US010421822B2

(12) United States Patent
Kelley et al.

(10) Patent No.: US 10,421,822 B2
(45) Date of Patent: Sep. 24, 2019

(54) ANTI-HTRA1 ANTIBODIES AND METHODS OF USE THEREOF

(71) Applicant: Genentech, Inc., South San Francisco, CA (US)

(72) Inventors: Robert F. Kelley, Petaluma, CA (US); Daniel K. Kirchhofer, Los Altos, CA (US); Joyce Lai, Fremont, CA (US); Chingwei V. Lee, Foster City, CA (US); Wei-Ching Liang, Foster City, CA (US); Michael T. Lipari, Santa Clara, CA (US); Kelly M. Loyet, Foster City, CA (US); Tao Sai, Foster City, CA (US); Menno Van Lookeren Campagne, San Francisco, CA (US); Yan Wu, Foster City, CA (US); Germaine Fuh, Pacifica, CA (US)

(73) Assignee: Genetech, Inc., South San Francisco, CA (US)

( * ) Notice: Subject to any disclaimer, the term of this patent is extended or adjusted under 35 U.S.C. 154(b) by 0 days.

(21) Appl. No.: 16/168,503

(22) Filed: Oct. 23, 2018

(65) Prior Publication Data

US 2019/0048097 A1     Feb. 14, 2019

Related U.S. Application Data

(62) Division of application No. 15/336,171, filed on Oct. 27, 2016.

(60) Provisional application No. 62/411,113, filed on Oct. 21, 2016, provisional application No. 62/345,669, filed on Jun. 3, 2016, provisional application No. 62/248,871, filed on Oct. 30, 2015.

(51) Int. Cl.
*C07K 16/40* (2006.01)
*A61K 39/395* (2006.01)
*A61K 39/00* (2006.01)

(52) U.S. Cl.
CPC .......... *C07K 16/40* (2013.01); *A61K 39/3955* (2013.01); *A61K 2039/507* (2013.01); *C07K 2317/24* (2013.01); *C07K 2317/34* (2013.01); *C07K 2317/53* (2013.01); *C07K 2317/55* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,376,110 A | 3/1983 | David et al. |
| 4,469,863 A | 9/1984 | Ts'o et al. |
| 4,476,301 A | 10/1984 | Imbach et al. |
| 4,485,045 A | 11/1984 | Regen |
| 4,486,530 A | 12/1984 | David et al. |
| 4,522,811 A | 6/1985 | Eppstein et al. |
| 4,544,545 A | 10/1985 | Ryan et al. |
| 4,816,567 A | 3/1989 | Cabilly et al. |
| 4,845,205 A | 7/1989 | Huynh Dinh et al. |
| 4,868,105 A | 9/1989 | Urdea et al. |
| 4,981,957 A | 1/1991 | Lebleu et al. |
| 5,013,556 A | 5/1991 | Woodle et al. |
| 5,023,243 A | 6/1991 | Tullis |
| 5,034,506 A | 7/1991 | Summerton et al. |
| 5,047,335 A | 9/1991 | Paulson et al. |
| 5,093,246 A | 3/1992 | Cech et al. |
| 5,118,800 A | 6/1992 | Smith et al. |
| 5,130,302 A | 7/1992 | Spielvogel et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,299 A | 1/1994 | Wong et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,367,066 A | 11/1994 | Urdea et al. |

(Continued)

FOREIGN PATENT DOCUMENTS

| | | |
|---|---|---|
| EP | 0073675 A1 | 3/1983 |
| EP | 0225807 B1 | 6/1987 |

(Continued)

OTHER PUBLICATIONS

"Roche initiates phase III trials for lampalizumab, first potential treatment for geographic atrophy (GA)," <http://www.roche.com/investors/updates/inv-update-2014-09-15.htm>, dated Sep. 15, 2014, retrieved on Feb. 1, 2017 (6 pages).

(Continued)

*Primary Examiner* — Daniel C Gamett
(74) *Attorney, Agent, or Firm* — Clark & Elbing LLP; Karen L. Elbing

(57) ABSTRACT

The present invention provides anti-HtrA1 antibodies (including bispecific anti-HtrA1 anti-Factor D antibodies) and methods of making and using the same, for example, in methods of treating HtrA1-associated disorders, ocular disorders, and/or complement-associated disorders.

52 Claims, 50 Drawing Sheets

(3 of 50 Drawing Sheet(s) Filed in Color)

Specification includes a Sequence Listing.

(56) References Cited

U.S. PATENT DOCUMENTS

| | | |
|---|---|---|
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,510,261 A | 4/1996 | Goochee et al. |
| 5,514,785 A | 5/1996 | Van Ness et al. |
| 5,519,126 A | 5/1996 | Hecht |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,567,811 A | 10/1996 | Misiura et al. |
| 5,569,825 A | 10/1996 | Lonberg et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,618,704 A | 4/1997 | Sanghvi et al. |
| 5,623,070 A | 4/1997 | Cook et al. |
| 5,625,050 A | 4/1997 | Beaton et al. |
| 5,625,126 A | 4/1997 | Lonberg et al. |
| 5,627,053 A | 5/1997 | Usman et al. |
| 5,633,425 A | 5/1997 | Lonberg et al. |
| 5,639,873 A | 6/1997 | Barascut et al. |
| 5,646,265 A | 7/1997 | McGee |
| 5,652,094 A | 7/1997 | Usman et al. |
| 5,658,873 A | 8/1997 | Bertsch-Frank et al. |
| 5,661,016 A | 8/1997 | Lonberg et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,698,046 A | 12/1997 | St Laurent et al. |
| 5,700,920 A | 12/1997 | Altmann et al. |
| 5,714,331 A | 2/1998 | Buchardt et al. |
| 5,739,277 A | 4/1998 | Presta et al. |
| 5,741,713 A | 4/1998 | Brown et al. |
| 5,750,373 A | 5/1998 | Garrard et al. |
| 5,750,692 A | 5/1998 | Cook et al. |
| 5,800,998 A | 9/1998 | Glucksmann |
| 5,837,492 A | 11/1998 | Tavtigian et al. |
| 5,891,628 A | 4/1999 | Reeders et al. |
| 6,004,794 A | 12/1999 | Karran et al. |
| 6,261,801 B1 | 7/2001 | Wei et al. |
| 6,274,376 B1 | 8/2001 | Black et al. |
| 6,274,720 B1 | 8/2001 | Lal et al. |
| 6,943,241 B2 | 9/2005 | Isogai et al. |
| 7,972,787 B2 | 7/2011 | Deangelis |
| 9,738,727 B2 | 8/2017 | Wu et al. |
| 2005/0059002 A1 | 3/2005 | Nie et al. |
| 2010/0129358 A1 | 5/2010 | Zhang et al. |
| 2010/0166743 A1 | 7/2010 | Zhang et al. |
| 2013/0129743 A1 | 5/2013 | Wu et al. |
| 2017/0145113 A1 | 5/2017 | Kelley et al. |
| 2017/0342163 A1 | 11/2017 | Wu et al. |

FOREIGN PATENT DOCUMENTS

| | | |
|---|---|---|
| EP | 0519463 A1 | 12/1992 |
| EP | 0332435 B2 | 10/1999 |
| WO | WO-84/03564 A1 | 9/1984 |
| WO | WO-91/03162 A1 | 3/1991 |
| WO | WO-92/07065 A1 | 4/1992 |
| WO | WO-93/06213 A1 | 4/1993 |
| WO | WO-93/15187 A1 | 8/1993 |
| WO | WO-99/07409 A1 | 2/1999 |
| WO | WO-99/32619 A1 | 7/1999 |
| WO | WO-99/55885 A2 | 11/1999 |
| WO | WO-00/01846 A2 | 1/2000 |
| WO | WO-00/08134 A2 | 2/2000 |
| WO | WO-00/44895 A1 | 8/2000 |
| WO | WO-00/44914 A1 | 8/2000 |
| WO | WO-01/29058 A1 | 4/2001 |
| WO | WO-01/36646 A1 | 5/2001 |
| WO | WO-03/080672 A1 | 10/2003 |
| WO | WO-2006/133295 A2 | 12/2006 |
| WO | WO-2008/067040 A2 | 6/2008 |
| WO | WO-2008/094370 A2 | 8/2008 |
| WO | WO-2008/101160 A2 | 8/2008 |
| WO | WO-2008/103299 A2 | 8/2008 |
| WO | WO-2009/046405 A2 | 4/2009 |
| WO | WO-2013/055998 A1 | 4/2013 |

OTHER PUBLICATIONS

"The siRNA user guide," <https://web.archive.org/web/20020220171546/http://www.mpibpc.gwdg.de/abteilungen/100/105/sirna.html>, retrieved on Aug. 20, 2015 (5 pages).

Ali et al. "Epidemiology and Biology of Insulin-like Growth Factor Binding Protein-3 (IGFBP-3) as an Anti-Cancer Molecule." BIOSIS Database Accession No. PREV200400113781, Hormone and Metabolic Research. 35(11-12):726-33 (2003) (Abstract Only).

Altschul et al., "Gapped BLAST and PSI-BLAST: a new generation of protein database search programs," Nucleic Acids Res. 25(17):3389-402 (1997).

Atlschul et al., "Basic local alignment search tool," J Mol Biol. 215(3): 403-10 (1990).

Bach et al., *Handbook of Monoclonal Antibodies*. Soldano Ferrone and Manfred P. Dierich, 303-59, 419-35 (1985).

Barbas et al., "In vitro evolution of a neutralizing human antibody to human immunodeficiency virus type 1 to enhance affinity and broaden strain cross-reactivity," Proc Natl Acad Sci U S A. 91(9):3809-13 (1994).

Bartel et al., 7: Using the two-hybrid system to detect protein-protein interactions. *Cellular Interactions in Development: A Practical Approach.* David A. Hartley, Oxford University Press, 153-179 (1993).

Beaucage et al., "Deoxynucleoside phosphoramidites—a new class of key intermediates for deoxypolynucleotide synthesis," Tetrahedron Lett. 22(20):1859-62 (1981).

Bird et al., "An international classification and grading system for age-related maculopathy and age-related macular degeneration. The International ARM Epidemiological Study Group," Surv Ophthalmol. 39(5):367-74 (1995).

Boerner et al., "Production of antigen-specific human monoclonal antibodies from in vitro-primed human splenocytes," J Immunol. 147(1):86-95 (1991).

Borchardt et al., "Synthetic receptor binding elucidated with an encoded combinatorial library," J Am Chem Soc. 116(1):373-374 (1994).

Borman, "DNA Chips Come of Age," Chemical & Engineering News. 74(50):42-3 (1996) (3 pages).

(56) References Cited

OTHER PUBLICATIONS

Boyd et al., "The effect of the removal of sialic acid, galactose and total carbohydrate on the functional activity of Campath-1H," Mol Immunol. 32(17-18):1311-8 (1995).
Brennan et al., "Preparation of bispecific antibodies by chemical recombination of monoclonal immunoglobulin G1 fragments," Science. 229(4708):81-3 (1985).
Brodeur et al., Mouse-Human Myeloma Partners for the Production of Heterohybridomas. *Monoclonal Antibody Production Techniques and Applications*. Lawrence B. Schook, University of Illinois, 51-63 (1987).
Burnham, "Polymers for delivering peptides and proteins," Am J Hosp Pharm. 51(2):210-8 (1994).
Capecchi, "Altering the genome by homologous recombination," Science. 244(4910):1288-92 (1989).
Cariello et al., "Resolution of a missense mutant in human genomic DNA by denaturing gradient gel electrophoresis and direct sequencing using in vitro DNA amplification: HPRT Munich," Am J Hum Genet. 42(5):726-34 (1988) (10 pages).
Carrillo et al., "The mutiple sequence alignment problem in biology," SIAM J Appl Math. 48(5):1073-82 (1988).
Carter et al., "High level *Escherichia coli* expression and production of a bivalent humanized antibody fragment," Biotechnology (N Y). 10(2):163-7 (1992).
Casset et al., "A peptide mimetic of an anti-CD4 monoclonal antibody by rational design," Biochem Biophys Res Commun. 307(1):198-205 (2003).
Chee et al., "Accessing genetic information with high-density DNA arrays," Science. 274(5287):610-4 (1996).
Chen et al., "Selection and analysis of an optimized anti-VEGF antibody: crystal structure of an affinity-matured Fab in complex with antigen," J Mol Biol. 293(4):865-81 (1999).
Chevray et al., "Protein interaction cloning in yeast: identification of mammalian proteins that react with the leucine zipper of Jun," Proc Natl Acad Sci U S A. 89(13):5789-93 (1992).
Chothia et al., "Domain association in immunoglobulin molecules. The packing of variable domains," J Mol Biol. 186(3):651-63 (1985).
Ciferri et al., "The trimeric serine protease HtrA1 forms a cage-like inhibition complex with an anti-HtrA1 antibody," Biochem J. 472(2):169-81 (2015).
Clackson et al., "Making antibody fragments using phage display libraries," Nature. 352(6336):624-8 (1991).
Clausen et al., "HTRA proteases: regulated proteolysis in protein quality control," Nat Rev Mol Cell Biol. 12(3):152-62 (2011).
Cole et al., The EBV-Hybridoma Technique and its Application to Human Lung Cancer. Monoclonal Antibodies and Cancer Therapy. Alan R. Liss, Inc., edited by Ralph A. Reisfeld and Stewart Sell. 77-96 (1985).
Conner et al., "Detection of sickle cell beta S-globin allele by hybridization with synthetic oligonucleotides," Proc Natl Acad Sci U S A. 80(1):278-82 (1983).
Cotton et al., "Reactivity of cytosine and thymine in single-base-pair mismatches with hydroxylamine and osmium tetroxide and its application to the study of mutations," Proc Natl Acad Sci U S A. 85(12):4397-401 (1988).
Cunningham et al., "High-resolution epitope mapping of hGH-receptor interactions by alanine-scanning mutagenesis," Science. 244(4908):1081-5 (1989).
David et al., "Protein iodination with solid state lactoperoxidase," Biochemistry. 13(5):1014-21 (1974).
De Pascalis et al., "Grafting of "abbreviated" complementarity-determining regions containing specificity-determining residues essential for ligand contact to engineer a less immunogenic humanized monoclonal antibody," J Immunol. 169(6):3076-84 (2002).
Dejneka et al., "Systemic rapamycin inhibits retinal and choroidal neovascularization in mice," Mol Vis. 10:964-72 (2004).
DeRisi et al., "Use of a cDNA microarray to analyse gene expression patterns in human cancer," Nat Genet. 14(4):457-60 (1996).
Devereux et al., "A comprehensive set of sequence analysis programs for the VAX," Nucleic Acids Res. 12(1 Pt 1):387-95 (1984).
Dewan et al., "HTRA1 promoter polymorphism in wet age-related macular degeneration," Science. 314(5801):989-92 (2006).
Donehower et al., "Mice deficient for p53 are developmentally normal but susceptible to spontaneous tumours," Nature. 356(6366):215-21 (1992).
Edwards et al., "Complement factor H polymorphism and age-related macular degeneration," Science. 308(5720):421-4 (2005).
Eigenbrot et al., "Structural and functional analysis of HtrA1 and its subdomains," Structure. 20(6):1040-50 (2012).
Elbashir et al., "Duplexes of 21-nucleotide RNAs mediate RNA interference in cultured mammalian cells," Nature. 411(6836):494-8 (2001).
Eppstein et al., "Biological activity of liposome-encapsulated murine interferon gamma is mediated by a cell membrane receptor," Proc Natl Acad Sci U S A. 82(11):3688-92 (1985).
Feil et al., "Ligand-activated site-specific recombination in mice," Proc Natl Acad Sci U S A. 93(20):10887-90 (1996).
Fields et al., "A novel genetic system to detect protein-protein interactions," Nature. 340(6230):245-6 (1989).
Finkelstein et al., "Use of denaturing gradient gel electrophoresis for detection of mutation and prospective diagnosis in late onset ornithine transcarbamylase deficiency," Genomics. 7(2):167-72 (1990).
Fishwild et al., "High-avidity human IgG kappa monoclonal antibodies from a novel strain of minilocus transgenic mice," Nat Biotechnol. 14(7):845-51 (1996).
Fodor, "Massively parallel genomics," Science. 277(5324):393, 395 (1997).
Fu et al., "The R345W mutation in EFEMP1 is pathogenic and causes AMD-like deposits in mice," Hum Mol Genet. 16(20):2411-22 (2007).
Fuh et al., "Structure-function studies of two synthetic anti-vascular endothelial growth factor Fabs and comparison with the Avastin Fab," J Biol Chem. 281(10):6625-31 (2006) (8 pages).
Gagneten et al., "Brief expression of a GFP cre fusion gene in embryonic stem cells allows rapid retrieval of site-specific genomic deletions," Nucleic Acids Res. 25(16):3326-31 (1997).
Ganesan et al., "Structural and mechanistic insight into how antibodies inhibit serine proteases," Biochem J. 430(2):179-89 (2010).
Goding, Nature of Antigens; Antibody Structure and Function; Genetics of Antibodies. *Monoclonal Antibodies: Principles and Practice: Production and Application of Monoclonal Antibodies in Cell Biology, Biochemistry and Immunology, Third Edition*. Academic Press Limited, 58-103 (1996).
Godowski et al., "Signal transduction and transcriptional regulation by glucocorticoid receptor-LexA fusion proteins," Science. 241(4867):812-6 (1988).
Griffiths et al., "Human anti-self antibodies with high specificity from phage display libraries," EMBO J. 12(2):725-34 (1993).
Grompe et al., "Scanning detection of mutations in human ornithine transcarbamoylase by chemical mismatch cleavage," Proc Natl Acad Sci U S A. 86(15):5888-92 (1989).
Grompe, "The rapid detection of unknown mutations in nucleic acids," Nat Genet. 5(2):111-7 (1993).
Hacia et al., "Detection of heterozygous mutations in BRCA1 using high density oligonucleotide arrays and two-colour fluorescence analysis," Nat Genet. 14(4):441-7 (1996).
Hannon, "RNA interference," Nature. 418(6894):244-51 (2002).
Hasty et al., "Introduction of a subtle mutation into the Hox-2.6 locus in embryonic stem cells," Nature. 350(6315):243-6 (1991).
Hawkins et al., "Selection of phage antibodies by binding affinity. Mimicking affinity maturation," J Mol Biol. 226(3):889-96 (1992).
Hoogenboom et al., "By-passing immunisation. Human antibodies from synthetic repertoires of germline VH gene segments rearranged in vitro," J Mol Biol. 227(2):381-8 (1992).
Hsu et al., "Differential N-glycan patterns of secreted and intracellular IgG produced in Trichoplusia ni cells," J Biol Chem. 272(14):9062-70 (1997).
Hunter et al., "Preparation of iodine-131 labelled human growth hormone of high specific activity," Nature. 194:495-6 (1962).

(56) References Cited

OTHER PUBLICATIONS

Hwang et al., "Hepatic uptake and degradation of unilamellar sphingomyelin/cholesterol liposomes: a kinetic study," Proc Natl Acad Sci U S A. 77(7):4030-4 (1980).
Iliades et al., "Triabodies: single chain Fv fragments without a linker form trivalent trimers," FEBS Lett. 409(3):437-41 (1997).
Jablonski et al., "Preparation of oligodeoxynucleotide-alkaline phosphatase conjugates and their use as hybridization probes," Nucleic Acids Res. 14(15):6115-28 (1986).
Jackson et al., "In vitro antibody maturation. Improvement of a high affinity, neutralizing antibody against IL-1 beta," J Immunol. 154(7):3310-9 (1995).
Jakobovits et al., "Analysis of homozygous mutant chimeric mice: deletion of the immunoglobulin heavy-chain joining region blocks B-cell development and antibody production," Proc Natl Acad Sci U S A. 90(6):2551-5 (1993).
Jakobovits et al., "Germ-line transmission and expression of a human-derived yeast artificial chromosome," Nature. 362(6417):255-8 (1993).
Jakobsdottir et al., "Susceptibility genes for age-related maculopathy on chromosome 10q26," Am J Hum Genet. 77(3):389-407 (2005).
Jefferis et al., "Glycosylation of antibody molecules: structural and functional significance," Chem Immunol. 65:111-28 (1997).
Johnson et al., "Human antibody engineering," Curr Opin Struct Biol. 3:564-71 (1993).
Jones et al., "Replacing the complementarity-determining regions in a human antibody with those from a mouse," Nature. 321(6069):522-5 (1986).
Justilien et al., "SOD2 knockdown mouse model of early AMD," Invest Ophthalmol Vis Sci. 48(10):4407-20 (2007).
Karan et al., "Lipofuscin accumulation, abnormal electrophysiology, and photoreceptor degeneration in mutant ELOVL4 transgenic mice: a model for macular degeneration," Proc Natl Acad Sci U S A. 102(11):4164-9 (2005).
Kinzler et al., "Identification of a gene located at chromosome 5q21 that is mutated in colorectal cancers," Science. 251(4999):1366-70 (1991).
Kortt et al., "Single-chain Fv fragments of anti-neuraminidase antibody NC10 containing five- and ten-residue linkers form dimers and with zero-residue linker a trimer," Protein Eng. 10(4):423-33 (1997).
Kozbor et al., "A human hybrid myeloma for production of human monoclonal antibodies," J Immunol. 133(6):3001-5 (1984).
Köhler et al., "Continuous cultures of fused cells secreting antibody of predefined specificity," Nature. 256(5517):495-7 (1975).
Lamminmäki et al., "Crystal structure of a recombinant anti-estradiol Fab fragment in complex with 17beta-estradiol," J Biol Chem. 276(39):36687-94 (2001).
Landegren et al. "DNA diagnostics—molecular techniques and automation," Science. 242(4876):229-37 (1988).
Le et al., "Population Pharmacokinetics and Pharmacodynamics of Lampalizumab Administered Intravitreally to Patients With Geographic Atrophy," CPT Pharmacometrics Syst Pharmacol. 4(10):595-604 (2015).
Lee et al., "Conversion of Xenopus ectoderm into neurons by NeuroD, a basic helix-loop-helix protein," Science. 268(5212):836-44 (1995).
Levin, "The occurence of lung cancer in man," Acta Unio Int Contra Cancrum. 9(3):531-41 (1953).
Lewis et al., "Efficient delivery of siRNA for inhibition of gene expression in postnatal mice," Nat Genet. 32(1):107-8 (2002).
Limbach et al., "Summary: the modified nucleosides of RNA," Nucleic Acids Res. 22(12):2183-96 (1994).
Lipshutz et al., "Using oligonucleotide probe arrays to access genetic diversity," Biotechniques. 19(3):442-7 (1995).
Lobe et al., "Conditional genome alteration in mice," Bioessays. 20(3):200-8 (1998).
Lockhart et al., "Expression monitoring by hybridization to high-density oligonucleotide arrays," Nat Biotechnol. 14(13):1675-80 (1996).
Lonberg et al., "Antigen-specific human antibodies from mice comprising four distinct genetic modifications," Nature. 368(6474):856-9 (1994).
Lonberg et al., "Human antibodies from transgenic mice," Int Rev Immunol. 13(1):65-93 (1995).
Ma et al., "A new class of yeast transcriptional activators," Cell. 51(1):113-9 (1987).
Ma et al., "Deletion analysis of GAL4 defines two transcriptional activating segments," Cell. 48(5):847-53 (1987).
Ma et al., "The carboxy-terminal 30 amino acids of GAL4 are recognized by GAL80," Cell. 50(1):137-42 (1987).
MacCallum et al., "Antibody-antigen interactions: contact analysis and binding site topography," J Mol Biol. 262(5):732-45 (1996).
Mage et al., Preparation of Fab and F(ab')2 Fragments from Monoclonal Antibodies. *Monoclonal Antibody Production Techniques and Applications*. Lawrence B. Schook, 79-97 (1987).
Marks et al., "By-passing immunization. Human antibodies from V-gene libraries displayed on phage," J Mol Biol. 222(3):581-97 (1991).
Marks et al., "By-passing immunization: building high affinity human antibodies by chain shuffling," Biotechnology (NY). 10(7):779-83 (1992).
Martin et al., "Irreversible coupling of immunoglobulin fragments to preformed vesicles. An improved method for liposome targeting," J Biol Chem. 257(1):286-8 (1982).
Matteucci et al., "Synthesis of deoxyoligonucleotides on a polymer support," J Am Chem Soc. 103:3185-91 (1981).
Matthews et al., "Analytical strategies for the use of DNA probes," Anal Biochem. 169(1):1-25 (1988).
McCafferty et al., "Phage antibodies: filamentous phage displaying antibody variable domains," Nature. 348(6301):552-4 (1990).
McCaffrey et al., "RNA interference in adult mice," Nature. 418(6893):38-9 (2002).
Mendez et al., "Functional transplant of megabase human immunoglobulin loci recapitulates human antibody response in mice," Nat Genet. 15(2):146-56 (1997).
Mifflin, "Use and applications of nucleic acid probes in the clinical laboratory," Clin Chem. 35(9):1819-25 (1989).
Modrich, "Mechanisms and biological effects of mismatch repair," Annu Rev Genet. 25:229-53 (1991).
Mombaerts et al., "RAG-1-deficient mice have no mature B and T lymphocytes," Cell. 68(5):869-77 (1992).
Moran et al., "Radio frequency tag encoded combinatorial library method for the discovery of tripeptide-substituted cinnamic acid inhibitors of the protein tyrosine phosphatase PTP1B," J Am Chem Soc. 117(43):10787-8 (1995).
Morimoto et al., "Single-step purification of F(ab')2 fragments of mouse monoclonal antibodies (immunoglobulins G1) by hydrophobic interaction high performance liquid chromatography using TSKgel Phenyl-5PW," J Biochem Biophys Methods. 24(1-2):107-17 (1992).
Morrison et al., "Chimeric human antibody molecules: mouse antigen-binding domains with human constant region domains," Proc Natl Acad Sci U S A. 81(21):6851-5 (1984).
Morrison, "Immunology. Success in specification," Nature. 368(6474):812-3 (1994).
Munson et al., "Ligand: a versatile computerized approach for characterization of ligand-binding systems," Anal Biochem. 107(1):220-39 (1980).
Nambu et al., "Combretastatin A-4 phosphate suppresses development and induces regression of choroidal neovascularization," Invest Ophthalmol Vis Sci. 44(8):3650-5 (2003).
Neuberger, "Generating high-avidity human Mabs in mice," Nat Biotechnol. 14(7):826 (1996).
Newton et al., "Analysis of any point mutation in DNA. The amplification refractory mutation system (ARMS)," Nucleic Acids Res. 17(7):2503-16 (1989).
Nguyen et al., "A two-step hybridization method for chemiluminescent detection of single copy genes," Biotechniques. 13(1):116-23 (1992).
Nielsen et al., "Sequence-selective recognition of DNA by strand displacement with a thymine-substituted polyamide," Science. 254(5037):1497-500 (1991).

(56) References Cited

OTHER PUBLICATIONS

Novack et al., "Detection of single base-pair mismatches in DNA by chemical modification followed by electrophoresis in 15% polyacrylamide gel," Proc Natl Acad Sci U S A. 83(3):586-90 (1986).
Novotný et al., "Structural invariants of antigen binding: comparison of immunoglobulin VL-VH and VL-VL domain dimers," Proc Natl Acad Sci U S A. 82(14):4592-6 (1985).
Nygren, "Conjugation of horseradish peroxidase to Fab fragments with different homobifunctional and heterobifunctional cross-linking reagents. A comparative study," J Histochem Cytochem. 30(5):407-12 (1982).
Oka et al., "HtrA1 serine protease inhibits signaling mediated by Tgfbeta family proteins," Development. 131(5):1041-53 (2004).
Orita et al., "Detection of polymorphisms of human DNA by gel electrophoresis as single-strand conformation polymorphisms," Proc Natl Acad Sci U S A. 86(8):2766-70 (1989).
Osterrieder et al., "Lessons from gene knockouts," Rev Sci Tech. 17(1):351-64 (1998).
Padlan et al., "Structure of an antibody-antigen complex: crystal structure of the HyHEL-10 Fab-lysozyme complex," Proc Natl Acad Sci USA. 86(15):5938-5942 (1989).
Pain et al., "Preparation of protein A-peroxidase monoconjugate using a heterobifunctional reagent, and its use in enzyme immunoassays," J Immunol Methods. 40(2):219-30 (1981).
Paul et al., "Effective expression of small interfering RNA in human cells," Nat Biotechnol. 20(5):505-8 (2002).
Perreault et al., "Mixed deoxyribo- and ribo-oligonucleotides with catalytic activity," Nature. 344(6266):565-7 (1990).
Philpott et al., "Lymphoid development in mice congenitally lacking T cell receptor alpha beta-expressing cells," Science. 256(5062):1448-52 (1992).
Pieken et al., "Kinetic characterization of ribonuclease-resistant 2'-modified hammerhead ribozymes," Science. 253(5017):314-7 (1991).
Riechmann et al., "Reshaping human antibodies for therapy," Nature. 332(6162):323-7 (1988).
Rigby et al., "Labeling deoxyribonucleic acid to high specific activity in vitro by nick translation with DNA polymerase I," J Mol Biol. 113(1):237-51 (1977).
Rosenfeld et al., "Ranibizumab: Phase III clinical trial results," Ophthalmol Clin North Am. 19(3):361-72 (2006).
Ruano et al., "Direct haplotyping of chromosomal segments from multiple heterozygotes via allele-specific PCR amplification," Nucleic Acids Res. 17(20):8392 (1989).
Rudikoff et al., "Single amino acid substitution altering antigen-binding specificity," Proc Natl Acad Sci U S A. 79(6):1979-83 (1982).
Saishin et al., "VEGF-TRAP(R1 R2) suppresses choroidal neovascularization and VEGF-induced breakdown of the blood-retinal barrier," J Cell Physiol. 195(2):241-8 (2003).
Saldanha, Molecular Engineering I: Humanization. *Handbook of Therapeutic Antibodies*. Wiley-VCH, 119-144 (2007).
Scaringe et al., "Chemical synthesis of biologically active oligoribonucleotides using beta-cyanoethyl protected ribonucleoside phosphoramidites," Nucleic Acids Res. 18(18):5433-41 (1990).
Schier et al., "Identification of functional and structural amino-acid residues by parsimonious mutagenesis," Gene. 169(2):147-55 (1996).
Sharrow et al., Overview of Flow Cytometry; Analysis of Flow Cytometry Data; Measurement of Intercellular Conjugates by Flow Cytometry. *Current Protocols in Immunology*. John Wiley & Sons, 5.1.1-5.1.8; 5.2.1-5.2.10; 5.6.1-5.6.8 (1991).
Shastry, "Gene disruption in mice: models of development and disease," Mol Cell Biochem. 181(1-2):163-79 (1998).
Shastry, "Genetic knockouts in mice: an update," Experientia. 51(11):1028-39 (1995).
Sheets et al., "Efficient construction of a large nonimmune phage antibody library: the production of high-affinity human single-chain antibodies to protein antigens," Proc Natl Acad Sci U S A. 95(11):6157-62 (1998).

Sheffield et al., "Attachment of a 40-base-pair G + C-rich sequence (GC-clamp) to genomic DNA fragments by the polymerase chain reaction results in improved detection of single-base changes," Proc Natl Acad Sci U S A. 86(1):232-6 (1989).
Sheffield et al., "Identification of novel rhodopsin mutations associated with retinitis pigmentosa by GC-clamped denaturing gradient gel electrophoresis," Am J Hum Genet. 49(4):699-706 (1991).
Shenk et al., "Biochemical method for mapping mutational alterations in DNA with S1 nuclease: the location of deletions and temperature-sensitive mutations in simian virus 40," Proc Natl Acad Sci U S A. 72(3):989-93 (1975).
Shi, "Mammalian RNAi for the masses," Trends Genet. 19(1):9-12 (2003).
Shinkai et al., "RAG-2-deficient mice lack mature lymphocytes owing to inability to initiate V(D)J rearrangement," Cell. 68(5):855-67 (1992).
Shoemaker et al., "Quantitative phenotypic analysis of yeast deletion mutants using a highly parallel molecular bar-coding strategy," Nat Genet. 14(4):450-6 (1996).
Sikela et al., "Screening an expression library with a ligand probe: isolation and sequence of a cDNA corresponding to a brain calmodulin-binding protein," Proc Natl Acad Sci U S A. 84(9):3038-42 (1987).
Smith et al., "Oxygen-induced retinopathy in the mouse," Invest Ophthalmol Vis Sci. 35(1):101-11 (1994).
Smith et al., Cardiac Glycoside-Specific Antibodies in the Treatment of Digitalis Intoxication. *Antibodies in Human Diagnosis and Therapy*. Edgar Haber and Richard M. Krause, 365-389 (1977).
Snouwaert et al., "An animal model for cystic fibrosis made by gene targeting," Science. 257(5073):1083-8 (1992).
Song et al., "RNA interference targeting Fas protects mice from fulminant hepatitis," Nat Med. 9(3):347-51 (2003).
Sui et al., "A DNA vector-based RNAi technology to suppress gene expression in mammalian cells," Proc Natl Acad Sci U S A. 99(8):5515-20 (2002).
Tamura et al., "Structural correlates of an anticarcinoma antibody: identification of specificity-determining residues (SDRs) and development of a minimally immunogenic antibody variant by retention of SDRs only," J Immunol. 164(3):1432-41 (2000) (11 pages).
Tanaka et al., "Choroidal neovascularization in transgenic mice expressing prokineticin 1: an animal model for age-related macular degeneration," Mol Ther. 13(3):609-16 (2006).
Tsuchiya et al., "Expression of mouse HtrA1 serine protease in normal bone and cartilage and its upregulation in joint cartilage damaged by experimental arthritis," Bone. 37(3):323-36 (2005).
Umaña et al., "Engineered glycoforms of an antineuroblastoma IgG1 with optimized antibody-dependent cellular cytotoxic activity," Nat Biotechnol. 17(2):176-80 (1999).
Usman et al., "Automated chemical synthesis of long oligoribunucleotides using 2'-O-silylated ribonucleoside 3'-O-phosphoramidites on a controlled-pore glass support: synthesis of a 43-nucleotide sequence similar to the 3'-half molecule of an *Escherichia coli* formylmethionine tRNA," J Am Chem Soc. 109(25):7845-54 (1987).
Usman et al., "Exploiting the chemical synthesis of RNA," Trends Biochem Sci. 17(9):334-9 (1992).
Vajdos et al., "Comprehensive functional maps of the antigen-binding site of an anti-ErbB2 antibody obtained with shotgun scanning mutagenesis," J Mol Biol. 320(2):415-28 (2002).
Valancius et al., "Double-strand gap repair in a mammalian gene targeting reaction," Mol Cell Biol. 11(9):4389-97 (1991).
Vaughan et al., "Human antibodies with sub-nanomolar affinities isolated from a large non-immunized phage display library," Nat Biotechnol. 14(3):309-14 (1996).
Verhoeyen et al., "Reshaping human antibodies: grafting an antilysozyme activity," Science. 239(4847):1534-6 (1988).
von Mehren et al., "Monoclonal antibody-based therapy," Curr Opin Oncol. 8(6):493-8 (1996).
Wartell et al., "Detecting base pair substitutions in DNA fragments by temperature-gradient gel electrophoresis," Nucleic Acids Res. 18(9):2699-705 (1990).
Waterhouse et al., "Combinatorial infection and in vivo recombination: a strategy for making large phage antibody repertoires," Nucleic Acids Res. 21(9):2265-6 (1993).

(56) References Cited

OTHER PUBLICATIONS

Wetmur et al., "Kinetics of renaturation of DNA," J Mol Biol. 31(3):349-70 (1968).
White et al., "Detecting single base substitutions as heteroduplex polymorphisms," Genomics. 12(2):301-6 (1992).
White et al., "Sets of linked genetic markers for human chromosomes," Annu Rev Genet. 22:259-79 (1988).
Wittwer et al., "Glycosylation at Asn-184 inhibits the conversion of single-chain to two-chain tissue-type plasminogen activator by plasmin," Biochemistry. 29(17):4175-80 (1990).
Wright et al., "Effect of glycosylation on antibody function: implications for genetic engineering," Trends Biotechnol. 15(1):26-32 (1997).
Wu et al., "Humanization of a murine monoclonal antibody by simultaneous optimization of framework and CDR residues," J Mol Biol. 294(1):151-62 (1999).
Wyss et al., "The structural role of sugars in glycoproteins," Curr Opin Biotechnol. 7(4):409-16 (1996).
Xia et al., "siRNA-mediated gene silencing in vitro and in vivo," Nat Biotechnol. 20(10):1006-10 (2002).
Yang et al., "A variant of the HTRA1 gene increases susceptibility to age-related macular degeneration," Science. 314(5801):992-3 (2006).
Yelton et al., "Affinity maturation of the BR96 anti-carcinoma antibody by codon-based mutagenesis," J Immunol. 155(4):1994-2004 (1995).
Yu et al., "RNA interference by expression of short-interfering RNAs and hairpin RNAs in mammalian cells," Proc Natl Acad Sci U S A. 99(9):6047-52 (2002).
Zamore et al., "siRNAs knock down hepatitis," Nat Med. 9(3):266-7 (2003) (3 pages).
Zola et al., Using monoclonal antibodies: Soluble antigens. *Monoclonal antibodies: A manual of techniques*. CRC Press, Inc., 147-158 (2000).
Zumbrunn et al., "Primary structure of a putative serine protease specific for IGF-binding proteins," FEBS Lett. 398(2-3):187-92 (1996).
Examination Report No. 1 for Australian Patent Application No. 2016344399, dated Nov. 26, 2018 (4 pages).
First Examination Report for New Zealand Patent Application No. 741780, dated Nov. 30, 2018 (6 pages).
International Preliminary Report on Patentability for International Patent Application No. PCT/US2016/059110, dated May 1, 2018 (12 pages).
International Search Report and Written Opinion for International Patent Application No. PCT/US2016/059110, dated Mar. 31, 2017 (23 pages).
Invitation to Pay Additional Fees for International Patent Application No. PCT/US2016/059110, dated Jan. 26, 2017 (9 pages).
Communication Pursuant to Article 94(3) for European Patent Application No. 16794157.4, dated Apr. 26, 2019 (5 pages).
Examination Report for Gulf Cooperation Council Patent Application No. 2016-32272, dated Dec. 12, 2018 (6 pages).

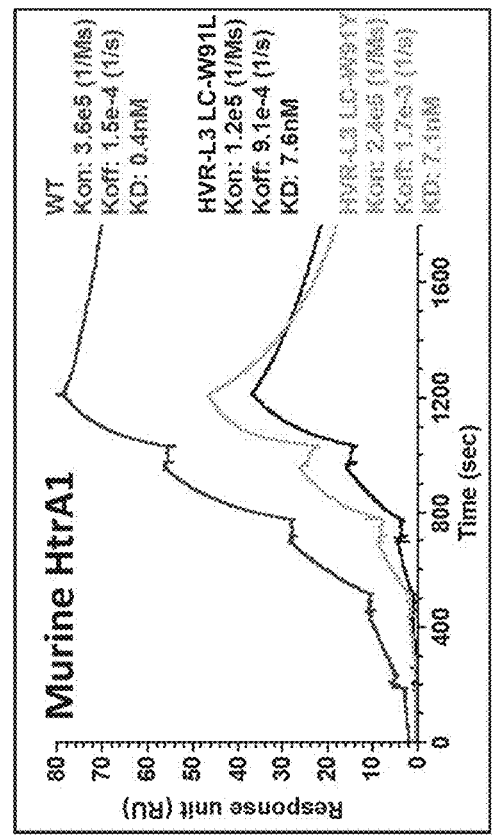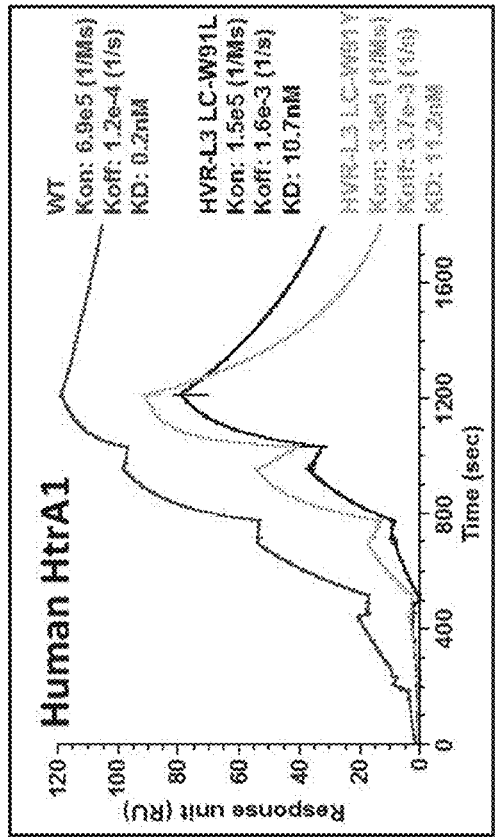
FIG. 11A
FIG. 11B

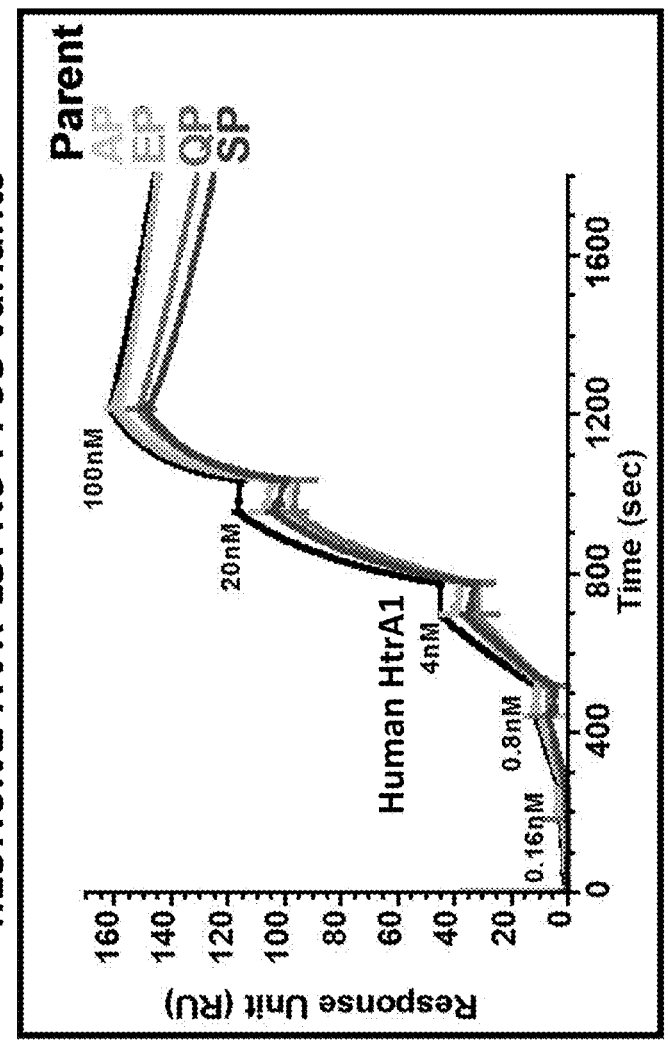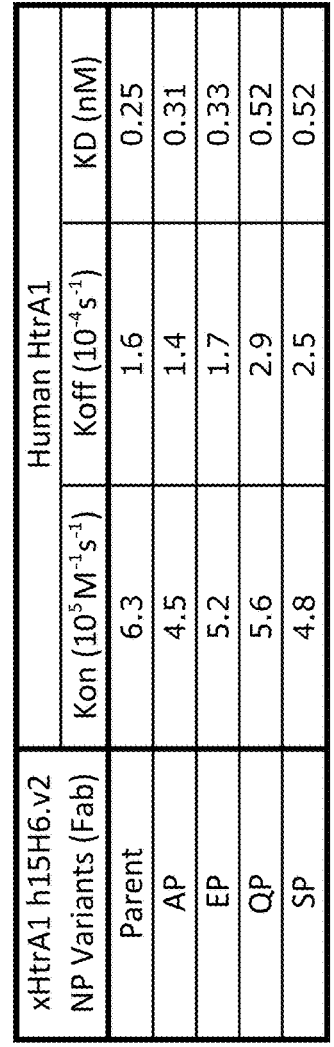
FIG. 12A
FIG. 12B

| xHtrA1 h15H6.v2 variants (Fab) | Human HtrA1-PD (N=2) | | |
|---|---|---|---|
| | Kon ($10^5 M^{-1}s^{-1}$) | Koff ($10^{-4} s^{-1}$) | KD (nM) |
| NP_DG (WT) | 4.9 ± 0.6 | 2.1 ± 0.2 | 0.4 ± 0.1 |
| AP_EG | 3.5 ± 0.1 | 2.1 ± 0.1 | 0.6 ± 0.1 |
| EP_EG | 4.5 ± 0.1 | 1.8 ± 0.1 | 0.4 ± 0.1 |
| QP_EG | 3.8 ± 0.1 | 2.9 ± 0.2 | 0.8 ± 0.1 |
| SP_EG | 3.5 ± 0.1 | 2.9 ± 0.1 | 0.8 ± 0.1 |

| Clones | FRET IC50 (nM) |
|---|---|
| h15H6.v2 FL | 5.9 ± 1.2 |
| h15H6.v2 Fab | 8.1 ± 0.6 |
| AP_EG Fab | 8.9 ± 2.6 |
| EP_EG Fab | 9.4 ± 1.3 |
| QP_EG Fab | 7.6 ± 0.7 |
| SP_EG Fab | 7.5 ± 3.1 |

FIG. 15A

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human Consensus K4 | D | I | V | M | T | Q | S | P | D | S | L | A | V | S | L | G | E | R | A | T | I | N | C | K | S | S | Q | S | V | L | Y | S | S | N | N | K | N | Y | L | A | W | Y |
| m19B12 | N | I | V | T | Q | S | P | A | S | L | A | V | S | L | G | Q | R | A | T | I | S | C | R | A | S | E | S | V | D | S | . | . | Y | G | K | S | F | M | H | W | Y | |
| h19B12.v1 | D | I | V | M | T | Q | S | P | D | S | L | A | V | S | L | G | E | R | A | T | I | N | C | R | A | S | E | S | V | D | S | . | . | Y | G | K | S | F | M | H | W | Y |

HVR-L1 – Contact  
HVR-L1 – Kabat

| Kabat number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human Consensus K4 | Q | Q | K | P | G | Q | P | P | K | L | L | I | Y | W | A | S | T | R | E | S | G | V | P | D | R | F | S | G | S | G | S | G | T | D | F | T | L | T | I | S | S | L |
| m19B12 | Q | Q | K | P | G | Q | P | P | K | L | L | I | Y | . | L | A | S | K | L | E | S | G | V | P | A | R | F | S | G | S | G | S | R | T | D | F | T | L | T | I | D | P | V |
| h19B12.v1 | Q | Q | K | P | G | Q | P | P | K | L | L | I | Y | . | L | A | S | K | L | E | S | G | V | P | D | R | F | S | G | S | G | S | G | T | D | F | T | L | T | I | S | S | L |

HVR-L2 – Contact  
HVR-L2 – Kabat

| Kabat number | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|---|---|
| Human Consensus K4 | Q | A | E | D | V | A | V | Y | Y | C | Q | Q | Y | . | . | . | . | . | . | . | . | . | . | T | K | V | E | I | K | (SEQ ID NO: 79) |
| m19B12 | E | A | D | D | A | A | T | Y | Y | C | Q | Q | N | N | E | D | P | Y | T | F | G | G | G | T | K | L | E | I | K | (SEQ ID NO: 56) |
| h19B12.v1 | Q | A | E | D | V | A | V | Y | Y | C | Q | Q | N | N | E | D | P | Y | T | F | G | Q | G | T | K | V | E | I | K | (SEQ ID NO: 46) |

HVR-L3 – Contact  
HVR-L3 – Kabat

FIG. 15B

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human Consensus VH3 | E | V | Q | L | V | E | S | G | G | G | L | V | Q | P | G | G | S | L | R | L | S | C | A | A | S | G | F | T | F | S | S | Y | A | M | S | W | V | R | Q | A | P | G |
| m19B12 | E | V | K | L | V | E | S | G | G | G | L | V | E | P | G | G | S | L | K | L | S | C | V | A | S | G | F | T | F | S | S | Y | I | M | S | W | V | R | Q | T | P | E |
| h19B12.v1 | E | V | Q | L | V | E | S | G | G | G | L | V | Q | P | G | G | S | L | R | L | S | C | A | A | S | G | F | T | F | S | S | Y | I | M | S | W | V | R | Q | A | P | G |

HVR-H1 - Contact: 30–35
HVR-H1 - Kabat: 31–35

| Kabat number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human Consensus VH3 | K | G | L | E | W | V | G | A | I | S | S | S | G | G | S | T | Y | Y | A | D | S | V | K | G | R | F | T | I | S | R | D | N | S | K | N | T | L | Y | L | Q | M | N |
| m19B12 | K | R | L | E | W | V | A | Y | I | S | N | G | G | T | T | Y | Y | S | D | T | H | K | G | R | F | T | I | S | R | D | N | A | K | N | T | L | Y | L | Q | M | S |
| h19B12.v1 | K | G | L | E | W | V | A | Y | I | S | N | G | G | T | T | Y | Y | S | D | T | I | K | G | R | F | T | I | S | R | D | N | S | K | N | T | L | Y | L | Q | M | N |

HVR-H2 - Contact: 47–58
HVR-H2 - Kabat: 50–65

| Kabat number | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 | | |
|---|---|---|---|---|---|---|---|---|---|---|---|---|---|---|---|---|---|---|---|---|---|---|---|---|---|---|---|---|---|---|---|---|---|---|---|---|---|---|---|
| Human Consensus VH3 | S | L | R | A | E | D | T | A | V | Y | Y | C | A | R | | | | | | | | | | | D | Y | W | G | Q | G | T | L | V | T | V | S | S | (SEQ ID NO: 80) | |
| m19B12 | T | L | K | S | E | D | T | A | I | Y | F | C | A | R | Q | N | F | R | S | D | G | S | S | M | D | Y | W | G | Q | G | T | A | V | T | V | S | S | (SEQ ID NO: 55) | |
| h19B12.v1 | S | L | R | A | E | D | T | A | V | Y | Y | C | A | R | Q | N | F | R | S | D | G | S | S | M | D | Y | W | G | Q | G | T | L | V | T | V | S | S | (SEQ ID NO: 45) | |

HVR-H3 - Contact: 93–101
HVR-H3 - Kabat: 95–102

FIG. 19

| HC | NNK | soft |
|---|---|---|
| 30K | x | |
| 30R | x | |
| 28K | x | x |
| 28R | x | |
| 34L | x | |
| 53A | | x |
| 58F | x | x |
| 100I | x | |
| 100aP | | x |

| LC | NNK | soft | NNK epistasis |
|---|---|---|---|
| 29R | | x | |
| 31H | x | | |
| 31E | x | x | |
| 53H | | x | |
| 53E | | x | |
| 89H | x | | |
| 92Y | x | | |
| 92K | | x | |
| 93I | | x | |
| 92K_32V | | | x |

FIG. 20

| Sample | $k_{on}$ (1/Ms) | $k_{off}$ (1/s) | KD (M) |
|---|---|---|---|
| LC3.HC3 | 8.01E+05 | 4.93E-05 | 6.16E-11 |
| LC3.HC1 | 8.85E+05 | 7.95E-05 | 8.98E-11 |
| APEG.LC37.HC13 | 4.31E+05 | 4.09E-05 | 9.50E-11 |
| APEG.LC3.HC1 | 4.28E+05 | 4.55E-05 | 1.06E-10 |
| h15H6.v4 (APEG.LC3.HC3) | 3.09E+05 | 3.29E-05 | 1.06E-10 |
| APEG.LC3.HC2 | 3.50E+05 | 4.08E-05 | 1.17E-10 |
| APEG.LC347.HC13 | 3.71E+05 | 4.88E-05 | 1.31E-10 |
| APEG.LC7.HC1 | 2.00E+05 | 2.75E-05 | 1.37E-10 |
| APEG.LC37.HC23 | 4.38E+05 | 6.41E-05 | 1.46E-10 |
| APEG.LC347.HC23 | 3.97E+05 | 6.47E-05 | 1.63E-10 |
| h15H6.v2 | 7.22E+05 | 1.58E-04 | 2.19E-10 |
| APEG.LC7.HC2 | 2.13E+05 | 6.60E-05 | 3.09E-10 |
| APEG.LC7.HC3 | 2.39E+05 | 7.93E-05 | 3.32E-10 |
| h15H6.v3 (h15H6.v2.APEG) | 3.15E+05 | 1.72E-04 | 5.46E-10 |

FIG. 21A

Light chain variable region

FIG. 21B

Heavy chain variable region

FIG. 22A

| Affinity Matured Variant | Protein Conc. (µM) | Protein Conc. (mg/mL) | IC50 Values (nM) | | | | | Maximal Inhibition (%) |
|---|---|---|---|---|---|---|---|---|
| | | | N of 1 | N of 2 | N of 3 | Average (nM) | StDev (nM) | |
| h15H6.v2.APEG (h15H6.v3) | 23.25 | 1.1 | 0.501 | 0.421 | 0.448 | 0.457 | 0.04 | 78.36 |
| APEG.LC3.HC1 | 7.40 | 0.35 | 0.437 | 0.404 | 0.482 | 0.441 | 0.04 | 92.72 |
| APEG.LC3.HC2 | 6.13 | 0.29 | 0.422 | 0.386 | 0.432 | 0.413 | 0.02 | 90.64 |
| APEG.LC3.HC3 (h15H6.v4) | 7.19 | 0.34 | 0.402 | 0.358 | 0.399 | 0.386 | 0.02 | 93.57 |
| APEG.LC7.HC1 | 6.34 | 0.3 | 0.415 | 0.582 | 0.506 | 0.501 | 0.08 | 92.64 |
| APEG.LC7.HC2 | 6.34 | 0.3 | 0.419 | 0.559 | 0.447 | 0.475 | 0.07 | 87.82 |
| APEG.LC7.HC3 | 6.55 | 0.31 | 0.377 | 0.539 | 0.456 | 0.457 | 0.08 | 93.71 |
| APEG.LC37.HC13 | 6.13 | 0.29 | 0.539 | 0.633 | 0.612 | 0.595 | 0.05 | 87.02 |
| APEG.LC37.HC23 | 5.07 | 0.24 | 0.556 | 0.441 | 0.522 | 0.506 | 0.06 | 94.69 |
| APEG.LC347.HC13 | 5.49 | 0.26 | 0.584 | 0.544 | 0.578 | 0.569 | 0.02 | 95.03 |
| APEG.LC347.HC23 | 6.55 | 0.31 | 0.594 | 0.517 | 0.561 | 0.557 | 0.04 | 94.97 |
| h15H6.v2 | 6.13 | 0.29 | 0.394 | 0.414 | 0.374 | 0.394 | 0.02 | 82.44 |
| LC3.HC1 | 5.07 | 0.24 | 0.442 | 0.492 | 0.424 | 0.453 | 0.04 | 92.09 |
| LC3.HC3 | 5.28 | 0.25 | 0.448 | 0.460 | 0.356 | 0.421 | 0.06 | 96.34 |

FIG. 24A

| Antibody | analysis | I | | II | | III | | IC50 mean | StDev | CV% |
|---|---|---|---|---|---|---|---|---|---|---|
| | | IC50 (nM) | slope | IC50 (nM) | slope | IC50 (nM) | slope | | | |
| h15H6.v4 mAb | RFU/s | 0.153 | 1.77 | 0.133 | 1.36 | 0.077 | 1.56 | 0.121 | 0.039 | 33% |
| YW505.94a mAb | RFU/s | 0.197 | 2.27 | 0.063 | 1.23 | 0.111 | 1.42 | 0.124 | 0.068 | 55% |
| h15H6.v4 Fab | RFU/s | 0.314 | 1.36 | 0.316 | 1.63 | 0.233 | 1.63 | 0.288 | 0.047 | 16% |
| h15H6.v2 Fab | RFU/s | 0.436 | 1.24 | 0.271 | 1.19 | 0.304 | 1.74 | 0.337 | 0.087 | 26% |

FIG. 24B

| Antibody | analysis | I | | II | | III | | IC90 mean | StDev | CV% |
|---|---|---|---|---|---|---|---|---|---|---|
| | | IC90 (nM) | slope | IC90 (nM) | slope | IC90 (nM) | slope | | | |
| h15H6.v4 mAb | RFU/s | 0.529433591 | 1.77 | 0.669114466 | 1.36 | 0.314908687 | 1.56 | 0.504 | 0.178 | 35% |
| YW505.94a mAb | RFU/s | 0.518605807 | 2.27 | 0.375965044 | 1.23 | 0.521584583 | 1.42 | 0.472 | 0.083 | 18% |
| h15H6.v4 Fab | RFU/s | 1.579714309 | 1.36 | 1.216499501 | 1.63 | 0.896975898 | 1.63 | 1.231 | 0.342 | 28% |
| h15H6.v2 Fab | RFU/s | 2.564701939 | 1.24 | 1.717329984 | 1.19 | 1.074703885 | 1.74 | 1.786 | 0.747 | 42% |

FIG. 25A

IC50's from 4-parameter fits:

| Antibody | analysis | IV | | V | | VI | | IC50 mean | StDev | CV% |
|---|---|---|---|---|---|---|---|---|---|---|
| | | IC50 (nM) | slope | IC50 (nM) | slope | IC50 (nM) | slope | | | |
| h15H6.v4 Fab | RFU/s | 0.102 | 1.49 | 0.172 | 1.56 | 0.208 | 1.28 | 0.161 | 0.054 | 34% |
| | RFU | 0.066 | 0.765 | 0.149 | 0.912 | 0.194 | 1.3 | 0.136 | 0.065 | 48% |

FIG. 25B

IC90's calculated from the IC50's and slopes of the above fits:

| Antibody | analysis | IV | | V | | VI | | IC90 mean | StDev | CV% |
|---|---|---|---|---|---|---|---|---|---|---|
| | | IC90 (nM) | slope | IC90 (nM) | slope | IC90 (nM) | slope | | | |
| h15H6.v4 Fab | RFU/s | 0.446 | 1.49 | 0.703 | 1.56 | 1.158 | 1.28 | 0.769 | 0.360 | 47% |
| | RFU | 1.167 | 0.765 | 1.658 | 0.912 | 1.052 | 1.3 | 1.292 | 0.322 | 25% |

FIG. 27C

Anti-HtrA1 Affinity Matured Variants
Endogenous HtrA1 Activity Assay IC50

| Affinity Matured Variant | IC50 | | | | Maximal Inhibition (%) | | | |
|---|---|---|---|---|---|---|---|---|
| | Expt. I | Expt. II | Average (nM) | StDev (nM) | Expt. I | Expt. II | Average (%) | StDev (%) |
| h15H6.v2.APEG (h15H6.v3) | 2.571 | 3.33 | 2.9505 | 0.54 | 76.41 | 63.39 | 69.9 | 9.21 |
| APEG.LC3.HC3 (h15H6.v4) | 1.004 | 1.246 | 1.125 | 0.17 | 83.49 | 76.67 | 80.08 | 4.82 |
| APEG.LC37.HC13 | 1.4815 | 1.822 | 1.65175 | 0.24 | 76.5 | 73.27 | 74.885 | 2.28 |
| APEG.LC347.HC3 | 1.7225 | 2.8415 | 2.282 | 0.79 | 81.26 | 75.79 | 78.525 | 3.87 |

FIG. 28

| Sample | $k_{on}$ (1/Ms) | $k_{off}$ (1/s) | KD (M) | IC50 FRET (nM) | StDev | IC90 FRET (nM) | StDev | Max inhibition |
|---|---|---|---|---|---|---|---|---|
| h15H6.v2 | 7.22E+05 | 1.58E-04 | 2.19E-10 | 0.44 | 0.08 | 1.87 | 0.66 | 91 |
| h15H6.v3 | 3.15E+05 | 1.72E-04 | 5.46E-10 | 0.41 | 0.12 | 2.77 | 2.07 | 77 |
| h15H6.v3 cyno | 4.05E+05 | 2.30E-04 | 5.67E-10 | n.d. | n.d. | n.d. | n.d. | n.d. |
| h15H6.v4 | 3.09E+05 | 3.29E-05 | 1.06E-10 | 0.30 | 0.10 | 1.19 | 0.04 | 100 |
| YW505.94a.28 | 1.69E+06 | 5.74E-03 | 3.40E-9 | 0.52 | 0.03 | 2.73 | 0.93 | 100 |

FIG. 29A
Human HtrA1 mqipraalpliliilaapslalpQLSRAGRSAPLAAGCPDRCEPARCPPQPEHCEGGRARDACGCCE
VCGAPEGAACGLQEGPCGEGLQCVVPFGVPASATVRRRAQAGLCVCASSEPVCGSDA
NTYANLCQLRAASRRSERLIRRPPVIVLQRGACGQGEDPNSLRHKYNFIADVEKIAP
AVVHIELFRKLPFSKREVPVASGSGFIVSEDGLIVTNAHVVTKNHRVKVELKNGATYE
AKIKDVDEKADIALIKIDHQGKLPVLLLGRSSELRPGEFVVAIGSPFSLQNTVTTGIVSTT
QRGGKELGLRNSDMDYIQTDAIINYGNSGGPLVNLDGEVIGINTLKVTAGISFAIPSDKI
KKFLTESHDRQAKGKAITSKKYIGIRMMSLTSSKAKELKDRHRDFPDVSGAYIIEVIPD
TPAEAGGLKENDVIISINGQSVVSANDVSDVIKRESTLNMVRRGNEDIMITVIPEEIDP (SEQ ID NO:121)

FIG. 29B
Murine HtrA1 mqshrtlslilliilaapslalPSGTGRSAPAATVCPEHCDPTRCAPPPTDCEGGRVRDACGCCEVC
GALEGAACGLQEGPCGEGLQCVVPFGVPASATVRRRAQAGLCVCASSEPVCGSDAKT
YTNLCQLRAASRRSEKLRQPPVIVLQRGACGQGEDPNSLRHKYNFIADVVEKIAPAV
VHIELYRKLPESKREVPVASGSGFIVSEDGLIVTNAHVVTKNRVKVELKNGATYEAKI
KDVDEKADIALIKIDHQGKLPVLLLGRSSELRPGEFVVAIGSPFSLQNTVTTGIVSTTQR
GGKELGLRNSDMDYIQTDAIINYGNSGGPLVNLDGEVIGINTLKVTAGISFAIPSDKIKK
FLTESHDRQAKGKAVTKKKYIGIRMMSLTSSKAKELKDRHRDFPDVLSGAYIIEVIPDT
PAEAGGLKENDVIISINGQSVVTANDVSDVIKKENTLNMVRRGNEDIVITVIPEEIDP (SEQ ID NO:155)

FIG. 30

VL Domain

| | Sequence | |
|---|---|---|
| WT | DIQVTQSPSSLSASVGDRVTITCITSTDIDDDMNWYQQKPGKVPKLLISGGNTLRPGVPSRFSGSGSGTDFTLTISSLQP EDVATYYCLQSDSLPYTFGQGTKVEIK | (SEQ ID NO: 120) |
| TM | DIQVTQSPSSLSASVGDRVTITCITSTDIESDMNWYQQKPGKVPKLLISGGNTLRPGVPSRFSGSGSGTDFTLTISSLQP EDVATYYCLQSDSLPYTFGQGTKVEIK | (SEQ ID NO: 133) |
| TM.D92E | DIQVTQSPSSLSASVGDRVTITCITSTDIESDMNWYQQKPGKVPKLLISGGNTLRPGVPSRFSGSGSGTDFTLTISSLQP EDVATYYCLQSESLPYTFGQGTKVEIK | (SEQ ID NO: 134) |
| SIESD | DIQVTQSPSSLSASVGDRVTITCITSTSIESDMNWYQQKPGKVPKLLISGGNTLRPGVPSRFSGSGSGTDFTLTISSLQP EDVATYYCLQSDSLPYTFGQGTKVEIK | (SEQ ID NO: 135) |
| SIESD.N103S | DIQVTQSPSSLSASVGDRVTITCITSTSIESDMNWYQQKPGKVPKLLISGGNTLRPGVPSRFSGSGSGTDFTLTISSLQP EDVATYYCLQSDSLPYTFGQGTKVEIK | (SEQ ID NO: 135) |

VH Domain

| | Sequence | |
|---|---|---|
| WT | EVQLVQSGPELKKPGASVKVSCKASGYTFTNYGMNWVRQAPGQGLEWMGWINTYTGETTYADDFKGRFVFSLDTSVSTAY LQISSLKAEDTAVYYCEREGGVNNWGQGTLVTVSS | (SEQ ID NO: 119) |
| TM | EVQLVQSGPELKKPGASVKVSCKASGYTFTNYGMNWVRQAPGQGLEWMGWINTYTGETTYAEDFKGRFVFSLDTSVSTAY LQISSLKAEDTAVYYCEREGGVNNWGQGTLVTVSS | (SEQ ID NO: 131) |
| TM.D92E | EVQLVQSGPELKKPGASVKVSCKASGYTFTNYGMNWVRQAPGQGLEWMGWINTYTGETTYAEDFKGRFVFSLDTSVSTAY LQISSLKAEDTAVYYCEREGGVNNWGQGTLVTVSS | (SEQ ID NO: 131) |
| SIESD | EVQLVQSGPELKKPGASVKVSCKASGYTFTNYGMNWVRQAPGQGLEWMGWINTYTGETTYAEDFKGRFVFSLDTSVSTAY LQISSLKAEDTAVYYCEREGGVNNWGQGTLVTVSS | (SEQ ID NO: 131) |
| SIESD.N103S | EVQLVQSGPELKKPGASVKVSCKASGYTFTNYGMNWVRQAPGQGLEWMGWINTYTGETTYAEDFKGRFVFSLDTSVSTAY LQISSLKAEDTAVYYCEREGGVNSWGQGTLVTVSS | (SEQ ID NO: 132) |

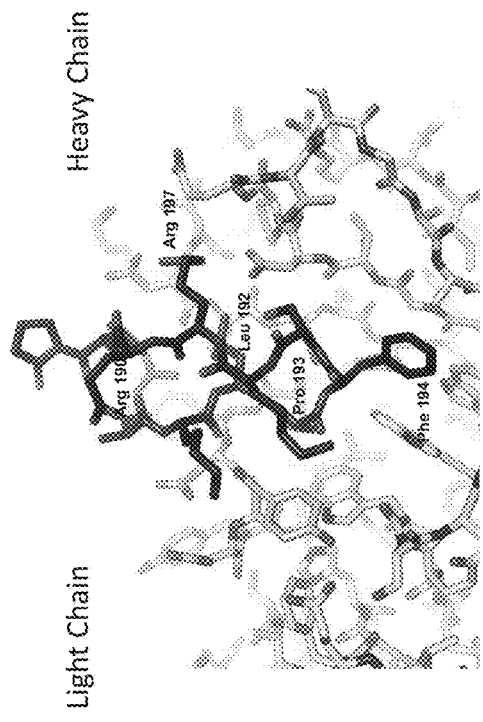
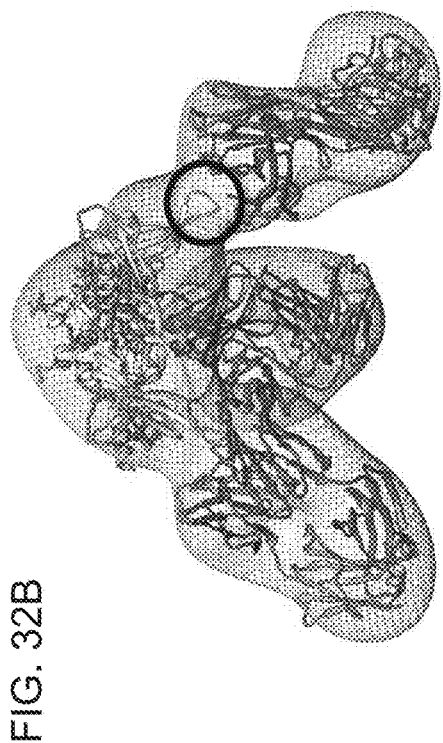
FIG. 32A
FIG. 32B

SEQUENCE LISTING

```
<160> NUMBER OF SEQ ID NOS: 160

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Met or Leu

<400> SEQUENCE: 1

Asp Ser Glu Xaa His
```

```
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Glu or Asp

<400> SEQUENCE: 2

Gly Val Asp Pro Glu Thr Xaa Gly Ala Ala Tyr Asn Gln Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Tyr Asp Tyr Asp Tyr Ala Leu Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Glu or Asn

<400> SEQUENCE: 4

Arg Ala Ser Ser Ser Val Xaa Phe Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asn, His or Glu

<400> SEQUENCE: 5

Ala Thr Ser Xaa Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ser or Tyr
```

```
<220> FEATURE:
<221> NAME/KEY: MISC_FEATURE
<222> LOCATION: (6)..(6)
<223> OTHER INFORMATION: Xaa is Ala or Asn

<400> SEQUENCE: 6

Gln Gln Trp Xaa Ser Xaa Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asp Ser Glu Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Gly Val Asp Pro Glu Thr Glu Gly Ala Ala Tyr Asn Gln Lys Phe Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Arg Ala Ser Ser Ser Val Glu Phe Ile His
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Ala Thr Ser Asn Leu Ala Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Gln Gln Trp Ser Ser Ala Pro Trp Thr
1               5

<210> SEQ ID NO 12
```

```
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (28)..(28)
<223> OTHER INFORMATION: Xaa is Lys or Thr
<220> FEATURE:
<221> NAME/KEY: MISC_FEATURE
<222> LOCATION: (30)..(30)
<223> OTHER INFORMATION: Xaa is Thr, Lys, or Arg

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Xaa Phe Xaa
            20                  25                  30

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Trp Val Arg Gln Ala Pro Gly Gln Gly Leu Glu Trp Ile Gly
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct

<400> SEQUENCE: 14

Arg Ala Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Thr Arg
            20                  25                  30

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Trp Gly Gln Gly Thr Leu Val Thr Val Ser Ser
1               5                   10

<210> SEQ ID NO 16
<211> LENGTH: 30
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr
            20                  25                  30
```

```
<210> SEQ ID NO 17
<211> LENGTH: 23
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Trp Tyr Gln Gln Lys Pro Gly Lys Ala Pro Lys Pro Leu Ile Ser
1               5                   10                  15

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Phe Gly Gln Gly Thr Lys Val Glu Ile Lys
1               5                   10

<210> SEQ ID NO 21
<211> LENGTH: 119
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Glu Gly Ala Ala Tyr Asn Gln Lys Phe
```

```
            50                  55                  60
Lys Gly Arg Ala Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                     85                  90                  95

Thr Arg Gly Tyr Asp Tyr Asp Tyr Ala Leu Asp Tyr Trp Gly Gln Gly
                100                 105                 110

Thr Leu Val Thr Val Ser Ser
            115

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
  1               5                  10                  15

Asp Arg Val Thr Ile Thr Cys Arg Ala Ser Ser Ser Val Glu Phe Ile
                 20                  25                  30

His Trp Tyr Gln Gln Lys Pro Gly Lys Ala Pro Lys Pro Leu Ile Ser
             35                  40                  45

Ala Thr Ser Asn Leu Ala Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Ala Pro Trp Thr
                 85                  90                  95

Phe Gly Gln Gly Thr Lys Val Glu Ile Lys
            100                 105

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Gln Gln Ser Gly Ala Glu Leu Val Arg Pro Gly Ala
  1               5                  10                  15

Ser Val Thr Leu Ser Cys Lys Ala Ser Gly Tyr Thr Phe Thr Asp Ser
                 20                  25                  30

Glu Met His Trp Val Lys Gln Thr Pro Val His Gly Leu Glu Trp Ile
             35                  40                  45

Gly Gly Val Asp Pro Glu Thr Asp Gly Ala Ala Tyr Asn Gln Lys Phe
         50                  55                  60

Lys Gly Lys Ala Thr Leu Thr Ala Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Gly Tyr Asp Tyr Asp Tyr Ala Leu Asp Tyr Trp Gly Gln Gly
                100                 105                 110

Thr Ser Val Thr Val Ser Ser
            115
```

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Phe Ile
                20                  25                  30

His Trp Tyr Gln Gln Lys Pro Gly Ser Ser Pro Lys Pro Trp Ile Ser
            35                  40                  45

Ala Thr Ser Asn Leu Ala Ser Gly Val Pro Pro Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105
```

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr
                20                  25                  30
```

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

```
Trp Val Lys Gln Thr Pro Val His Gly Leu Glu Trp Ile Gly
1               5                   10
```

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

```
Lys Ala Thr Leu Thr Ala Asp Lys Ser Ser Thr Ala Tyr Met Glu
1               5                   10                  15

Leu Arg Ser Leu Thr Ser Glu Asp Ser Ala Val Tyr Tyr Cys Thr Arg
                20                  25                  30
```

<210> SEQ ID NO 28
<211> LENGTH: 11

```
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Ser Val Thr Val Ser Ser
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asn Ile Val Val Thr Gln Ser Pro Ala Ser Leu Ala Val Ser Leu Gly
1               5                   10                  15

Gln Arg Ala Thr Ile Ser Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Ala Arg Phe Ser Gly Ser Gly Ser Arg Thr Asp Phe Thr
1               5                   10                  15

Leu Thr Ile Asp Pro Val Glu Ala Asp Asp Ala Ala Thr Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Gly Gly Thr Lys Leu Glu Ile Lys
1               5                   10

<210> SEQ ID NO 33

<400> SEQUENCE: 33

000

<210> SEQ ID NO 34

<400> SEQUENCE: 34
```

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Ser Tyr Ile Met Ser
1               5

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Tyr Ile Ser Asn Gly Gly Gly Thr Thr Tyr Tyr Ser Asp Thr Ile Lys
1               5                   10                  15

Gly

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct

<400> SEQUENCE: 41

Gln Asn Phe Arg Ser Asp Gly Ser Ser Met Asp Tyr
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42

Arg Ala Ser Glu Ser Val Asp Ser Tyr Gly Lys Ser Phe Met His
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

Leu Ala Ser Lys Leu Glu Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Gln Gln Asn Asn Glu Asp Pro Tyr Thr
1               5

<210> SEQ ID NO 45
<211> LENGTH: 121
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Ala Pro Gly Lys Gly Leu Glu Trp Val
        35                  40                  45

Ala Tyr Ile Ser Asn Gly Gly Gly Thr Thr Tyr Tyr Ser Asp Thr Ile
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Asn Phe Arg Ser Asp Gly Ser Ser Met Asp Tyr Trp Gly
            100                 105                 110

Gln Gly Thr Leu Val Thr Val Ser Ser
        115                 120

<210> SEQ ID NO 46
<211> LENGTH: 111
<212> TYPE: PRT
<213> ORGANISM: Artificial Sequence
<220> FEATURE:
<223> OTHER INFORMATION: Synthetic Construct

<400> SEQUENCE: 46

Asp Ile Val Met Thr Gln Ser Pro Asp Ser Leu Ala Val Ser Leu Gly
1               5                   10                  15

-continued

Glu Arg Ala Thr Ile Asn Cys Arg Ala Ser Glu Ser Val Asp Ser Tyr
            20                  25                  30

Gly Lys Ser Phe Met His Trp Tyr Gln Gln Lys Pro Gly Gln Pro Pro
        35                  40                  45

Lys Leu Leu Ile Tyr Leu Ala Ser Lys Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Val Glu Ile Lys
            100                 105                 110

<210> SEQ ID NO 47
<211> LENGTH: 30
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 48
<211> LENGTH: 14
<212> TYPE: PRT
<213> ORGANISM: Artificial Sequence
<220> FEATURE:
<223> OTHER INFORMATION: Synthetic Construct

<400> SEQUENCE: 48

Trp Val Arg Gln Ala Pro Gly Lys Gly Leu Glu Trp Val Ala
1               5                   10

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Trp Gly Gln Gly Thr Leu Val Thr Val Ser Ser
1               5                   10

<210> SEQ ID NO 51
<211> LENGTH: 23

```
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Trp Tyr Gln Gln Lys Pro Gly Gln Pro Pro Lys Leu Leu Ile Tyr
1               5                   10                  15

<210> SEQ ID NO 53
<211> LENGTH: 32
<212> TYPE: PRT
<213> ORGANISM: Artificial Sequence
<220> FEATURE:
<223> OTHER INFORMATION: Synthetic Construct

<400> SEQUENCE: 53

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Phe Gly Gln Gly Thr Lys Val Glu Ile Lys
1               5                   10

<210> SEQ ID NO 55
<211> LENGTH: 121
<212> TYPE: PRT
<213> ORGANISM: Artificial Sequence
<220> FEATURE:
<223> OTHER INFORMATION: Synthetic Construct

<400> SEQUENCE: 55

Glu Val Lys Leu Val Glu Ser Gly Gly Gly Leu Val Glu Pro Gly Gly
1               5                   10                  15

Ser Leu Lys Leu Ala Cys Val Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Tyr Ile Ser Asn Gly Gly Gly Thr Thr Tyr Tyr Ser Asp Thr Ile
    50                  55                  60

Lys Gly Arg Phe Thr Ile Ser Arg Asp Asn Ala Lys Asn Thr Leu Tyr
65                  70                  75                  80
```

Leu Gln Met Ser Thr Leu Lys Ser Glu Asp Thr Ala Ile Tyr Phe Cys
                85                  90                  95

Ala Arg Gln Asn Phe Arg Ser Asp Gly Ser Ser Met Asp Tyr Trp Gly
            100                 105                 110

Gln Gly Thr Ala Val Thr Val Ser Ser
        115                 120

<210> SEQ ID NO 56
<211> LENGTH: 111
<212> TYPE: PRT
<213> ORGANISM: Artificial Sequence
<220> FEATURE:
<223> OTHER INFORMATION: Synthetic Construct

<400> SEQUENCE: 56

Asn Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Lys Ser Phe Met His Trp Tyr Gln Gln Lys Pro Gly Gln Pro Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 57
<211> LENGTH: 30
<212> TYPE: PRT
<213> ORGANISM: Artificial Sequence
<220> FEATURE:
<223> OTHER INFORMATION: Synthetic Construct

<400> SEQUENCE: 57

Glu Val Lys Leu Val Glu Ser Gly Gly Gly Leu Val Glu Pro Gly Gly
1               5                   10                  15

Ser Leu Lys Leu Ala Cys Val Ala Ser Gly Phe Thr Phe Ser
            20                  25                  30

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Trp Val Arg Gln Thr Pro Glu Lys Arg Leu Glu Trp Val Ala
1               5                   10

<210> SEQ ID NO 59
<211> LENGTH: 32
<212> TYPE: PRT
<213> ORGANISM: Artificial Sequence
<220> FEATURE:
<223> OTHER INFORMATION: Synthetic Construct

<400> SEQUENCE: 59

```
Arg Phe Thr Ile Ser Arg Asp Asn Ala Lys Asn Thr Leu Tyr Leu Gln
1               5                   10                  15

Met Ser Thr Leu Lys Ser Glu Asp Thr Ala Ile Tyr Phe Cys Ala Arg
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: Synthetic Construct

<400> SEQUENCE: 60

Trp Gly Gln Gly Thr Ala Val Thr Val Ser Ser
1               5                   10

<210> SEQ ID NO 61
<211> LENGTH: 23
<212> TYPE: PRT
<213> ORGANISM: Artificial Sequence
<220> FEATURE:
<223> OTHER INFORMATION: Synthetic Construct

<400> SEQUENCE: 61

Asn Ile Val Val Thr Gln Ser Pro Ala Ser Leu Ala Val Ser Leu Gly
1               5                   10                  15

Gln Arg Ala Thr Ile Ser Cys
            20

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Trp Tyr Gln Gln Lys Pro Gly Gln Pro Pro Lys Leu Leu Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: Synthetic Construct

<400> SEQUENCE: 63

Gly Val Pro Ala Arg Phe Ser Gly Ser Gly Ser Arg Thr Asp Phe Thr
1               5                   10                  15

Leu Thr Ile Asp Pro Val Glu Ala Asp Asp Ala Ala Thr Tyr Tyr Cys
            20                  25                  30

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Phe Gly Gly Gly Thr Lys Leu Glu Ile Lys
1               5                   10
```

```
<210> SEQ ID NO 65
<211> LENGTH: 121
<212> TYPE: PRT
<213> ORGANISM: Artificial Sequence
<220> FEATURE:
<223> OTHER INFORMATION: Synthetic Construct

<400> SEQUENCE: 65

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Tyr Ile Ser Asn Gly Gly Thr Thr Tyr Tyr Pro Asp Thr Ile
    50                  55                  60

Lys Gly Arg Phe Thr Ile Ser Arg Asp Asn Ala Lys Asn Thr Leu Tyr
65                  70                  75                  80

Leu Gln Met Asn Thr Leu Lys Ser Glu Asp Thr Ala Ile Tyr Phe Cys
                85                  90                  95

Ala Arg Gln Asn Phe Arg Ser Asp Gly Ser Ser Met Asp Tyr Trp Gly
            100                 105                 110

Gln Gly Thr Ser Val Thr Val Ser Ser
        115                 120

<210> SEQ ID NO 66
<211> LENGTH: 111
<212> TYPE: PRT
<213> ORGANISM: Artificial Sequence
<220> FEATURE:
<223> OTHER INFORMATION: Synthetic Construct

<400> SEQUENCE: 66

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Ser
            20                  25                  30

Gly Arg Ser Phe Met His Trp Tyr Gln Gln Lys Pro Gly Gln Pro Pro
        35                  40                  45

Arg Leu Leu Ile Tyr Leu Ala Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Asn Leu Glu Ile Lys
            100                 105                 110

<210> SEQ ID NO 67
<211> LENGTH: 117
<212> TYPE: PRT
<213> ORGANISM: Artificial Sequence
<220> FEATURE:
<223> OTHER INFORMATION: Synthetic Construct

<400> SEQUENCE: 67

Asp Val His Leu Val Glu Ser Gly Gly Gly Leu Val Arg Pro Gly Gly
1               5                   10                  15

Ser Arg Lys Leu Ser Cys Glu Ala Ser Gly Phe Thr Phe Ser Ser Phe
            20                  25                  30
```

Gly Met His Trp Val Arg Gln Ala Pro Glu Lys Gly Leu Glu Trp Val
         35                  40                  45

Ala Phe Ile Thr Ser Asp Ser Ser Thr Ile Tyr Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Thr Arg Ser Gly Asp Asp Tyr Leu Asp Tyr Trp Gly Gln Gly Thr Thr
            100                 105                 110

Leu Thr Val Ser Ser
            115

<210> SEQ ID NO 68
<211> LENGTH: 111
<212> TYPE: PRT
<213> ORGANISM: Artificial Sequence
<220> FEATURE:
<223> OTHER INFORMATION: Synthetic Construct

<400> SEQUENCE: 68

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Thr Ser
             20                  25                  30

Ser Ser Ser Tyr Met His Trp Tyr Gln Gln Lys Pro Gly Gln Pro Pro
         35                  40                  45

Lys Val Phe Ile Lys Tyr Ala Ser Asn Leu Glu Ser Gly Val Pro Ala
 50                  55                  60

Arg Phe Ser Gly Ser Gly Ser Gly Thr Asp Phe Thr Leu Ser Ile His
 65                  70                  75                  80

Pro Val Glu Glu Glu Asp Thr Ala Thr Tyr Tyr Cys Gln His Ser Trp
                 85                  90                  95

Glu Ile Pro Phe Thr Phe Gly Gly Gly Thr Lys Leu Glu Ile Lys
            100                 105                 110

<210> SEQ ID NO 69
<211> LENGTH: 119
<212> TYPE: PRT
<213> ORGANISM: Artificial Sequence
<220> FEATURE:
<223> OTHER INFORMATION: Synthetic Construct

<400> SEQUENCE: 69

Glu Val Met Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Val Met Ser Trp Val Arg Gln Thr Pro Glu Lys Arg Leu Glu Trp Val
         35                  40                  45

Ala Ala Ile Ser Gly Gly Gly Asp Tyr Thr Tyr Tyr Pro Asp Ser Leu
 50                  55                  60

Lys Gly Arg Phe Thr Ile Ser Arg Asp Asn Ala Arg Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg Val Asp Tyr Asp Glu Tyr Ser Phe Glu Tyr Trp Gly Gln Gly

Thr Ala Leu Thr Val Ser Ser
            115

<210> SEQ ID NO 70
<211> LENGTH: 111
<212> TYPE: PRT
<213> ORGANISM: Artificial Sequence
<220> FEATURE:
<223> OTHER INFORMATION: Synthetic Construct

<400> SEQUENCE: 70

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
            100                 105

<210> SEQ ID NO 72
<211> LENGTH: 106
<212> TYPE: PRT
<213> ORGANISM: Artificial Sequence
<220> FEATURE:
<223> OTHER INFORMATION: Synthetic Construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Trp Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 73
<211> LENGTH: 106
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 74
<211> LENGTH: 106
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ala Pro Trp Thr
                85                  90                  95

Phe Gly Gln Gly Thr Lys Val Glu Ile Lys

```
                    100                 105

<210> SEQ ID NO 75
<211> LENGTH: 112
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 76
<211> LENGTH: 119
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115

<210> SEQ ID NO 77
<211> LENGTH: 119
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Ser
         20                  25                  30

Glu Met His Trp Val Arg Gln Ala Pro Gly Gln Gly Leu Glu Trp Ile
         35                  40                  45

Gly Gly Val Asp Pro Glu Thr Asp Gly Ala Ala Tyr Asn Gln Lys Phe
     50                  55                  60

Lys Gly Arg Ala Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Gly Tyr Asp Tyr Asp Tyr Ala Leu Asp Tyr Trp Gly Gln Gly
             100                 105                 110

Thr Leu Val Thr Val Ser Ser
            115
```

<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
         20                  25                  30

Glu Met His Trp Val Arg Gln Ala Pro Gly Gln Gly Leu Glu Trp Ile
         35                  40                  45

Gly Gly Val Asp Pro Glu Thr Glu Gly Ala Ala Tyr Asn Gln Lys Phe
     50                  55                  60

Lys Gly Arg Ala Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Gly Tyr Asp Tyr Asp Tyr Ala Leu Asp Tyr Trp Gly Gln Gly
             100                 105                 110

Thr Leu Val Thr Val Ser Ser
            115
```

<210> SEQ ID NO 79
<211> LENGTH: 113
<212> TYPE: PRT
<213> ORGANISM: Artificial Sequence
<220> FEATURE:
<223> OTHER INFORMATION: Synthetic Construct

<400> SEQUENCE: 79

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
         20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
```

```
                65                  70                  75                  80
Ile Ser Ser Leu Gln Ala Glu Asp Val Ala Val Tyr Tyr Cys Gln Gln
                    85                  90                  95

Tyr Tyr Ser Thr Pro Phe Thr Phe Gly Gln Gly Thr Lys Val Glu Ile
                100                 105                 110

Lys

<210> SEQ ID NO 80
<211> LENGTH: 112
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Gly Ala Ile Ser Ser Ser Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Tyr Trp Gly Gln Gly Thr Leu Val Thr Val Ser Ser
                100                 105                 110

<210> SEQ ID NO 81
<211> LENGTH: 106
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Arg Val Asn Phe Ile
                20                  25                  30

His Trp Tyr Gln Gln Lys Pro Gly Lys Ala Pro Lys Pro Leu Ile Ser
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
                100                 105

<210> SEQ ID NO 82
<211> LENGTH: 106
<212> TYPE: PRT
<213> ORGANISM: Artificial Sequence
<220> FEATURE:
<223> OTHER INFORMATION: Synthetic Construct
```

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val His Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 83
<211> LENGTH: 106
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Glu Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 84
<211> LENGTH: 106
<212> TYPE: PRT
<213> ORGANISM: Artificial Sequence
<220> FEATURE:
<223> OTHER INFORMATION: Synthetic Construct

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Asn Phe Ile
            20                  25                  30

His Trp Tyr Gln Gln Lys Pro Gly Lys Ala Pro Lys Pro Leu Ile Ser
        35                  40                  45

Ala Thr Ser His Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 85
<211> LENGTH: 106
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
        35                  40                  45

Ala Thr Ser Glu Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 86
<211> LENGTH: 106
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Ser Asn Pro Trp Thr
                85                  90                  95

Phe Gly Gln Gly Thr Lys Val Glu Ile Lys
            100                 105

<210> SEQ ID NO 87
<211> LENGTH: 106
<212> TYPE: PRT
<213> ORGANISM: Artificial Sequence
<220> FEATURE:
<223> OTHER INFORMATION: Synthetic Construct

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Ser Asn Pro Trp Thr
                85                  90                  95

Phe Gly Gln Gly Thr Lys Val Glu Ile Lys
            100                 105

<210> SEQ ID NO 88
<211> LENGTH: 106
<212> TYPE: PRT
<213> ORGANISM: Artificial Sequence
<220> FEATURE:
<223> OTHER INFORMATION: Synthetic Construct

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Lys Ser Asn Pro Trp Thr
                85                  90                  95

Phe Gly Gln Gly Thr Lys Val Glu Ile Lys
            100                 105

<210> SEQ ID NO 89
<211> LENGTH: 106
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Asn Phe Ile
            20                  25                  30

His Trp Tyr Gln Gln Lys Pro Gly Lys Ala Pro Lys Pro Leu Ile Ser
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ile Asn Pro Trp Thr
                85                  90                  95
```

Phe Gly Gln Gly Thr Lys Val Glu Ile Lys
            100                 105

<210> SEQ ID NO 90
<211> LENGTH: 106
<212> TYPE: PRT
<213> ORGANISM: Artificial Sequence
<220> FEATURE:
<223> OTHER INFORMATION: Synthetic Construct

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Asn Val Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Lys Ser Asn Pro Trp Thr
                85                  90                  95

Phe Gly Gln Gly Thr Lys Val Glu Ile Lys
            100                 105

<210> SEQ ID NO 91
<211> LENGTH: 106
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Glu Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Ser Asn Pro Trp Thr
                85                  90                  95

Phe Gly Gln Gly Thr Lys Val Glu Ile Lys
            100                 105

<210> SEQ ID NO 92
<211> LENGTH: 106
<212> TYPE: PRT
<213> ORGANISM: Artificial Sequence
<220> FEATURE:
<223> OTHER INFORMATION: Synthetic Construct

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Glu Phe Ile
            20                  25                  30

His Trp Tyr Gln Gln Lys Pro Gly Lys Ala Pro Lys Pro Leu Ile Ser
            35                  40                  45

Ala Thr Ser His Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Ser Asn Pro Trp Thr
                85                  90                  95

Phe Gly Gln Gly Thr Lys Val Glu Ile Lys
            100                 105

<210> SEQ ID NO 93
<211> LENGTH: 119
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Asp Ser
            20                  25                  30

Glu Met His Trp Val Arg Gln Ala Pro Gly Gln Gly Leu Glu Trp Ile
            35                  40                  45

Gly Gly Val Asp Pro Glu Thr Asp Gly Ala Ala Tyr Asn Gln Lys Phe
50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
            115

<210> SEQ ID NO 94
<211> LENGTH: 119
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asp Ser
            20                  25                  30

Glu Met His Trp Val Arg Gln Ala Pro Gly Gln Gly Leu Glu Trp Ile
            35                  40                  45

Gly Gly Val Asp Pro Glu Thr Asp Gly Ala Ala Tyr Asn Gln Lys Phe
50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
                100                 105                 110

Thr Leu Val Thr Val Ser Ser
        115

<210> SEQ ID NO 95
<211> LENGTH: 119
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
                100                 105                 110

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
                100                 105                 110

Thr Leu Val Thr Val Ser Ser
        115

<210> SEQ ID NO 97
<211> LENGTH: 119
<212> TYPE: PRT

<213> ORGANISM: Artificial Sequence
<220> FEATURE:
<223> OTHER INFORMATION: Synthetic Construct

<400> SEQUENCE: 97

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Leu His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115
```

<210> SEQ ID NO 98
<211> LENGTH: 119
<212> TYPE: PRT
<213> ORGANISM: Artificial Sequence
<220> FEATURE:
<223> OTHER INFORMATION: Synthetic Construct

<400> SEQUENCE: 98

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Ala Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115
```

<210> SEQ ID NO 99
<211> LENGTH: 119
<212> TYPE: PRT
<213> ORGANISM: Artificial Sequence
<220> FEATURE:
<223> OTHER INFORMATION: Synthetic Construct

<400> SEQUENCE: 99

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30
```

```
Glu Met His Trp Val Arg Gln Ala Pro Gly Gln Gly Leu Glu Trp Ile
        35                  40                  45

Gly Gly Val Asp Pro Glu Thr Asp Gly Ala Phe Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
            115

<210> SEQ ID NO 100
<211> LENGTH: 119
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Ile Ala Leu Asp Tyr Trp Gly Gln Gly
            100                 105                 110

Thr Leu Val Thr Val Ser Ser
            115

<210> SEQ ID NO 101
<211> LENGTH: 119
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
```

-continued

```
                85                  90                  95
Thr Arg Gly Tyr Asp Tyr Asp Tyr Pro Leu Asp Tyr Trp Gly Gln Gly
            100                 105                 110
Thr Leu Val Thr Val Ser Ser
        115

<210> SEQ ID NO 102
<211> LENGTH: 119
<212> TYPE: PRT
<213> ORGANISM: Artificial Sequence
<220> FEATURE:
<223> OTHER INFORMATION: Synthetic Construct

<400> SEQUENCE: 102

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Lys Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Artificial Sequence
<220> FEATURE:
<223> OTHER INFORMATION: Synthetic Construct

<400> SEQUENCE: 103

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Arg Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Asp Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115

<210> SEQ ID NO 104
<211> LENGTH: 119
```

```
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Glu Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser
        115

<210> SEQ ID NO 105
<211> LENGTH: 106
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Glu Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Ser Ala Pro Trp Thr
                85                  90                  95

Phe Gly Gln Gly Thr Lys Val Glu Ile Lys
            100                 105

<210> SEQ ID NO 106
<211> LENGTH: 119
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Lys Asp Ser
            20                  25                  30

Glu Met His Trp Val Arg Gln Ala Pro Gly Gln Gly Leu Glu Trp Ile
```

```
                35                  40                  45
Gly Gly Val Asp Pro Glu Thr Glu Gly Ala Ala Tyr Asn Gln Lys Phe
         50                  55                  60

Lys Gly Arg Ala Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Gly Tyr Asp Tyr Asp Tyr Ala Leu Asp Tyr Trp Gly Gln Gly
             100                 105                 110

Thr Leu Val Thr Val Ser Ser
         115

<210> SEQ ID NO 107
<211> LENGTH: 119
<212> TYPE: PRT
<213> ORGANISM: Artificial Sequence
<220> FEATURE:
<223> OTHER INFORMATION: Synthetic Construct

<400> SEQUENCE: 107

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Arg Asp Ser
             20                  25                  30

Glu Met His Trp Val Arg Gln Ala Pro Gly Gln Gly Leu Glu Trp Ile
         35                  40                  45

Gly Gly Val Asp Pro Glu Thr Glu Gly Ala Ala Tyr Asn Gln Lys Phe
     50                  55                  60

Lys Gly Arg Ala Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Arg Gly Tyr Asp Tyr Asp Tyr Ala Leu Asp Tyr Trp Gly Gln Gly
             100                 105                 110

Thr Leu Val Thr Val Ser Ser
         115

<210> SEQ ID NO 108
<211> LENGTH: 106
<212> TYPE: PRT
<213> ORGANISM: Artificial Sequence
<220> FEATURE:
<223> OTHER INFORMATION: Synthetic Construct

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Ser Val Glu Phe Ile
             20                  25                  30

His Trp Tyr Gln Gln Lys Pro Gly Lys Ala Pro Lys Pro Leu Ile Ser
         35                  40                  45

Ala Thr Ser His Leu Ala Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Tyr Ser Ala Pro Trp Thr
                 85                  90                  95
```

Phe Gly Gln Gly Thr Lys Val Glu Ile Lys
            100                 105

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Gly Tyr Thr Phe Thr Asn Tyr Gly Met Asn
1               5                   10

<210> SEQ ID NO 110
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa is Asp or Glu

<400> SEQUENCE: 110

Trp Ile Asn Thr Tyr Thr Gly Glu Thr Thr Tyr Ala Xaa Asp Phe Lys
1               5                   10                  15
Gly

<210> SEQ ID NO 111
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Asn or Ser

<400> SEQUENCE: 111

Glu Gly Gly Val Xaa Asn
1               5

<210> SEQ ID NO 112
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Asp or Ser
<220> FEATURE:
<221> NAME/KEY: MISC_FEATURE
<222> LOCATION: (7)..(7)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Asp or Ser

<400> SEQUENCE: 112

Ile Thr Ser Thr Xaa Ile Xaa Xaa Asp Met Asn
1               5                   10

<210> SEQ ID NO 113

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

Gly Gly Asn Thr Leu Arg Pro
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asp or Glu

<400> SEQUENCE: 114

Leu Gln Ser Xaa Ser Leu Pro Tyr Thr
1               5

<210> SEQ ID NO 115
<211> LENGTH: 17
<212> TYPE: PRT
<213> ORGANISM: Artificial Sequence
<220> FEATURE:
<223> OTHER INFORMATION: Synthetic Construct

<400> SEQUENCE: 115

Trp Ile Asn Thr Tyr Thr Gly Glu Thr Thr Tyr Ala Asp Asp Phe Lys
1               5                   10                  15

Gly

<210> SEQ ID NO 116
<211> LENGTH: 6
<212> TYPE: PRT
<213> ORGANISM: Artificial Sequence
<220> FEATURE:
<223> OTHER INFORMATION: Synthetic Construct

<400> SEQUENCE: 116

Glu Gly Gly Val Asn Asn
1               5

<210> SEQ ID NO 117
<211> LENGTH: 11
<212> TYPE: PRT
<213> ORGANISM: Artificial Sequence
<220> FEATURE:
<223> OTHER INFORMATION: Synthetic Construct

<400> SEQUENCE: 117

Ile Thr Ser Thr Asp Ile Asp Asp Asp Met Asn
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

<400> SEQUENCE: 118
```

Leu Gln Ser Asp Ser Leu Pro Tyr Thr
1               5

<210> SEQ ID NO 119
<211> LENGTH: 115
<212> TYPE: PRT
<213> ORGANISM: Artificial Sequence
<220> FEATURE:
<223> OTHER INFORMATION: Synthetic Construct

<400> SEQUENCE: 119

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser
        115

<210> SEQ ID NO 120
<211> LENGTH: 106
<212> TYPE: PRT
<213> ORGANISM: Artificial Sequence
<220> FEATURE:
<223> OTHER INFORMATION: Synthetic Construct

<400> SEQUENCE: 120

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Thr Lys Val Glu Ile Lys
            100                 105

<210> SEQ ID NO 121
<211> LENGTH: 480
<212> TYPE: PRT
<213> ORGANISM: Homo sapiens

<400> SEQUENCE: 121

Met Gln Ile Pro Arg Ala Ala Leu Leu Pro Leu Leu Leu Leu Leu Leu
1               5                   10                  15

```
Ala Ala Pro Ala Ser Ala Gln Leu Ser Arg Ala Gly Arg Ser Ala Pro
             20                  25                  30

Leu Ala Ala Gly Cys Pro Asp Arg Cys Glu Pro Ala Arg Cys Pro Pro
         35                  40                  45

Gln Pro Glu His Cys Glu Gly Arg Ala Arg Asp Ala Cys Gly Cys
 50                  55                  60

Cys Glu Val Cys Gly Ala Pro Glu Gly Ala Ala Cys Gly Leu Gln Glu
 65              70                  75                      80

Gly Pro Cys Gly Glu Gly Leu Gln Cys Val Val Pro Phe Gly Val Pro
                 85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
                260                 265                 270

Leu Arg Pro Gly Glu Phe Val Val Ala Ile Gly Ser Pro Phe Ser Leu
    275                 280                 285

Gln Asn Thr Val Thr Thr Gly Ile Val Ser Thr Thr Gln Arg Gly Gly
290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His
        355                 360                 365

Asp Arg Gln Ala Lys Gly Lys Ala Ile Thr Lys Lys Tyr Ile Gly
    370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

Val Ile Pro Asp Thr Pro Ala Glu Ala Gly Gly Leu Lys Glu Asn Asp
            420                 425                 430

Val Ile Ile Ser Ile Asn Gly Gln Ser Val Val Ser Ala Asn Asp Val
```

```
                    435                 440                 445
Ser Asp Val Ile Lys Arg Glu Ser Thr Leu Asn Met Val Val Arg Arg
        450                 455                 460

Gly Asn Glu Asp Ile Met Ile Thr Val Ile Pro Glu Ile Asp Pro
465                 470                 475                 480

<210> SEQ ID NO 122
<211> LENGTH: 4
<212> TYPE: PRT
<213> ORGANISM: Artificial Sequence
<220> FEATURE:
<223> OTHER INFORMATION: Synthetic Construct

<400> SEQUENCE: 122

Cys Pro Pro Cys
1

<210> SEQ ID NO 123
<211> LENGTH: 17
<212> TYPE: PRT
<213> ORGANISM: Artificial Sequence
<220> FEATURE:
<223> OTHER INFORMATION: Synthetic Construct

<400> SEQUENCE: 123

Gly Val Asp Pro Glu Thr Asp Gly Ala Ala Tyr Asn Gln Lys Phe Lys
1               5                   10                  15

Gly

<210> SEQ ID NO 124
<211> LENGTH: 10
<212> TYPE: PRT
<213> ORGANISM: Artificial Sequence
<220> FEATURE:
<223> OTHER INFORMATION: Synthetic Construct

<400> SEQUENCE: 124

Arg Ala Ser Ser Ser Val Asn Phe Ile His
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gln Gln Trp Ser Ser Asn Pro Trp Thr
1               5

<210> SEQ ID NO 126
<211> LENGTH: 253
<212> TYPE: PRT
<213> ORGANISM: Homo sapiens

<400> SEQUENCE: 126

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
                20                  25                  30

Glu Ala His Ala Arg Pro Tyr Met Ala Ser Val Gln Leu Asn Gly Ala
        35                  40                  45
```

```
His Leu Cys Gly Gly Val Leu Val Ala Glu Gln Trp Val Leu Ser Ala
 50                  55                  60

Ala His Cys Leu Glu Asp Ala Asp Gly Lys Val Gln Val Leu Leu
 65                  70                  75                  80

Gly Ala His Ser Leu Ser Gln Pro Glu Pro Ser Lys Arg Leu Tyr Asp
                 85                  90                  95

Val Leu Arg Ala Val Pro His Pro Asp Ser Gln Pro Asp Thr Ile Asp
                100                 105                 110

His Asp Leu Leu Leu Gln Leu Ser Glu Lys Ala Thr Leu Gly Pro
                115                 120                 125

Ala Val Arg Pro Leu Pro Trp Gln Arg Val Asp Arg Asp Val Ala Pro
130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
                180                 185                 190

Leu Met Cys Ala Glu Ser Asn Arg Arg Asp Ser Cys Lys Gly Asp Ser
                195                 200                 205

Gly Gly Pro Leu Val Cys Gly Gly Val Leu Glu Gly Val Val Thr Ser
210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 127
<211> LENGTH: 115
<212> TYPE: PRT
<213> ORGANISM: Artificial Sequence
<220> FEATURE:
<223> OTHER INFORMATION: Synthetic Construct

<400> SEQUENCE: 127

Gln Val Gln Leu Gln Gln Ser Gly Ala Glu Leu Val Lys Pro Gly Ala
 1               5                   10                  15

Ser Val Lys Leu Ser Cys Lys Ala Ser Gly Tyr Thr Phe Thr Ser Tyr
                 20                  25                  30

Tyr Met Tyr Trp Val Lys Glu Arg Pro Gly Gln Gly Leu Glu Trp Ile
                 35                  40                  45

Gly Glu Ile Asn Pro Thr Asn Gly Gly Thr Asn Phe Asn Glu Lys Phe
 50                  55                  60

Lys Ser Lys Ala Thr Leu Thr Val Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Gly Gly Phe Ala Tyr Trp Gly Gln Gly Thr Leu Val Thr
                100                 105                 110

Val Ser Ala
        115

<210> SEQ ID NO 128
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 128

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asp
            20                  25                  30

Val Ala Trp Phe Gln Gln Lys Pro Gly Gln Ser Pro Arg Gly Leu Ile
        35                  40                  45

Tyr Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ser Gly Thr Lys Val Glu Ile Lys
            100                 105
```

<210> SEQ ID NO 129
<211> LENGTH: 464
<212> TYPE: PRT
<213> ORGANISM: Artificial Sequence
<220> FEATURE:
<223> OTHER INFORMATION: Synthetic Construct

<400> SEQUENCE: 129

```
Met Gly Trp Ser Cys Ile Ile Leu Phe Leu Val Ala Thr Ala Thr Gly
1               5                   10                  15

Ala Tyr Ala Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Tyr Met Tyr Trp Val Lys Glu Arg Pro Gly Gln Gly Leu
    50                  55                  60

Glu Trp Ile Gly Glu Ile Asn Pro Thr Asn Gly Thr Asn Phe Asn
65                  70                  75                  80

Glu Lys Phe Lys Ser Lys Ala Thr Leu Thr Val Asp Thr Ser Ser Asn
                85                  90                  95

Thr Ala Tyr Met Gln Leu Ser Ser Leu Thr Ser Glu Asp Ser Ala Val
                100                 105                 110

Tyr Tyr Cys Ala Arg Glu Gly Gly Phe Ala Tyr Trp Gly Gln Gly Thr
            115                 120                 125

Leu Val Thr Val Ser Ala Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240
```

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 130
<211> LENGTH: 233
<212> TYPE: PRT
<213> ORGANISM: Artificial Sequence
<220> FEATURE:
<223> OTHER INFORMATION: Synthetic Construct

<400> SEQUENCE: 130

Met Gly Trp Ser Cys Ile Ile Leu Phe Leu Val Ala Thr Ala Thr Gly
1               5                   10                  15

Val His Ser Asp Ile Val Met Thr Gln Ser Gln Lys Phe Met Ser Thr
            20                  25                  30

Ser Val Gly Asp Arg Val Ser Val Thr Cys Lys Ala Ser Gln Asn Val
        35                  40                  45

Asp Thr Asp Val Ala Trp Phe Gln Gln Lys Pro Gly Gln Ser Pro Arg
    50                  55                  60

Gly Leu Ile Tyr Ser Ala Ser Arg Tyr Ser Gly Val Pro Asp Arg
65                  70                  75                  80

Phe Thr Gly Ser Gly Ser Gly Thr Asp Phe Thr Leu Thr Ile Ser Asn
                85                  90                  95

Val Gln Ser Glu Asp Leu Ala Glu Tyr Phe Cys Gln Gln Tyr Asn Asn
            100                 105                 110

Tyr Pro Leu Thr Phe Gly Ser Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 131
<211> LENGTH: 115
<212> TYPE: PRT
<213> ORGANISM: Artificial Sequence
<220> FEATURE:
<223> OTHER INFORMATION: Synthetic Construct

<400> SEQUENCE: 131

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser
        115

<210> SEQ ID NO 132
<211> LENGTH: 115
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
```

```
                    85                  90                  95

Glu Arg Glu Gly Gly Val Ser Asn Trp Gly Gln Gly Thr Leu Val Thr
                100                 105                 110

Val Ser Ser
        115

<210> SEQ ID NO 133
<211> LENGTH: 106
<212> TYPE: PRT
<213> ORGANISM: Artificial Sequence
<220> FEATURE:
<223> OTHER INFORMATION: Synthetic Construct

<400> SEQUENCE: 133

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Thr Lys Val Glu Ile Lys
            100                 105

<210> SEQ ID NO 134
<211> LENGTH: 106
<212> TYPE: PRT
<213> ORGANISM: Artificial Sequence
<220> FEATURE:
<223> OTHER INFORMATION: Synthetic Construct

<400> SEQUENCE: 134

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Glu Ser Leu Pro Tyr
                85                  90                  95

Thr Phe Gly Gln Thr Lys Val Glu Ile Lys
            100                 105

<210> SEQ ID NO 135
<211> LENGTH: 106
<212> TYPE: PRT
<213> ORGANISM: Artificial Sequence
<220> FEATURE:
<223> OTHER INFORMATION: Synthetic Construct

<400> SEQUENCE: 135
```

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Thr Lys Val Glu Ile Lys
            100                 105

<210> SEQ ID NO 136
<211> LENGTH: 115
<212> TYPE: PRT
<213> ORGANISM: Artificial Sequence
<220> FEATURE:
<223> OTHER INFORMATION: Synthetic Construct

<400> SEQUENCE: 136

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Glu Ile Asn Asn Leu Lys Asn Glu Asp Met Ala Thr Tyr Phe Cys
                85                  90                  95

Glu Arg Glu Gly Gly Val Asp Asn Trp Gly Gln Gly Thr Thr Leu Thr
            100                 105                 110

Val Ser Ser
    115

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Gly Gly Asn Thr Leu Arg Pro Gly Val Pro Ser Arg Phe Ser Ser
    50                  55                  60

Ser Gly Tyr Gly Ala Asp Phe Val Phe Thr Ile Asp Asn Met Leu Ser

```
                65                  70                  75                  80
            Glu Asp Val Ala Asp Tyr Tyr Cys Leu Gln Ser Asp Asn Leu Pro Tyr
                            85                  90                  95
            Thr Phe Gly Gly Gly Thr Arg Leu Glu Ile Lys
                        100                 105

<210> SEQ ID NO 138

<400> SEQUENCE: 138

000

<210> SEQ ID NO 139
<211> LENGTH: 23
<212> TYPE: DNA
<213> ORGANISM: Artificial Sequence
<220> FEATURE:
<223> OTHER INFORMATION: Synthetic Construct

<400> SEQUENCE: 139
tttyttgtcc accktggtgc tgc                                             23

<210> SEQ ID NO 140
<211> LENGTH: 19
<212> TYPE: DNA
<213> ORGANISM: Artificial Sequence
<220> FEATURE:
<223> OTHER INFORMATION: Synthetic Construct

<400> SEQUENCE: 140
gtagaagttg ttcaagaag                                                  19

<210> SEQ ID NO 141
<211> LENGTH: 22
<212> TYPE: DNA
<213> ORGANISM: Artificial Sequence
<220> FEATURE:
<223> OTHER INFORMATION: Synthetic Construct

<400> SEQUENCE: 141
cargtcamdg tcactgrctc ag                                              22

<210> SEQ ID NO 142
<211> LENGTH: 21
<212> TYPE: DNA
<213> ORGANISM: Artificial Sequence
<220> FEATURE:
<223> OTHER INFORMATION: Synthetic Construct

<400> SEQUENCE: 142
gaggcacctc cagatgttaa c                                               21

<210> SEQ ID NO 143
<211> LENGTH: 23
<212> TYPE: DNA
<213> ORGANISM: Artificial Sequence
<220> FEATURE:
<223> OTHER INFORMATION: Synthetic Construct

<400> SEQUENCE: 143
actgctcact ggatggtggg aag                                             23

<210> SEQ ID NO 144
<211> LENGTH: 47
<212> TYPE: DNA
```

```
<213> ORGANISM: Artificial Sequence
<220> FEATURE:
<223> OTHER INFORMATION: Synthetic Construct

<400> SEQUENCE: 144
gcaactgcaa ctggagtaca ttcacaaatt gttctctccc agtctcc          47

<210> SEQ ID NO 145
<211> LENGTH: 44
<212> TYPE: DNA
<213> ORGANISM: Artificial Sequence
<220> FEATURE:
<223> OTHER INFORMATION: Synthetic Construct

<400> SEQUENCE: 145
ggatacagtt ggtgcagcat cagcccgttt gatttccagc ttgg             44

<210> SEQ ID NO 146
<211> LENGTH: 47
<212> TYPE: DNA
<213> ORGANISM: Artificial Sequence
<220> FEATURE:
<223> OTHER INFORMATION: Synthetic Construct

<400> SEQUENCE: 146
gcaactgcaa ctggagcgta cgcccaggtc cagctgcagc agtctgg          47

<210> SEQ ID NO 147
<211> LENGTH: 48
<212> TYPE: DNA
<213> ORGANISM: Artificial Sequence
<220> FEATURE:
<223> OTHER INFORMATION: Synthetic Construct

<400> SEQUENCE: 147
gggcccttgg tggaggctga ggagacggtg actgaggttc cttgaccc         48

<210> SEQ ID NO 148
<211> LENGTH: 47
<212> TYPE: DNA
<213> ORGANISM: Artificial Sequence
<220> FEATURE:
<223> OTHER INFORMATION: Synthetic Construct

<400> SEQUENCE: 148
gcaactgcaa ctggagtaca ttcaaacatt gtggtgaccc aatctcc          47

<210> SEQ ID NO 149
<211> LENGTH: 44
<212> TYPE: DNA
<213> ORGANISM: Artificial Sequence
<220> FEATURE:
<223> OTHER INFORMATION: Synthetic Construct

<400> SEQUENCE: 149
ggatacagtt ggtgcagcat cagcccgctt tatttccagc ttgg             44

<210> SEQ ID NO 150
<211> LENGTH: 53
<212> TYPE: DNA
<213> ORGANISM: Artificial Sequence
<220> FEATURE:
<223> OTHER INFORMATION: Synthetic Construct

<400> SEQUENCE: 150
gcaactgcaa ctggagcgta cgccgaggtg aagctggtgg aatctggggg agg   53
```

<210> SEQ ID NO 151
<211> LENGTH: 48
<212> TYPE: DNA
<213> ORGANISM: Artificial Sequence
<220> FEATURE:
<223> OTHER INFORMATION: Synthetic Construct

<400> SEQUENCE: 151
gggcccttgg tggaggctga ggagacggtg actgcggttc cttgaccc                48

<210> SEQ ID NO 152
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: N-term Mca
<220> FEATURE:
<221> NAME/KEY: MOD_RES
<222> LOCATION: (9)..(9)
<223> OTHER INFORMATION: Lys(DNP)

<400> SEQUENCE: 152

Ile Arg Arg Val Ser Tyr Ser Phe Lys Lys
1               5                   10

<210> SEQ ID NO 153
<211> LENGTH: 234
<212> TYPE: PRT
<213> ORGANISM: Artificial Sequence
<220> FEATURE:
<223> OTHER INFORMATION: Synthetic Construct

<400> SEQUENCE: 153

Met Lys His Gln His Gln His Gln His Gln His Gln Met His
1               5                   10                  15

Gln Ser Thr Ala Ala Gly Gln Gly Gln Glu Asp Pro Asn Ser Leu
                20                  25                  30

Arg His Lys Tyr Asn Phe Ile Ala Asp Val Val Glu Lys Ile Ala Pro
            35                  40                  45

Ala Val Val His Ile Glu Leu Tyr Arg Lys Leu Pro Phe Ser Lys Arg
        50                  55                  60

Glu Val Pro Val Ala Ser Gly Ser Gly Phe Ile Val Ser Glu Asp Gly
65                  70                  75                  80

Leu Ile Val Thr Asn Ala His Val Val Thr Asn Lys Asn Arg Val Lys
                85                  90                  95

Val Glu Leu Lys Asn Gly Ala Thr Tyr Glu Ala Lys Ile Lys Asp Val
            100                 105                 110

Asp Glu Lys Ala Asp Ile Ala Leu Ile Lys Ile Asp His Gln Gly Lys
        115                 120                 125

Leu Pro Val Leu Leu Leu Gly Arg Ser Ser Glu Leu Arg Pro Gly Glu
    130                 135                 140

Phe Val Val Ala Ile Gly Ser Pro Phe Ser Leu Gln Asn Thr Val Thr
145                 150                 155                 160

Thr Gly Ile Val Ser Thr Thr Gln Arg Gly Gly Lys Glu Leu Gly Leu
                165                 170                 175

Arg Asn Ser Asp Met Asp Tyr Ile Gln Thr Asp Ala Ile Ile Asn Tyr
            180                 185                 190

Gly Asn Ser Gly Gly Pro Leu Val Asn Leu Asp Gly Glu Val Ile Gly
            195                 200                 205

Ile Asn Thr Leu Lys Val Thr Ala Gly Ile Ser Phe Ala Ile Pro Ser
    210                 215                 220

Asp Lys Ile Lys Lys Phe Leu Thr Glu Ser
225                 230

<210> SEQ ID NO 154
<211> LENGTH: 228
<212> TYPE: PRT
<213> ORGANISM: Artificial Sequence
<220> FEATURE:
<223> OTHER INFORMATION: Synthetic Construct

<400> SEQUENCE: 154

Met Gly Ser Ser His His His His His His Ser Ser Gly Leu Val Pro
1               5                   10                  15

Arg Gly Ser His Met Asp Pro Asn Ser Leu Arg His Lys Tyr Asn Phe
            20                  25                  30

Ile Ala Asp Val Val Glu Lys Ile Ala Pro Ala Val Val His Ile Glu
        35                  40                  45

Leu Phe Arg Lys Leu Pro Phe Ser Lys Arg Glu Val Pro Val Ala Ser
    50                  55                  60

Gly Ser Gly Phe Ile Val Ser Glu Asp Gly Leu Ile Val Thr Asn Ala
65                  70                  75                  80

His Val Val Thr Asn Lys His Arg Val Lys Val Glu Leu Lys Asn Gly
                85                  90                  95

Ala Thr Tyr Glu Ala Lys Ile Lys Asp Val Asp Glu Lys Ala Asp Ile
            100                 105                 110

Ala Leu Ile Lys Ile Asp His Gln Gly Lys Leu Pro Val Leu Leu Leu
        115                 120                 125

Gly Arg Ser Ser Glu Leu Arg Pro Gly Glu Phe Val Val Ala Ile Gly
    130                 135                 140

Ser Pro Phe Ser Leu Gln Asn Thr Val Thr Thr Gly Ile Val Ser Thr
145                 150                 155                 160

Thr Gln Arg Gly Gly Lys Glu Leu Gly Leu Arg Asn Ser Asp Met Asp
                165                 170                 175

Tyr Ile Gln Thr Asp Ala Ile Ile Asn Tyr Gly Asn Ser Gly Gly Pro
            180                 185                 190

Leu Val Asn Leu Asp Gly Glu Val Ile Gly Ile Asn Thr Leu Lys Val
        195                 200                 205

Thr Ala Gly Ile Ser Phe Ala Ile Pro Ser Asp Lys Ile Lys Lys Phe
    210                 215                 220

Leu Thr Glu Ser
225

<210> SEQ ID NO 155
<211> LENGTH: 480
<212> TYPE: PRT
<213> ORGANISM: Mus musculus

<400> SEQUENCE: 155

Met Gln Ser Leu Arg Thr Thr Leu Leu Ser Leu Leu Leu Leu Leu Leu
1               5                   10                  15

Ala Ala Pro Ser Leu Ala Leu Pro Ser Gly Thr Gly Arg Ser Ala Pro
            20                  25                  30

Ala Ala Thr Val Cys Pro Glu His Cys Asp Pro Thr Arg Cys Ala Pro

```
                35                  40                  45
Pro Pro Thr Asp Cys Glu Gly Arg Val Arg Asp Ala Cys Gly Cys
         50                  55                  60
Cys Glu Val Cys Gly Ala Leu Glu Gly Ala Ala Cys Gly Leu Gln Glu
65                   70                  75                   80
Gly Pro Cys Gly Glu Gly Leu Gln Cys Val Pro Phe Gly Val Pro
                 85                  90                  95
Ala Ser Ala Thr Val Arg Arg Arg Ala Gln Ala Gly Leu Cys Val Cys
                100                 105                 110
Ala Ser Ser Glu Pro Val Cys Gly Ser Asp Ala Lys Thr Tyr Thr Asn
                115                 120                 125
Leu Cys Gln Leu Arg Ala Ala Ser Arg Arg Ser Glu Lys Leu Arg Gln
        130                 135                 140
Pro Pro Val Ile Val Leu Gln Arg Gly Ala Cys Gly Gln Gly Gln Glu
145                 150                 155                 160
Asp Pro Asn Ser Leu Arg His Lys Tyr Asn Phe Ile Ala Asp Val Val
                165                 170                 175
Glu Lys Ile Ala Pro Ala Val Val His Ile Glu Leu Tyr Arg Lys Leu
            180                 185                 190
Pro Phe Ser Lys Arg Glu Val Pro Val Ala Ser Gly Ser Gly Phe Ile
        195                 200                 205
Val Ser Glu Asp Gly Leu Ile Val Thr Asn Ala His Val Val Thr Asn
210                 215                 220
Lys Asn Arg Val Lys Val Glu Leu Lys Asn Gly Ala Thr Tyr Glu Ala
225                 230                 235                 240
Lys Ile Lys Asp Val Asp Glu Lys Ala Asp Ile Ala Leu Ile Lys Ile
                245                 250                 255
Asp His Gln Gly Lys Leu Pro Val Leu Leu Leu Gly Arg Ser Ser Glu
                260                 265                 270
Leu Arg Pro Gly Glu Phe Val Val Ala Ile Gly Ser Pro Phe Ser Leu
            275                 280                 285
Gln Asn Thr Val Thr Thr Gly Ile Val Ser Thr Thr Gln Arg Gly Gly
        290                 295                 300
Lys Glu Leu Gly Leu Arg Asn Ser Asp Met Asp Tyr Ile Gln Thr Asp
305                 310                 315                 320
Ala Ile Ile Asn Tyr Gly Asn Ser Gly Gly Pro Leu Val Asn Leu Asp
                325                 330                 335
Gly Glu Val Ile Gly Ile Asn Thr Leu Lys Val Thr Ala Gly Ile Ser
                340                 345                 350
Phe Ala Ile Pro Ser Asp Lys Ile Lys Lys Phe Leu Thr Glu Ser His
            355                 360                 365
Asp Arg Gln Ala Lys Gly Lys Ala Val Thr Lys Lys Tyr Ile Gly
        370                 375                 380
Ile Arg Met Met Ser Leu Thr Ser Ser Lys Ala Lys Glu Leu Lys Asp
385                 390                 395                 400
Arg His Arg Asp Phe Pro Asp Val Leu Ser Gly Ala Tyr Ile Ile Glu
                405                 410                 415
Val Ile Pro Asp Thr Pro Ala Glu Ala Gly Gly Leu Lys Glu Asn Asp
                420                 425                 430
Val Ile Ile Ser Ile Asn Gly Gln Ser Val Val Thr Ala Asn Asp Val
            435                 440                 445
Ser Asp Val Ile Lys Lys Glu Asn Thr Leu Asn Met Val Val Arg Arg
        450                 455                 460
```

Gly Asn Glu Asp Ile Val Ile Thr Val Ile Pro Glu Ile Asp Pro
465                 470                 475                 480

<210> SEQ ID NO 156
<211> LENGTH: 104
<212> TYPE: PRT
<213> ORGANISM: Artificial Sequence
<220> FEATURE:
<223> OTHER INFORMATION: Synthetic Construct

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Glu Pro Lys Ser Cys Asp Lys Thr His Thr
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Pro Ala Pro Glu Leu Leu Gly Gly Pro
1               5

<210> SEQ ID NO 159
<211> LENGTH: 213
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Glu Phe Ile
            20                  25                  30

His Trp Tyr Gln Gln Lys Pro Gly Lys Ala Pro Lys Pro Leu Ile Ser
        35                  40                  45

Ala Thr Ser Asn Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ala Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 160
<211> LENGTH: 223
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Asp Ser
            20                  25                  30

Glu Met His Trp Val Arg Gln Ala Pro Gly Gln Gly Leu Glu Trp Ile
        35                  40                  45

Gly Gly Val Asp Pro Glu Thr Glu Gly Ala Ala Tyr Asn Gln Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Thr Arg Gly Tyr Asp Tyr Asp Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
-continued

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp
    210                 215                 220
```

ANTI-HTRA1 ANTIBODIES AND METHODS OF USE THEREOF

FIELD OF THE INVENTION

The invention relates generally to anti-HtrA1 antibodies and methods of using the same.

BACKGROUND OF THE INVENTION

The serine protease HtrA serine peptidase 1 (HtrA1) (PRSS11; Clan PA, family 51) belongs to an evolutionarily conserved family of HtrA proteins. In humans, HtrA1, HtrA3, and HtrA4 share the same domain architecture: an N-terminal IGFBP-like module and a Kazal-like module, a protease domain with trypsin-like fold, and a C-terminal PDZ domain. The physiological relevance of HtrA1 has been firmly established by the identification of human loss-of-function mutations causing familial ischemic cerebral small-vessel disease. The molecular mechanism involves deficient TGFβ inhibition by HtrA1 resulting in increased TGFβ signaling. Dysregulated TGF signaling by aberrant HtrA1 expression may also contribute to arthritic disease, perhaps in conjunction with HtrA1-mediated degradation of various extracellular matrix components, or indirectly via up-regulation of matrix metalloproteases. In addition, human genetic studies identified a strong correlation between progression of age-related macular degeneration (AMD) and a SNP in the HtrA1 promoter region which results in increased HtrA1 transcript levels (see, e.g., Dewan et al., Science 314:989-992, 2006 and Yang et al., Science 314:992-993, 2006).

AMD is a progressive chronic disease of the central retina with significant consequences for visual acuity. Late forms of the disease are the leading cause of vision loss in industrialized countries. For the Caucasian population ≥40 years of age, the prevalence of early AMD is estimated at about 6.8% and advanced AMD at about 1.5%. The prevalence of late AMD increases dramatically with age rising to about 11.8% after 80 years of age. Two types of AMD exist, non-exudative (dry) and exudative (wet) AMD. The more common dry AMD involves atrophic and hypertrophic changes in the retinal pigment epithelium (RPE) underlying the central retina (macula) as well as deposits (drusen) on the RPE. Advanced dry AMD can result in significant retinal damage, including geographic atrophy (GA), with irreversible vision loss. Moreover, patients with dry AMD can progress to the wet form, in which abnormal blood vessels called choroidal neovascular membranes (CNVMs) develop under the retina, leak fluid and blood, and ultimately cause a blinding disciform scar in and under the retina.

There remains a need for anti-HtrA1 antibodies with improved properties, such as binding affinity, stability, and inhibitory (blocking) activity, as well as therapeutic and diagnostic uses thereof.

SUMMARY OF THE INVENTION

The present invention provides anti-HtrA1 antibodies and methods of using the same for therapeutic and diagnostic purposes. The anti-HtrA1 antibodies of the invention are highly potent and have a high binding affinity for HtrA1. The improved properties of the antibodies of the invention make them suitable for use in therapy.

In one aspect, the invention encompasses an isolated antibody that specifically binds to an HtrA1 epitope, where the HtrA1 epitope comprises at least one amino acid of the HtrA1 protein selected from the group consisting of Arg190, Leu192, Pro193, Phe194, and Arg197, where the amino acid numbering refers to the numbering for the human HtrA1 precursor protein.

In one embodiment, the HtrA1 epitope comprises at least one amino acid of the HtrA1 protein selected from the group consisting of Leu192, Pro193, and Arg197.

In another embodiment, the HtrA1 epitope comprises at least two amino acids of the HtrA1 protein selected from the group consisting of Leu192, Pro193, and Arg197.

In a particular embodiment, the HtrA1 epitope comprises the HtrA1 amino acids Leu192, Pro193, and Arg197.

In another embodiment, the HtrA1 epitope comprises the HtrA1 amino acids Arg190, Leu192, Pro193, and Arg197.

In an additional embodiment, the HtrA1 epitope comprises the HtrA1 amino acids Arg190, Leu192, Pro193, Phe194, and Arg197.

In one aspect, the invention features an isolated antibody that specifically binds human HtrA serine peptidase 1 (HtrA1) with a KD of about 550 pM or lower. In some embodiments, the antibody specifically binds human HtrA1 with a KD between about 40 pM and about 550 pM. In some embodiments, the antibody specifically binds human HtrA1 with a KD between about 40 pM and about 250 pM. In some embodiments, the antibody specifically binds human HtrA1 with a KD between about 50 pM and about 125 pM. In some embodiments, the antibody specifically binds human HtrA1 with a KD of about 110 pM. In some embodiments, the antibody specifically binds human HtrA1 with a KD of about 60 pM. In some embodiments, the KD is measured by surface plasmon resonance (SPR) (e.g., BIACORE® SPR). In some embodiments, the SPR is performed as described herein (e.g., in the Examples section).

In some embodiments, any one of the preceding antibodies is capable of inhibiting the activity of HtrA1. In some embodiments, the antibody inhibits the activity of the protease domain of human HtrA1 (huHtrA1-PD) with a 50% inhibitory concentration (IC50) of 1.5 nM or lower. In some embodiments, the antibody inhibits the activity of huHtrA1-PD with an IC50 of 0.25 nM to about 0.5 nM. In some embodiments, the antibody inhibits the activity of huHtrA1-PD with an IC50 of about 0.3 nM. In some embodiments, the inhibitory activity is an in vitro FRET-based blocking assay measurement. In some embodiments, the in vitro FRET-based blocking assay comprises cleavage of an H2-Opt probe (e.g., SEQ ID NO: 152). In some embodiments, the in vitro FRET-based blocking assay is performed as described herein (e.g., in the Examples).

In some embodiments of the above aspect, the antibody comprises a binding domain comprising: (a) an HVR-H1 comprising the amino acid sequence of DSEX$_1$H (SEQ ID NO: 1), wherein X$_1$ is Met or Leu; (b) an HVR-H2 comprising the amino acid sequence of GVDPETX$_2$GAAYNQKFKG (SEQ ID NO: 2), wherein X$_2$ is Glu or Asp; and (c) an HVR-H3 comprising the amino acid sequence of GYDYDYALDY (SEQ ID NO: 3). In some embodiments, the antibody comprises a binding domain comprising: (a) an HVR-H1 comprising the amino acid sequence of DSEMH (SEQ ID NO: 7); (b) an HVR-H2 comprising the amino acid sequence of GVDPETEGAAYNQKFKG (SEQ ID NO: 8); and (c) an HVR-H3 comprising the amino acid sequence of GYDYDYALDY (SEQ ID NO: 3). In some embodiments, the antibody further comprises: (a) an FR-H1 comprising the amino acid sequence of EVQLVQSGAEVKKPGASVKVSCKASGYX$_1$FX$_2$ (SEQ ID NO: 12), wherein X$_1$ is Lys or Thr and X$_2$ is Thr, Lys, or Arg; (b) an FR-H2 comprising the amino acid sequence of WVRQAPGQGLEWIG (SEQ ID NO: 13); (c) an FR-H3 comprising the amino acid sequence of RATITRDTST-STAYLELSSLRSEDTAVYYCTR (SEQ ID NO: 14); and (d) an FR-H4 comprising the amino acid sequence of WGQGTLVTVSS (SEQ ID NO: 15). In some embodiments, the antibody further comprises: (a) an FR-H1 comprising the amino acid sequence of EVQLVQSGAEVKKPGASVK-VSCKASGYKFT (SEQ ID NO: 16); (b) an FR-H2 comprising the amino acid sequence of WVRQAPGQGLEWIG (SEQ ID NO: 13); (c) an FR-H3 comprising the amino acid sequence of RATITRDTSTSTAYLELSSLRSED-TAVYYCTR (SEQ ID NO: 14); and (d) an FR-H4 comprising the amino acid sequence of WGQGTLVTVSS (SEQ ID NO: 15).

In some embodiments of the above aspect, the binding domain further comprises: (a) an HVR-L1 comprising the amino acid sequence of RASSSVX$_3$FIH (SEQ ID NO: 4), wherein X$_3$ is Glu or Asn; (b) an HVR-L2 comprising the amino acid sequence of ATSX$_4$LAS (SEQ ID NO: 5), wherein X$_4$ is Asn, His or Glu; and (c) an HVR-L3 comprising the amino acid sequence of QQWX$_5$SX$_6$PWT (SEQ ID NO: 6), wherein X$_5$ is Ser or Tyr and X$_6$ is Ala or Asn. In some embodiments, the binding domain further comprises: (a) an HVR-L1 comprising the amino acid sequence of RASSSVEFIH (SEQ ID NO: 9); (b) an HVR-L2 comprising the amino acid sequence of ATSNLAS (SEQ ID NO: 10); and (c) an HVR-L3 comprising the amino acid sequence of QQWSSAPWT (SEQ ID NO: 11). In some embodiments, the antibody further comprises: (a) an FR-L1 comprising the amino acid sequence of DIQMTQSPSSLSASVGDRVTITC (SEQ ID NO: 17); (b) an FR-L2 comprising the amino acid sequence of WYQQK-PGKAPKPLIS (SEQ ID NO: 18); (c) an FR-L3 comprising the amino acid sequence of GVPSRFSGSGSGTDFTLTISS-LQPEDFATYYC (SEQ ID NO: 19); and (d) an FR-L4 comprising the amino acid sequence of FGQGTKVEIK (SEQ ID NO: 20).

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 21; (b) a light chain variable (VL) domain comprising an amino acid sequence having at least 95% sequence identity to the amino acid sequence of SEQ ID NO: 22; or (c) a VH domain as in (a) and a VL domain as in (b). In some embodiments, the VH domain further comprises: (a) an FR-H1 comprising the amino acid sequence of EVQLVQSGAEVKKPGASVKVSCKAS-GYKFT (SEQ ID NO: 16); (b) an FR-H2 comprising the amino acid sequence of WVRQAPGQGLEWIG (SEQ ID NO: 13); (c) an FR-H3 comprising the amino acid sequence of RATITRDTSTSTAYLELSSLRSEDTAVYYCTR (SEQ ID NO: 14); and (d) an FR-H4 comprising the amino acid sequence of WGQGTLVTVSS (SEQ ID NO: 15). In some embodiments, the VH domain comprises the amino acid sequence of SEQ ID NO: 21. In some embodiments, the VL domain further comprises: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKPLIS (SEQ ID NO: 18); (c) an FR-L3 comprising the amino acid sequence of GVPSRF-SGSGSGTDFTLTISSLQPEDFATYYC (SEQ ID NO: 19); and (d) an FR-L4 comprising the amino acid sequence of FGQGTKVEIK (SEQ ID NO: 20). In some embodiments, the VL domain comprises the amino acid sequence of SEQ ID NO: 22.

In another aspect, the invention features an isolated antibody that specifically binds HtrA1, wherein the antibody comprises a binding domain comprising the following six HVRs: (a) an HVR-H1 comprising the amino acid sequence of DSEX$_1$H (SEQ ID NO: 1), wherein X$_1$ is Met or Leu; (b) an HVR-H2 comprising the amino acid sequence of GVDPETX$_2$GAAYNQKFKG (SEQ ID NO: 2), wherein X$_2$ is Glu or Asp; (c) an HVR-H3 comprising the amino acid sequence of GYDYDYALDY (SEQ ID NO: 3); (d) an HVR-L1 comprising the amino acid sequence of RASSSVX$_3$FIH (SEQ ID NO: 4), wherein X$_3$ is Glu or Asn; (e) an HVR-L2 comprising the amino acid sequence of ATSX$_4$LAS (SEQ ID NO: 5), wherein X$_4$ is Asn, His or Glu; and (f) an HVR-L3 comprising the amino acid sequence of QQWX$_5$SX$_6$PWT (SEQ ID NO: 6), wherein X$_5$ is Ser or Tyr and X$_6$ is Ala or Asn. In some embodiments, the binding domain comprises the following six HVRs: (a) an HVR-H1 comprising the amino acid sequence of DSEMH (SEQ ID NO: 7); (b) an HVR-H2 comprising the amino acid sequence of GVDPETEGAAYNQKFKG (SEQ ID NO: 8); (c) an HVR-H3 comprising the amino acid sequence of GYDY-DYALDY (SEQ ID NO: 3); (d) an HVR-L1 comprising the amino acid sequence of RASSSVEFIH (SEQ ID NO: 9); (e) an HVR-L2 comprising the amino acid sequence of ATSN-LAS (SEQ ID NO: 10); and (f) an HVR-L3 comprising the amino acid sequence of QQWSSAPWT (SEQ ID NO: 11).

In another aspect, the invention features an isolated antibody that specifically binds HtrA1, wherein the antibody comprises a binding domain comprising (a) a VH domain comprising an amino acid sequence having at least 95% sequence identity to the amino acid sequence of SEQ ID NO: 21; (b) a VL domain comprising an amino acid sequence having at least 95% sequence identity to the amino acid sequence of SEQ ID NO: 22; or (c) a VH domain as in (a) and a VL domain as in (b). In some embodiments, the VH domain further comprises: (a) an FR-H1 comprising the amino acid sequence of EVQLVQSGAEVKKPGASVK-VSCKASGYKFT (SEQ ID NO: 16); (b) an FR-H2 comprising the amino acid sequence of WVRQAPGQGLEWIG (SEQ ID NO: 13); (c) an FR-H3 comprising the amino acid sequence of RATITRDTSTSTAYLELSSLRSED-TAVYYCTR (SEQ ID NO: 14); and (d) an FR-H4 comprising the amino acid sequence of WGQGTLVTVSS (SEQ ID NO: 15). In some embodiments, the VH domain comprises the amino acid sequence of SEQ ID NO: 21. In some embodiments, the VL domain further comprises: (a) an FR-L1 comprising the amino acid sequence of DIQMTQSPSSLSASVGDRVTITC (SEQ ID NO: 17); (b) an FR-L2 comprising the amino acid sequence of WYQQK-PGKAPKPLIS (SEQ ID NO: 18); (c) an FR-L3 comprising the amino acid sequence of GVPSRFSGSGSGTDFTLTISS-LQPEDFATYYC (SEQ ID NO: 19); and (d) an FR-L4 comprising the amino acid sequence of FGQGTKVEIK (SEQ ID NO: 20). In some embodiments, the VL domain comprises the amino acid sequence of SEQ ID NO: 22.

In another aspect, the invention features an isolated antibody that specifically binds HtrA1, wherein the antibody comprises a binding domain comprising (a) a VH domain comprising an amino acid sequence having at least 99% sequence identity to the amino acid sequence of SEQ ID NO: 21 and (b) a VL domain comprising an amino acid sequence having at least 99% sequence identity to the amino acid sequence of SEQ ID NO: 22.

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 23; (b) a light chain variable (VL) domain comprising an amino acid sequence having at least 95% sequence identity to the amino acid sequence of SEQ ID NO: 24; or (c) a VH domain as in (a) and a VL domain as in (b). In some embodiments, the VH domain further comprises: (a) an FR-H1 comprising the amino acid sequence of QVQLQQSGAELVRPGASVTLSCKALSCK-ASGYTFT (SEQ ID NO: 24); (b) an FR-H2 comprising the amino acid sequence of WVKQTPVHGLEWIG (SEQ ID NO: 25); (c) an FR-H3 comprising the amino acid sequence of KATLTADKSSSTAYMELRSLTSEDSAVYYCTR (SEQ ID NO: 26); and (d) an FR-H4 comprising the amino acid sequence of WGQGTSVTVSS (SEQ ID NO: 27). In some embodiments, the VH domain comprises the amino acid sequence of SEQ ID NO: 23. In some embodiments, the VL domain further comprises: (a) an FR-L1 comprising the amino acid sequence of NIVVTQSPASLAVSLGQRATISC (SEQ ID NO: 29); (b) an FR-L2 comprising the amino acid sequence of WYQQKPGQPPKLLIY (SEQ ID NO: 30); (c) an FR-L3 comprising the amino acid sequence of GVPARF-SGSGSRTDFTLTIDPVEADDAATYYC (SEQ ID NO: 31); and (d) an FR-L4 comprising the amino acid sequence of FGGGTKLEIK (SEQ ID NO: 32). In some embodiments, the VL domain comprises the amino acid sequence of SEQ ID NO: 24.

In another aspect, the invention features an isolated antibody that specifically binds HtrA1, wherein the antibody comprises a binding domain comprising (a) a VH domain comprising an amino acid sequence having at least 99% sequence identity to the amino acid sequence of SEQ ID NO: 23 and (b) a VL domain comprising an amino acid sequence having at least 99% sequence identity to the amino acid sequence of SEQ ID NO: 24.

In another aspect, the invention features an isolated antibody that specifically binds HtrA1, wherein the antibody comprises a binding domain comprising the following six HVRs: (a) an HVR-H1 comprising the amino acid sequence of SYIMS (SEQ ID NO: 39); (b) an HVR-H2 comprising the amino acid sequence of YISNGGGTTYYSDTIKG (SEQ ID NO: 40); (c) an HVR-H3 comprising the amino acid sequence of QNFRSDGSSMDY (SEQ ID NO: 41); (d) an HVR-L1 comprising the amino acid sequence of RASES-VDSYGKSFMH (SEQ ID NO: 42); (e) an HVR-L2 comprising the amino acid sequence of LASKLES (SEQ ID NO: 43); and (f) an HVR-L3 comprising the amino acid sequence of QQNNEDPYT (SEQ ID NO: 44).

In another aspect, the invention features an isolated antibody that specifically binds HtrA1, wherein the antibody comprises a binding domain comprising (a) a VH domain comprising an amino acid sequence having at least 95% sequence identity to the amino acid sequence of SEQ ID NO: 45; (b) a VL domain comprising an amino acid sequence having at least 95% sequence identity to the amino acid sequence of SEQ ID NO: 46; or (c) a VH domain as in (a) and a VL domain as in (b). In some embodiments, the VH domain further comprises: (a) an FR-H1 comprising the amino acid sequence of EVQLVESGGGLVQPGGSLRLS-CAASGFTFS (SEQ ID NO: 47); (b) an FR-H2 comprising the amino acid sequence of WVRQAPGKGLEWVA (SEQ ID NO: 48); (c) an FR-H3 comprising the amino acid sequence of RFTISRDNSKNTLYLQMNSLRAEDTAVYY-CAR (SEQ ID NO: 49); and (d) an FR-H4 comprising the amino acid sequence of WGQGTLVTVSS (SEQ ID NO: 50). In some embodiments, the VH domain comprises the amino acid sequence of SEQ ID NO: 45. In some embodiments, the VL domain further comprises: (a) an FR-L1 comprising the amino acid sequence of DIVMTQSPD-SLAVSLGERATINC (SEQ ID NO: 51); (b) an FR-L2 comprising the amino acid sequence of WYQQKPGQPP-KLLIY (SEQ ID NO: 52); (c) an FR-L3 comprising the amino acid sequence of GVPDRFSGSGSGTDFTLTISS-LQAEDVAVYYC (SEQ ID NO: 53); and (d) an FR-L4 comprising the amino acid sequence of FGQGTKVEIK (SEQ ID NO: 54). In some embodiments, the VL domain comprises the amino acid sequence of SEQ ID NO: 46.

In another aspect, the invention features an isolated antibody that specifically binds HtrA1, wherein the antibody comprises a binding domain comprising (a) a VH domain comprising an amino acid sequence having at least 99% sequence identity to the amino acid sequence of SEQ ID NO: 45 and (b) a VL domain comprising an amino acid sequence having at least 99% sequence identity to the amino acid sequence of SEQ ID NO: 46.

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 55; (b) a light chain variable (VL) domain comprising an amino acid sequence having at least 95% sequence identity to the amino acid sequence of SEQ ID NO: 56; or (c) a VH domain as in (a) and a VL domain as in (b). In some embodiments, the VH domain further comprises: (a) an FR-H1 comprising the amino acid sequence of EVKLVESGGGLVEPGGSLKLACVAS-GFTFS (SEQ ID NO: 57); (b) an FR-H2 comprising the amino acid sequence of WVRQTPEKRLEWVA (SEQ ID NO: 58); (c) an FR-H3 comprising the amino acid sequence of RFTISRDNAKNTLYLQMSTLKSEDTAIYFCAR (SEQ ID NO: 59); and (d) an FR-H4 comprising the amino acid sequence of WGQGTAVTVSS (SEQ ID NO: 60). In some embodiments, the VH domain comprises the amino acid sequence of SEQ ID NO: 55. In some embodiments, the VL domain further comprises: (a) an FR-L1 comprising the amino acid sequence of NIVVTQSPASLAVSLGQRATISC (SEQ ID NO: 61); (b) an FR-L2 comprising the amino acid sequence of WYQQKPGQPPKLLIY (SEQ ID NO: 62); (c) an FR-L3 comprising the amino acid sequence of GVPARF-SGSGSRTDFTLTIDPVEADDAATYYC (SEQ ID NO: 63); and (d) an FR-L4 comprising the amino acid sequence of FGGGTKLEIK (SEQ ID NO: 64). In some embodiments, the VL domain comprises the amino acid sequence of SEQ ID NO: 56.

In another aspect, the invention features an isolated antibody that specifically binds HtrA, wherein the antibody comprises a binding domain comprising (a) a VH domain comprising an amino acid sequence having at least 99% sequence identity to the amino acid sequence of SEQ ID NO: 55 and (b) a VL domain comprising an amino acid sequence having at least 99% sequence identity to the amino acid sequence of SEQ ID NO: 56.

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 65; (b) a light chain variable (VL) domain comprising an amino acid sequence having at least 95% sequence identity to the amino acid sequence of SEQ ID NO: 66; or (c) a VH domain as in (a) and a VL domain as in (b).

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 67; (b) a light chain variable (VL) domain comprising an amino acid sequence having at least 95% sequence identity to the amino acid sequence of SEQ ID NO: 68; or (c) a VH domain as in (a) and a VL domain as in (b).

In another aspect, the invention features an isolated antibody that specifically binds HtrA1, wherein the antibody comprises a binding domain comprising (a) a heavy chain variable (VH) domain comprising an amino acid sequence having at least 95% sequence identity to the amino acid sequence of SEQ ID NO: 69; (b) a light chain variable (VL) domain comprising an amino acid sequence having at least 95% sequence identity to the amino acid sequence of SEQ ID NO: 70; or (c) a VH domain as in (a) and a VL domain as in (b).

In some embodiments of any of the preceding aspects, the antibody is monoclonal, human, humanized, or chimeric. In particular embodiments, the antibody is monoclonal, humanized, or chimeric.

In some embodiments of any of the preceding aspects, the antibody is an antibody fragment that binds to HtrA1. In some embodiments, the antibody fragment is selected from the group consisting of Fab, Fab'-SH, Fv, scFV, and (Fab')$_2$ fragments. In some embodiments, the antibody fragment is an Fab. In some embodiments, the Fab comprises a truncation in the hinge region of the heavy chain constant region. In some embodiments, the Fab comprises a truncation in the upper hinge of the heavy chain constant region. In some embodiments, the heavy chain constant region terminates at position 221 (EU numbering). In some embodiments, the amino acid residue at position 221 is an aspartic acid (Asp) residue. In some embodiments, the heavy chain constant region comprises the amino acid sequence of SEQ ID NO: 156. In some embodiments, the antibody comprises the heavy chain amino acid sequence of SEQ ID NO: 160. In some embodiments, the antibody comprises the light chain amino acid sequence of SEQ ID NO: 159. In some embodiments, the antibody comprises the heavy chain amino acid sequence of SEQ ID NO: 160 and the light chain amino acid sequence of SEQ ID NO: 159.

In some embodiments, the Fab is an IgG1 Fab.

In some embodiments of any of the preceding aspects, the antibody is a full-length antibody. In some embodiments, the antibody is an IgG antibody. In some embodiments, the antibody is a monospecific antibody.

In some embodiments of any of the preceding aspects, the antibody is a bispecific antibody. In some embodiments, the bispecific antibody comprises a second binding domain that binds to Factor D. In some embodiments, the second binding domain comprises the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu. In some embodiments, the second binding domain comprises the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some embodiments, the second binding domain comprises (a) a VH domain comprising an amino acid sequence having at least 95% sequence identity to the amino acid sequence of SEQ ID NO: 119; (b) a VL domain comprising an amino acid sequence having at least 95% sequence identity to the amino acid sequence of SEQ ID NO: 120; or (c) a VH domain as in (a) and a VL domain as in (b). In some embodiments, the VH domain comprises the amino acid sequence of SEQ ID NO: 119. In some embodiments, the VL domain comprises the amino acid sequence of SEQ ID NO: 120.

In another aspect, the invention features an isolated antibody that specifically binds both HtrA1 and Factor D, wherein the antibody comprises a first binding domain that specifically binds HtrA1 comprising the following six HVRs: (a) an HVR-H1 comprising the amino acid sequence of DSEMH (SEQ ID NO: 7); (b) an HVR-H2 comprising the amino acid sequence of GVDPETEGAAYNQKFKG (SEQ ID NO: 8); (c) an HVR-H3 comprising the amino acid sequence of GYDYDYALDY (SEQ ID NO: 3), (d) an HVR-L1 comprising the amino acid sequence of RASSSVEFIH (SEQ ID NO: 9); (e) an HVR-L2 comprising the amino acid sequence of ATSNLAS (SEQ ID NO: 10); and (f) an HVR-L3 comprising the amino acid sequence of QQWSSAPWT (SEQ ID NO: 11); and a second binding domain that specifically binds Factor D comprising the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118).

In another aspect, the invention features an isolated antibody that specifically binds both HtrA1 and Factor D, wherein the antibody comprises a first binding domain that specifically binds HtrA1 comprising (a) a VH domain comprising an amino acid sequence having at least 99% sequence identity to the amino acid sequence of SEQ ID NO: 21 and (b) a VL domain comprising an amino acid sequence having at least 99% sequence identity to the amino acid sequence of SEQ ID NO: 22, and a second binding domain that specifically binds Factor D comprising (a) a VH domain comprising an amino acid sequence having at least 99% sequence identity to the amino acid sequence of SEQ ID NO: 119 and (b) a VL domain comprising an amino acid sequence having at least 99% sequence identity to the amino acid sequence of SEQ ID NO: 120.

In some embodiments of the above aspects, the invention encompasses an isolated antibody that specifically binds to an HtrA1 epitope, where the HtrA1 epitope comprises at least one amino acid of the HtrA1 protein selected from the group consisting of Arg190, Leu192, Pro193, Phe194, and Arg197, where the amino acid numbering refers to the numbering for the human HtrA1 precursor protein.

In one embodiment, the HtrA1 epitope comprises at least one amino acid of the HtrA1 protein selected from the group consisting of Leu192, Pro193, and Arg197.

In a particular embodiment, the HtrA1 epitope comprises the HtrA1 amino acids Leu192, Pro193, and Arg197.

In another embodiment, the HtrA1 epitope comprises the HtrA1 amino acids Arg190, Leu192, Pro193, and Arg197.

In an additional embodiment, the HtrA1 epitope comprises the HtrA1 amino acids Arg190, Leu192, Pro193, Phe194, and Arg197.

In another aspect, the invention features an isolated nucleic acid encoding any of the antibodies described herein. In another aspect, the invention features a vector (e.g., an expression vector) comprising the isolated nucleic acid for expressing the antibody. In another aspect, the invention features host cells comprising the preceding nucleic acids and/or vectors. In some embodiments, the host cell is a mammalian cell. In some embodiments, the mammalian cell is a Chinese hamster ovary (CHO) cell or a 293 cell. In some embodiments, the host cell is a prokaryotic cell. In some embodiments, the prokaryotic cell is E. coli.

In another aspect, the invention features a method of producing any of the antibodies described herein, the method comprising culturing a host cell that comprises any of the preceding vectors (e.g., expression vectors) in a culture medium. In some embodiments, the method further comprises recovering the antibody from the host cell or the culture medium.

In another aspect, the invention features a composition comprising any one of the preceding antibodies. In some embodiments, the composition further comprises a pharmaceutically acceptable carrier, excipient, or diluent. In some embodiments, the composition is a pharmaceutical composition. In some embodiments, the pharmaceutical composition is lyophilized. In some embodiments, the composition further comprises a Factor D binding antagonist. In some embodiments, the Factor D binding antagonist is an anti-Factor D antibody or an antigen-binding fragment thereof. In some embodiments, the antigen-binding fragment is an Fab or an (Fab')$_2$. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some embodiments, the anti-Factor D antibody or antigen-binding fragment thereof comprises (a) a VH domain comprising an amino acid sequence having at least 95% sequence identity to the amino acid sequence of SEQ ID NO: 119; (b) a VL domain comprising an amino acid sequence having at least 95% sequence identity to the amino acid sequence of SEQ ID NO: 120; or (c) a VH domain as in (a) and a VL domain as in (b). In some embodiments, the VH domain comprises the amino acid sequence of SEQ ID NO: 119. In some embodiments, the VL domain comprises the amino acid sequence of SEQ ID NO: 120. In some embodiments, the anti-Factor D antigen-binding antibody fragment is lampalizumab.

In another aspect, the invention encompasses a combination therapy comprising any of the preceding anti-HtrA1 antibodies and a Factor D antagonist. In a particular embodiment, the Factor D antagonist is an anti-Factor D antibody. In a particular embodiment, the Factor D antagonist is lampalizumab. In a particular embodiment, the anti-Factor D antagonist is administered sequentially.

In some aspects, any one of the preceding antibodies can be used as a medicament.

In some aspects, any one of the preceding antibodies can be used in treating an HtrA1-associated disorder or an ocular disorder. In some embodiments, the HtrA1-associated disorder or the ocular disorder is age-related macular degeneration (AMD), diabetic retinopathy, retinopathy of prematurity, or polypoidal choroidal vasculopathy. In some embodiments, the HtrA1-associated disorder or the ocular disorder is AMD. In some embodiments, the AMD is early dry AMD, intermediate dry AMD, or advanced dry AMD. In some embodiments, the advanced dry AMD is geographic atrophy.

In some aspects, any one of the preceding antibodies can be used in the manufacture of a medicament for treating an HtrA1-associated disorder or an ocular disorder. In some embodiments, the HtrA1-associated disorder or the ocular disorder is AMD, diabetic retinopathy, retinopathy of prematurity, or polypoidal choroidal vasculopathy. In some embodiments, the HtrA1-associated disorder or the ocular disorder is AMD. In some embodiments, the AMD is early dry AMD, intermediate dry AMD, or advanced dry AMD. In some embodiments, the advanced dry AMD is geographic atrophy. In some embodiments, the medicament is formulated for use in combination with a Factor D binding antagonist. In some embodiments, the Factor D binding antagonist is an anti-Factor D antibody or an antigen-binding fragment thereof. In some embodiments, the antigen-binding fragment is an Fab or an (Fab')$_2$. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO:

115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some embodiments, the anti-Factor D antibody or antigen-binding fragment thereof comprises (a) a VH domain comprising an amino acid sequence having at least 95% sequence identity to the amino acid sequence of SEQ ID NO: 119; (b) a VL domain comprising an amino acid sequence having at least 95% sequence identity to the amino acid sequence of SEQ ID NO: 120; or (c) a VH domain as in (a) and a VL domain as in (b). In some embodiments, the VH domain comprises the amino acid sequence of SEQ ID NO: 119. In some embodiments, the VL domain comprises the amino acid sequence of SEQ ID NO: 120. In some embodiments, the anti-Factor D antigen-binding fragment is lampalizumab.

In another aspect, the invention features a method of treating an HtrA1-associated disorder or an ocular disorder in a subject in need thereof, the method comprising administering a therapeutically effective amount of the antibody of any one of the preceding antibodies. In some embodiments, the HtrA1-associated disorder or the ocular disorder is AMD, diabetic retinopathy, retinopathy of prematurity, or polypoidal choroidal vasculopathy. In some embodiments, the HtrA1-associated disorder or the ocular disorder is AMD. In some embodiments, the AMD is early dry AMD, intermediate dry AMD, or advanced dry AMD. In some embodiments, the advanced dry AMD is geographic atrophy. In some embodiments, the method further comprises administering a Factor D binding antagonist.

In another aspect, the invention features a method for inhibiting retinal or photoreceptor cell degeneration in a subject, the method comprising administering to the subject an effective amount of any one of the preceding antibodies, thereby inhibiting retinal or photoreceptor cell degeneration.

In another aspect, the invention features a method for inhibiting HtrA1 serine protease activity in an eye of a subject, the method comprising administering to the subject an effective amount of any one of the preceding antibodies, thereby inhibiting HtrA1 serine protease activity in the eye. In some embodiments, the method further comprises administering a Factor D binding antagonist.

In another aspect, the invention features a method of treating an HtrA1-associated disorder or a complement-associated disorder in a subject in need thereof, the method comprising administering to the subject a therapeutically effective amount of an HtrA1 binding antagonist and a Factor D binding antagonist. In some embodiments, the HtrA1-associated disorder or the complement-associated disorder is an ocular disorder. In some embodiments, the ocular disorder is selected from the group consisting of AMD, diabetic retinopathy, choroidal neovascularization (CNV), uveitis, diabetic macular edema, pathological myopia, von Hippel-Lindau disease, histoplasmosis of the eye, central retinal vein occlusion, corneal vascularization, and retinal neovascularization. In some embodiments, the ocular disorder is AMD. In some embodiments, the AMD is early dry AMD, intermediate dry AMD, or advanced dry AMD. In some embodiments, the advanced dry AMD is geographic atrophy. In some embodiments, the HtrA1 binding antagonist is an anti-HtrA1 antibody or an antigen-binding fragment thereof. In some embodiments, the antigen-binding fragment is selected from the group consisting of Fab, Fab'-SH, Fv, scFV, and (Fab')$_2$ fragments. In some embodiments, the antigen-binding fragment is an Fab. In some embodiments, the Fab comprises a truncation in the upper hinge of the heavy chain constant region. In some embodiments, the heavy chain constant region terminates at position 221 (EU numbering). In some embodiments, the amino acid residue at position 221 is an aspartic acid (Asp) residue. In some embodiments, the heavy chain constant region comprises the amino acid sequence of SEQ ID NO: 156. In some embodiments, the antibody comprises the heavy chain amino acid sequence of SEQ ID NO: 160. In some embodiments, the antibody comprises the light chain amino acid sequence of SEQ ID NO: 159. In some embodiments, the antibody comprises the heavy chain amino acid sequence of SEQ ID NO: 160 and the light chain amino acid sequence of SEQ ID NO: 159. In some embodiments, the Fab is an IgG1 Fab.

In another aspect, the invention features a method of treating an HtrA1-associated disorder or a complement-associated disorder in a subject in need thereof, the method comprising administering to the subject a therapeutically effective amount of any one of the preceding antibodies and a therapeutically effective amount of a Factor D binding antagonist.

In some embodiments of any of the preceding aspects, the Factor D binding antagonist is an anti-Factor D antibody or an antigen-binding fragment thereof. In some embodiments, the antigen-binding fragment is an Fab or an (Fab')$_2$. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu. In some embodiments, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some embodiments, the anti-Factor D antibody or antigen-binding fragment thereof comprises (a) a VH domain comprising an amino acid sequence having at least 95% sequence identity to the amino acid sequence of SEQ ID NO: 119; (b) a VL domain comprising an amino acid sequence having at least 95% sequence identity to the amino acid sequence of SEQ ID NO: 120; or (c) a VH domain as in (a) and a VL domain as in (b). In some embodiments, the VH domain comprises the amino acid sequence of SEQ ID NO: 119. In some embodiments, the VL domain comprises the amino acid sequence of SEQ ID NO: 120. In some embodiments, the anti-Factor D antigen-binding fragment is lampalizumab.

In some embodiments of any of the preceding aspects, the HtrA1-associated disorder or the complement-associated disorder is an ocular disorder. In some embodiments, the ocular disorder is selected from the group consisting of AMD, diabetic retinopathy, choroidal neovascularization (CNV), uveitis, diabetic macular edema, pathological myopia, von Hippel-Lindau disease, histoplasmosis of the eye, central retinal vein occlusion, corneal vascularization, and retinal neovascularization. In some embodiments, the ocular disorder is AMD. In some embodiments, the AMD is early dry AMD, intermediate dry AMD, or advanced dry AMD. In some embodiments, the advanced dry AMD is geographic atrophy.

In some embodiments of any of the preceding aspects, the antibody is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions. In some embodiments, the antibody is administered intravitreally, ocularly, intraocularly, juxtasclerally, subtenonly, superchoroidally, or topically. In some embodiments, the antibody is administered intravitreally by injection. In some embodiments, the antibody is administered topically by eye drop or ointment. In some embodiments, the antibody is administered by a long-acting delivery system. In particular embodiments, the long-acting delivery system is a PLGA-based solid implant or an implantable port delivery system.

In some embodiments of any of the preceding aspects, the subject is a human.

BRIEF DESCRIPTION OF THE DRAWINGS

The application file contains at least one drawing executed in color. Copies of this patent or patent application with color drawings will be provided by the Office upon request and payment of the necessary fee.

FIG. 2C shows the initial and end results of the assay for buffer, E medium (a nutrient-rich medium from CLONACELL™), and conditioned medium. 100% indicates complete inhibition.

In FIG. 3A, 40 nM of muHtrA1-PD was used in a ratio of 40 μl muHtrA1-PD to 60 μl hybridoma supernatant. In FIG. 3B, 20 nM of huHtrA1-PD was used in a ratio of 40 μl huHtrA1-PD to 60 μl hybridoma supernatant. Antibody YW505.94 ("94 IgG") served as a positive control. Buffer and CM served as negative controls.

FIG. 6A shows a sequence alignment of amino acid sequences of the heavy chain variable region (VH) of antibody clones 19B12, 20E2, 3A5, 12A5, and 15H6.

FIG. 6B shows a sequence alignment of the amino acid sequences of the light chain variable region (VL) of antibody clones 19B12, 20E2, 3A5, 12A5, and 15H6.

FIGS. 8A-8B show sequence alignments of the amino acid sequences of the VL (FIG. 8A) and VH (FIG. 8B) of anti-HtrA1 antibody clones m15H6, H15H6.v1, H15H6.v2, and h15H6.v2.APEG (also referred to herein as "h15H6.v3") compared to the human consensus κ1 sequence (FIG. 8A) or VH1 sequence (FIG. 8B). HVR sequences are delimited by the denoted boxes for each of the antibody clones. The HVR sequences according to the Kabat definition are underlined. Residues shown in white text in shaded boxes indicates residues that are different between the human consensus VH1 sequence and the anti-HtrA1 antibody clones.

FIG. 9A shows the results from binding of m15H6 Fab to huHtrA1. FIG. 9B shows the results from binding of m15H6 Fab to muHtrA1. FIG. 9C shows the results from binding of h15H6.v1 to huHtrA1. FIG. 9D shows the results from binding of h15H6.v1 to huHtrA1. The $K_{on}$, $K_{off}$, and KD determined from each analysis are shown as text inside each graph.

FIGS. 11A-11B are graphs showing the results of BIACORE™ SPR analysis comparing binding of antibody clone h15H6.v2 and the HVR-L3 LC-W91L and LC-W91Y variants to murine (FIG. 11A) or human (FIG. 11B) HtrA1. The antibodies used were in Fab format. The $K_{on}$, $K_{off}$, and KD determined from each analysis are shown as text inside each graph.

FIG. 12A is a graph showing the results of BIACORE™ SPR analysis comparing binding of antibody clone h15H6.v2 (parent) and the indicated variants at VL position 94 (i.e., LC-N94A LC-P95 (AP), LC-N94E LC-P95 (EP), LC-N94Q LC-P95 (QP), and LC-N94S LC-P95 (SP)) to huHtrA1. The antibodies used were in Fab format. The graph shows response units (RU) as a function of time (sec).

FIG. 12B is a table that summarizes the results of the BIACORE™ SPR analysis shown in FIG. 12A.

FIGS. 15A-15B show sequence alignments of the amino acid sequences of the VL (FIG. 15A) and VH (FIG. 15B) of anti-HtrA1 antibody clones m19B12 and h19B12.v1 compared to the human consensus κ4 sequence (FIG. 15A) or VH3 sequence (FIG. 15B). HVR sequences are delimited by the denoted boxes for each of the antibody clones. The HVR sequences according to the Kabat definition are underlined. Residues shown in white text in shaded boxes indicates residues that are different between the human consensus VH1 sequence and the anti-HtrA1 antibody clones.

FIG. 16A shows the results from binding of m19B12 Fab to huHtrA1. FIG. 16B shows the results from binding of m19B12 Fab to muHtrA1. FIG. 16C shows the results from binding of h19B12.v1 Fab to huHtrA1. FIG. 16D shows the results from binding of h19B12.v1 Fab to huHtrA1. The $K_{on}$, $K_{off}$, and KD for each analysis are shown as text inside each graph.

FIG. 19 is a table showing mutations identified as being enriched in the sorted sample as compared to the unsorted sample from the NNK libraries and/or soft randomization libraries of the VH and VL of h15v6.v2.

FIG. 20 is a table showing the results of BIACORE™ SPR analysis of binding of the indicated affinity matured Fab antibody variant clones. The $K_{on}$, $K_{off}$, and KD for each affinity matured antibody variant clone obtained from this analysis are shown as compared to h15H6.v2 and h15H6.v2.APEG (also referred to as h15H6.v3).

FIGS. 21A-21B show sequence alignments of the amino acid sequences of the VL (FIG. 21A) and VH (FIG. 21B) of affinity matured variant anti-HtrA1 antibody clones.

FIG. 22A is a table summarizing the results of the indicated affinity matured variant anti-HtrA1 Fab antibody clones to inhibit the activity of HtrA1 as assessed in FRET-based H2-Opt activity assays. The table shows the results from 3 independent experiments as well as the average and standard deviation (StDev). These experiments employed a rate (RFU/s) analysis.

FIGS. 24A-24B are tables showing IC50 (FIG. 24A) and IC90 (FIG. 24B) results for the indicated h15H6 antibody variant formats from a first set of three independent experiments. The IC50 values were determined using 4-parameter fits. The IC90 values were determined from the IC50 values and the slopes of the fits. Experiment I corresponds to the data shown in FIGS. 23A-23F. CV %, coefficient of variation. The data were analyzed using a rate (RFU/s) approach.

FIGS. 25A-25B are tables showing IC50 (FIG. 25A) and IC90 (FIG. 25B) results for the indicated h15H6 antibody variant formats from a second set of three independent experiments. The IC50 values were determined using 4-parameter fits. The IC90 values were determined from the IC50 values and the slopes of the fits. The data were analyzed using either a rate (RFU/s) approach or an endpoint (RFU) approach.

FIG. 27C is a table summarizing the results of the endogenous HtrA1 activity assays depicted in FIGS. 27A and 27B.

FIG. 28 is a table summarizing the kinetic binding properties and inhibitory activity of the indicated h15H6.v2 Fab variants and derivatives. YW505.94a.28 (see, e.g., WO 2013/055998) served as a positive control. All of the h15H6 Fab variants and derivatives showed improved affinity and improved potency when compared with YW505.94a.28 Fab, with h15H6.v4 Fab showing approximately a 30-fold improvement in affinity when compared with this antibody.

FIG. 29A shows the amino acid sequence of human HtrA1. The mature sequence is shown in capital letters, the protease domain is underlined, and residues N224 and K248 are shaded.

FIG. 29B shows the amino acid sequence of murine HtrA1. The mature sequence is shown in capital letters, and the protease domain is underlined.

FIG. 30 shows an alignment of light and heavy chain variable domains of a reference anti-Factor D antibody ("WT") and its select variants. HVRs within the variable domains are underlined. Residue substitutions in the variants are shown in bold.

FIGS. 32A-32B depict the binding of 15H6.v4 Fab to HtrA1, and show that the HtrA1 epitope bound by 15H6.v4 Fab is distinct from the epitope bound by YW505.94 Fab. FIG. 32A depicts the interaction between the 15H6.v4 Fab and its epitope on the HtrA1 protein, as determined by X-ray crystallography. The 15H6.v4 Fab binds to the LA loop of the HtrA1 protein (see, for example, Glaza P et al. (2015) PLoS One 10(6):e0131142). The structure shown in FIG. 32B was generated using electron microscopy. The circle shows the 15H6V.4 Fab epitope on the HtrA1 protein.

DETAILED DESCRIPTION OF THE INVENTION

I. Definitions

Figure 1A:
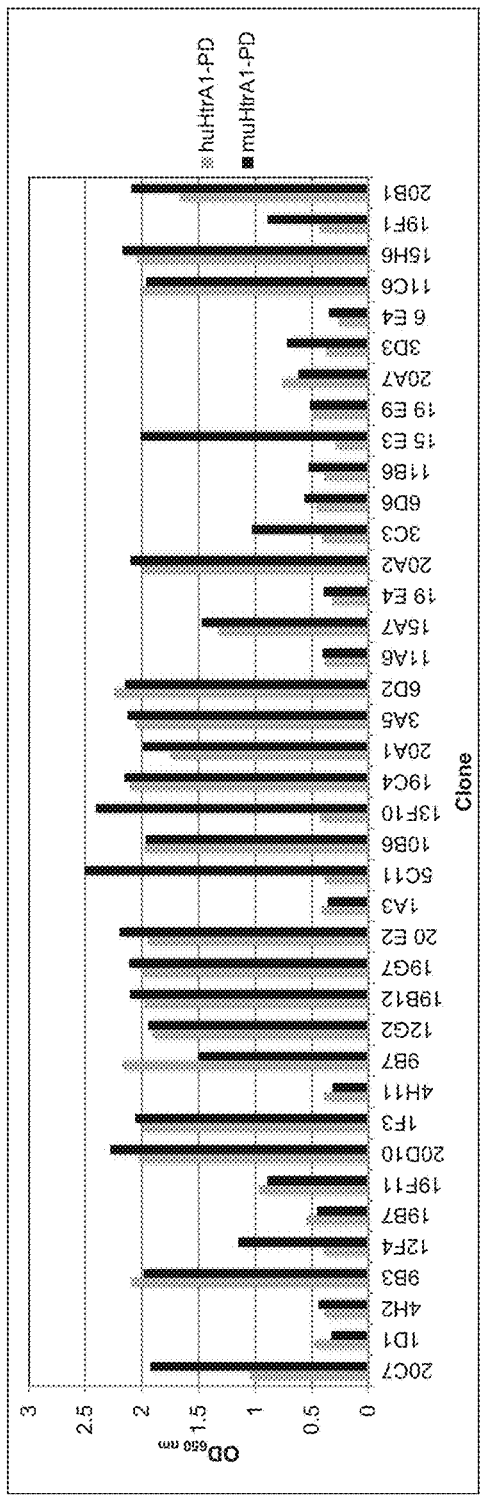
FIGS. 1A-1B are graphs showing that the majority of enzyme-linked immunosorbent assay (ELISA)-positive hybridoma clones showed similar reactivity profiles to both human (hu) and murine (mu) HtrA1 protease domain (PD). The graphs show the optical density at 650 nm ($OD_{650nm}$) for each of the indicated 75 clones. Background signal in this assay was <0.05 $OD_{650nm}$. The human and murine HtrA1 protease domains share 91% homology.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Active" or "activity" or "biological activity" in the context of an antibody of the present invention is the ability to antagonize (partially or fully inhibit) a biological activity of its target, for example, in vitro and/or in vivo. One example of a biological activity of an antibody is the ability to achieve a measurable improvement in the state, e.g., pathology, of a disorder associated with its target. For example, for an anti-HtrA1 antibody, the disorder may be an HtrA1-associated disorder, such as, for example, AMD (e.g., geographic atrophy). The activity of an anti-HtrA1 antibody can be determined in in vitro or in vivo tests, including binding assays, activity assays (e.g., FRET-based activity assays (e.g., using an H2-Opt substrate) or mass spectrometry-based activity assays), using a relevant animal model, or human clinical trials. In another example, for an anti-Factor D antibody (e.g., an anti-HtrA1/anti-Factor D antibody), the disorder may be a complement-associated disorder, such as, for example, a complement-associated ocular disorder. The activity of an anti-Factor D antibody can be determined in in vitro or in vivo tests, including binding assays, alternative pathway hemolysis assays (e.g., assays measuring inhibition of the alternative pathway complement activity or activation), using a relevant animal model, or human clinical trials.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs) and/or framework regions (FRs), compared to a parent antibody which does not possess such alterations, such alterations resulting in an improvement in the affinity of the antibody for antigen.

The terms "anti-HtrA1 antibody" and "an antibody that specifically binds to HtrA1" refer to an antibody that is capable of binding HtrA1 with sufficient affinity such that the antibody is useful as a diagnostic and/or therapeutic agent in targeting HtrA1. In one embodiment, the extent of binding of an anti-HtrA1 antibody to an unrelated, non-HtrA1 protein is less than about 10% of the binding of the antibody to HtrA1 as measured, e.g., by a radioimmunoassay (RIA). In certain embodiments, an antibody that binds to HtrA1 has a dissociation constant (KD) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-HtrA1 antibody binds to an epitope of HtrA1 that is conserved among HtrA1 from different species. An anti-HtrA1 antibody may be, for example, any anti-HtrA1 antibody described herein or in International Patent Application Publication No. WO 2013/055998, which is incorporated herein by reference in its entirety.

The terms "anti-Factor D antibody" and "an antibody that specifically binds to Factor D" refer to an antibody that is capable of binding Factor D with sufficient affinity such that the antibody is useful as a diagnostic and/or therapeutic agent in targeting Factor D, for example, in such a manner so as to inhibit or substantially reduce complement activation. In one embodiment, the extent of binding of an anti-Factor D antibody to an unrelated, non-Factor D protein is less than about 10% of the binding of the antibody to Factor D as measured, e.g., by an RIA. In certain embodiments, an antibody that binds to Factor D has a dissociation constant (KD) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-Factor D antibody binds to an epitope of Factor D that is conserved among Factor D from different species. An anti-Factor D antibody may be any anti-Factor D antibody described herein and/or in U.S. Pat. Nos. 8,067,002; 8,273,352; and 8,268,310; and U.S. patent application Ser. No. 14/700,853, each of which is incorporated herein by reference in their entirety.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md. (1991).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Plückthun in *The Pharmacology of*

*Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA*, 90:6444-6448, 1993.

A "blocking" antibody or an "antagonist" antibody is one which inhibits or reduces biological activity of the antigen it binds. Certain blocking antibodies or antagonist antibodies substantially or completely inhibit the biological activity of the antigen.

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 Å the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g., B cell receptor); and B cell activation.

"Framework" or "framework region" or "FR" refers to variable domain residues other than hypervariable region (HVR) residues. The FR of a variable domain generally consists of four FR domains: FR1, FR2, FR3, and FR4.

The terms "full-length antibody," "intact antibody," and "whole antibody" are used herein interchangeably to refer to an antibody having a structure substantially similar to a native antibody structure or having heavy chains that contain an Fc region as defined herein.

The "hinge region" is generally defined as stretching from 216-238 (EU numbering) or 226-251 (Kabat numbering) of human IgG1. The hinge can be further divided into three distinct regions, the upper, middle (e.g., core), and lower hinge. In certain embodiments, the hinge region of a human IgG1 antibody is generally defined as follows:

The upper hinge comprises amino acids having the sequence EPKSCDKTHT (SEQ ID NO: 157). In certain embodiments, the upper hinge comprises the amino acids at positions 216-225 (EU numbering) or 226-238 (Kabat numbering).

The middle (e.g., core) hinge comprises amino acids having the sequence CPPC (SEQ ID NO: 122). In certain embodiments, the core hinge comprises the amino acids at positions 226-229 (EU numbering) or 239-242 (Kabat numbering).

The lower hinge comprises amino acids having the sequence PAPELLGGP (SEQ ID NO: 158). In certain embodiments, the lower hinge comprises the amino acids at positions 230-238 (EU numbering) or 243-251 (Kabat numbering).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup Ill as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr Op. Struct. Biol.* 2:593-596 (1992).

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, J. Mol. Biol. 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). Accordingly, the HVR and FR sequences generally appear in the following sequence in VH (or VL): FR1-H1 (L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The terms "variable domain residue numbering as in Kabat," "Kabat amino acid residue," or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., J. Chromatogr. B 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively 10-10 M or lower, alternatively $10^{-11}$ M or lower, alternatively $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

A "nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell. In some embodiments, the nucleic acid encodes an anti-HtrA1 antibody. In other embodiments, the nucleic acid may encode an anti-Factor D antibody (e.g., an anti-HtrA1/anti-Factor D antibody).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % O/amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A protein, including an antibody, is said to be "stable" if it essentially retains the intact conformational structure and biological activity. Various analytical techniques for measuring protein stability are available in the art and are reviewed in, e.g., Peptide and Protein Drug Delivery, 247-301, Vincent Lee Ed., Marcel Dekker, Inc., New York, N.Y., Pubs. (1991) and Jones (1993) *Adv. Drug Delivery Rev.* 10: 29-90. An antibody variant with "improved stability" refers to an antibody variant that is more stable comparing to the starting reference antibody. Preferably, antibody variants with improved stability are variants of the reference (wild-type) antibodies in which specific amino acid residues are altered for the purpose of improving physical stability, and/or chemical stability, and/or biological activity, and/or reducing immunogenicity of the native antibodies.

The term "isomerization" refers generally to a chemical process by which a chemical compound is transformed into any of its isomeric forms, i.e., forms with the same chemical composition but with different structure or configuration and, hence, generally with different physical and chemical properties. Specifically used herein is aspartate isomerization, a process wherein one or more aspartic acid (D or Asp) residue(s) of a polypeptide have been transformed to isoaspartic acid residue(s). See, e.g., Geiger et al., *J. Biol. Chem.* 262:785-94, 1987.

The term "deamidation" refers generally to a chemical reaction wherein an amide functional group is removed from an organic compound. Specifically used herein is asparagine deamidation, a process wherein one or more asparagine (N or Asn) residue(s) of a polypeptide (e.g., an antibody) have been converted to aspartic acid (D or Asp), i.e., the neutral amide side chain has been converted to a residue with an overall acidic property. See, e.g., Xie et al., *J. Pharm. Sci.* 88:8-13, 1999.

An "oxidized" variant of a polypeptide molecule (e.g., an antibody) is a polypeptide wherein one or more methionine (M or Met) or tryptophan (W or Trp) residue(s) of the original polypeptide have been converted to sulfone or sulfoxide through the sulfur of methionine. Oxidation may be prevented by converting methionine (M or Met) to leucine (L or Leu) or isoleucine (I or Ile). See, e.g., Amphlett et al., *Pharm. Biotechnol.,* 9:1-140, 1996.

Amino acid residues "prone" to certain identified physical or chemical processes (e.g., isomerization, deamidation, or oxidation) refer to those residues within a specific protein molecule that have been identified to have the propensity to undergo the identified processes such as isomerization, deamidation, or oxidation. Their propensities are often determined by their relative positions within the primary and/or conformational structure of the protein. For example, it has been shown that the first Asp in an Asp-XXX motif (wherein XXX can be Asp, Gly, His, Ser or Thr) is prone to Asp isomerization due to the involvement of its adjacent residue, where some other Asp within the same protein may not possess such propensity. Assays for identifying residues prone to certain processes within a specific protein molecule are known in the art. See, e.g., Cacia et al., *Biochem.* 35:1897-1903, 1996.

The term "HtrA serine peptidase 1 (HtrA1)" or "HtrA1," as used interchangeably herein, refers to any native HtrA1 from any vertebrate source, including mammals such as primates (e.g., humans) and rodents (e.g., mice and rats), unless otherwise indicated. The term encompasses "full-length," unprocessed HtrA1 as well as any form of HtrA1 that results from processing in the cell. The term also encompasses naturally occurring variants of HtrA1, e.g., splice variants or allelic variants. The amino acid sequence of an exemplary human HtrA11 is shown in SEQ ID NO: 121 (see FIG. 29A). The UniProt Accession number for human HtrA1 is Q92743. The amino acid sequence of an exemplary murine HtrA1 is shown in SEQ ID NO: 155 (see FIG. 29B). The UniProt Accession number for murine HtrA1 is Q9R118. As described herein, amino acid residues of huHtrA1 and muHtrA1 are made with reference to SEQ ID NO: 121 and SEQ ID NO: 155, respectively. Amino acid positions are specified by the one letter amino acid code followed by its position within SEQ ID NO: 121 or SEQ ID NO: 155 (see FIG. 29B). As shown in FIG. 29A, the mature sequence of human HtrA1 comprises a sequence starting at glutamine at position 23 of SEQ ID NO: 121 and ending at proline at position 480 of SEQ ID NO:121, e.g., Q23-P480. Exemplary fragments of human HtrA1 include fragments comprising, consisting essentially of, or consisting of amino acids D161-K379. HtrA1 is also known in the art as protease, serine, 11 (IGF binding) (PRSS11), ARMD7, HtrA, and IGFBP5-protease.

The term "HtrA1" also encompasses "HtrA1 variants," which means an active HtrA1 polypeptide having at least about 80% amino acid sequence identity to a native sequence HtrA1 polypeptide, such as SEQ ID NO: 121 or SEQ ID NO: 155. Ordinarily, a HtrA1 variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with a native HtrA1 sequence, e.g., SEQ ID NO: 121 or SEQ ID NO: 155.

The term "HtrA1 binding antagonist" is used in the broadest sense, and includes any molecule that is capable of neutralizing, blocking, partially or fully inhibiting, abrogating, reducing or interfering with an HtrA1 biological activity. HtrA1 binding antagonists include, without limitation, anti-HtrA1 antibodies, and antibody variants thereof, antigen-binding fragments thereof, other binding polypeptides, peptides, and non-peptide small molecules, that bind to HtrA1 and are capable of neutralizing, blocking, partially or fully inhibiting, abrogating, reducing or interfering with HtrA1 activities, such as the ability of HtrA1 to cleave a substrate in vitro (e.g., an H2-Opt substrate or casein) or in vivo (e.g., the ability of HtrA1 to contribute to the pathology of an ocular disorder (e.g, AMD (e.g., geographic atrophy)).

The term "Factor D," as used herein, refers to native sequence and variant Factor D polypeptides. Factor D is also known in the art as complement factor D (CFD), C3 proactivator convertase, properdin factor D esterase, and adipsin.

A "native sequence Factor D" is a polypeptide having the same amino acid sequence as a Factor D polypeptide derived from nature, regardless of its mode of preparation. Thus, native sequence Factor D can be isolated from nature or can be produced by recombinant and/or synthetic means. In addition to a mature Factor D protein, such as a mature human Factor D protein (see, e.g., NCBI Reference Sequence NM_001928, SEQ ID NO: 126), the term "native sequence Factor D," specifically encompasses naturally occurring precursor forms of Factor D (e.g., an inactive preprotein, which is proteolytically cleaved to produce the active form), naturally-occurring variant forms (e.g., alternatively spliced forms) and naturally-occurring allelic variants of Factor D, as well as structural conformational variants of Factor D molecules having the same amino acid sequence as a Factor D polypeptide derived from nature. The UniProt Accession Number for human Factor D is P00746. Factor D polypeptides of non-human animals, including higher primates and non-human mammals, are specifically included within this definition.

"Factor D variant" means an active Factor D polypeptide having at least about 80% amino acid sequence identity to a native sequence Factor D polypeptide, such as the native sequence human Factor D polypeptide (e.g., NM_001928, SEQ ID NO: 126). Ordinarily, a Factor D variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature human amino acid sequence (e.g., NM_001928, SEQ ID NO: 126).

The term "Factor D binding antagonist" is used in the broadest sense, and includes any molecule that is capable of neutralizing, blocking, partially or fully inhibiting, abrogating, reducing or interfering with a Factor D biological activity. Factor D binding antagonists include, without limitation, anti-Factor D antibodies, and antibody variants thereof, antigen-binding fragments thereof, other binding polypeptides, peptides, and non-peptide small molecules, that bind to Factor D and are capable of neutralizing, blocking, partially or fully inhibiting, abrogating, reducing or interfering with Factor D activities, such as the ability of Factor D to participate in the pathology of a complement-associated eye condition.

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein, VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib).

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) *Cancer Res.* 57:4593-4599, including but not limited to the antibody known as bevacizumab (BV; AVASTIN®).

The anti-VEGF antibody "ranibizumab" also known as "LUCENTIS®" or "rhuFab V2" is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48,000 daltons. See WO 98/45331 and US 2003/0190317. Additional preferred antibodies include the G6 or B20 series antibodies (e.g., G6-31, B20-4.1), as described in PCT Application Publication Nos. WO 2005/012359 and WO 2005/044853, which are each incorporated herein by reference in their entirety. For additional preferred antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89. Additional anti-VEGF antibodies include anti-VEGF antibodies described in PCT Application Publication No. WO 2009/155724.

The term "IL-6 binding antagonist" refers to a molecule that decreases, blocks, inhibits, abrogates or interferes with signal transduction resulting from the interaction of IL-6 with one or more of its binding partners, such as an interleukin-6 receptor (IL-6R) (also called CD126) and/or gp130 (also called CD130). Exemplary IL-6 binding antagonists include, for example, anti-IL-6 antagonists (including anti-IL-6 antibodies, e.g., EBI-031 (Eleven Biotherapeutics)) and anti-IL-6R antagonists (including anti-IL-6R antibodies, e.g., tocilizumab (ACTEMRA®). A "small molecule" is defined herein to have a molecular weight below about 600, preferable below about 1000 daltons.

A "disorder" is any condition that would benefit from treatment with the antibody. This includes chronic and acute disorders or diseases including those pathological conditions which predispose the mammal to the disorder in question. Non-limiting examples of disorders to be treated herein include HtrA1-associated disorders, ocular disorders, and/or complement-associated disorders.

The term "HtrA1-associated disorder," as used herein, refers in the broadest sense to any disorder or condition associated with abnormal HtrA1 expression or activities. In some embodiments, HtrA1-associated disorders are associated with excess HtrA1 levels or activity in which atypical symptoms may manifest due to the levels or activity of HtrA1 locally (e.g., in an eye) and/or systemically in the body. Exemplary HtrA1-associated disorders include HtrA1-associated ocular disorders, which include, but are not limited to, for example, age-related macular degeneration (AMD), including wet (exudative) AMD (including early, intermediate, and advanced wet AMD) and dry (non-exudative) AMD (including early, intermediate, and advanced dry AMD (e.g., geographic atrophy (GA)).

As used herein, the term "ocular disorder" includes, but is not limited to, disorders of the eye including macular degenerative diseases such as age-related macular degeneration (AMD), including wet (exudative) AMD (including early, intermediate, and advanced wet AMD) and dry (non-exudative) AMD (including early, intermediate, and advanced dry AMD (e.g., geographic atrophy (GA)); diabetic retinopathy (DR) and other ischemia-related retinopathies; endophthalmitis; uveitis; choroidal neovascularization (CNV); retinopathy of prematurity (ROP); polypoidal choroidal vasculopathy (PCV); diabetic macular edema; pathological myopia; von Hippel-Lindau disease; histoplasmosis of the eye; Central Retinal Vein Occlusion (CRVO); corneal neovascularization; and retinal neovascularization. In some embodiments, the ocular disorder is AMD (e.g., GA).

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia, or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis, and pancreatitis. The disorder may be the result of an adverse drug reaction, drug allergy, IL-2 induced vascular leakage syndrome, or radiographic contrast media allergy. It also includes autoimmune disease such as systemic lupus erythematosus, myasthenia gravis, rheumatoid arthritis, Alzheimer's disease, and multiple sclerosis. Complement activation is also associated with transplant rejection. Complement activation is also associated with ocular disorders, such as complement-associated ocular disorders.

The term "complement-associated ocular disorder" is used in the broadest sense and includes all eye conditions the pathology of which involves complement, including the classical and the alternative pathways, and in particular the alternative pathway of complement. Complement-associated ocular disorders include, without limitation, macular degenerative diseases, such as all stages of age-related macular degeneration (AMD), choroidal neovascularization (CNV), uveitis, diabetic and other ischemia-related retinopathies, endophthalmitis, uveitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, AMD includes wet AMD (including early, intermediate, and advanced wet AMD) and dry AMD (including early, intermediate, and advanced dry AMD (e.g., geographic atrophy (GA)). In a further example, dry (non-exudative) AMD may include the presence of hard drusen, soft drusen, geographic atrophy, and/or pigment clumping. Early AMD may include, for example, multiple small to one or more non-extensive medium sized drusen. Intermediate AMD may include, for example, extensive medium drusen to one or more large drusen. See, e.g., Ferris et al., *AREDS Report No.* 18: Sallo et al., *Eye Res,* 34(3):238-40, 2009; Jager et al., *New Engl J. Med.,* 359(1):1735, 2008. In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, the complement-associated ocular disorder is intermediate dry AMD. In one example, complement-associated ocular disorder is geographic atrophy. In one example, the complement-associated ocular disorder is wet AMD (e.g., choroidal neovascularization (CNV)).

The above lists are not all-inclusive, and it will be understood that a disease or disorder may fall within various categories. For example, AMD can be categorized in some instances as an HtrA1-associated disorder, an ocular disorder, and a complement-associated disorder.

As used herein, "administering" is meant a method of giving a dosage of a compound (e.g., an anti-HtrA1 antibody of the invention, a nucleic acid encoding an anti-HtrA1 antibody of the invention) or a composition (e.g., a pharmaceutical composition, e.g., a pharmaceutical composition including an anti-HtrA1 antibody of the invention) to a subject. The compositions utilized in the methods described herein can be administered, for example, intravitreally (e.g., by intravitreal injection), ocularly (e.g., by ocular injection), intraocularly (e.g., by intraocular injection), juxtasclerally (e.g., by juxtascleral injection), subtenonly (e.g., by subtenon injection), superchoroidally (e.g., by superchoroidal injection), topically (e.g., by eye drop), intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, intratumorally, peritoneally, subcutaneously, subconjunctivally, intravesicularly, mucosally, intrapericardially, intraumbilically, intraorbitally, orally, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In particular embodiments, the antibodies described herein (e.g., anti-HtrA1 antibodies, anti-Factor D antibodies, and anti-HtrA1/anti-Factor D antibodies) are administered by intravitreal injection.

Administration "in combination with" one or more further therapeutic agents includes simultaneous (concurrent) and consecutive administration in any order.

The terms "long-acting delivery," "sustained-release," and "controlled release" are used generally to describe a delivery mechanism using formulation, dosage form, device, or other types of technologies to achieve the prolonged or extended release or bioavailability of a therapeutic agent (e.g., an antibody of the invention). It may refer to technologies that provide prolonged or extended release or bioavailability of the drug to the general systemic circulation or a subject or to local sites of action in a subject including (but not limited to) cells, tissues, organs, joints, regions, and the like. Furthermore, these terms may refer to a technology that is used to prolong or extend the release of the drug from a formulation or dosage form, or they may refer to a technology used to extend or prolong the bioavailability or the pharmacokinetics or the duration of action of the drug to a subject, or they may refer to a technology that is used to extend or prolong the pharmacodynamic effect elicited by a formulation.

A "long-acting formulation," a "sustained release formulation," or a "controlled release formulation" is a pharmaceutical formulation, dosage form, or other technology that is used to provide long-acting delivery. In one aspect, the controlled release is used to improve a therapeutic agent's local bioavailability, specifically ocular residence time in the context of ocular delivery. "Increased ocular residence time" refers to the post-delivery period during which the delivered ocular drug remains effective both in terms of quality (e.g., activity) and in terms of quantity (e.g., effective amount). In addition to or in lieu of high dose and controlled release, the drug can be modified post-translationally, such as via PEGylation, to achieve increased in vivo half-life.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. A "subject" may be a "patient."

The term "package insert" is used to refer to instructions customarily included in commercial packages of therapeutic products, that contain information about the indications, usage, dosage, administration, combination therapy, contraindications and/or warnings concerning the use of such therapeutic products.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "pharmaceutical formulation" refers to a preparation which is in such form as to permit the biological activity of an active ingredient contained therein to be effective, and which contains no additional components which are unacceptably toxic to a subject to which the formulation would be administered.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of the disease or disorder, alleviation of symptoms, diminishment of any direct or indirect pathological consequences of the disease or disorder, decreasing the rate of disease progression, amelioration or palliation of the disease or disorder state, and remission or improved prognosis. In some embodiments, antibodies of the invention are used to delay development of a disease or disorder or to slow the progression of a disease or disorder. In some examples, the disorder is an HtrA1-associated disorder, an ocular disorder, and/or a complement-associated disorder, for example, AMD (e.g., GA).

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "library" refers to a plurality of antibody or antibody fragment sequences (e.g., anti-HtrA1 antibodies of the invention), or the nucleic acids that encode these sequences, the sequences being different in the combination of variant amino acids that are introduced into these sequences, for example, as described herein.

A "mutation" is a deletion, insertion, or substitution of a nucleotide(s) relative to a reference nucleotide sequence, such as a wild-type sequence.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art. A codon set typically is represented by 3 capital letters in italics, e.g., NNK, NNS, XYZ, DVK and the like. Synthesis of oligonucleotides with selected nucleotide "degeneracy" at certain positions is well known in that art, for example the TRIM approach (Knappek et al., *J. Mol. Biol.* 296:57-86, 1999; Garrard et al., *Gene* 128:103, 1993). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

"Phage display" is a technique by which variant polypeptides are displayed as fusion proteins to at least a portion of coat protein on the surface of phage, for example, filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. See, for example, Wells et al., *Curr. Opin. Struct. Biol.,* 3:355-362, 1992, and references cited therein. In a monovalent phage display, a protein or peptide library is fused to a gene III or a portion thereof, and expressed at low levels in the presence of wild-type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. See, e.g., Lowman et al., *Methods: A companion to Methods in Enzymology,* 3:205-216, 1991.

A "variant" or "mutant" of a starting or reference polypeptide (e.g., a reference antibody or its variable domain(s)/HVR(s)), is a polypeptide that (1) has an amino acid sequence different from that of the starting or reference polypeptide and (2) was derived from the starting or reference polypeptide through either natural or artificial (man-made) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "reference antibody," as used herein, refers to an antibody or fragment thereof whose antigen-binding sequence serves as the template sequence upon which diversification according to the criteria described herein is performed. An antigen-binding sequence generally includes an antibody variable region, preferably at least one HVR, preferably including framework regions.

"Enriched," as used herein, means that an entity (e.g., an amino acid residue alteration) is present at a higher frequency in a sorted library as compared to a corresponding reference library (e.g., an unsorted library, or a library that has been sorted for a different or non-relevent antigen). In contrast, "depleted" means that an entity (for example, an amino acid residue alteration) is present at a lower frequency in a sorted library as compared to a corresponding reference library (e.g., an unsorted library, or a library that has been sorted for a different or non-relevent antigen). The term "neutral," when used in reference to methods of identifying amino acid residue variants, means that an entity is neither enriched nor depleted, in other words, it is present at approximately the same frequency in a sorted library as compared to a corresponding reference library (e.g., an unsorted library, or a library that has been sorted for a different or non-relevent antigen).

By "isoelectric point (pI)" is meant the pH at which a molecule (e.g., a protein, such as an antibody) carries no net electrical charge, also referred to in the art as "pH(I)" or "IEP."

II. Compositions and Methods

The invention provides novel antibodies that bind to HtrA1, and methods of making and using the same, for example, for therapeutic and diagnostic uses. Antibodies of the invention are useful, e.g., for the diagnosis or treatment of various disorders, including HtrA1-associated disorders, ocular disorders, and/or complement-associated disorders, including age-related macular degeneration (e.g., geographic atrophy).

A. Exemplary Anti-HtrA1 Antibodies

In one aspect, the invention is based, in part, on antibodies that specifically bind to HtrA1. Antibodies of the invention are useful, for example, for the treatment or diagnosis of disorders including HtrA1-associated disorders, ocular disorders, and/or complement-associated disorders, including age-related macular degeneration (e.g., geographic atrophy).

The invention provides isolated antibodies that specifically bind to HtrA1. In some instances, the HtrA1 is human HtrA1 (huHtrA1). In other instances, the HtrA1 is murine HtrA1 (muHtrA1). In certain instances, an anti-HtrA1 antibody of the invention specifically binds huHtrA1 with a KD of 100 nM or lower (e.g., 100 nM or lower, 10 nM or lower, 5 nM or lower, 2.5 nM or lower, 1 nM or lower, 100 pM or lower, 10 pM or lower, 1 pM or lower, or 0.1 pM or lower). For example, in some instances, an anti-HtrA1 antibody of the invention specifically binds huHtrA1 with a KD of 1 nM or lower (e.g., 1 nM or lower, 900 pM or lower, 800 pM or lower, 700 pM or lower, 600 pM or lower, 550 pM or lower, 500 pM or lower, 400 pM or lower, 300 pM or lower, 200 pM or lower, 150 pM or lower, 125 pM or lower, 100 pM or lower, 75 pM or lower, 50 pM or lower, 25 pM or lower, or 1 pM or lower). In some instances, the anti-HtrA1 antibody binds huHtrA1 with a KD between about 40 pM and about 700 pM (e.g., between about 40 pM and about 700 pM, between about 40 pM and about 600 pM, between about 40 pM and about 550 pM, between about 40 pM and about 500 pM, between about 40 pM and about 400 pM, between about 40 pM and about 300 pM, between about 40 pM and about 250 pM, between about 50 pM and about 200 pM, between about 50 pM and about 175 pM, between about 50 pM and about 150 pM, between about 50 pM and about 125 pM, between about 70 pM and about 125 pM, or between about 50 pM and about 125 pM). In some instances, the anti-HtrA1 antibody binds huHtrA1 with a KD of about 110 pM. In some instances, the anti-HtrA1 antibody binds huHtrA1 with a KD of about 60 pM. Any of the preceding KD values may represent the binding affinity of an anti-HtrA1 antibody of the invention (e.g., a Fab of an anti-HtrA1 antibody of the invention) to the protease domain (PD) of huHtrA1 (huHtrA1-PD), for example, as measured using BIACORE® surface plasmon resonance, for example, as described herein.

In some instances, an anti-HtrA1 antibody of the invention is capable of inhibiting the activity of HtrA1. In some instances, the antibody inhibits the activity of the protease domain of huHtrA1-PD with a 50% inhibitory concentration (IC50) of 10 nM or lower (e.g., 10 nM or lower, 5 nM or lower, 2 nM or lower, 1.5 nM or lower, 1 nM or lower, 900 pM or lower, 800 pM or lower, 700 pM or lower, 600 pM or lower, 500 pM or lower, 400 pM or lower, 300 pM or lower, 200 pM or lower, 100 pM or lower, 50 pM or lower, or 1 pM or lower). In some instances, the anti-HtrA1 antibody inhibits the activity of huHtrA1-PD with an IC50 of between about 0.25 nM and about 1 nM (e.g., between about 0.25 nM and about 1 nM, between about 0.25 nM and about 0.9 nM, between about 0.25 nM and about 0.8 nM, between about 0.25 nM and about 0.7 nM, between about 0.25 nM and about 0.6 nM, between about 0.25 nM and about 0.5 nM, or between about 0.25 nM and about 0.4 nM). In some instances, the anti-HtrA1 antibody inhibits the activity of huHtrA1-PD with an IC50 of about 0.3 nM. In any of the preceding instances, the inhibitory activity may be an in vitro FRET-based blocking assay measurement. In some instances, the in vitro FRET-based blocking assay comprises cleavage of an H2-Opt probe (e.g., (Mca)IRRV-SYSF(Dnp)KK (SEQ ID NO: 152). In any of the preceding instances, the IC50 value may be based on the ability of the anti-HtrA1 in bivalent format (e.g., IgG format) to inhibit huHtrA1-PD activity.

The invention also encompasses an isolated antibody that specifically binds to an HtrA1 epitope, where the HtrA1 epitope comprises at least one amino acid of the HtrA1 protein selected from the group consisting of Arg190, Leu192, Pro193, Phe194, and Arg1197, where the amino acid numbering refers to the numbering for the human HtrA1 precursor protein. In one embodiment, the human HtrA1 precursor protein has the sequence of SEQ ID NO: 121. In one embodiment, the HtrA1 epitope comprises at least one amino acid of the HtrA1 protein selected from the group consisting of Leu192, Pro193, and Arg197.

In one embodiment, the HtrA1 epitope comprises at least two amino acids of the HtrA1 protein selected from the group consisting of Leu192, Pro193, and Arg197. In a particular embodiment, the HtrA1 epitope comprises the HtrA1 amino acids Leu192, Pro193, and Arg197. In another embodiment, the HtrA1 epitope comprises the HtrA1 amino acids Arg190, Leu1192, Pro193, and Arg197. In an additional embodiment, the HtrA1 epitope comprises the HtrA1 amino acids Arg190, Leu1192, Pro193, Phe194, and Arg197.

In some embodiments, the anti-HtrA1 antibody when bound to HtrA1 is positioned 4 angstroms or less from one or more of amino acids Arg190, Leu192, Pro193, Phe194, and Arg197. In some embodiments, the distance between the antibody and the one or more amino acids is determined by crystallography, for example using the crystallography methods described in the Examples.

In some instances, the anti-HtrA1 antibody may include at least one, two, three, four, five, or six hypervariable regions (HVRs) selected from: (a) HVR-H1 comprising the amino acid sequence of DSEX$_1$H (SEQ ID NO: 1), wherein X$_1$ is Met or Leu; (b) HVR-H2 comprising the amino acid sequence of GVDPETX$_2$GAAYNQKFKG (SEQ ID NO: 2), wherein X$_2$ is Glu or Asp; (c) HVR-H3 comprising the amino acid sequence of GYDYDYALDY (SEQ ID NO: 3); (d) HVR-L1 comprising the amino acid sequence of RASSSVX$_3$FIH (SEQ ID NO: 4), wherein X$_3$ is Glu or Asn; (e) HVR-L2 comprising the amino acid sequence of ATSX$_4$LAS (SEQ ID NO: 5), wherein X$_4$ is Asn, His or Glu; and (f) HVR-L3 comprising the amino acid sequence of QQWX$_5$SX$_6$PWT (SEQ ID NO: 6), wherein X$_5$ is Ser or Tyr and X$_6$ is Ala or Asn, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

For instance, the anti-HtrA1 antibody may include at least one, two, three, four, five, or six HVRs selected from (a) HVR-H1 comprising the amino acid sequence of DSEMH (SEQ ID NO: 7); (b) HVR-H2 comprising the amino acid sequence of GVDPETEGAAYNQKFKG (SEQ ID NO: 8); (c) HVR-H3 comprising the amino acid sequence of GYDYDYALDY (SEQ ID NO: 3); (d) HVR-L1 comprising the amino acid sequence of RASSSVEFIH (SEQ ID NO: 9); (e) HVR-L2 comprising the amino acid sequence of ATSNLAS (SEQ ID NO: 10); and (f) HVR-L3 comprising the amino acid sequence of QQWSSAPWT (SEQ ID NO: 11), or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 3 or 7-11.

In some instances, any of the preceding anti-HtrA1 antibodies may include one, two, three, or four of the following heavy chain variable domain (VH) framework regions (FRs): (a) an FR-H1 comprising the amino acid sequence of EVQLVQSGAEVKKPGASVKVSCKASGYX$_1$FX$_2$ (SEQ ID NO: 12), wherein X$_1$ is Lys or Thr and X$_2$ is Thr, Lys, or Arg; (b) an FR-H2 comprising the amino acid sequence of WVRQAPGQGLEWIG (SEQ ID NO: 13); (c) an FR-H3 comprising the amino acid sequence of RATITRDTSTSTAYLELSSLRSEDTAVYYCTR (SEQ ID NO: 14); and (d) an FR-H4 comprising the amino acid sequence of WGQGTLVTVSS (SEQ ID NO: 15).

In some instances, any of the preceding anti-HtrA1 antibodies may include one, two, three, or four of the following light chain variable domain (VL) FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKPLIS (SEQ ID NO: 18); (c) an FR-L3 comprising the amino acid sequence of GVPSRFSGSGSGTDFTLTISSLQPEDFATYYC (SEQ ID NO: 19); and (d) an FR-L4 comprising the amino acid sequence of FGQGTKVEIK (SEQ ID NO: 20).

For example, in some instances, the anti-HtrA1 antibody includes the following six HVRs: (a) an HVR-H1 comprising the amino acid sequence of DSEMH (SEQ ID NO: 7); (b) an HVR-H2 comprising the amino acid sequence of GVDPETEGAAYNQKFKG (SEQ ID NO: 8); (c) an HVR-H3 comprising the amino acid sequence of GYDYDYALDY (SEQ ID NO: 3); (d) an HVR-L1 comprising the amino acid sequence of RASSSVEFIH (SEQ ID NO: 9); (e) an HVR-L2 comprising the amino acid sequence of ATSNLAS (SEQ ID NO: 10); and (f) an HVR-L3 comprising the amino acid sequence of QQWSSAPWT (SEQ ID NO: 11). In some instances, the anti-HtrA1 antibody includes the following four heavy chain variable domain FRs: (a) an FR-H1 comprising the amino acid sequence of EVQLVQSGAEVKKPGASVKVSCKASGYKFT (SEQ ID NO: 16); (b) an FR-H2 comprising the amino acid sequence of WVRQAPGQGLEWIG (SEQ ID NO: 13); (c) an FR-H3 comprising the amino acid sequence of RATITRDTSTSTAYLELSSLRSEDTAVYYCTR (SEQ ID NO: 14); and (d) an FR-H4 comprising the amino acid sequence of WGQGTLVTVSS (SEQ ID NO: 15). In further instances, the anti-HtrA1 antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKPLIS (SEQ ID NO: 18); (c) an FR-L3 comprising the amino acid sequence of GVPSRFSGSGSGTDFTLTISSLQPEDFATYYC (SEQ ID NO: 19); and (d) an FR-L4 comprising the amino acid sequence of FGQGTKVEIK (SEQ ID NO: 20). In some instances, the anti-HtrA1 antibody includes (a) a VH domain comprising an amino acid sequence of SEQ ID NO: 21 and (b) a VL domain comprising an amino acid sequence of SEQ ID NO: 22. In some instances, the anti-HtrA1 antibody is APEG.LC3.HC3.

In another example, in some instances, the anti-HtrA1 antibody includes the following six HVRs: (a) an HVR-H1 comprising the amino acid sequence of DSEMH (SEQ ID NO: 7); (b) an HVR-H2 comprising the amino acid sequence of GVDPETDGAAYNQKFKG (SEQ ID NO: 123); (c) an HVR-H3 comprising the amino acid sequence of GYDYDYALDY (SEQ ID NO: 3); (d) an HVR-L1 comprising the amino acid sequence of RASSSVNFIH (SEQ ID NO: 124); (e) an HVR-L2 comprising the amino acid sequence of ATSNLAS (SEQ ID NO: 10); and (f) an HVR-L3 comprising the amino acid sequence of QQWSSAPWT (SEQ ID NO: 125). In some instances, the anti-HtrA1 antibody includes the following four heavy chain variable domain FRs: (a) an FR-H1 comprising the amino acid sequence of QVQLQQSGAELVRPGASVTLSCKASGYTFT (SEQ ID NO: 25); (b) an FR-H2 comprising the amino acid sequence of WVKQTPVHGLEWIG (SEQ ID NO: 26); (c) an FR-H3 comprising the amino acid sequence of KATLTADKSSSTAYMELRSLTSEDSAVYYCTR (SEQ ID NO: 27); and (d) an FR-H4 comprising the amino acid sequence of WGQGTSVTVSS (SEQ ID NO: 28). In further instances, the anti-HtrA1 antibody includes the following four light chain variable domain FRs: (a) an FR-L1 comprising the amino acid sequence of NIVVTQSPASLAVSLGQRATISC (SEQ ID NO: 29); (b) an FR-L2 comprising the amino acid sequence of WYQQKPGQPPKLLIY (SEQ ID NO: 30); (c) an FR-L3 comprising the amino acid sequence of GVPARFSGSGSRTDFTLTIDPVEADDAATYYC (SEQ ID NO: 31); and (d) an FR-L4 comprising the amino acid sequence of FGGGTKLEIK (SEQ ID NO: 32). In some instances, the anti-HtrA1 antibody includes (a) a VH domain comprising an amino acid sequence of SEQ ID NO: 23 and (b) a VL domain comprising an amino acid sequence of SEQ ID NO: 24. In some instances, the anti-HtrA1 antibody is 15H6 (also referred to as m15H6).

In another example, the anti-HtrA1 antibody may include at least one, two, three, four, five, or six HVRs selected from (a) HVR-H1 comprising the amino acid sequence of SYIMS (SEQ ID NO: 39); (b) HVR-H2 comprising the amino acid sequence of YISNGGGTTYYSDTIKG (SEQ ID NO: 40); (c) HVR-H3 comprising the amino acid sequence of QNFRSDGSSMDY (SEQ ID NO: 41); (d) HVR-L1 comprising the amino acid sequence of RASESVDSYGKSFMH (SEQ ID NO: 42); (e) HVR-L2 comprising the amino acid sequence of LASKLES (SEQ ID NO: 43); and (f) HVR-L3 comprising the amino acid sequence of QQNNEDPYT (SEQ ID NO: 44), or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 39-44.

In some instances, any of the preceding anti-HtrA1 antibodies may include one, two, three, or four of the following heavy chain variable domain FRs: (a) an FR-H1 comprising the amino acid sequence of EVQLVESGGGLVQPGGSL-RLSCAASGFTFS (SEQ ID NO: 47) or EVKLVES-GGGLVEPGGSLKLACVASGFTFS (SEQ ID NO: 57); (b) an FR-H2 comprising the amino acid sequence of WVRQAPGKGLEWVA (SEQ ID NO: 48) or WVRQT-PEKRLEWVA (SEQ ID NO: 58); (c) an FR-H3 comprising the amino acid sequence of RFTISRDNSKNTLYLQMNSL-RAEDTAVYYCAR (SEQ ID NO: 49) or RFTISRD-NAKNTLYLQMSTLKSEDTAIYFCAR (SEQ ID NO: 59); and (d) an FR-H4 comprising the amino acid sequence of WGQGTLVTVSS (SEQ ID NO: 50) or WGQGTAVTVSS (SEQ ID NO: 60).

In some instances, any of the preceding anti-HtrA1 antibodies may include one, two, three, or four of the following light chain variable domain FRs: (a) an FR-L1 comprising the amino acid sequence of DIVMTQSPDSLAVSLGERAT-INC (SEQ ID NO: 51) or NIVVTQSPASLAVS-LGQRATISC (SEQ ID NO: 61); (b) an FR-L2 comprising the amino acid sequence of WYQQKPGQPPKLLIY (SEQ ID NO: 52) or WYQQKPGQPPKLLIY (SEQ ID NO: 62); (c) an FR-L3 comprising the amino acid sequence of GVP-DRFSGSGSGTDFTLTISSLQAEDVAVYYC (SEQ ID NO: 53) or GVPARFSGSGSRTDFTLTIDPVEADDAATYYC (SEQ ID NO: 63); and (d) an FR-L4 comprising the amino acid sequence of FGQGTKVEIK (SEQ ID NO: 54) or FGGGTKLEIK (SEQ ID NO: 64).

For example, in some instances, the anti-HtrA1 antibody includes the following six HVRs: SYIMS (SEQ ID NO: 39); (b) HVR-H2 comprising the amino acid sequence of YIS-NGGGTTYYSDTIKG (SEQ ID NO: 40); (c) HVR-H3 comprising the amino acid sequence of QNFRSDGSSMDY (SEQ ID NO: 41); (d) HVR-L1 comprising the amino acid sequence of RASESVDSYGKSFMH (SEQ ID NO: 42); (e) HVR-L2 comprising the amino acid sequence of LASKLES (SEQ ID NO: 43); and (f) HVR-L3 comprising the amino acid sequence of QQNNEDPYT (SEQ ID NO: 44). In some instances, the anti-HtrA1 antibody includes the following four heavy chain variable domain FRs: (a) an FR-H1 comprising the amino acid sequence of EVQLVES-GGGLVQPGGSLRLSCAASGFTFS (SEQ ID NO: 47); (b) an FR-H2 comprising the amino acid sequence of WVRQAPGKGLEWVA (SEQ ID NO: 48); (c) an FR-H3 comprising the amino acid sequence of RFTISRDNSKNT-LYLQMNSLRAEDTAVYYCAR (SEQ ID NO: 49); and (d) an FR-H4 comprising the amino acid sequence of WGQGTLVTVSS (SEQ ID NO: 50). In further instances, the anti-HtrA1 antibody includes the following four light chain variable domain FRs: (a) an FR-L1 comprising the amino acid sequence of DIVMTQSPDSLAVSLGERATINC (SEQ ID NO: 51); (b) an FR-L2 comprising the amino acid sequence of WYQQKPGQPPKLLIY (SEQ ID NO: 52); (c) an FR-L3 comprising the amino acid sequence of GVPDRF-SGSGSGTDFTLTISSLQAEDVAVYYC (SEQ ID NO: 53); and (d) an FR-L4 comprising the amino acid sequence of FGQGTKVEIK (SEQ ID NO: 54). In some instances, the anti-HtrA1 antibody includes (a) a VH domain comprising an amino acid sequence of SEQ ID NO: 45 and (b) a VL domain comprising an amino acid sequence of SEQ ID NO: 46. In some instances, the anti-HtrA1 antibody is h19B12.v1.

In another example, in some instances, the anti-HtrA1 antibody includes the following six HVRs: SYIMS (SEQ ID NO: 39); (b) HVR-H2 comprising the amino acid sequence of YISNGGGTTYYSDTIKG (SEQ ID NO: 40); (c) HVR-H3 comprising the amino acid sequence of QNFRS-DGSSMDY (SEQ ID NO: 41); (d) HVR-L1 comprising the amino acid sequence of RASESVDSYGKSFMH (SEQ ID NO: 42); (e) HVR-L2 comprising the amino acid sequence of LASKLES (SEQ ID NO: 43); and (f) HVR-L3 comprising the amino acid sequence of QQNNEDPYT (SEQ ID NO: 44). In some instances, the anti-HtrA1 antibody includes the following four heavy chain variable domain FRs: (a) an FR-H1 comprising the amino acid sequence of EVKLVESGGGLVEPGGSLKLACVASGFTFS (SEQ ID NO: 57); (b) an FR-H2 comprising the amino acid sequence of WVRQTPEKRLEWVA (SEQ ID NO: 58); (c) an FR-H3 comprising the amino acid sequence of RFTISRDNAKNT-LYLQMSTLKSEDTAIYFCAR (SEQ ID NO: 59); and (d) an FR-H4 comprising the amino acid sequence of WGQG-TAVTVSS (SEQ ID NO: 60). In further instances, the anti-HtrA1 antibody includes the following four light chain variable domain FRs: (a) an FR-L1 comprising the amino acid sequence of NIVVTQSPASLAVSLGQRATISC (SEQ ID NO: 61); (b) an FR-L2 comprising the amino acid sequence of WYQQKPGQPPKLLIY (SEQ ID NO: 62); (c) an FR-L3 comprising the amino acid sequence of GVPARF-SGSGSRTDFTLTIDPVEADDAATYYC (SEQ ID NO: 63); and (d) an FR-L4 comprising the amino acid sequence of FGGGTKLEIK (SEQ ID NO: 64). In some instances, the anti-HtrA1 antibody includes (a) a VH domain comprising an amino acid sequence of SEQ ID NO: 55 and (b) a VL domain comprising an amino acid sequence of SEQ ID NO: 56. In some instances, the anti-HtrA1 antibody is 19B12 (also referred to as m19B12).

In another example, an anti-HtrA1 antibody of the invention includes one, two, three, four, five, or six of the HVRs of antibody 20E2 light and heavy chain variable domains (SEQ ID NOs: 66 and 65, respectively), and wherein (i) the HVR-L1 sequence comprises Kabat amino acid residues 24-34, the HVR-L2 sequence comprises Kabat amino acid residues 50-56, and the HVR-L3 sequence comprises Kabat amino acid residues 89-97 of SEQ ID NO: 66, and (ii) the HVR-H1 sequence comprises Kabat amino acid residues 31-35, the HVR-H2 sequence comprises Kabat amino acid residues 50-65, and the HVR-H3 sequence comprises Kabat amino acid residues 95-102 of SEQ ID NO: 65, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of the above HVRs of antibody 20E2. In some instances, the anti-HtrA1 antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, SEQ ID NOs: 65; (b) a VL domain comprising an amino acid sequence having at least about 90% sequence (e.g., at least 91%, 92%, 93%, 94%, 95%, 96%, 97%, 98%, or 99% sequence identity) to, or the sequence of, SEQ ID NO: 66; or (c) a VH domain as in (a) and a VL domain as in (b). In some instances, the antibody comprises a VH domain comprising the amino acid sequence of SEQ ID NO: 65 and a VL domain comprising the amino acid sequence of SEQ ID NO: 66.

In another example, an anti-HtrA1 antibody of the invention includes one, two, three, four, five, or six of the HVRs of antibody 3A5 light and heavy chain variable domains (SEQ ID NOs: 68 and 67, respectively), and wherein (i) the HVR-L1 sequence comprises Kabat amino acid residues 24-34, the HVR-L2 sequence comprises Kabat amino acid residues 50-56, and the HVR-L3 sequence comprises Kabat amino acid residues 89-97 of SEQ ID NO: 68, and (ii) the HVR-H1 sequence comprises Kabat amino acid residues 31-35, the HVR-H2 sequence comprises Kabat amino acid residues 50-65, and the HVR-H3 sequence comprises Kabat amino acid residues 95-102 of SEQ ID NO: 67, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of the above HVRs of antibody 3A5. In some instances, the anti-HtrA1 antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, SEQ ID NOs: 67; (b) a VL domain comprising an amino acid sequence having at least about 90% sequence (e.g., at least 91%, 92%, 93%, 94%, 95%, 96%, 97%, 98%, or 99% sequence identity) to, or the sequence of, SEQ ID NO: 68; or (c) a VH domain as in (a) and a VL domain as in (b). In some instances, the antibody comprises a VH domain comprising the amino acid sequence of SEQ ID NO: 67 and a VL domain comprising the amino acid sequence of SEQ ID NO: 68.

In another example, an anti-HtrA1 antibody of the invention includes one, two, three, four, five, or six of the HVRs of antibody 12A5 light and heavy chain variable domains (SEQ ID NOs: 70 and 69, respectively), and wherein (i) the HVR-L1 sequence comprises Kabat amino acid residues 24-34, the HVR-L2 sequence comprises Kabat amino acid residues 50-56, and the HVR-L3 sequence comprises Kabat amino acid residues 89-97 of SEQ ID NO: 70, and (ii) the HVR-H1 sequence comprises Kabat amino acid residues 31-35, the HVR-H2 sequence comprises Kabat amino acid residues 50-65, and the HVR-H3 sequence comprises Kabat amino acid residues 95-102 of SEQ ID NO: 69, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of the above HVRs of antibody 12A5. In some instances, the anti-HtrA1 antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, SEQ ID NOs: 69; (b) a VL domain comprising an amino acid sequence having at least about 90% sequence (e.g., at least 91%, 92%, 93%, 94%, 95%, 96%, 97%, 98%, or 99% sequence identity) to, or the sequence of, SEQ ID NO: 70; or (c) a VH domain as in (a) and a VL domain as in (b). In some instances, the antibody comprises a VH domain comprising the amino acid sequence of SEQ ID NO: 69 and a VL domain comprising the amino acid sequence of SEQ ID NO: 70.

In some instances, the anti-HtrA1 antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, any one of SEQ ID NOs: 21, 23, 76, 77, 78, 93-101, 106, or 107; (b) a VL domain comprising an amino acid sequence having at least about 90% sequence (e.g., at least 91%, 92%, 93%, 94%, 95%, 96%, 97%, 98%, or 99% sequence identity) to, or the sequence of, any one of SEQ ID NOs: 22, 24, 72-74, 81-92, 105, or 108; or (c) a VH domain as in (a) and a VL domain as in (b). For example, in some instances, the antibody comprises a VH domain comprising the amino acid sequence of SEQ ID NO: 21 and a VL domain comprising the amino acid sequence of SEQ ID NO: 22. In some instances, the antibody comprises a VH domain comprising the amino acid sequence of SEQ ID NO: 23 and a VL domain comprising the amino acid sequence of SEQ ID NO: 24. In some instances, the antibody comprises a VH domain comprising the amino acid sequence of SEQ ID NO: 76 and a VL domain comprising the amino acid sequence of SEQ ID NO: 72. In some instances, the antibody comprises a VH domain comprising the amino acid sequence of SEQ ID NO: 77 and a VL domain comprising the amino acid sequence of SEQ ID NO: 73. In some instances, the antibody comprises a VH domain comprising the amino acid sequence of SEQ ID NO: 78 and a VL domain comprising the amino acid sequence of SEQ ID NO: 74. In some instances, the antibody comprises a VH domain comprising the amino acid sequence of SEQ ID NO: 77 and a VL domain comprising the amino acid sequence of SEQ ID NO: 87. In some instances, the antibody comprises a VH domain comprising the amino acid sequence of SEQ ID NO: 95 and a VL domain comprising the amino acid sequence of SEQ ID NO: 73. In some instances, the antibody comprises a VH domain comprising the amino acid sequence of SEQ ID NO: 94 and a VL domain comprising the amino acid sequence of SEQ ID NO: 73. In some instances, the antibody comprises a VH domain comprising the amino acid sequence of SEQ ID NO: 93 and a VL domain comprising the amino acid sequence of SEQ ID NO: 73. In some instances, the antibody comprises a VH domain comprising the amino acid sequence of SEQ ID NO: 77 and a VL domain comprising the amino acid sequence of SEQ ID NO: 83. In some instances, the antibody comprises a VH domain comprising the amino acid sequence of SEQ ID NO: 97 and a VL domain comprising the amino acid sequence of SEQ ID NO: 73. In some instances, the antibody comprises a VH domain comprising the amino acid sequence of SEQ ID NO: 77 and a VL domain comprising the amino acid sequence of SEQ ID NO: 85. In some instances, the antibody comprises a VH domain comprising the amino acid sequence of SEQ ID NO: 77 and a VL domain comprising the amino acid sequence of SEQ ID NO: 84. In some instances, the antibody comprises a VH domain comprising the amino acid sequence of SEQ ID NO: 100 and a VL domain comprising the amino acid sequence of SEQ ID NO: 73. In some instances, the antibody comprises a VH domain comprising the amino acid sequence of SEQ ID NO: 99 and a VL domain comprising the amino acid sequence of SEQ ID NO: 73. In some instances, the antibody comprises a VH domain comprising the amino acid sequence of SEQ ID NO: 101 and a VL domain comprising the amino acid sequence of SEQ ID NO: 73. In some instances, the antibody comprises a VH domain comprising the amino acid sequence of SEQ ID NO: 77 and a VL domain comprising the amino acid sequence of SEQ ID NO: 86. In some instances, the antibody comprises a VH domain comprising the amino acid sequence of SEQ ID NO:

96 and a VL domain comprising the amino acid sequence of SEQ ID NO: 73. In some instances, the antibody comprises a VH domain comprising the amino acid sequence of SEQ ID NO: 77 and a VL domain comprising the amino acid sequence of SEQ ID NO: 82. In some instances, the antibody comprises a VH domain comprising the amino acid sequence of SEQ ID NO: 77 and a VL domain comprising the amino acid sequence of SEQ ID NO: 88. In some instances, the antibody comprises a VH domain comprising the amino acid sequence of SEQ ID NO: 77 and a VL domain comprising the amino acid sequence of SEQ ID NO: 81. In some instances, the antibody comprises a VH domain comprising the amino acid sequence of SEQ ID NO: 77 and a VL domain comprising the amino acid sequence of SEQ ID NO: 89. In some instances, the antibody comprises a VH domain comprising the amino acid sequence of SEQ ID NO: 98 and a VL domain comprising the amino acid sequence of SEQ ID NO: 73. In some instances, the antibody comprises a VH domain comprising the amino acid sequence of SEQ ID NO: 77 and a VL domain comprising the amino acid sequence of SEQ ID NO: 90. In some instances, the antibody comprises a VH domain comprising the amino acid sequence of SEQ ID NO: 95 and a VL domain comprising the amino acid sequence of SEQ ID NO: 83. In some instances, the antibody comprises a VH domain comprising the amino acid sequence of SEQ ID NO: 93 and a VL domain comprising the amino acid sequence of SEQ ID NO: 83. In some instances, the antibody comprises a VH domain comprising the amino acid sequence of SEQ ID NO: 94 and a VL domain comprising the amino acid sequence of SEQ ID NO: 87. In some instances, the antibody comprises a VH domain comprising the amino acid sequence of SEQ ID NO: 97 and a VL domain comprising the amino acid sequence of SEQ ID NO: 83. In some instances, the antibody comprises a VH domain comprising the amino acid sequence of SEQ ID NO: 94 and a VL domain comprising the amino acid sequence of SEQ ID NO: 83. In some instances, the antibody comprises a VH domain comprising the amino acid sequence of SEQ ID NO: 95 and a VL domain comprising the amino acid sequence of SEQ ID NO: 87. In some instances, the antibody comprises a VH domain comprising the amino acid sequence of SEQ ID NO: 94 and a VL domain comprising the amino acid sequence of SEQ ID NO: 85. In some instances, the antibody comprises a VH domain comprising the amino acid sequence of SEQ ID NO: 97 and a VL domain comprising the amino acid sequence of SEQ ID NO: 87. In some instances, the antibody comprises a VH domain comprising the amino acid sequence of SEQ ID NO: 93 and a VL domain comprising the amino acid sequence of SEQ ID NO: 87. In some instances, the antibody comprises a VH domain comprising the amino acid sequence of SEQ ID NO: 93 and a VL domain comprising the amino acid sequence of SEQ ID NO: 84. In some instances, the antibody comprises a VH domain comprising the amino acid sequence of SEQ ID NO: 97 and a VL domain comprising the amino acid sequence of SEQ ID NO: 85. In some instances, the antibody comprises a VH domain comprising the amino acid sequence of SEQ ID NO: 95 and a VL domain comprising the amino acid sequence of SEQ ID NO: 85. In some instances, the antibody comprises a VH domain comprising the amino acid sequence of SEQ ID NO: 93 and a VL domain comprising the amino acid sequence of SEQ ID NO: 85. In some instances, the antibody comprises a VH domain comprising the amino acid sequence of SEQ ID NO: 97 and a VL domain comprising the amino acid sequence of SEQ ID NO: 84. In some instances, the antibody comprises a VH domain comprising the amino acid sequence of SEQ ID NO: 95 and a VL domain comprising the amino acid sequence of SEQ ID NO: 84. In some instances, the antibody comprises a VH domain comprising the amino acid sequence of SEQ ID NO: 94 and a VL domain comprising the amino acid sequence of SEQ ID NO: 84. In some instances, the antibody comprises a VH domain comprising the amino acid sequence of SEQ ID NO: 104 and a VL domain comprising the amino acid sequence of SEQ ID NO: 22. In some instances, the antibody comprises a VH domain comprising the amino acid sequence of SEQ ID NO: 106 and a VL domain comprising the amino acid sequence of SEQ ID NO: 105. In some instances, the antibody comprises a VH domain comprising the amino acid sequence of SEQ ID NO: 107 and a VL domain comprising the amino acid sequence of SEQ ID NO: 105. In some instances, the antibody comprises a VH domain comprising the amino acid sequence of SEQ ID NO: 106 and a VL domain comprising the amino acid sequence of SEQ ID NO: 108. In some instances, the antibody comprises a VH domain comprising the amino acid sequence of SEQ ID NO: 107 and a VL domain comprising the amino acid sequence of SEQ ID NO: 108.

In some instances, any of the preceding anti-HtrA1 antibodies may include one, two, three, or four of the following heavy chain variable domain framework regions (FRs): (a) an FR-H1 comprising the amino acid sequence of EVQLVQSGAEVKKPGASVKVSCKASGYX$_1$FX$_2$ (SEQ ID NO: 12), wherein X$_1$ is Lys or Thr and X$_2$ is Thr, Lys, or Arg; (b) an FR-H2 comprising the amino acid sequence of WVRQAPGQGLEWIG (SEQ ID NO: 13); (c) an FR-H3 comprising the amino acid sequence of RATITRDTST-STAYLELSSLRSEDTAVYYCTR (SEQ ID NO: 14); and (d) an FR-H4 comprising the amino acid sequence of WGQGTLVTVSS (SEQ ID NO: 15). In other instances, any of the preceding anti-HtrA1 antibody may include one, two, three, or four of the following heavy chain variable domain FRs: (a) an FR-H1 comprising the amino acid sequence of QVQLQQSGAELVRPGASVTLSCKASGYTFT (SEQ ID NO: 25); (b) an FR-H2 comprising the amino acid sequence of WVKQTPVHGLEWIG (SEQ ID NO: 26); (c) an FR-H3 comprising the amino acid sequence of KATL-TADKSSSTAYMELRSLTSEDSAVYYCTR (SEQ ID NO: 27); and (d) an FR-H4 comprising the amino acid sequence of WGQGTSVTVSS (SEQ ID NO: 28).

In some instances, any of the preceding anti-HtrA1 antibodies may include one, two, three, or four of the following light chain variable domain FRs: (a) an FR-L1 comprising the amino acid sequence of DIQMTQSPSSLSAS-VGDRVTITC (SEQ ID NO: 17); (b) an FR-L2 comprising the amino acid sequence of WYQQKPGKAPKPLIS (SEQ ID NO: 18); (c) an FR-L3 comprising the amino acid sequence of GVPSRFSGSGSGTDFTLTISSLQPEDFA-TYYC (SEQ ID NO: 19); and (d) an FR-L4 comprising the amino acid sequence of FGQGTKVEIK (SEQ ID NO: 20). In other instances, any of the preceding anti-HtrA1 antibody may include one, two, three, or four of the following light chain variable domain FRs: (a) an FR-L1 comprising the amino acid sequence of NIVVTQSPASLAVSLGQRATISC (SEQ ID NO: 29); (b) an FR-L2 comprising the amino acid sequence of WYQQKPGQPPKLLIY (SEQ ID NO: 30); (c) an FR-L3 comprising the amino acid sequence of GVPARF-SGSGSRTDFTLTIDPVEADDAATYYC (SEQ ID NO: 31); and (d) an FR-L4 comprising the amino acid sequence of FGGGTKLEIK (SEQ ID NO: 32).

In some instances, the anti-HtrA1 antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, any one of SEQ ID NOs: 45, 55, 65, 67, or 69; (b) a VL domain comprising an amino acid sequence having at least about 90% sequence (e.g., at least 91%, 92%, 93%, 94%, 95%, 96%, 97%, 98%, or 99% sequence identity) to, or the sequence of, any one of SEQ ID NOs: 46, 56, 66, 68, or 70; or (c) a VH domain as in (a) and a VL domain as in (b). For example, in some instances, the antibody comprises a VH domain comprising the amino acid sequence of SEQ ID NO: 45 and a VL domain comprising the amino acid sequence of SEQ ID NO: 46. In some instances, the antibody comprises a VH domain comprising the amino acid sequence of SEQ ID NO: 55 and a VL domain comprising the amino acid sequence of SEQ ID NO: 56. In some instances, the antibody comprises a VH domain comprising the amino acid sequence of SEQ ID NO: 65 and a VL domain comprising the amino acid sequence of SEQ ID NO: 66. In some instances, the antibody comprises a VH domain comprising the amino acid sequence of SEQ ID NO: 67 and a VL domain comprising the amino acid sequence of SEQ ID NO: 68. In some instances, the antibody comprises a VH domain comprising the amino acid sequence of SEQ ID NO: 69 and a VL domain comprising the amino acid sequence of SEQ ID NO: 70.

In some instances, the invention provides an isolated antibody that specifically binds HtrA1, wherein the antibody comprises (a) a VH domain comprising the amino acid sequence of SEQ ID NO: 21 and (b) a VL domain comprising the amino acid sequence of SEQ ID NO: 22, such as the antibody referred to herein as APEG.LC3.HC3.

In some instances, the invention provides an isolated antibody that specifically binds HtrA1, wherein the antibody comprises (a) a VH domain comprising the amino acid sequence of SEQ ID NO: 45 and (b) a VL domain comprising the amino acid sequence of SEQ ID NO: 46, such as the antibody referred to herein as h19B6.v1.

In certain instances, the invention provides an anti-HtrA1 antibody that binds to the same epitope as any one of the preceding antibodies. In some instances, the invention provides an anti-HtrA1 antibody that competes for binding to HtrA1 with any one of the preceding antibodies.

In certain embodiments, any of the preceding anti-HtrA1 antibodies may have one or more of the following properties: (i) binds to HtrA1 with a ratio of 1 variable domain to one subunit of an HtrA1 trimer (e.g., a Fab binds to an HtrA1 trimer with a ratio of 3 Fab to 1 HtrA1 trimer, and an IgG binds to an HtrA1 trimer with a ratio of 3 IgG to 2 HtrA1 trimers), (ii) for antibodies comprising two variable domains, binds to HtrA1 in a manner that results in the forming a "cage" similar to that shown in FIG. 9 of U.S. Patent Application Publication US 2013/0129743, (iii) does not prevent trimer formation of HtrA1, (iv) cross-reacts with murine HtrA1; (v) does not cross-react with HtrA2, HtrA3 and/or HtrA4; (vi) binds to HtrA1 competitively with anti-HtrA1 antibody YW505.94.28a (see, e.g., WO 2013/055998), (vii) inhibits complex formation between HtrA1 and a1-antitrypsin (AIAT). In some embodiments, the invention provides an antibody that binds to the same epitope as any of the preceding antibodies.

In a further aspect, an anti-HtrA1 antibody according to any of the above embodiments may incorporate any of the features, singly or in combination, as described in Sections 1-8 of Section C "Antibody Properties and Features" below.

B. Exemplary Anti-Factor D Antibodies

The invention provides anti-Factor D antibodies that may be used with the anti-HtrA1 antibodies of the invention, for example, in methods of treating a disorder, including an HtrA1-associated disorder, an ocular disorder, and/or a complement-associated disorder (e.g., AMD (e.g., geographic atrophy)). The invention also provides multispecific (e.g., bispecific) antibodies that specifically bind to HtrA1 and Factor 20 D (e.g., anti-HtrA1/anti-Factor D antibodies). Any suitable anti-Factor D antibody may be used in the compositions and methods of the invention. As a non-limiting example, any anti-Factor D antibody described herein and/or in U.S. Pat. Nos. 8,067,002; 8,268,310; 8,273, 352; and/or in U.S. patent application Ser. No. 14/700,853 may be used in the compositions and methods of the present invention.

For example, in some instances, the anti-Factor D antibody may comprise an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the monoclonal antibody 166-32 produced from the hybridoma deposited with the American Type Culture Collection (ATCC) and designated HB12476. For example, in some instances, the anti-Factor D antibody comprises (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 136; (b) a VL domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 137; or (c) a VH domain as in (a) and a VL domain as in (b). For example, in some instances, the anti-Factor D antibody comprises a VH domain comprising the amino acid sequence of SEQ ID NO: 136 and a VL domain comprising the amino acid sequence of SEQ ID NO: 137, such as the anti-Factor D monoclonal antibody 166-32. In some instances, the anti-Factor D antibody is a humanized derivative of monoclonal antibody 166-32. In some embodiments, the anti-Factor D antibody binds to the same epitope as monoclonal antibody 166-32. In some instances, the anti-Factor D antibody is an antibody fragment derived from monoclonal antibody 166-32. In some instances, the antibody fragment derived from monoclonal antibody 166-32 is an Fab, Fab'-SH, Fv, scFv, or an (Fab')₂ fragment. In some embodiments, the antibody fragment derived from monoclonal antibody 166-32 is an Fab.

In some instances, humanized derivatives of monoclonal antibody 166-32 may be employed in the compositions and methods of the invention. For example, any humanized derivative of monoclonal antibody 166-32 described, for example, in U.S. Pat. No. 8,067,002 may be used in the compositions and methods of the invention. Exemplary humanized derivatives of monoclonal antibody 166-32 described in U.S. Pat. No. 8,067,002 include, for example, humanized anti-Factor D antibody clones #111, #56, #250, and #416. The amino acid sequences of the VH and VL domains of humanized anti-Factor D antibody clones #111, #56, #250, and #416 are shown, for example, in FIG. 5 of U.S. Pat. No. 8,067,002. In some instances, the anti-Factor D antibody may comprise an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, anti-Factor D antibody clone #111, #56, #250, or #416.

In some instances, modified or variant humanized anti-Factor D antibodies, and fragments thereof, may be used in the compositions and methods of the invention. For example, any modified or variant version of humanized anti-Factor D antibody clone #111 described, for example, in U.S. Pat. No. 8,273,352 may be used in the compositions and methods of the invention, for example, antibody clone 238 or 238-1. In some instances, the anti-Factor D antibody may comprise an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, anti-Factor D antibody clone 238 or 238-1.

In some instances, the anti-Factor D antibody or antigen-binding fragment thereof may include at least one, two, three, four, five, or six HVRs selected from (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVXN (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 109-114. For example, in some instances, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu.

For example, in some instances, the anti-Factor D antibody or antigen-binding fragment thereof may include at least one, two, three, four, five, or six HVRs selected from (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118), or a combination of one or more of the above HVRs and one or more variants thereof having at least 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 109, 113, or 115-118. For example, in some instances, the anti-Factor D antibody or antigen-binding fragment thereof comprises the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118).

In some instances, the anti-Factor D antibody comprises (a) a VH domain comprising an amino acid sequence having at least about 90% sequence identity (e.g., at least 91%, 92%, 93%, 94%, 95%, 96%, 97%, 98%, or 99% sequence identity) to, or the sequence of, any one of SEQ ID NOs: 119, 131, or 132; (b) a VL domain comprising an amino acid sequence having at least about 90%/i sequence identity (e.g., at least 91%, 92%, 93%, 94%, 95%, 96%, 97%, 98%, or 99% sequence identity) to, or the sequence of, any one of SEQ ID NOs: 120, 133, 134, or 135; or (c) a VH as in (a) and a VL as in (b). For example, in some instances, the antibody comprises a VH domain comprising the amino acid sequence of SEQ ID NO: 119 and a VL domain comprising the amino acid sequence of SEQ ID NO: 120. In other instances, the antibody comprises a VH domain comprising the amino acid sequence of SEQ ID NO: 131 and a VL domain comprising the amino acid sequence of SEQ ID NO: 133. In other instances, the antibody comprises a VH domain comprising the amino acid sequence of SEQ ID NO: 131 and a VL domain comprising the amino acid sequence of SEQ ID NO: 134. In other instances, the antibody comprises a VH domain comprising the amino acid sequence of SEQ ID NO: 131 and a VL domain comprising the amino acid sequence of SEQ ID NO: 135. In other instances, the antibody comprises a VH domain comprising the amino acid sequence of SEQ ID NO: 132 and a VL domain comprising the amino acid sequence of SEQ ID NO: 135. Any of the anti-Factor D antibodies shown in FIG. 30, or a variant thereof, or a fragment thereof, may be used in the compositions and methods of the invention. In some embodiments, the anti-Factor D antibody or antigen-binding fragment thereof a VH domain comprising the amino acid sequence of SEQ ID NO: 119 and a VL domain comprising the amino acid sequence of SEQ ID NO: 120. In some instances, the anti-Factor D antigen-binding antibody fragment is lampalizumab having CAS registry number 1278466-20-8.

In another example, in some instances, the anti-Factor D antibody is or is derived from a 20D12 antibody, for example, as described in U.S. Pat. No. 8,268,310. In one example, the anti-Factor D antibody includes one, two, three, four, five, or six of the HVRs of antibody 20D12 light and heavy chain variable domains (SEQ ID NOs: 128 and 127, respectively), and wherein (i) the HVR-L1 sequence comprises Kabat amino acid residues 24-34, the HVR-L2 sequence comprises Kabat amino acid residues 50-56, and the HVR-L3 sequence comprises Kabat amino acid residues 89-97 of SEQ ID NO: 128, and (ii) the HVR-H1 sequence comprises Kabat amino acid residues 31-35, the HVR-H2 sequence comprises Kabat amino acid residues 50-65, and the HVR-H3 sequence comprises Kabat amino acid residues 95-102 of SEQ ID NO: 127, or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of the above HVRs of antibody 20D12.

In some instances, the anti-Factor D antibody comprises (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 127; (b) a VL domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 128; or (c) a VH domain as in (a) and a VL domain as in (b). For example, in some instances, the anti-Factor D antibody comprises a VH domain comprising the amino acid sequence of SEQ ID NO: 127 and a VL domain comprising the amino acid sequence of SEQ ID NO: 128, such as the anti-Factor D antibody 20D12. In some instances, the anti-Factor D antibody comprises a heavy chain comprising the amino acid sequence of SEQ ID NO: 129 and a light chain comprising the amino acid sequence of SEQ ID NO: 130. In some instances, the anti-Factor D antibody is a humanized derivative of monoclonal antibody 20D12. In some embodiments, the anti-Factor D antibody binds to the same epitope as monoclonal antibody 20D12 or a humanized derivative thereof. In some instances, the anti-Factor D antibody is an antibody fragment derived from monoclonal antibody 20D12 or a humanized derivative thereof. In some instances, the antibody fragment derived from monoclonal antibody 20D12 or a humanized derivative thereof is an Fab, Fab'-SH, Fv, scFv, or an (Fab')$_2$ fragment. In some embodiments, the antibody fragment derived from monoclonal antibody 20D12 or a humanized derivative thereof is an Fab.

In some instances, fragments of any of the preceding anti-Factor D antibodies (e.g., antigen-binding fragments) may be used in the compositions and methods of the invention. The antibody fragments of the present invention may be, for example, Fab, Fab', F(ab')$_2$, scFv, (scFv)$_2$, dAb, hypervariable region (HVR) fragments, linear antibodies, single-chain antibody molecules, minibodies, diabodies, or multispecific antibodies formed from antibody fragments. In a further embodiment, an anti-Factor D antibody fragment (e.g., antigen-binding fragment) that is capable of penetrating substantially all of the retina may be used in the compositions and methods of the invention. In an even further embodiment, an anti-Factor D antibody fragment (e.g., antigen-binding fragment) that is capable of penetrating throughout the entire thickness of the retina may be used in the compositions and methods of the invention.

In some instances, the invention may include the use of humanized anti-Factor D antibodies, wherein a Fab fragment of such antibodies have a half life of at least 3, 5, 7, 10, or 12 days after administration into a mammalian eye (e.g., human) via a single intravitreal injection. In another embodiment, the invention may include the use of humanized anti-Factor D antibodies, wherein a Fab fragment of such antibodies inhibits alternative pathway (AP) complement activation for at least 40, 45, 50, 55, 60, 65, 70, 75, 80, 85, 90, 95, 100, 105, 110, or 115 days after administration into a mammalian eye (e.g., human) via a single intravitreal injection. In another embodiment, the invention may include the use of humanized anti-Factor D antibodies, wherein the concentration of a Fab fragment of such antibodies that inhibits alternative pathway (AP) complement activation is maintatained in retinal tissue for at least 40, 45, 50, 55, 60, 65, 70, 75, 80 or 85 days after administration into a mammalian eye (e.g., human) via a single intravitreal injection. In another embodiment, the invention may include the use of humanized anti-Factor D antibodies, wherein the concentration of a Fab fragment of such antibodies that inhibits alternative pathway (AP) complement activation is maintained in the vitreous humor for at least 80, 85, 90, 95, 100, 105, 110, or 115 days after administration into a mammalian eye (e.g., human) via a single intravitreal injection. In one example, the invention includes use of a fragment of said anti-Factor D antibodies (e.g., antigen-binding fragments).

In some instances, any of the preceding anti-Factor D antibodies binds Factor D with a KD of about 20 nM or lower in its monovalent form (e.g., the KD of the antibody as a Fab fragment to Factor D). In some instances, an antibody provided herein binds Factor D with a KD of about 10 nM or lower in its monovalent form. In some instances, an antibody provided herein binds Factor D with a KD of about 5 nM or lower in its monovalent form. In some instances, an antibody provided herein binds Factor D with a KD of about 2 nM or lower in its monovalent form. For example, in some instances, the antibody binds Factor D with a KD between about 0.5 pM and about 2 nM (e.g., about 0.5 pM, about 1 pM, about 2 pM, about 3 pM, about 4 pM, about 5 pM, about 6 pM, about 7 pM, about 8 pM, about 9 pM, about 10 pM, about 15 pM, about 20 pM, about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM) in its monovalent form. In some instances, the antibody binds Factor D with a KD between about 0.5 pM and about 100 pM in its monovalent form. In some instances, the antibody binds Factor D with a KD of about 0.5 pM in its monovalent form. In some instances, the antibody binds Factor D with a KD of below about 10 pM in its monovalent form.

In some instances, any of the preceding anti-Factor D antibodies binds Factor D with a KD of about 10 nM or lower in its bivalent form (e.g., the KD of the antibody as an IgG to Factor D). In some instances, an antibody provided herein binds Factor D with a KD of about 5 nM or lower in its bivalent form. In some instances, an antibody provided herein binds Factor D with a KD of about 2 nM or lower in its bivalent form. For example, in some instances, the antibody binds Factor D with a KD between about 0.5 pM and about 2 nM (e.g., about 0.5 pM, about 1 pM, about 2 pM, about 3 pM, about 4 pM, about 5 pM, about 6 pM, about 7 pM, about 8 pM, about 9 pM, about 10 pM, about 15 pM, about 20 pM, about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nriM, about 1.8 nM, about 1.9 nM, or about 2 nM) in its bivalent form. In some instances, the antibody binds Factor D with a KD between about 0.5 pM and about 100 pM in its bivalent form. In some instances, the antibody binds Factor D with a KD of about 0.5 pM in its bivalent form. In some instances, the antibody binds Factor D with a KD of below about 10 pM in its bivalent form.

In a further aspect, an anti-Factor D antibody according to any of the above embodiments may incorporate any of the features, singly or in combination, as described in Sections 1-8 of Section C "Antibody Properties and Features" below.

C. Antibody Properties and Features

The antibodies described herein (e.g., anti-HtrA1 antibodies and anti-Factor D antibodies, as described above, as well as anti-HtrA1/anti-Factor D antibodies described below), as well as any of the antibodies for use in a method described herein, may have any of the features, singly or in combination, described in Sections 1-8 below.

1. Antibody Affinity

In certain embodiments, an antibody provided herein (e.g., an anti-HtrA1 antibody, an anti-Factor D antibody, or a bispecific anti-HtrA1 anti-Factor D antibody) has a dissociation constant (KD) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). For example, in some instances, an antibody provided herein binds human HtrA1 (huHtrA1) with a KD of about 10 nM or lower. In some instances, an antibody provided herein binds huHtrA1 with a KD of about 5 nM or lower. In some instances, an antibody provided herein binds huHtrA1 with a KD of about 2 nM or lower. For example, in some instances, the antibody binds huHtrA1 with a KD between about 25 pM and about 2 nM (e.g., about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM). In some instances, the antibody binds huHtrA1 with a KD between about 75 pM and about 600 pM (e.g., about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM). In some instances, the antibody binds huHtrA1 with a KD between about 75 pM and about 500 pM. In some instances, the antibody binds huHtrA1 with a KD between about 75 pM and about 400 pM. In some instances, the antibody binds huHtrA1 with a KD between about 75 pM and about 300 pM. In some instances, the antibody binds huHtrA1 with a KD between about 75 pM and about 200 pM. In some instances, the antibody binds huHtrA1 with a KD between about 75 pM and about 150 pM. In some instances, the antibody binds huHtrA1 with a KD between about 75 pM and about 125 pM. In some instances, the antibody binds huHtrA1 with a KD between about 75 pM and about 100 pM. In some instances, the antibody binds huHtrA1 with a KD of about 80 pM. In some instances, the antibody binds huHtrA1 with a KD of about 60 pM. In some instances, the antibody binds huHtrA1 with a KD of about 40 pM.

In one embodiment, KD is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, KD is measured using a BIACORE® surface plasmon resonance (SPR) assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN®-20) surfactant (PBST) at 25° C. at a flow rate of approximately 25 µl/min. Association rates ($k_{on}$) and dissociation rates (ko) are calculated using a simple one-to-one *Langmuir* binding model (BIACORE® Evaluation Software version 3.2) by simultaneously fitting the association and dissociation sensorgrams. The equilibrium dissociation constant (KD) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette. KD may also be measured using a BIA-CORE® SPR assay as described in the Examples below.

2. Antibody Stability

The invention provides antibodies with enhanced stability, for example, as compared to a reference anti-HtrA1 antibody. The stability of an antibody may be determined using any method known in the art, for example, spectroscopy (e.g., mass spectroscopy), differential scanning fluorimetry (DSF), circular dichroism (CD), intrinsic protein fluorescence, differential scanning calorimetry, light scattering (e.g., dynamic light scattering (DLS) and static light scattering (SLS), self-interaction chromatography (SIC). The anti-HtrA1 antibody may have, for example, an enhanced melting temperature ($T_m$), temperature of aggregation ($T_{agg}$), or other metrics of stability compared to a reference anti-HtrA1 antibody.

The invention provides antibodies with reduced deamidation compared to a reference anti-HtrA1 antibody. Deamidation can be reduced or prevented as described herein and/or using methods known in the art. The invention also provides antibodies with reduced oxidation (e.g., tryptophan oxidation, for example at position LC-W91), for example, as compared to a reference anti-HtrA1 antibody. Oxidation (e.g., tryptophan oxidation) can be reduced or prevented as described herein and/or using methods known in the art. The invention also provides antibodies with reduced isomerization, for example, as compared to a reference anti-HtrA1 antibody. Isomerization can be reduced or prevented as described herein and/or using methods known in the art.

3. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

In some instances, an antibody (e.g., an anti-HtrA1 antibody) provided herein is an Fab. In some embodiments, the Fab comprises a truncation in the hinge region (e.g., the upper hinge) of the heavy chain constant region. In some embodiments, the Fab heavy chain constant region terminates at position 221 (EU numbering). In some embodiments, the amino acid residue at position 221 is an aspartic acid residue (D221). In some embodiments, the heavy chain constant region of the Fab comprises an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the amino acid sequence of SEQ ID NO: 156. In some embodiments, the antibody comprises the heavy chain amino acid sequence of SEQ ID NO: 160. In some embodiments, the antibody comprises the light chain amino acid sequence of SEQ ID NO: 159. In some embodiments, the antibody comprises the heavy chain amino acid sequence of SEQ ID NO: 160 and the light chain amino acid sequence of SEQ ID NO: 159. In some embodiments, the Fab is an IgG1 Fab.

In some instances, the Fab binds to HtrA1 and may include at least one, two, three, four, five, or six HVRs selected from (a) HVR-H1 comprising the amino acid sequence of DSEMH (SEQ ID NO: 7); (b) HVR-H2 comprising the amino acid sequence of GVDPETEGAAYNQKFKG (SEQ ID NO: 8); (c) HVR-H3 comprising the amino acid sequence of GYDYDYALDY (SEQ ID NO: 3); (d) HVR-L1 comprising the amino acid sequence of RASSSVEFIH (SEQ ID NO: 9); (e) HVR-L2 comprising the amino acid sequence of ATSNLAS (SEQ ID NO: 10); and (f) HVR-L3 comprising the amino acid sequence of QQWSSAPVWT (SEQ ID NO: 11), or a combination of one or more of the above HVRs and one or more variants thereof having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 3 or 7-11. In some instances, such a Fab may include a truncation in the hinge region (e.g., the upper hinge) of the heavy chain constant region. In some embodiments, the Fab heavy chain constant region terminates at position 221 (EU numbering). In some embodiments, the amino acid residue at position 221 is Asp (D221). In some embodiments, the heavy chain constant region of the Fab comprises an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the amino acid sequence of SEQ ID NO: 156. In some instances, the Fab includes the following six HVRs: (a) an HVR-H1 comprising the amino acid sequence of DSEMH (SEQ ID NO: 7); (b) an HVR-H2 comprising the amino acid sequence of GVDPETEGAAYNQKFKG (SEQ ID NO: 8); (c) an HVR-H3 comprising the amino acid sequence of GYDYDYALDY (SEQ ID NO: 3); (d) an HVR-L1 comprising the amino acid sequence of RASSSVEFIH (SEQ ID NO: 9); (e) an HVR-L2 comprising the amino acid sequence of ATSNLAS (SEQ ID NO: 10); and (f) an HVR-L3 comprising the amino acid sequence of QQWSSAPVWT (SEQ ID NO: 11), and further includes a heavy chain constant region comprising the amino acid sequence of SEQ ID NO: 156.

In some instances, the Fab binds to HtrA1 and comprises (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the amino acid sequence of SEQ ID NO: 21; (b) a VL domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the amino acid sequence of SEQ ID NO: 22; and (c) a truncation in the hinge region (e.g., the upper hinge) of the heavy chain constant region. In some embodiments, the Fab heavy chain constant region terminates at position 221 (EU numbering). In some embodiments, the amino acid residue at position 221 is Asp (D221). In some embodiments, the heavy chain constant region of the Fab comprises an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the amino acid sequence of SEQ ID NO: 156. In some embodiments, the antibody comprises the heavy chain amino acid sequence of SEQ ID NO: 160. In some embodiments, the antibody comprises the light chain amino acid sequence of SEQ ID NO: 159. In some embodiments, the antibody comprises the heavy chain amino acid sequence of SEQ ID NO: 160 and the light chain amino acid sequence of SEQ ID NO: 159.

In some instances, the Fab binds to HtrA1 and comprises (a) a VH domain comprising the amino acid sequence of SEQ ID NO: 21; (b) a VL domain comprising the amino acid sequence of SEQ ID NO: 22; and (c) a heavy chain constant region comprising the amino acid sequence of SEQ ID NO: 156.

4. Chimeric and Humanized Antibodies

In certain embodiments, an antibody provided herein is a chimeric antibody. Certain chimeric antibodies are described, for example, in U.S. Pat. No. 4,816,567; and Morrison et al., *Proc. Natl. Acad. Sci. USA*, 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, for example, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, for example, in Almagro and Fransson, *Front. Biosci.* 13:1619-1633 (2008), and are further described, for example, in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al., *J. Immunoi.* 151:2296 (1993)); framework regions derived from the consensus sequence of human antibodies of a particular subgroup of light or heavy chain variable regions (see, e.g., Carter et al., *Proc. Natl. Acad. Sci. USA*, 89:4285 (1992); and Presta et al., *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5. Human Antibodies

In certain embodiments, an antibody provided herein is a human antibody. Human antibodies can be produced using various techniques known in the art. Human antibodies are described generally in van Dijk et al., *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

6. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

7. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of HtrA1. In certain embodiments, one of the binding specificities is for HtrA1 and the other is for any other antigen (e.g., a second biological molecule, e.g., Factor D). Accordingly, the bispecific antibody may have binding specificity for HtrA1 and Factor D. Bispecific antibodies can be prepared as full length antibodies or antibody fragments. Any of the anti-HtrA1 antibodies described herein may be used to engineer a multispecific antibody (e.g., a bispecific antibody), for example an anti-HtrA1/anti-Factor D bispecific antibody. Any of the anti-Factor D antibodies described herein and/or known in the art may be used to engineer such an anti-HtrA1/anti-Factor D bispecific antibody.

For example, in some instances, a bispecific anti-HtrA1 antibody comprising a first binding domain that specifically binds HtrA1 comprising at least one, two, three, four, five, or six hypervariable regions (HVRs) selected from: (a) HVR-H1 comprising the amino acid sequence of DSEX$_1$H (SEQ ID NO: 1), wherein X$_1$ is Met or Leu; (b) HVR-H2 comprising the amino acid sequence of GVDPETX$_1$GAAYNQKFKG (SEQ ID NO: 2), wherein X$_1$ is Glu or Asp; (c) HVR-H3 comprising the amino acid sequence of GYDYDYALDY (SEQ ID NO: 3); (d) HVR-L1 comprising the amino acid sequence of RASSSVX$_3$FIH (SEQ ID NO: 4), wherein X$_3$ is Glu or Asn; (e) HVR-L2 comprising the amino acid sequence of ATSX$_4$LAS (SEQ ID NO: 5), wherein X$_4$ is Asn, His or Glu; and (f) HVR-L3 comprising the amino acid sequence of QQWX$_5$SX$_6$PWT (SEQ ID NO: 6), wherein X$_5$ is Ser or Tyr and X$_6$ is Ala or Asn, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6, may have a second binding domain that binds to Factor D. The second binding domain that specifically binds to Factor D may, for example, include at least one, two, three, four, five, or six HVRs selected from (a) an HVR-H1 comprising the amino acid sequence of GYTFTNYGMN (SEQ ID NO: 109); (b) an HVR-H2 comprising the amino acid sequence of WINTYTGETTYAXDFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 109-114.

For example, in some instances, a bispecific anti-HtrA1 antibody comprising a first binding domain that specifically binds HtrA1 comprising at least one, two, three, four, five, or six hypervariable regions (HVRs) selected from: (a) HVR-H1 comprising the amino acid sequence of DSEMH (SEQ ID NO: 7); (b) HVR-H2 comprising the amino acid sequence of GVDPETEGAAYNQKFKG (SEQ ID NO: 8); (c) HVR-H3 comprising the amino acid sequence of GYDYDYALDY (SEQ ID NO: 3); (d) HVR-L1 comprising the amino acid sequence of RASSSVEFIH (SEQ ID NO: 9); (e) HVR-L2 comprising the amino acid sequence of ATSNLAS (SEQ ID NO: 10); and (f) HVR-L3 comprising the amino acid sequence of QQWSSAPWT (SEQ ID NO: 11), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 3 or 7-11, may have a second binding domain that binds to Factor D. The second binding domain that specifically binds to Factor D may, for example, include at least one, two, three, four, five, or six HVRs selected from (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 109, 113, or 115-118.

In particular embodiments, the invention provides a bispecific anti-HtrA1 antibody that specifically binds both HtrA1 and Factor D, wherein the antibody comprises a first binding domain that specifically binds HtrA1 comprising the following six HVRs: (a) an HVR-H1 comprising the amino acid sequence of DSEMH (SEQ ID NO: 7); (b) an HVR-H2 comprising the amino acid sequence of GVDPETEGAAYN-QKFKG (SEQ ID NO: 8); (c) an HVR-H3 comprising the amino acid sequence of GYDYDYALDY (SEQ ID NO: 3); (d) an HVR-L1 comprising the amino acid sequence of RASSSVEFIH (SEQ ID NO: 9); (e) an HVR-L2 comprising the amino acid sequence of ATSNLAS (SEQ ID NO: 10); and (f) an HVR-L3 comprising the amino acid sequence of QQWSSAPWT (SEQ ID NO: 11); and a second binding domain that specifically binds Factor D comprising the following six HVRs: (a) an HVR-H1 comprising the amino acid sequence of GYTFTNYGMN (SEQ ID NO: 109); (b) an HVR-H2 comprising the amino acid sequence of WIN-TYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some instances, the second binding domain comprises one, two, three, four, five, or six HVRs of the anti-Factor D antigen-binding antibody fragment lampalizumab.

In some instances, a bispecific anti-HtrA1 antibody comprises a first binding domain that specifically binds HtrA1 comprising (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 21; (b) a VL domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 22; or (c) a VH domain as in (a) and a VL domain as in (b), such as APEG.LC3.HC3, may have a second binding domain that binds to Factor D. The second binding domain that specifically binds to Factor D may, for example, comprise (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 119; (b) a VL domain comprising an amino acid sequence having at least about 80% sequence identity (e.g., at least 81%, 82%, 83%, 84%, 85%, 86%, 87%, 88%, 89%, 90%, 91%, 92%,92%, 93%, 94%, 95%, 96%, 97%, 98%, or 99% sequence identity) to, or the sequence of, SEQ ID NO: 120; or (c) a VH domain as in (a) and a VL domain as in (b). In some instances, the second binding domain that specifically binds to Factor D may comprise (a) a VH domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-Factor D antigen-binding antibody fragment lampalizumab; (b) a VL domain comprising an amino acid sequence having at least about 80% sequence identity (e.g., at least 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-Factor D antigen-binding antibody fragment lampalizumab; or (c) a VH domain as in (a) and a VL domain as in (b).

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see,e.g., Gruber et al., *J. immunol.*, 152:5368 (1994)); and preparing trispecific antibodies as described, for example, in Tutt et al., *J. Immunol.* 147:60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to HtrA1 as well as another, different antigen (see, e.g., US 2008/0069820).

8. Antibody Variants

In certain embodiments, amino acid sequence variants (e.g., antibody variants including one or more amino acid residue alterations) of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile:
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues and/or FR residues of a parent antibody (e.g., a humanized or human antibody). Generally, the resulting variant(s) selected for further study will have modifications (e.g., improvements) in certain biological properties (e.g., increased affinity, increased stability, increased expression, altered pI, and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury, *Methods Mol Biol.* 207:179-196 (2008)), and/or residues that contact antigen, with the resulting variant VH or VL being tested for binding affinity. Affinity maturation by constructing and reselecting from secondary libraries has been described, for example, in Hoogenboom et al., in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

In certain embodiments, substitutions, insertions, or deletions may occur within one or more FRs so long as such alterations do not substantially reduce the ability of the antibody to bind antigen. Such alterations may, for example, improve antibody affinity and/or stability (e.g., as assessed by an increased melting temperature).

Examples of framework region residues or HVR region residues to modify include possible deamidation sites (i.e., asparagine (N or Asn)), oxidation sites (i.e., methionine (M or Met) or tryptophan (W or Trp)) or pyroglutamate conversion sites (i.e., glutamine (Q or Gln)), wherein modification at such sites prevent or reduce deamidation and/or oxidation and/or pyroglutamate conversion, respectively.

To prevent or reduce the formation of deamidated variants, asparagine (N or Asn) may be mutated to alanine (A or Ala), glutamine (Q or Gln) or serine (S or Ser). To prevent or reduce the formation of oxidated variants, methionine (Met) or tryptophan (W or Trp) may be mutated to leucine (L) or isoleucine (I). To prevent or reduce the formation of pyroglutamate variants, glutamine (Q or Gln) may be mutated to glutamate (E or Glu). See, e.g., Amphlett et al., *Pharm. Biotechnol.,* 9:1-140, 1996. Alternatively, or in addition, one or more alterations (e.g., substitutions) of framework region residues may be in the Fc region in the parent antibody.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue.

Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, US Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986): US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid residue alteration (e.g., a substitution) at one or more amino acid positions. In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991).

Non-limiting examples of in vitro assays to assess ADCC activity of a molecule of interest are described in U.S. Pat. No. 5,500,362 (see, e.g., Hellstrom et al., *Proc. Nat'l Acad. Sci. USA* 83:7059-7063 (1986) and Hellstrom et al., *Proc. Nat'l Acad. Sci. USA* 82:1499-1502 (1985); U.S. Pat. No. 5,821,337; and Bruggemann et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc., Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al., *Proc. Nat'l Acad. Sci. USA* 95:652-656 (1998). C1q binding assays may also be carried out to confirm that the antibody is unable to bind C1q and hence lacks CDC activity. See, for example, C1q and C3c binding ELISA in WO 2006/029879 and WO 2005/100402. To assess complement activation, a CDC assay may be performed (see, e.g., Gazzano-Santoro et al., *J. Immunol Methods* 202:163 (1996); Cragg et al., *Blood* 101:1045-1052 (2003); and Cragg et al., *Blood* 103:2738-2743 (2004)). FcRn binding and in vivo clearance/half life determinations can also be performed using methods known in the art (see, e.g., Petkova et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al., *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immrunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, and the like.

The antibody-polymer conjugates can be made using any suitable technique for derivatizing antibody with polymers. It will be appreciated that the invention is not limited to conjugates utilizing any particular type of linkage between an antibody or antibody fragment and a polymer.

In one aspect, the conjugates of the invention include species wherein a polymer is covalently attached to a specific site or specific sites on the parental antibody, i.e., polymer attachment is targeted to a particular region or a particular amino acid residue or residues in the parental antibody or antibody fragment. Site specific conjugation of polymers is most commonly achieved by attachment to cysteine residues in the parental antibody or antibody fragment. In such embodiments, the coupling chemistry can, for example, utilize the free sulfhydryl group of a cysteine residue not in a disulfide bridge in the parental antibody. The polymer can be activated with any functional group that is capable of reacting specifically with the free sulfhydryl or thiol group(s) on the parental antibody, such as maleimide, sulfhydryl, thiol, triflate, tesylate, aziridine, exirane, and 5-pyridyl functional groups. The polymer can be coupled to the parental antibody using any protocol suitable for the chemistry of the coupling system selected, such as the protocols and systems described in U.S. Pat. Nos. 4,179,337 and 7,122,636; and Jevsevar et al., *Biotech. J.* 5:113-128, 2010.

In one embodiment, one or more cysteine residue(s) naturally present in the parental antibody is (are) used as attachment site(s) for polymer conjugation. In another embodiment, one or more cysteine residue(s) is (are) engineered into a selected site or sites in the parental antibody for the purpose of providing a specific attachment site or sites for polymer.

In one aspect, the invention encompasses antibody fragment-polymer conjugates, wherein the antibody fragment is a Fab, and the polymer is attached to one or more cysteine residue in the light or heavy chain of the Fab fragment that would ordinarily form the inter-chain disulfide bond linking the light and heavy chains.

In another aspect, the invention encompasses antibody fragment-polymer conjugates, wherein the antibody fragment is a Fab', and the polymer attachment is targeted to the hinge region of the Fab' fragment. In one embodiment, one or more cysteine residue(s) naturally present in the hinge region of the antibody fragment is (are) used to attach the polymer. In another embodiment, one or more cysteine residues is (are) engineered into the hinge region of the Fab' fragment for the purpose of providing a specific attachment site or sites for polymer. In one embodiment, a Fab fragment of the invention (e.g., an anti-HtrA1 Fab fragment, an anti-Factor D Fab fragment, or an anti-HtrA1/anti-Factor D Fab fragment) is modified by adding one cysteine at the C'-terminal end for the purpose of providing one attachment site for polymer conjugation. In another embodiment, the Fab fragment of the invention is modified by adding four additional residues, Cys-Pro-Pro-Cys (SEQ ID NO: 122), at the C'-terminal end for the purpose of providing two attachment sites for polymer conjugation.

One commonly used antibody conjugation is PEGylation, wherein one or more polyethylene glycol (PEG) polymers are covalently attached to the constant region of the antibody. See U.S. Pat. Nos. 4,179,337 and 7,122,636. PEG polymers of different sizes (e.g., from about 500 D to about 300,000 D) and shapes (e.g., linear or branched) have been known and widely used in the field. The polymers useful for the present invention may be obtained commercially (e.g., from Nippon Oil and Fats; Nektar Therapeutics; Creative PEGWorks) or prepared from commercially-available starting materials using conventional chemical procedures. PEGylation changes the physical and chemical properties of the antibody drug, and may results in improved pharmacokinetic behaviors such as improved stability, decreased immunogenicity, extended circulating life, as well as increased residence time. In another embodiment, any antibody described herein (e.g., an anti-HtrA1 antibody of the invention) may be conjugated to hyaluronic acid (HA).

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f) Isoelectric Point Variants

The invention provides antibodies variants with altered isoelectric points. For example, the invention provides antibodies variants with a reduced isoelectric point (pI), for example, as compared to a reference anti-HtrA1 antibody. In some instances, the surface charge is reduced at physiological pH. In some instances, the anti-HtrA1 antibody has a pI equal to or lower than about 8 (e.g., about 8, about 7, about 6, about 5, or about 4). In some instances, the antibody has a pI from about 4 to about 8 (e.g., about 4, about 5, about 6, about 7, or about 8). In some instances, the anti-HtrA1 antibody has a pI from about 5 to about 7 (e.g., about 5, about 6, or about 7). In some instances, the anti-HtrA1 antibody has a pI from about 5 to about 6 (e.g., about 5.1, about 5.2, about 5.3, about 5.4, about 5.5, about 5.6, about 5.7, about 5.8, about 5.9, or about 6).

Antibodies of the invention may be engineered to have a reduced pI, for example, by substituting wild-type amino acid residues at a given position with an amino acid having a lower pI. The pI of an amino acid can be determined based on the pKa values of the amine ($-NH_2$), carboxylic acid ($-COOH$), and side-chain of the amino acid, which are known in the art. In some embodiments, surface-exposed amino acid residues may be substituted to reduce the pI of an antibody. In one embodiment, surface-exposed amino acid residues may be substituted with glutamate (E). In one embodiment, surface-exposed amino acid residues may be substituted with aspartate (D).

D. Recombinant Methods and Compositions

Any of the antibodies (e.g., anti-HtrA1 antibodies) described herein may be produced using recombinant methods and compositions, for example, as described in U.S. Pat. No. 4,816,567. In one embodiment, an isolated nucleic acid encoding an anti-HtrA1 antibody described herein is provided. Such a nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such a nucleic acid are provided. In a further embodiment, a host cell comprising such a nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell or lymphoid cell (e.g., YO, NSO, Sp20 cell). In one embodiment, a method of making an anti-HtrA1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HtrA1 antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells ($T_M4$ cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as YO, NSO and Sp2/0. For a review of certain mammalian host cell lines suitable for antibody production, see, for example, Yazaki and Wu, *Methods in Molecular Biology, Vol.* 248 (B. K. C. Lo, ed., Humana Press, Totowa, N.J.), pp. 255-268 (2003).

E. Assays

Anti-HtrA1 antibodies (e.g., anti-HtrA1 antibodies and anti-HtrA1/anti-Factor D antibodies) provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, surface plasmon resonance assays (e.g., BIACORE®), etc.

In one aspect, antigen binding activity (e.g., as indicated by KD) is measured using a BIACORE® surface plasmon resonance (SPR) assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN®-20) surfactant (PBST) at 25° C. at a flow rate of approximately 25 µl/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant (KD) is calculated as the ratio $k_{off}/k_{on}$. See, for example, Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette. KD may also be measured using a BIA-CORE® SPR assay as described in the Examples below.

In another aspect, competition assays may be used to identify an antibody that competes with an antibody as described herein for binding to HtrA1. In certain embodiments, such a competing antibody binds to the same epitope (e.g., a linear or a conformational epitope) that is bound by an antibody as described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized HtrA1 is incubated in a solution comprising a first labeled antibody that binds to HtrA1 and a second unlabeled antibody that is being tested for its ability to compete with the first antibody for binding to HtrA1. The second antibody may be present in a hybridoma supernatant. As a control, immobilized HtrA1 is incubated in a solution comprising the first labeled antibody but not the second unlabeled antibody. After incubation under conditions permissive for binding of the first antibody to HtrA1, excess unbound antibody is removed, and the amount of label associated with immobilized HtrA1 is measured. If the amount of label associated with immobilized HtrA1 is substantially reduced in the test sample relative to the control sample, then that indicates that the second antibody is competing with the first antibody for binding to HtrA1. See Harlow and Lane (1988) *Antibodies: A Laboratory Manual* ch.14 (Cold Spring Harbor Laboratory, Cold Spring Harbor, N.Y.).

2. Activity Assays

In one aspect, assays are provided for identifying anti-HtrA1 antibodies thereof having biological activity. Biological activity may include, for example, inhibiting, blocking, antagonizing, suppressing, interfering, modulating and/or reducing one or more biological activities of HtrA1. Antibodies having such biological activity in vivo and/or in vitro are also provided.

In certain embodiments, an antibody of the invention is tested for such biological activity. In certain embodiments, an anti-HtrA1 antibody binds to HtrA1 and reduces or inhibits its serine protease activity for one or more HtrA1 substrates, including, for example, the H2-Opt substrate, α-casein, β-casein, or BODIPY® FL casein substrates as described in the Examples below, or any other suitable HtrA1 substrate. In certain embodiments, an anti-HtrA1 antibody inhibits HtrA1 serine protease activity with an $IC_{50}$ of less than 50 nM, 30 nM, 25 nM, 20 nM, 15 nM, 10 nM, 5 nM, 3 nM, 2.5 nM, 2 nM, 1 nM, 800 pM, 600 pM, 500 pM, 400 pM, 300 pM, 200 pM, 100 pM, 50 pM, or less for one or more HtrA1 substrates. In certain embodiments, an anti-HtrA1 antibody protects photoreceptor cells from degradation, protects the thickness of the outer nuclear layer, or protects electroretinogram functional activity in an ocular disease model, such as the constant light exposure mouse model described in Example 10 of U.S. 2013/0129743.

To determine whether an anti-Factor D antibody, or variant or fragment thereof (e.g., antigen-binding fragment) is capable of binding to Factor D and exerting a biological effect, for example, inhibition of alternative pathway hemolysis, hemolytic inhibition assays using rabbit red blood cells (RBCs) may be used, including those described in Example 2 of U.S. Pat. No. 8,273,352, which is incorporated herein by reference in its entirety. Such hemolytic inhibition may be determined using standard assays (Kostavasili et al., *J. Immunology* 158:1763-72, 1997; Wiesmann et al., *Nature* 444:159-60, 2006). Activation of complement in such assays may be initiated with serum or plasma. Appropriate concentrations of Factor D in serum or plasma (Pascual et al., *Kidney International* 34:529-536, 1998; Complement Facts Book, Bernard J. Morley and Mark J. Walport, editors, *Academic Press* (2000); Barnum et al., *J. Irnmunol Methods*, 67: 303-309, 1984) can be routinely determined according to methods known in the art, including those that have been described in references such as Pascual et al., supra and Barnum et al., supra, and Example 4 of U.S. Pat. No. 8,273,352. The anti-Factor D antibodies described herein are generally capable of inhibiting biological activities associated with Factor D. For example, at a concentration of 18 µg/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107).

3. Stability Assays

In one aspect, assays are provided for determining the stability (e.g., thermostability) of an anti-HtrA1 antibody. For example, the stability of an antibody may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The stability of an assay may be determined as described herein, for example, using mass spectrometry as described, for example, in Example 4, for example in the context of a AAPH stress test and/or a thermal stress test.

F. Methods and Compositions for Diagnostics and Detection

In certain embodiments, any of the anti-HtrA1 antibodies provided herein is useful for detecting the presence of HtrA1 in a biological sample. The term "detecting" as used herein encompasses quantitative or qualitative detection. In certain embodiments, a biological sample comprises a cell or tissue, such as a sample comprising photoreceptor cells, retinal pigment epithelium cells, cells of the outer nuclear layer, the inner nuclear layer, Muller cells, ciliary epithelium, or retinal tissue. In some embodiments, a biological sample comprises a bodily fluid, e.g., vitreous or blood.

In one embodiment, an anti-HtrA1 antibody for use in a method of diagnosis or detection is provided. In a further aspect, a method of detecting the presence of HtrA1 in a biological sample is provided. In certain embodiments, the method comprises contacting the biological sample with an anti-HtrA1 antibody as described herein under conditions permissive for binding of the anti-HtrA1 antibody to HtrA1, and detecting whether a complex is formed between the anti-HtrA1 antibody and HtrA1. Such method may be an in vitro or in vivo method. In one embodiment, an anti-HtrA1 antibody is used to select subjects eligible for therapy with an anti-HtrA1 antibody, for example, where HtrA1 is a biomarker for selection of patients.

In certain embodiments, a patient suitable for treatment with an anti-HtrA1 antibody may be identified by detecting one or more polymorphisms in the HtrA1 gene or HtrA1 control sequence, such as the HtrA1 promoter polymorphism rs11200638(G/A) (see e.g., DeWan et al., *Science* 314: 989-992, 2006, which is incorporated herein by reference in its entirety).

Exemplary disorders that may be diagnosed using an antibody of the invention include, but are not limited to, HtrA-associated disorders, ocular disorders, complement-associated disorders, and preeclampsia. In some instances, the ocular disorder includes, but is not limited to, for example, AMD, including wet AMD (including early, intermediate, and advanced wet AMD) and dry AMD (including early, intermediate, and advanced dry AMD (e.g., geographic atrophy (GA)), diabetic retinopathy (DR), retinopathy of prematurity (ROP), or polypoidal choroidal vasculopathy (PCV).

In some embodiments, preeclampsia may be diagnosed using an antibody of the invention. In some embodiments, an increased level of HtrA1 in a sample derived from a subject relative to a reference level of HtrA1 may indicate that the subject has, or is susceptible to, preeclampsia. See, e.g., Teoh et al. *Placenta* 36(9):990-995, 2015. In some embodiments, serum HtrA1 levels may be detected using an antibody of the invention. In other embodiments, placental HtrA1 levels may be detected using an antibody of the invention.

In certain embodiments, labeled anti-HtrA1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, for example, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the sample may be fresh or frozen or may be embedded in paraffin and fixed with a preservative such as formalin, for example.

G. Diagnostic Kits

As a matter of convenience, an antibody of the present invention (e.g., an anti-HtrA1 antibody or an anti-HtrA1/anti-Factor D antibody) can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

H. Pharmaceutical Formulations

Therapeutic formulations of the antibody or antibody variant thereof (e.g., an anti-HtrA1 antibody or an anti-HtrA1/anti-Factor D antibody of the invention) may be prepared for storage as lyophilized formulations or aqueous solutions by mixing the polypeptide having the desired degree of purity with optional "pharmaceutically-acceptable" carriers, excipients, or stabilizers typically employed in the art (all of which are termed "excipients"). For example, buffering agents, stabilizing agents, preservatives, isotonifiers, non-ionic detergents, antioxidants and other miscellaneous additives. See e.g., *Remington's Pharmaceutical Sciences*, 16$^{th}$ edition, A. Osol, Ed. (1980). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.), and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers, sometimes known as "stabilizers," may be added to ensure isotonicity of liquid compositions of the present invention and include polhydric sugar alcohols, preferably trihydric or higher sugar alcohols, such as glycerin, erythritol, arabitol, xylitol, sorbitol, and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (i.e., <10 residues); proteins such as human serum albumin, bovine serum albumin, gelatin, or immunoglobulins; hydrophylic polymers, such as polyvinylpyrrolidone; monosaccharides, such as xylose, mannose, fructose, and glucose; disaccharides such as lactose, maltose, and sucrose; and trisaccacharides such as raffinose; and polysaccharides such as dextran. Stabilizers may be present in the range from 0.1 to 10,000 weights per part of weight active protein.

Non-ionic surfactants or detergents (also known as "wetting agents") may be added to help solubilize the therapeutic protein (e.g., antibody) as well as to protect the therapeutic protein against agitation-induced aggregation, which also permits the formulation to be exposed to shear surface stress without causing denaturation of the protein. Suitable non-ionic surfactants include polysorbates (20, 80, and the like), polyoxamers (184, 188, and the like), PLURONIC® polyols, polyoxyethylene sorbitan monoethers (TWEEN®-20, TWEEN®-80, and the like). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g., starch), chelating agents (e.g., EDTA), antioxidants (e.g., ascorbic acid, methionine, and vitamin E), and cosolvents. The formulation herein may also contain more than one active compound as necessary for the particular indication being treated, preferably those with complementary activities that do not adversely affect each other. For example, it may be desireable to include an HtrA1 binding antagonist (e.g., an anti-HtrA1 antibody) and a Factor D binding antagonist (e.g., an anti-Factor D antibody) in the formulation. In another example, for treating an ocular disorder associated with undesired neovascularization, such as wet AMD, it may be desirable to further provide an anti-angiogenic therapy, such as a VEGF antagonist therapy, for example, LUCENTIS® (ranibizumab). Such active ingredients are suitably present in combination in amounts that are effective for the purpose intended.

The active ingredients may also be entrapped in microcapsule prepared, for example, by coascervation techniques or by interfacial polymerization, for example, hyd roxymethylcellu lose, or gelatin-microcapsule and poly-(methylmethacylate) microcapsule, respectively, in colloidal drug delivery systems (for example, liposomes, albumin micropheres, microemulsions, nano-particles, and nanocapsules), or in macroemulsions. Such techniques are disclosed in *Remington's Pharmaceutical Sciences,* 16th edition, A. Osal, Ed. (1980).

Sustained release preparations may be prepared. Suitable examples of sustained-release preparations include semipermeable matrices of solid hydrophobic polymers containing the antibody, or antibody variant or fragment (e.g., antigen-binding fragment) thereof, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylenevinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thiodisulfide interchange, stabilization may be achieved by modifying sulfhydryl residues, lyophilizing from acidic solutions, controlling moisture content, using appropriate additives, and developing specific polymer matrix compositions.

I. Therapeutic Methods and Compositions

Any of the anti-HtrA1 antibodies provided herein (e.g., anti-HtrA1 antibodies and anti-HtrA1/anti-Factor D antibodies) may be used in therapeutic methods.

In one aspect, an anti-HtrA1 antibody for use as a medicament is provided. In further aspects, the invention provides an anti-HtrA1 antibody for use in treating an HtrA1-associated disorder. In some embodiments, the HtrA1-associated disorder is AMD, including wet AMD (including early, intermediate, and advanced wet AMD) and dry AMD (including early, intermediate, and advanced dry AMD (e.g., geographic atrophy (GA)). In some instances, the AMD is advanced dry AMD (e.g., GA).

In another embodiment, the invention provides an anti-HtrA1 antibody for use in treating an ocular disorder. In some instances, the ocular disorder is AMD, including wet (exudative) AMD (including early, intermediate, and advanced wet AMD) and dry (nonexudative) AMD (including early, intermediate, and advanced dry AMD (e.g., GA); diabetic retinopathy (DR) and other ischemia-related retinopathies; endophthalmitis; uveitis; choroidal neovascularization (CNV); retinopathy of prematurity (ROP); polypoidal choroidal vasculopathy (PCV); diabetic macular edema; pathological myopia; von Hippel-Lindau disease; histoplasmosis of the eye; Central Retinal Vein Occlusion (CRVO); corneal neovascularization; or retinal neovascularization. In some embodiments, the ocular disorder is AMD (e.g., advanced dry AMD (e.g., GA)).

In another aspect, an anti-HtrA1 antibody for use in a method of treatment is provided. In certain instances, the invention provides an anti-HtrA1 antibody for use in a method of treating a subject having an HtrA1-associated disorder comprising administering to the individual an effective amount of the anti-HtrA1 antibody. In some embodiments, the HtrA1-associated disorder is AMD, including wet AMD (including early, intermediate, and advanced wet AMD) and dry AMD (including early, intermediate, and advanced dry AMD (e.g., GA)). In some instances, AMD is advanced dry AMD (e.g., GA).

In another instance, the invention provides an anti-HtrA1 antibody for use in a method of treating a subject having an ocular disorder comprising administering to the individual an effective amount of the anti-HtrA1 antibody. In some instances, the ocular disorder is AMD, including wet (exudative) AMD (including early, intermediate, and advanced wet AMD) and dry (nonexudative) AMD (including early, intermediate, and advanced dry AMD (e.g., GA); DR and other ischemia-related retinopathies; endophthalmitis; uveitis; CNV; ROP; PCV; diabetic macular edema; pathological myopia; von Hippel-Lindau disease; histoplasmosis of the eye; CRVO; corneal neovascularization; or retinal neovascularization. In some embodiments, the ocular disorder is AMD (e.g., advanced dry AMD (e.g., GA)).

In some instances, the invention provides an anti-HtrA1 antibody for use in inhibiting retinal or photoreceptor cell degeneration in a subject. In other instances, the invention provides an anti-HtrA1 antibody for use in inhibiting HtrA1 serine protease activity in an eye of a subject. A "subject" according to any of the above uses may be a human.

The invention provides for the use of an anti-HtrA1 antibody in the manufacture or preparation of a medicament. For example, in one instance, the medicament is for treatment of an HtrA1-associated disorder. In a further instance, the medicament is for use in a method of treating an HtrA1-associated disorder comprising administering to a subject having an HtrA1-associated disorder an effective amount of the medicament. In any of the preceding uses of medicaments, the method may include administering to the individual an effective amount of at least one additional therapeutic agent, e.g., as described below. In some embodiments, the HtrA1-associated disorder is AMD, including wet AMD (including early, intermediate, and advanced wet AMD) and dry AMD (including early, intermediate, and advanced dry AMD (e.g., GA)). In some instances, the AMD is advanced dry AMD (e.g., GA).

In another instance, the medicament is for use in a method of treating an ocular disorder comprising administering to the subject having an ocular disorder an effective amount of the medicament. In some instances, the ocular disorder is AMD, including wet (exudative) AMD (including early, intermediate, and advanced wet AMD) and dry (nonexudative) AMD (including early, intermediate, and advanced dry AMD (e.g., GA); DR and other ischemia-related retinopathies; endophthalmitis; uveitis; CNV; ROP; PCV; diabetic macular edema; pathological myopia; von Hippel-Lindau disease; histoplasmosis of the eye; CRVO; corneal neovascularization; or retinal neovascularization. In some embodiments, the ocular disorder is AMD (e.g., advanced dry AMD (e.g., GA)).

The invention provides a method for treating an HtrA1-associated disorder. In one embodiment, the method comprises administering to a subject having an HtrA1-associated disorder an effective amount of an anti-HtrA1 antibody. In some embodiments, the HtrA1-associated disorder is AMD, including wet AMD (including early, intermediate, and advanced wet AMD) and dry AMD (including early, intermediate, and advanced dry AMD (e.g., GA)). In some instances, the AMD is advanced dry AMD (e.g., GA). In further instances, the method further comprises administering to the individual an effective amount of at least one additional therapeutic agent, as described below. A "subject" according to any of the above methods may be a human.

The invention provides a method for treating an ocular disorder. In one embodiment, the method comprises administering to a subject having an ocular disorder an effective amount of an anti-HtrA1 antibody. In some instances, the ocular disorder is AMD, including wet (exudative) AMD (including early, intermediate, and advanced wet AMD) and dry (nonexudative) AMD (including early, intermediate, and advanced dry AMD (e.g., GA); DR and other ischemia-related retinopathies; endophthalmitis; uveitis; CNV; ROP; PCV; diabetic macular edema; pathological myopia; von Hippel-Lindau disease; histoplasmosis of the eye; CRVO; corneal neovascularization; or retinal neovascularization. In some embodiments, the ocular disorder is AMD (e.g., advanced dry AMD (e.g., GA)).

The invention provides a method of treating an HtrA1-associated disorder, an ocular disorder, and/or a complement-associated disorder in a subject in need thereof, the method comprising administering to the subject a therapeutically effective amount of an HtrA1 binding antagonist and/or a Factor D binding antagonist. In some embodiments, the HtrA1-associated disorder or complement-associated disorder is an ocular disorder. In some embodiments, the ocular disorder is selected from the group consisting of AMD, diabetic retinopathy, choroidal neovascularization (CNV), uveitis, diabetic macular edema, pathological myopia, von Hippel-Lindau disease, histoplasmosis of the eye, central retinal vein occlusion, corneal vascularization, and retinal neovascularization. In some instances, the the ocular disorder is AMD, including wet AMD (including early, intermediate, and advanced wet AMD) and dry AMD (including early, intermediate, and advanced dry AMD (e.g., GA)). In some instances, the AMD is advanced dry AMD (e.g., GA). In any of the preceding embodiments, the HtrA1-binding antagonist may be an anti-HtrA1 antibody or antigen-binding fragment thereof, for example, any anti-HtrA1 antibody or antigen-binding fragment thereof described herein. In some embodiments, the antigen-binding antibody fragment is selected from the group consisting of Fab, Fab'-SH, Fv, scFV, and (Fab')$_2$ fragments. In some embodiments, the antigen-binding antibody fragment is an Fab. In some embodiments, the Fab comprises a truncation in the hinge region (e.g., the upper hinge) of the heavy chain constant region. In some embodiments, the Fab heavy chain constant region terminates at position 221 (EU numbering). In some embodiments, the amino acid residue at position 221 is an aspartic acid residue. In some embodiments, the heavy chain constant region of the Fab comprises the amino acid sequence of SEQ ID NO: 156. In some embodiments, the Fab is an IgG1 Fab. In some instances, the Factor D binding antagonist is an anti-Factor D antibody or antigen-binding fragment thereof, for example, any of the anti-Factor D antibodies described herein.

In another aspect, the invention provides for the use of a bispecific antibody that specifically binds both HtrA1 and Factor D or an antigen-binding antibody fragment thereof in the manufacture of a medicament for treating a HtrA1-associated disorder, an ocular disorder, and/or a complement-associated disorder. In some embodiments, the HtrA1-associated disorder and/or complement associated disorder is an ocular disorder. In some instances, the ocular disorder is AMD, including wet AMD (including early, intermediate, and advanced wet AMD) and dry AMD (including early, intermediate, and advanced dry AMD (e.g., GA)). In some embodiments, the AMD is advanced dry AMD (e.g., GA). The bispecific antibody may comprise a binding domain that specifically binds HtrA1 that is derived from any of the anti-HtrA1 antibodies described herein. The bispecific antibody may comprise a binding domain that specifically binds Factor D that is derived from any of the anti-Factor D antibodies described herein. In some embodiments, the antigen-binding antibody fragment is a Fab fragment or an (Fab')$_2$ fragment.

Any of the anti-Factor D antibodies or antigen-binding fragments thereof described herein and/or known in the art may be used in any of the preceding methods or uses. For example, in some instances, the anti-Factor D antibody or antigen-binding fragment thereof may include the following six HVRs: (a) an HVR-H1 comprising the amino acid sequence of GYTFTNYGMN (SEQ ID NO: 109); (b) an HVR-H2 comprising the amino acid sequence of WINTYTGETTYAX$_1$DFKG (SEQ ID NO: 110), wherein X$_1$ is Asp or Glu; (c) an HVR-H3 comprising the amino acid sequence of EGGVX$_1$N (SEQ ID NO: 111), wherein X$_1$ is Asn or Ser; (d) an HVR-L1 comprising the amino acid sequence of ITSTX$_1$IX$_2$X$_3$DMN (SEQ ID NO: 112), wherein X$_1$ is Asp or Ser, X$_2$ is Asp or Glu, and X$_3$ is Asp or Ser; (e) an HVR-L2 comprising the amino acid sequence of GGNTLRP (SEQ ID NO: 113); and (f) an HVR-L3 comprising the amino acid sequence of LQSX$_1$SLPYT (SEQ ID NO: 114), wherein X$_1$ is Asp or Glu. In some instances, the anti-Factor D antibody or antigen-binding fragment thereof includes the following six HVRs: (a) an HVR-H1 comprising the amino acid sequence of GYTFTNYGMN (SEQ ID NO: 109); (b) an HVR-H2 comprising the amino acid sequence of WINTYTGETTYADDFKG (SEQ ID NO: 115); (c) an HVR-H3 comprising the amino acid sequence of EGGVNN (SEQ ID NO: 116); (d) an HVR-L1 comprising the amino acid sequence of ITSTDIDDMN (SEQ ID NO: 117); (e) an HVR-L2 comprising the amino acid sequence of GGNTLRP (SEQ ID NO: 113); and (f) an HVR-L3 comprising the amino acid sequence of LQSDSLPYT (SEQ ID NO: 118). In some embodiments, the anti-Factor D antibody or antigen-binding fragment thereof includes (a) a VH domain comprising an amino acid sequence having at least 90% sequence identity to the amino acid sequence of SEQ ID NO: 119; (b) a VL domain comprising an amino acid sequence having at least 90% sequence identity to the amino acid sequence of SEQ ID NO: 120; or (c) a VH domain as in (a) and a VL domain as in (b). In some instances, the VH domain comprises the amino acid sequence of SEQ ID NO: 119. In some instances, the VL domain comprises the amino acid sequence of SEQ ID NO: 120. In some instances, the anti-Factor D antigen-binding antibody fragment is lampalizumab having CAS registry number 1278466-20-8.

It is contemplated that the antibody of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents (e.g., mice and rats) and other mammals in which preclinical studies are performed. Such mammals may be established animal models for a disease to be treated with the antibody or may be used to study toxicity of the antibody of interest. In each of these embodiments, dose escalation studies may be performed in the mammal.

In a further aspect, the invention provides pharmaceutical formulations comprising any of the anti-HtrA1 antibodies provided herein, for example, for use in any of the above therapeutic methods. In one embodiment, a pharmaceutical formulation comprises any of the anti-HtrA1 antibodies provided herein and a pharmaceutically acceptable carrier.

In another embodiment, a pharmaceutical formulation comprises any of the anti-HtrA1 antibodies provided herein and at least one additional therapeutic agent, for example, as described below.

In any of the therapeutic uses and methods described herein, the anti-HtrA1 antibody may be an Fab. In some embodiments, the Fab comprises a truncation in the hinge region (e.g., the upper hinge region) of the heavy chain constant region. In some embodiments, the Fab heavy chain constant region terminates at position 221 (EU numbering). In some embodiments, the amino acid residue at position 221 is an aspartic acid residue. In some embodiments, the heavy chain constant region of the Fab comprises the amino acid sequence of SEQ ID NO: 156. In some embodiments, the Fab is an IgG1 Fab.

An antibody of the invention (and any additional therapeutic agent) for prevention or treatment of an ocular disease or condition can be administered by any suitable means, including but not limited to, for example, ocular, intraocular, and/or intravitreal injection, and/or juxtascleral injection, and/or subtenon injection, and/or superchoroidal injection, and/or topical administration in the form of eye drops and/or ointment. Such antibodies of the invention may be delivered by a variety of methods, for example, intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a mini pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular, or intravitreal administration can be prepared by methods and using excipients known in the art. An important feature for efficient treatment is proper penetration through the eye. Unlike diseases of the front of the eye, where drugs can be delivered topically, retinal diseases typically benefit from a more site-specific approach. Eye drops and ointments rarely penetrate the back of the eye, and the blood-ocular barrier hinders penetration of systemically administered drugs into ocular tissue. Accordingly, a method of choice for drug delivery to treat retinal disease, such as AMD and CNV, is typically direct intravitreal injection. Intravitreal injections are usually repeated at intervals which depend on the patient's condition, and the properties and half-life of the drug delivered. For intraocular (e.g., intravitreal) penetration, usually molecules of smaller size are preferred.

Eyes have many biophysical and anatomic features that can render ocular drug delivery challenging. For example, blood-ocular barriers are defense mechanisms for protect the eye from infection, but at the same time make it hard for drug to penetrate, especially for diseases in the posterior segments of the eye. Consequently, high-dose administration is often desired to achieve and maintain drug's onsite bioavailability (e.g., ocular residence time) in order to improve efficacy. Meanwhile, the limited space in the back of the eye restrains the drug volume to be delivered, which in turn may favor drugs to be delivered in a high concentration formulation.

Patients with ocular disorders (e.g., AMD (e.g., geographic atrophy)) can also be benefited from long acting/slow released delivery of therapeutics. Less frequent dosing would provide improved convenience to the patient, have potential benefits of decreased infection rate and increased clinical efficacy. Controlled release of high dose drugs could also minimize drug side effects. Two promising systems for long-acting delivery are PLGA-based solid implants and an implantable port delivery system (PDS). Both systems have the potential to provide near zero-order release kinetics for an extended period of time. For PLGA implants, the protein drug is encapsulated in a hydrophobic polymer matrix and drug release is accomplished via slow hydrolysis of the polymer. The rate of release can be controlled by changing the drug loading, polymer hydrophobicity, or polymer molecular weight. The PDS is a refillable device where release into the vitreous is controlled by a porous metal membrane comprising a titanium frit. Since the reservoir has a low volume, a high protein concentration is required for effective delivery with the PDS.

In addition to or in lieu of high concentration and long acting delivery, increased bioavailability (e.g., ocular residence time) of the drug can be achieved, or facilitated, by posttranslational modifications, wherein the protein drug is covalently conjugated with natural or synthetic polymers such as polysialylation, HESylation (conjugation with hydroxyethyl starch) and PEGylation. See, e.g., Chen et al., *Expert. Opin. Drug Deliv.* 8:1221-36, 2011; Kontermann, *BioDrugs* 23:93-109, 2011. PEGylation, the covalent attachment of polymer polyethylene glycol (PEG) to a protein, is a well-established technology especially useful for extending the half-life of antibody fragment therapeutics. Jevsevar et al., *Biotech. J.* 5:113-128, 2010.

The conditions that a drug is exposed to vary depending on the delivery system used. For incorporation into solid PLGA implants, lyophilized or spray-dried drug is used. Implants are produced using a hot-melt extrusion process such that the drug is briefly exposed to temperatures approaching 90° C. Although the drug remains in solid state for the duration of release, degradation of PLGA may expose the drug to a low pH environment. In contrast, drug delivered with the PDS is maintained at high concentration in liquid state and exposed to vitreous which is characterized as a reducing environment at physiological ionic strength and pH.

The amount of antibody or antibody variant thereof which will be effective in the treatment of a particular ocular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

Additional suitable administration means include parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein. In some instances, the anti-HtrA1 antibody may be administered intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, topically, transdermally, by inhalation, by injection, by implantation, by infusion, by continuous infusion, by localized perfusion bathing target cells directly, by catheter, by lavage, in cremes, or in lipid compositions.

The efficacy of the treatment of ocular disorders (e.g., complement-associated ocular disorders), such as AMD or CNV, can be measured by various endpoints commonly used in evaluating intraocular diseases. For example, vision loss can be assessed. Vision loss can be evaluated by any method known in the art and/or described herein, including but not limited to, for example, measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, and the like. Ocular assessments can be done, e.g., which include, but are not limited to, e.g., performing eye exam, measuring intraocular pressure, assessing visual acuity, measuring slitlamp pressure, assessing intraocular inflammation, and the like.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg, 0.2 mg/kg, 0.4 mg/kg, 0.6 mg/kg, 0.8 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg) of antibody can be an initial candidate dosage for administration to the patient, whether, for example, by one or more separate administrations, or by continuous infusion. In some embodiments, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs.

In some instances, a fixed dose of an anti-HtrA1 antibody of the invention is administered, for example, to an eye. In some instances, about 0.1 mg to about 10 mg or about 5-15 mg of an anti-HtrA1 antibody of the invention is administered to an eye, e.g., about 0.1 mg/eye to about 0.5 mg/eye, about 0.5 mg/eye to about 1 mg/eye, about 1 mg/eye to about 1.5 mg/eye, about 1.5 mg/eye to about 2 mg/eye, about 2 mg/eye to about 2.5 mg/eye, about 2.5 mg/eye to about 3 mg/eye, about 3 mg/eye to about 3.5 mg/eye, about 3.5 mg/eye to about 4 mg/eye, about 4 mg/eye to about 4.5 mg/eye, about 4.5 mg/eye to about 5 mg/eye, about 5 mg/eye to about 5.5 mg/eye, about 5.5 mg/eye to about 6 mg/eye, about 6 mg/eye to about 6.5 mg/eye, about 6.5 mg/eye to about 7 mg/eye, about 7 mg/eye to about 7.5 mg/eye, about 7.5 mg/eye to about 8 mg/eye, about 8 mg/eye to about 8.5 mg/eye, about 8.5 mg/eye to about 9 mg/eye, about 9 mg/eye to about 9.5 mg/eye, or about 9.5 mg/eye to about 10 mg/eye. In some instances, the antibody is used at about 0.1 mg/eye to about 2 mg/eye, about 0.1 mg/eye to about 3 mg/eye, about 0.1 mg/eye to about 5 mg/eye, about 0.1 mg/eye to about 6 mg/eye, about 0.1 mg/eye to about 7 mg/eye, about 0.1 mg/eye to about 8 mg/eye, about 0.1 mg/eye to about 9 mg/eye, about 0.1 mg/eye to about 10 mg/eye, about 0.5 mg/eye to about 2 mg/eye, about 0.5 mg/eye to about 3 mg/eye, about 1 mg/eye to about 3 mg/eye, or about 2 mg/eye to about 5 mg/eye. In some instances, a fixed dose of an anti-HtrA1 antibody of about 0.5 mg/eye, about 1 mg/eye, about 1.5 mg/eye, about 2 mg/eye, about 2.5 mg/eye, about 3 mg/eye, about 3.5 mg/eye, about 4 mg/eye, about 4.5 mg/eye, about 5 mg/eye, about 5.5 mg/eye, about 6 mg/eye, about 6.5 mg/eye, about 7 mg/eye, about 7.5 mg/eye, about 8 mg/eye, about 8.5 mg/eye, about 9 mg/eye, about 9.5 mg/eye, about 10 mg/eye, or more is used. In a particular instance, for example, a fixed dose of an anti-HtrA1 antibody is administered at about 2 mg/eye.

In some embodiments the dose may be administered once a week, once every two weeks, once every three weeks, once every four weeks, once every five weeks, once every six weeks, once every seven weeks, once every eight weeks, once every nine weeks, once every ten weeks, once every eleven weeks, or once every twelve weeks.

An HtrA1 binding antagonist (e.g., an anti-HtrA1 antibody of the invention) can be administered alone or in combination with at least a second therapeutic compound. Administration of the HtrA1 binding antagonist (e.g., an anti-HtrA1 antibody of the invention) and any second therapeutic compound can be done simultaneously, e.g., as a single composition or as two or more distinct compositions using the same or different administration routes. Alternatively, or additionally the administration can be done sequentially, in any order. In certain embodiments, intervals ranging from minutes to days, to weeks to months, can be present between the administrations of the two or more compositions. For example, the HtrA1 binding antagonist (e.g., an anti-HtrA1 antibody of the invention) may be administered first, followed by the second therapeutic compound. However, simultaneous administration or administration of the second therapeutic compound prior to the HtrA1 binding antagonist (e.g., an anti-HtrA1 antibody of the invention) is also contemplated. In one example, the HtrA1 binding antagonist is an anti-HtrA1 10 antibody, for example, any anti-HtrA1 antibody described herein or known in the art. In one example, the second therapeutic compound is a Factor D binding antagonist. In a further example, the Factor D binding antagonist is an anti-Factor D antibody, for example, any anti-Factor D antibody described herein or known in the art. In particular embodiments, the anti-Factor D antibody is lampalizumab. In further embodiments, the anti-Factor D antibody is administered at a dose of 1-15 mgs, for example at a dose of 10 mgs. In particular embodiments, the lampalizumab is administered once every two weeks, once every three weeks, or once every four weeks. In certain embodiments, an additional therapeutic agent is a therapeutic agent suitable for treatment of an ocular disorder associated with undesirable neovascularization in the eye, such as, for example, wet AMD. Suitable therapeutic agents include, for example, anti-angiogenic therapies such as VEGF antagonists (e.g., anti-VEGF antibodies and antibody fragments, including LUCENTIS® (ranibizumab), and anti-VEGFR1 antibodies and related molecules (e.g., aflibercept (VEGF Trap-Eye; EYLEA®)); inhibitors of the complement system, such as complement factor C2 antagonists (including, for example, anti-CFC2 antibodies); and anti-inflammatory agents, such as IL-6 binding antagonists (e.g., tocilizumab (ACTEMRA®) and EBI-031 (Eleven Biotherapeutics)). In other embodiments, treatment of a disease or disorder associated with undesirable ocular neovascularization may involve a combination of an anti-HtrA1 antibody and photodynamic therapy (e.g., with MACUGEN™ or VISUDYNE™).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the HtrA1 binding antagonist (e.g., anti-HtrA1 antibody) and administration of an additional therapeutic agent occur within about one month, or within about one, two or three weeks, or within about one, two, three, four, five, or six days, of each other.

It is understood that any of the above formulations or therapeutic methods may be carried out using an immunoconjugate of the invention in place of or in addition to an anti-HtrA1 antibody.

J. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Development of Stable, High-potency, High-affinity Antibodies that Bind HtrA1

The goal of the following experiments was to discover new anti-HtrA1 antibodies having higher potency and higher affinity for HtrA1.

First, mHtrA1 knock-out mice were generated. It was necessary to use knock-out mice because initial efforts to generate hybridomas from mice expressing HtrA1 were not successful, likely because the murine and human HtrA11 proteins share 98% sequence identify.

Next, the HtrA1 knock-out mice were immunized with the protease domain of mHtrA1. The resulting hybridomas were screened by ELISA and 75 ELISA positive clones were identified. The 75 clones were tested for the ability to inhibit cleavage of an HtrA1 protease substrate. 10 of the 75 clones were shown to inhibit HtrA1 protease activity.

Seven of these clones were selected for further analysis based on their ability to inhibit protease activity, to bind human and murine HtrA1, and to selectively bind muHtrA1 over muHtrA3 and muHtrA4. These seven clones underwent further screening and four were found to have improved potency for HtrA1 when compared with the control antibody YW505.94. Two of these antibodies, 15H6 and 9B12, were selected for further development based on their preferred molecular profile, including potency and selectivity.

The hypervariable regions of the selected antibodies were grafted onto a human framework as outlined below. The importance of the mouse light chain Vernier references was tested for 15H6 by individually swapping these residues and testing binding to human and mouse HtrA1. One substitution abolished binding, two reduced binding, two affected only binding to murine HtrA1, and three did not have a significant impact on binding. These three substitutions were introduced into antibody 15H6.v1 to make antibody 15H6.v2

15H6.v2 was then was engineered to improve its stability. Potentially unstable residues that could lead to oxidation (W91 in HVR-L3), clipping (N94 P95 in HVR-LC), and deamidation (D55 G56 in HVR-H2) were identified. Substitutions of W91 substantially impacted binding. Four substitutions at position N94 were tested. Two of these substitutions impacted binding, but two were selected for additional analysis. Four substitutions at position D55 were tested. Only one of these substitutions showed comparable binding to the parent molecule.

The next step was to improve the affinity of h15H6.v2 binding to HtrA1. As a first step, deep sequencing was used to investigate the structure/function relationship for h15H6.v2. Of the many individual mutations tested in this experiment, approximately 19 individual mutations were found to improve affinity for HtrA1. Antibodies containing combinations the LC and HC mutations with the slowest off-rate were designed and tested, resulting in the identification of variant antibodies having improved potency and affinity for HtrA1. Variants having the best affinity and potency were also engineered to introduce the stabilizing substitutions described above. Of the resulting variants, h15H6.v4 was found to have the highest potency against HtrA1.

The structure of h15H6.v4 in Fab format bound to HtrA1 was determined by X-ray crystallography and electron microscopy. This structural analysis revealed that the h15H6.v4 Fab binds closely to the "LA loop" of the HtrA1 protein. The epitope bound by h15H6.v4 is distinct from that bound by control antibody YW505.94. Although it is not intended that the present invention be bound by any particular mechanism, it is possible that the close interaction between h15H6.v4 and the LA loop of HtrA1 explains the significantly improved affinity and potency of this antibody when compared with YW505.94.

The experiments described above are outlined in greater detail below.

Example 1: Generation of Anti-HtrA1 Antibodies Using Hybridoma Approaches

A. Media and Antibodies

CLONACELL™-HY Medium B (Cat#03802), Medium C (Cat#03803), Medium D (Cat#03804) and Medium E (Cat#03805) were from StemCell Technologies. CYTOFUSION® Medium C (Cat# LCM-C) used for electrofusion was from Cyto Pulse Sciences. Allophycocyanin (APC)-labeled goat F(ab')$_2$ anti-mouse Ig was from SouthernBiotech (Cat#1012-11), horseradish peroxidase (HRP)-conjugated goat anti-mouse IgG Fc antibody was from Sigma. TMB (3,3',5,5'-tetramethylbenzidine) One Component HRP Microwell Substrate (Cat# TMBW-1000-01) and TMB Stop Reagent (Cat# BSTP-1000-01) were from BioFx Laboratories.

B. In Vivo Immunization of Mice

Five HtrA1-knockout mice (HtrA1.noneo.BALB.ko.C1-3) were immunized with purified His-tagged recombinant murine HtrA1 protease domain (referred to herein as muHtrA1-PD-His, SEQ ID NO: 153; see Example 2 of WO 2013/055998) suspended in monophosphoryl lipid A/trehalose dicorynomycolate adjuvant by footpad injection (2 μg/injection per mouse) at 3 to 4 day intervals for a total of 12 boosts, followed by 2 pre-fusion boosts with antigen in phosphate-buffered saline (PBS). Three days after the final boost, lymphocytes from immunized mice spleens and lymph nodes were harvested and isolated. muHtrA1-PD-His was prepared for injection by purification as described in Example 2 of WO 2013/055998.

C. Cell Fusion, Hybridoma Screening, and Subcloning

Isolated mouse spleen cells from two mice (numbers 748 and 749) were fused with SP2/0 myeloma cells (American Type Culture Collection) using the Cyto Pulse CEEF-50 apparatus (Cyto Pulse Sciences). Briefly, after washing twice with CYTOFUSION® Medium C, the isolated spleen cells and SP2/0 cells were mixed at a 1:1 ratio and then resuspended in CYTOFUSION® Medium C at a concentration of 10 million cells/ml. Electrofusion was performed according to the manufacturer's guidance. Fused cells were cultured in CLONACELL™-HY Medium C overnight at 37° C. in a 7% CO$_2$ incubator. The next day, the fused cells were centrifuged and then resuspended in 10 ml CLONACELL™-HY Medium C and then gently mixed with 90 ml methylcellulose-based CLONACELL™-HY Medium D containing the selective reagents hypoxanthine, aminopterin and thymidine (HAT). The cells were plated into 40×100 mm Petri dishes (Cat#351029, Becton Dickinson) and allowed to grow in 37° C. in a 7% CO$_2$ incubator. After 10 days incubation, 1429 single hybridoma clones were picked using a CLONEPIX™ system (Genetix, United Kingdom) and transferred into 15×96-well cell culture plates (#353075, Becton Dickinson) with 200 μl/well CLONACELL™-HY Medium E. Hybridoma culture media were changed, and 3 days later hybridoma supernatants were screened by enzyme-linked immunosorbent assay (ELISA) to assay for binding to muHtrA1-PD-His.

Figure 1B:
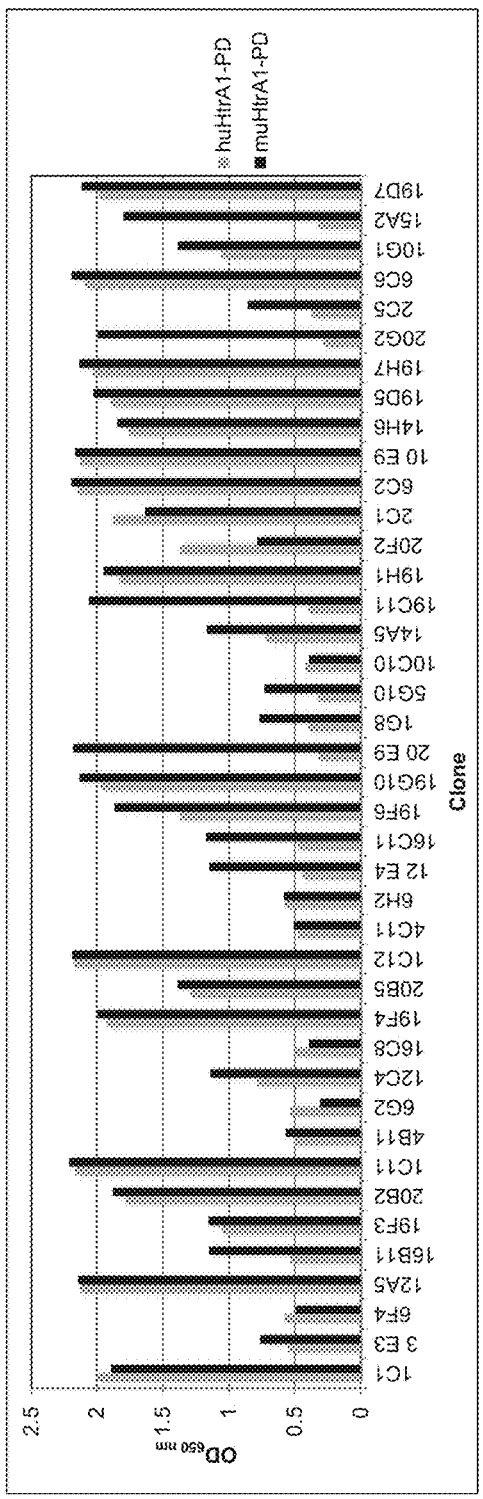

ELISA was performed according to a standard protocol. Briefly, 96-well microtiter ELISA plates (Greiner, Germany) were coated with 100 μl/well muHtrA1-PD-His or huHtrA1-PD-His (SEQ ID NO: 154) at 2 μg/ml in 0.05 M carbonate buffer (pH 9.6) at 4° C. overnight. After washing three times with wash buffer (0.05% TWEEN®20 in PBS, Sigma), plates were blocked with 100 μl ELISA assay diluents with BSA. 100 μl of cultured supernatants or diluted purified monoclonal antibodies (mAbs) were added and incubated for 1 h at room temperature. The plates were washed three times and incubated with HRP-conjugated goat anti-mouse IgG Fc for 1 h. After washing three times, bound enzyme was detected by addition of 100 μl/well of the TMB substrate (BioFX Laboratories) for 5 min. The reactions were stopped by adding 100 μl/well of stop reagent (BioFX Laboratories), followed by detection of color at absorbance 650 nm ($A_{650\ nm}$). 105 initial ELISA-positive supernatants were identified. After expansion and culturing for 3 days, these clones were rescreened in a subsequent ELISA which confirmed that 75 out of the 105 clones were still ELISA-positive for binding to muHtrA1-PD-His (FIGS. 1A and 1B). The majority of these 75 clones also bound to human HtrA1 protease domain (FIGS. 1A and 1B).

Figure 2A:
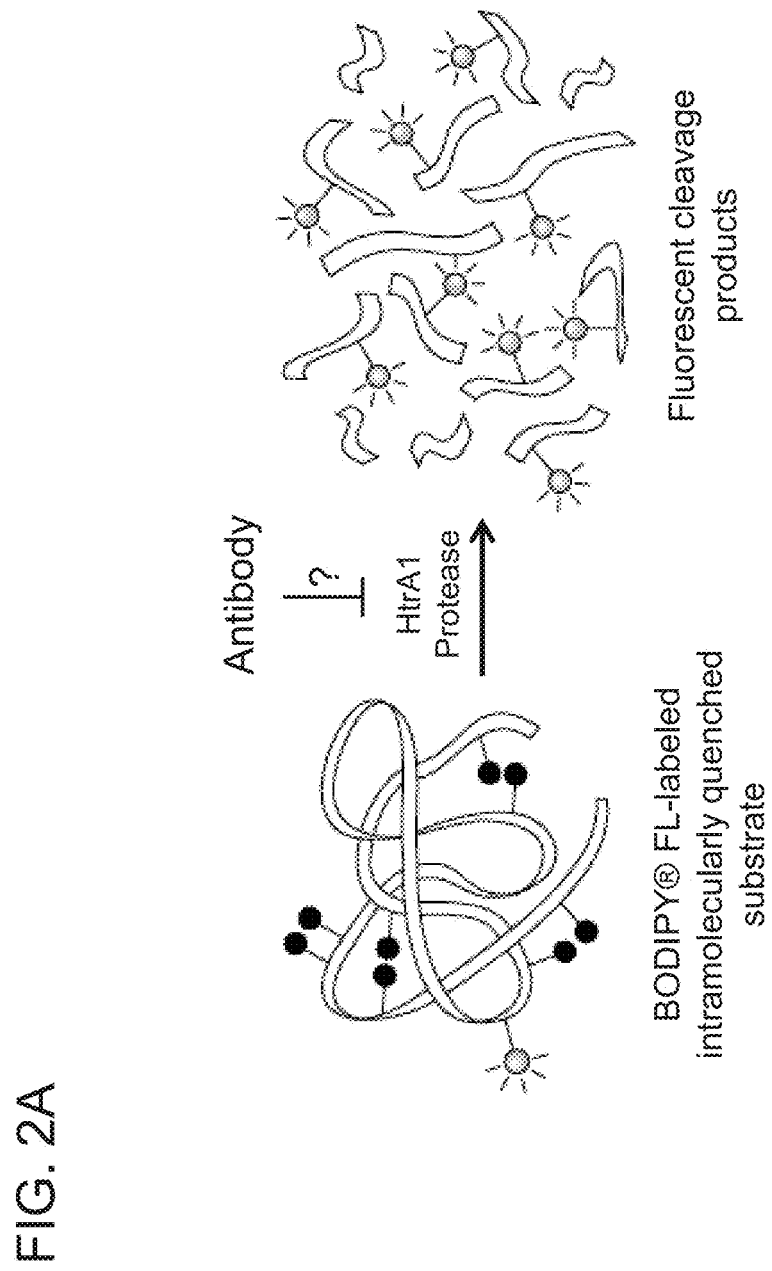
FIG. 2A is a schematic diagram of a blocking assay used to determine the ability of the indicated anti-HtrA1 hybridoma clone supernatants to inhibit HtrA1-PD-mediated cleavage of a BODIPY® FL-labeled fluorescent substrate.
Figure 2C:
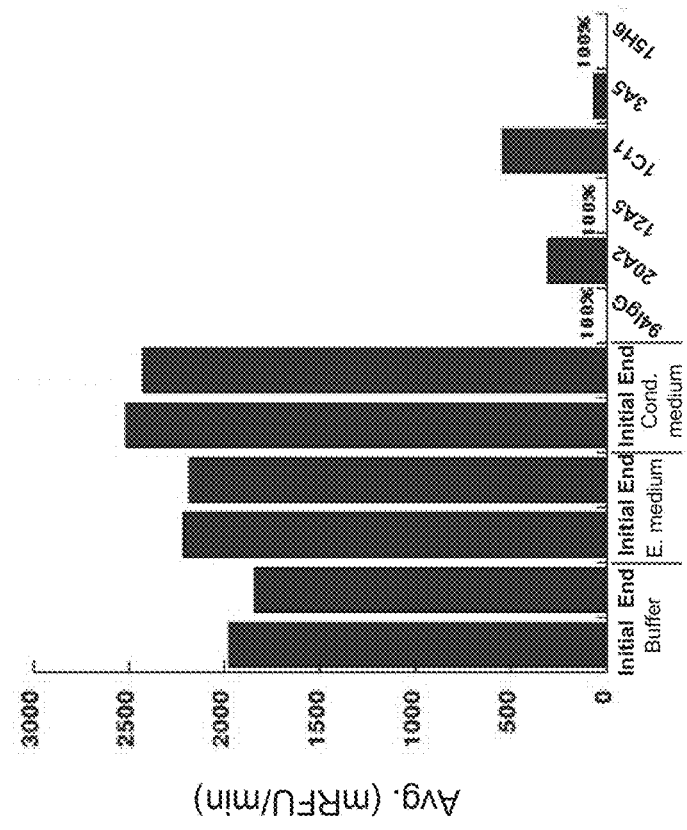
FIGS. 2B-2C are graphs showing that 10 anti-HtrA1 hybridoma clone supernatants markedly inhibited human HtrA1-PD-mediated substrate cleavage using the blocking assay described in FIG. 2A and Example 1. The graphs show the average fluorescent signal (milli relative fluorescent units (mRFU)/min) for the hybridoma supernatants from the indicated clones. Antibody YW505.94 (also referred to as "94 IgG," see International Patent Application Publication No. WO 2013/055998, which is incorporated herein by reference in its entirety) at 10 μg/ml in conditioned media (CM or cond. medium) served as a positive control to show that the assay showed no changes due to media and is stable over the assay time. Buffer or media served as negative controls.
Figure 2B:
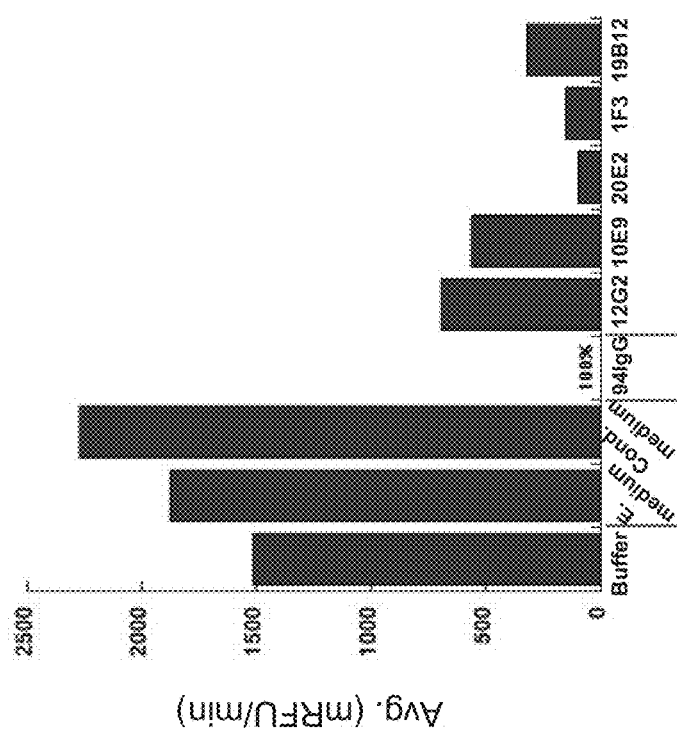
Figure 3A:
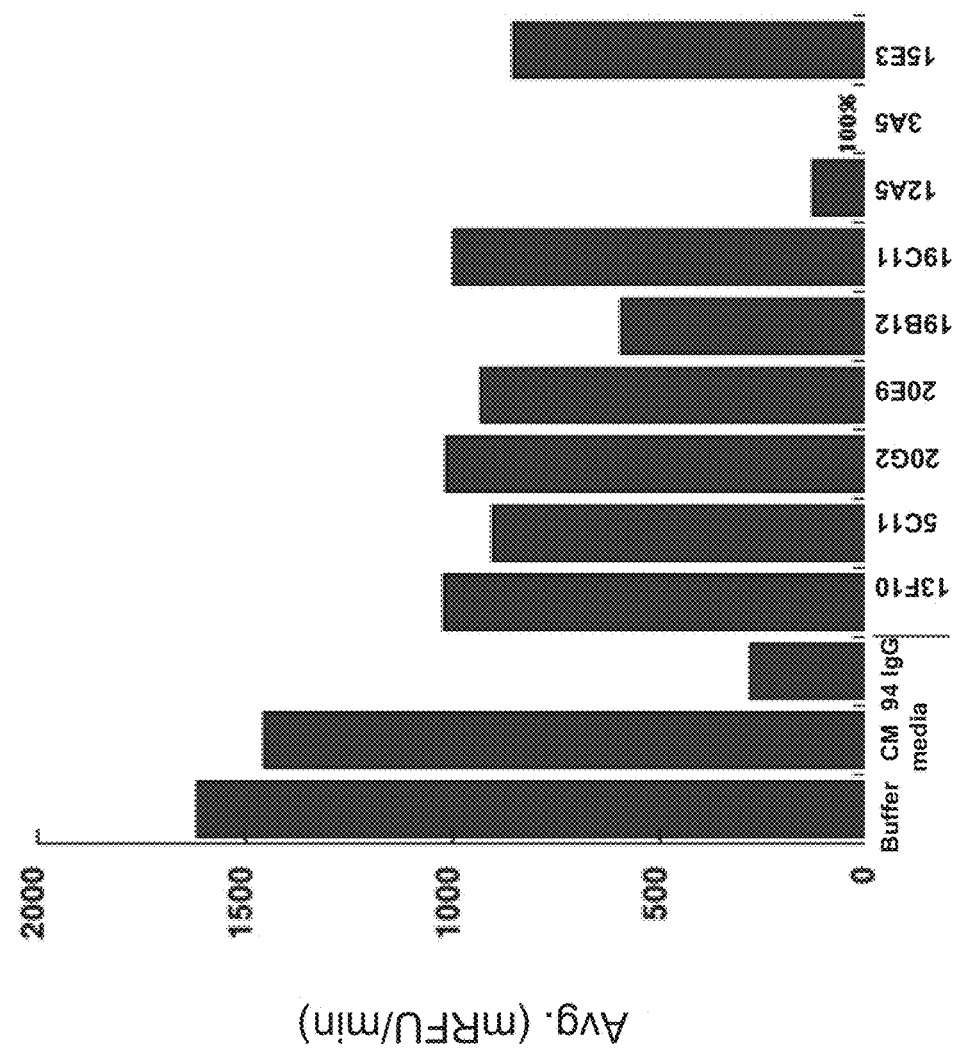
FIGS. 3A-3B are graphs showing the ability of the indicated hybridoma supernatants to inhibit cleavage of a fluorescent substrate by muHtrA1-PD (FIG. 3A) or huHtrA1-PD (FIG. 3B).
Figure 3B:
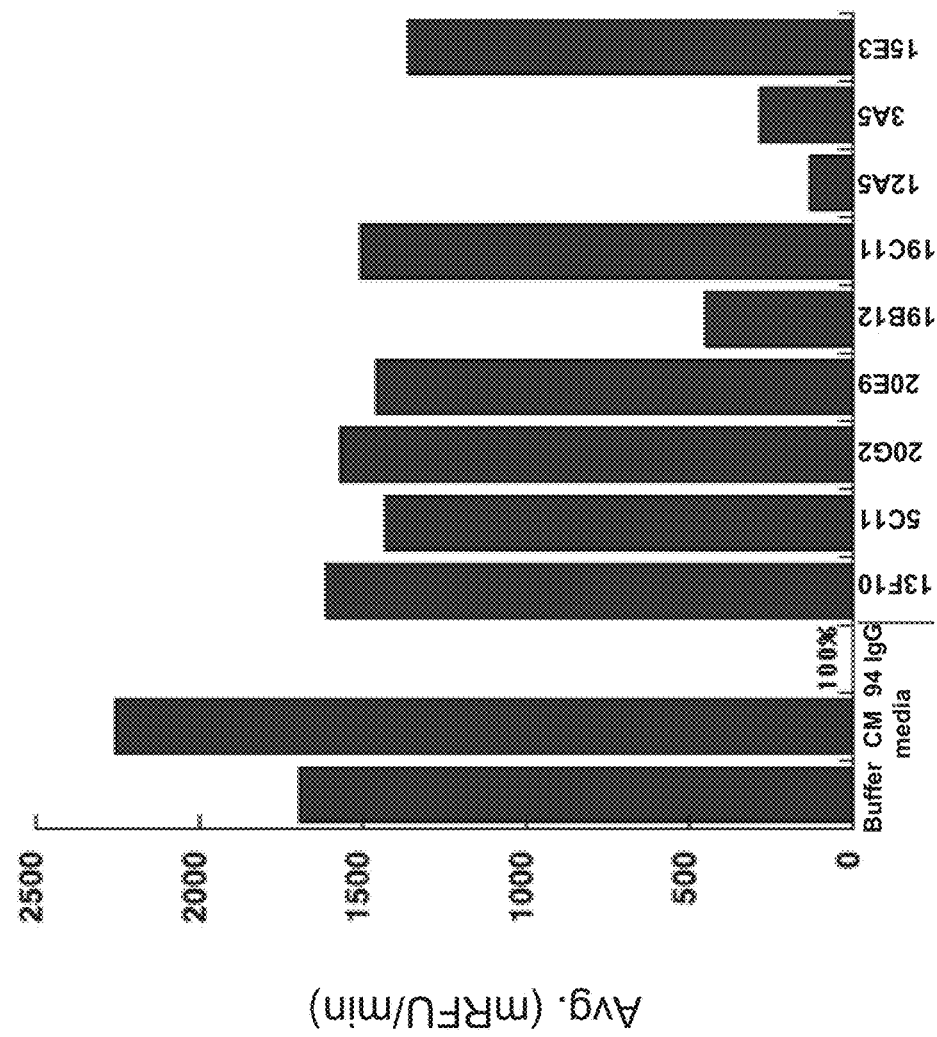

The 75 ELISA-positive clones were next tested using an in vitro assay to assess the ability of the hybridoma supernatant to inhibit cleavage of a substrate by the human HtrA1 protease domain (huHtrA1-PD-His; SEQ ID NO: 154). The ENZCHEK® Green Fluorescence Protease Assay (Thermo-Fisher Scientific) assay was used. This assay employs a casein derivative that is heavily labeled with the pH-insensitive green fluorescent BODIPY® FL dye as a substrate. The fluorescence of the BODIPY® FL dye is intramolecularly quenched in the full-length labeled substrate. Cleavage of the substrate by huHtrA1-PD releases fluorescent BODIPY® FL-labeled peptides, resulting in an increase in fluorescence signal (FIG. 2A). Briefly, the hybridoma supernatant and HtrA1-PD (20 nM hHtrA1-PD; 40 μl hHtrA1-PD to 60 μl supernatant) were incubated in a buffer (50 mM Tris, 200 mM NaCl, 0.25% CHAPS, pH 8.0) in a final volume of 200 μl for 20 min at 37° C. 5 μg/ml of the BODIPY® FL-labeled substrate was added, and the fluorescence (milli relative fluorescence units (mRFU)/min) was read for 20 min. Using this blocking assay, 10 out of the 75 clones were found to inhibit human HtrA1-PD-mediated substrate cleavage (FIGS. 2B and 2C). FIGS. 3A and 3B show a comparison of the ability of a subset of clones to inhibit the activity of muHtrA1-PD compared to huHtrA1-PD.

After at least 2 rounds of single cell subcloning by limiting dilution, 7 clones with varying characteristics (20E2, 19B12, 12A5, 3A5, 15H6, 15E3, and 19G10) were scaled up and the supernatants were collected for antibody purification and further assessment. These clones were chosen, in part, based on the ability to inhibit HtrA1 activity in vitro and binding to muHtrA3 (19B12). The 7 clones were also tested for the ability to detect muHtrA1 in an immunohistochemistry as well as for the ability to bind murine HtrA3-PD and murine HtrA4-PD (as assessed by ELISA). Table 2 shows a summary of qualitative properties of these 7 clones.

TABLE 2

Properties of 7 Final Clones Selected for Antibody Purification

| Clone | Isotype | Binds muHtrA1-PD | Binds huHtrA1-PD | Blocks hu/muHtrA1-PD Substrate Cleavage | muHtrA1 IHC positive | Binds muHtrA3-PD | Binds muHtrA4-PD |
|---|---|---|---|---|---|---|---|
| 20E2 | mIgG2a | Yes | Yes | Yes | No | No | No |
| 19B12 | mIgG2a | Yes | Yes | Yes | No | Slightly | No |
| 12A5 | mIgG2b | Yes | Yes | Yes | Yes | No | Yes |
| 3A5 | mIgG2a | Yes | Yes | Yes | Yes | No | No |
| 15H6 | mIgG2a | Yes | Yes | Yes | Yes | No | No |
| 15E3 | mIgG2a | Yes | No | Slightly | No | Yes | Yes |
| 19G10 | mIgG2a | Yes | Yes | No | Yes | Yes | Yes |

The next step was to determine whether the seven antibodies selected above inhibited HtrA1-mediated cleavage as measured in a FRET Assay.

The hybridoma supernatants were purified by Protein A affinity chromatography, followed by sterile filtration (0.2 μm pore size, Nalge Nunc International, NY, USA), and storage at 4° C. in PBS. The purified monoclonal antibodies were confirmed by ELISA and FACS before further testing in functional assays. The isotypes of purified mAbs were determined by the ISOSTRIP™ mouse monoclonal antibody isotyping kit (Roche Diagnostics Corporation).

Figure 4A:
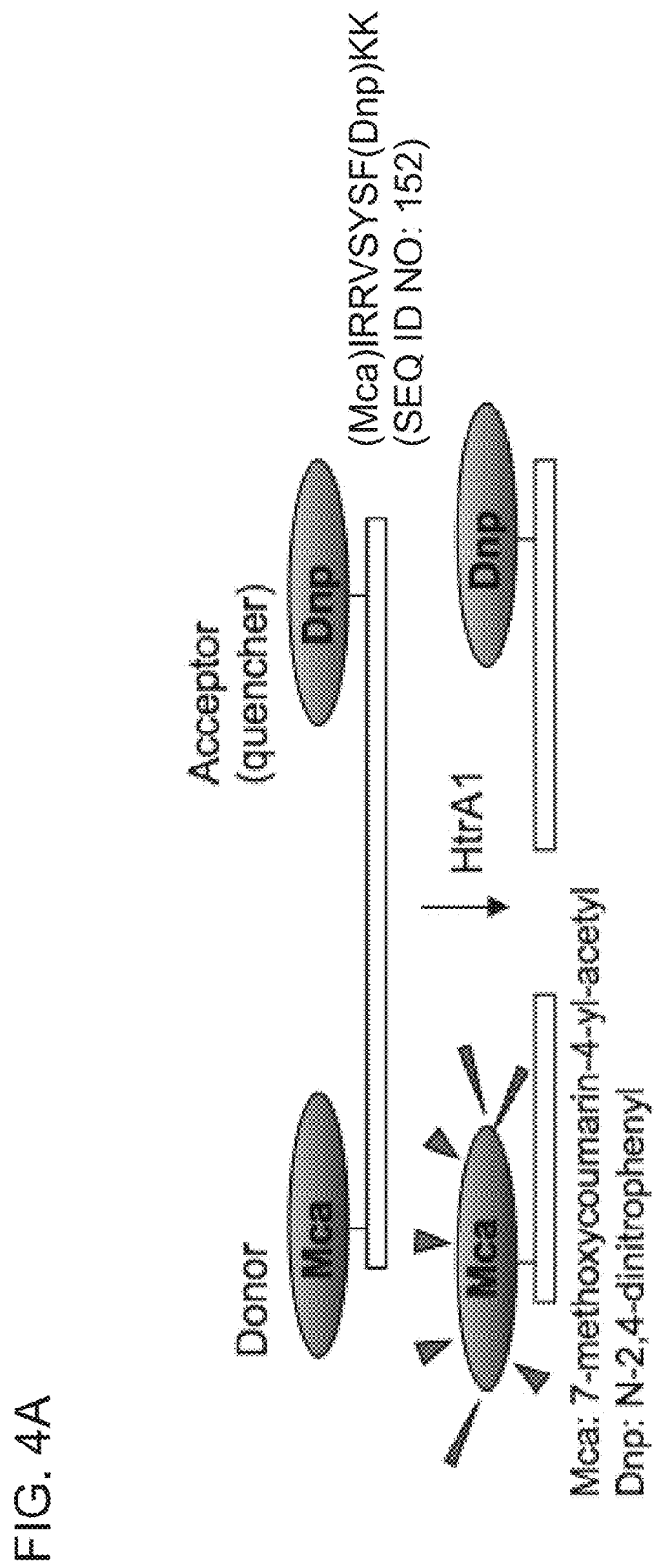
FIG. 4A is a schematic diagram of a FRET-based blocking assay used to determine the ability of purified anti-HtrA1 antibody clones to inhibit HtrA1-PD-mediated cleavage of a FRET-based substrate, H2-Opt.
Figure 4B:
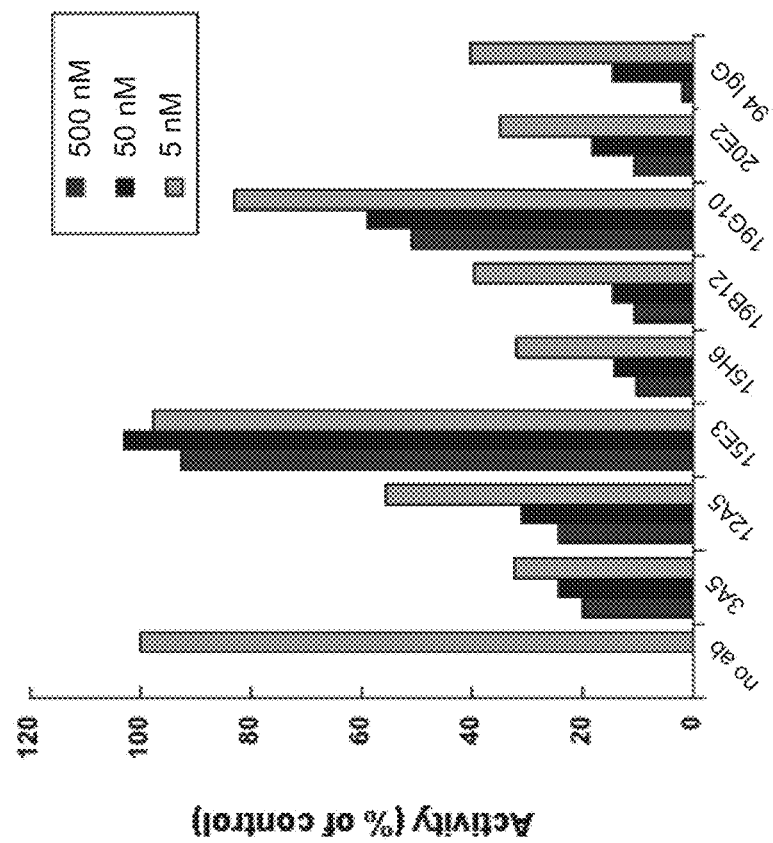
FIGS. 4B-4C are graphs showing that purified antibody clones 15H6, 19B12, 3A5, 12A5, and 20E2 retained the ability to inhibit murine (FIG. 4B) and human (FIG. 4C) HtrA1-PD-mediated substrate cleavage. The addition of no antibody ("no ab") served as a negative control, while antibody YW505.94 ("94 IgG") served as a positive control. The purified antibodies were added at concentrations of 5 nM, 50 nM, or 500 nM. 15 nM or muHtrA1-PD-Fc was used in the assay presented in FIG. 4B, while 3 nM of huHtrA1-PD-Fc was used in the assay presented in FIG. 4C.
Figure 4C:
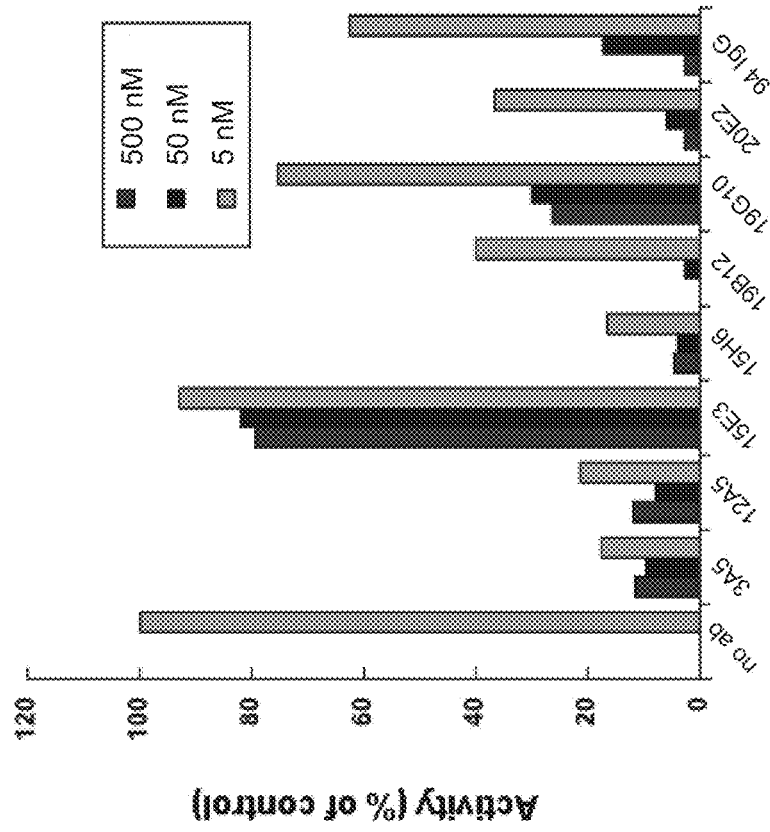

The purified antibodies were tested for the ability to inhibit the activity of HtrA1 in a FRET-based blocking assay (e.g., H2-Opt assay). In this assay, the ability of the antibody to inhibit the cleavage of a fluorescence resonance energy transfer (FRET, also referred to as Farster resonance energy transfer) substrate was determined. The FRET peptide substrate H2-Opt, which has a molecular weight of 1600 Da, includes the donor Mca (7-methoxycoumarin-4-yl-acetyl) and the acceptor (quencher) Dnp (N-2,4-dinitrophenyl). The full-length sequence of the FRET peptide substrate is (Mca) IRRVSYSF(Dnp)KK (SEQ ID NO: 152). In the intact peptide substrate, the quenching moiety Dnp quenches the fluorescence of the Mca donor. Proteolytic cleavage of the FRET peptide substrate separates the fluorophore and quencher, thereby relieving the quenching of Mca fluorescence and resulting in an increased fluorescent signal (FIG. 4A). The assay was performed using the H2-Opt assay conditions described below in Example 3, Section F. The time-dependent increase in fluorescence intensity is related to the extent of substrate hydrolysis. The antibodies were tested at concentrations of 5 nM, 50 nM, and 500 nM. Five of the purified anti-HtrA1 antibodies (15H6, 19B12, 3A5, 12A5, and 20E2) retained the ability to block human and murine HtrA1-PD-mediated substrate cleavage (FIGS. 4B and 4C).

Figure 5B:
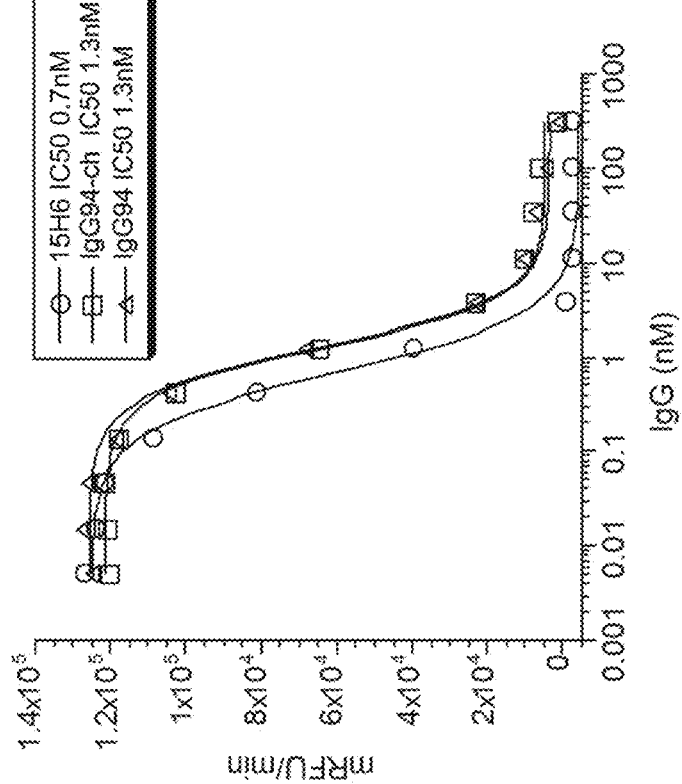
FIGS. 5A-5B are graphs showing that the indicated purified mIgG antibody clones inhibit full-length human HtrA1 (huHtrA1-FL)-mediated cleavage of a FRET peptide substrate. The graph shows activity (mRFU/min) as a function of IgG concentration. huHtrA1-FL was added at a concentration of 5 nM. YWV505.94 in IgG format ("IgG94") and a chimeric variant thereof ("IgG94-ch") as described in Cifferi et al. (2015) Biochem. J. 472(2):169-81 served as positive controls. The half maximal inhibitory concentration (IC50) for each antibody clone is shown.
Figure 5A:
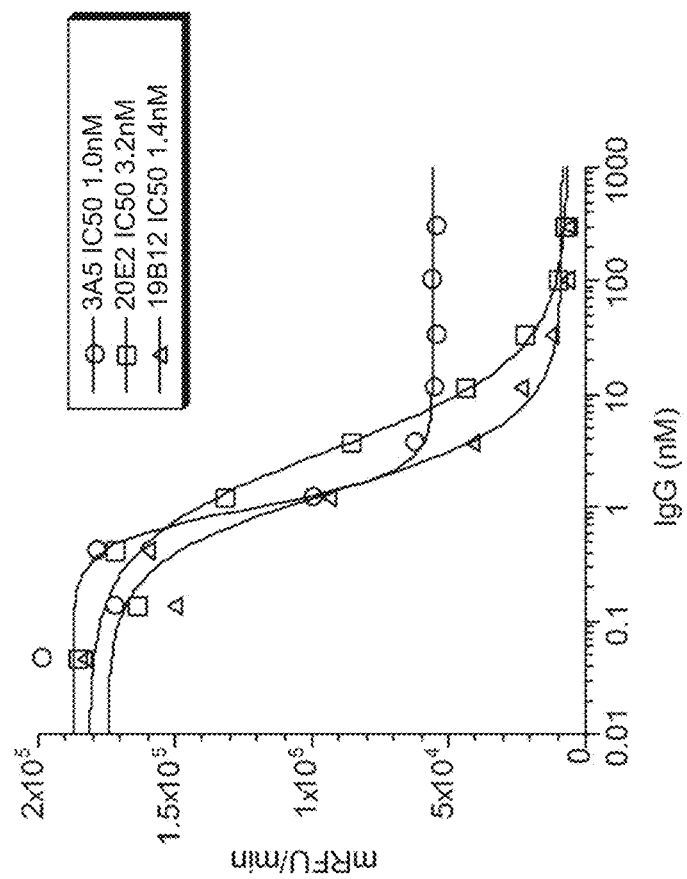
Figure 5D:
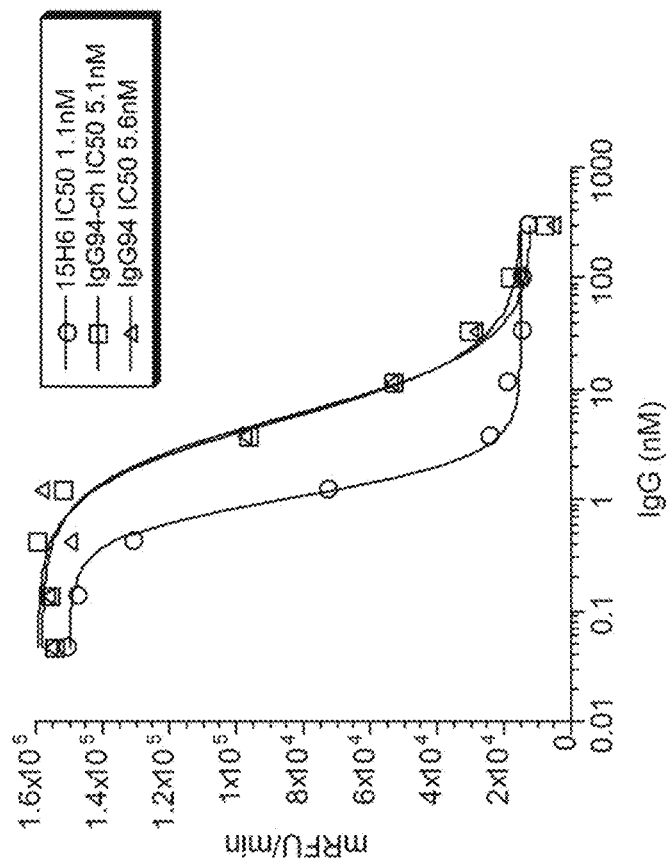
FIGS. 5C-5D are graphs showing that the indicated purified mIgG antibody clones inhibit muHtrA1-FL-mediated cleavage of a FRET peptide substrate. The graph shows activity (mRFU/min) as a function of IgG concentration. muHtrA1-FL was added at 5 nM. IgG94 and IgG94-ch served as positive controls as described in the Figure description for FIGS. 5A and 5B. The half maximal inhibitory concentration (IC50) is shown.
Figure 5C:
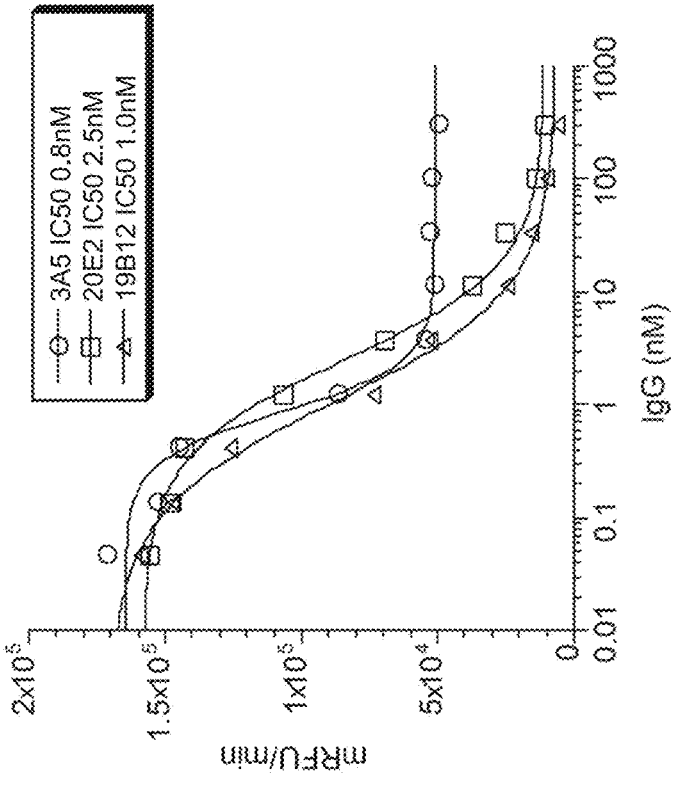
Figure 6A:
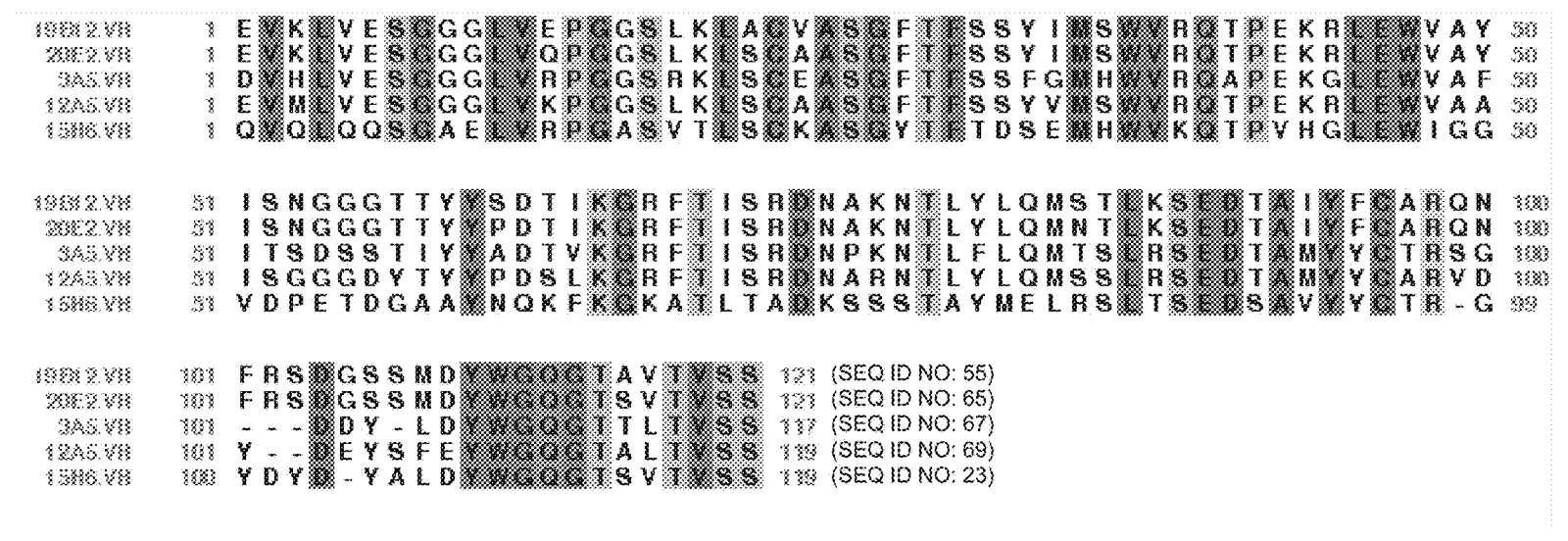
Figure 6B:
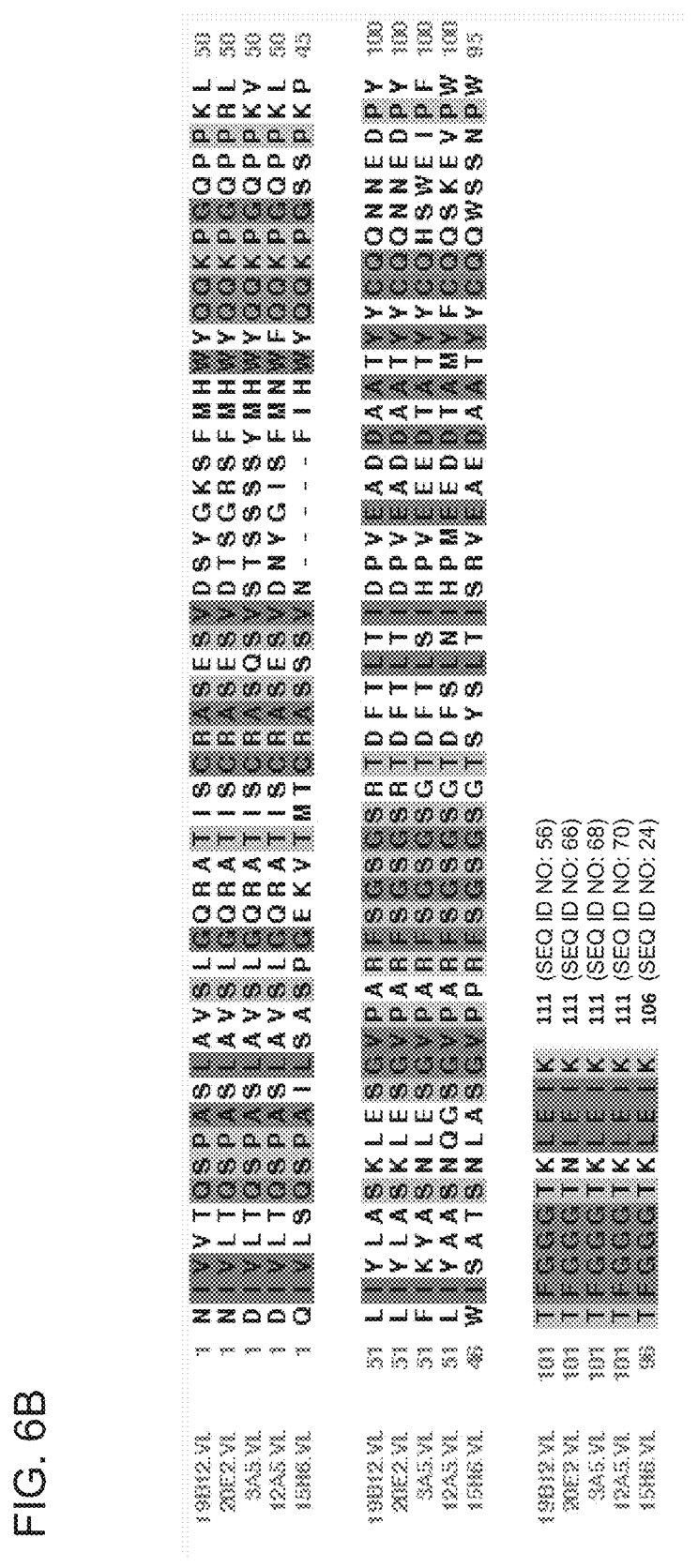

Next, the ability of the purified antibodies to inhibit full-length HtrA1-mediated substrate cleavage was tested. The FRET-based blocking assay described in the preceding paragraph was employed using purified full-length (FL) muHtrA1 or huHtrA1. muHtrA1-FL and huHtrA1-FL were purified as described in Example 2 of WO 2013/055998. The purified antibodies, including 15H6 and 19B12, inhibited the activity of huHtrA1-FL (FIGS. 5A-5B) and muHtrA1-FL (FIGS. 5C-5D). In this assay, clone 15H6 inhibited huHtrA1-FL with an IC50 of 0.7 nM, which was approximately two-fold improved compared to the IC50 of the positive control antibody YW505.94. 15H6 inhibited muHtrA1-FL with an IC50 of 1.1 nM, which was almost 5-fold improved compared to the positive control antibody YW505.94. Clone 19B12 inhibited huHtrA1-FL with an IC50 of 1.4 nM, and inhibited muHtrA1-FL with an IC50 of 1.0 nM. The selected antibodies were sequenced as described below in Section D. The sequences of these five antibodies are shown in FIG. 6A and FIG. 6B. Two antibodies, 15H6 and 19B12, were selected for further development based on their preferred molecular profile including their potency and their selectivity. The reformatting of these antibodies is described below in Section E, D. Antibody Sequencing from Hybridoma Clones i. Cloning Variable Region Gene Sequences from Hybridoma Cells Using 5'-Rapid Amplification of cDNA Ends (5'-RACE) in a 96-Well Format For each hybridoma clone, about 25 μl of log-phase-growing cells (0.5-1.0×10⁶ cells/ml) were transferred from tissue culture plates to wells of a 96-well U-bottom plate. 150 μl of cold 1×PBS was then added to wash the cells before spinning down at 1000 rpm for 5 min. The supernatant was removed and the cell pellet was resuspended in 25 μl of cold 1×PBS.

ii. Reverse Transcription-Polymerase Chain Reaction (RT-PCR) Reaction

A master mix consisting of the following was prepared (for 50 wells) in an Eppendorf tube: 2.5 μl of RNASE-OUT™ (Invitrogen #10777019), 12.5 μl of 10× Synthesis Buffer (5× SUPERSCRIPT® buffer), 12.5 μl of dithiothreitol (DTT) (0.1M Invitrogen #P/NY00147), 6.25 μl of dNTPs (10 mM Invitrogen #18427-013), 12.5 μl of 2.5% nonyl phenoxypolyethoxylethanol (NP-40), 6.25 μl of bovine serum albumin (BSA) at 2 mg/ml (BioLabs #9001S), 25 μl of RACE4muHC primer (1:100 in PCR grade water) (Race 3 kappa primer was substituted for sequencing the light chain (LC)), 37.5 μl of PCR-grade water, and 10 μl of SUPERSCRIPT@ 3 enzyme (Invitrogen #18080-093). The Race4muHC degenerate primer nucleotide sequence is TTT YTT GTC CAC CKT GGT GCT GC (SEQ ID NO: 139), where Y encodes for C or T, and K encodes for G or T. The Race 3 kappa primer nucleotide sequence is GTA GAA GTT GTT CAA GAA G (SEQ ID NO: 140).

2.5 μl/well of master mix was then transferred to a 96-well PCR reaction plate. 1 μl of cells/well was added to the plate, the plate was spun briefly for 30 seconds, and then the plate was shaken. The plate was set into the PCR machine and the program was set to 30 min at 45° C. followed by 30 minutes at 50° C. This plate was labeled as Plate A.

iii. Tailing Reaction

A 10× stock tailing buffer was made with the following ingredients (for 50 wells): 5 μl of 1 M MgCl₂, 5 μl of 0.1 M DTT, 5 μl of 1 M Tris pH 7.5, 10 μl of 100 mM dGTP, and 25 μl of PCR-grade water.

A working solution was made with the following ingredients (for 50 wells): 50 μl of the 10× stock tailing buffer, 312.5 µl of PCR-grade water, and 12.5 µl of 300-unit Terminal Deoxynucleotidyl Transferase (TdT) (Promega #M828A/C).

This working solution was then added to the PCR reaction Plate A at 7.5 µl/well. Plate A was then placed into the PCR machine for 1 h at 37° C. followed by 5 min at 65° C. This plate was labeled as Plate A/B to distinguish tailing of this plate.

iv. First PCR Reaction

A master mix consisting of the following was prepared (for 50 wells) in a 15-mL Falcon tube: 1050 µl of PCR-grade water, 500 µl of 5×GC cDNA PCR reaction buffer, 500 µl of GC-melt reagent (Clontech #S1091), 50 µl of the forward primer DC5dn, 50 µl of Race7muHC (Race 2 kappa primer for LC), 50 µl of dNTP (10 mM), and 50 µl of GC ADVANTAGE® polymerase (Clontech #S1088). The Race7muHC degenerate primer nucleotide sequence is CAR GTC AMD GTC ACT GRC TCA G (SEQ ID NO: 141), where R encodes either A or G, M encodes either A or C, and D encodes either G or A or T. The Race 2 kappa primer nucleotide sequence is GAG GCA CCT CCA GAT GTT AAC (SEQ ID NO: 142).

45 µl of this master mix was then transferred into wells of a new PCR reaction plate and 1 µl of the template from Plate A/B was then added. This plate was then placed into the PCR machine and run under a Touchdown PCR method with decreasing annealing temperatures, as listed below. This plate was labeled Plate C.

Touchdown PCR Method:

96° C. for 4 min 3 cycles of [96° C. for 45 sec, 64° C. for 30 sec, 68° C. for 90 sec], 3 cycles of [96° C. for 45 sec, 61° C. for 30 sec, 68° C. for 90 sec], 3 cycles of [96° C. for 45 sec, 58° C. for 30 sec, 68° C. for 90 sec], 3 cycles of [96° C. for 45 sec, 57° C. for 30 sec, 68° C. for 90 sec], 3 cycles of [96° C. for 45 sec, 55° C. for 30 sec, 68° C. for 90 sec]

25 cycles of [96° C. for 45 sec, 52° C. for 30 sec, 68° C. for 90 sec]

68° C. for 5 min, followed by a 4° C. end hold.

Afterwards, 3 µl of PCR product was run on a 2% ethidium bromide (EtBr) E-GEL® and bands were checked. ExoI/shrimp alkaline phosphatase (SAP) was added at 10 µl/well and placed in the PCR machine for 45 min at 37° C. followed by 15 min at 85° C. ExoI/SAP master mix was made for 50 wells: 2.5 µl of 20 unit/µl Exonuclease I (Fermentas #EN0582), 25 µl of SAP (USB #70092Y), 472.5 µl of PCR-grade water. A 1:4 dilution of the PCR product was made in water. The Race7muHC primer was used for sequencing the heavy chain (HC) and the Race7.1muLC primer was used for sequencing the LC. The Race7.1 muLC primer nucleotide sequence is ACT GCT CAC TGG ATG GTG GGA AG (SEQ ID NO: 143).

v. Gel Filtration and Mass Spectrometry Characterization

For gel filtration analysis, 10 ml of purified sample was injected onto TSK-GEL® Super SW3000 (4.6 mm inner diameter×30 cm, TOSOH Bioscience) at 0.35 ml/min using 200 mM $K_2PO_4$, 250 mM KCl, pH 7.0 as the mobile phase. Approximately 2 mg of purified IgG was reduced with 50 mM dithioreitol at 37° C. for 20 min and analyzed by time-of-flight (TOF) mass spectrometry (Agilent LC/MS 6224) after on-line reversed-phase separation using a PLRP-S column (Agilent) and acetonitrile gradient. Intact masses were determined by maximum entropy deconvolution of collected m/z spectra using MassHunter Qualitative Analysis software (Agilent).

vi. Results

The sequences of the heavy chain variable region (VH) for 19B12, 20E2, 3A5, 12A5, and 15H6 are shown in FIG. 6A. The sequences of the light chain variable region (VL) for 19B12, 20E2, 3A5, 12A5, and 15H6 are shown in FIG. 6B. These clones have unique heavy and light chains. Mass spectrometry data corroborated the sequence data (see Tables 3 and 4) (see, e.g., Bos et al. *Biotechnol. Bioeng.* 112(9): 1832-1842, 2015).

TABLE 3

HC Masses as determined by Mass Spectrometry

| Clone | HC Masses (Daltons) |
|---|---|
| 19B12 | 51130 |
|  | 50968 |
| 20E2 | 51006 |
|  | 51168 |
| 3A5 | 50684 |
|  | 50846 |
| 12A5 | 51355 |
|  | 51193 |
| 15H6 | 50828 |
|  | 50666 |
|  | 50990 |

TABLE 4

LC Masses as determined by Mass Spectrometry

| Clone | LC Masses (Daltons) |
|---|---|
| 19B12 | 23970 |
| 20E2 | 23963 |
| 3A5 | 23966 |
| 12A5 | 23895 |
| 15H6 | 23230 |

E. Reformatting Antibodies 15H6 and 19B12 i. TOPO® Cloning of Antibodies 15H6 and 19B12

TOPO® cloning was performed to confirm the variable region sequences of antibody clones 15H6 and 19B12 obtained from direct sequencing of the 5'-RACE PCR products (described above). The TOPO® TA cloning reaction was done as described in the pCR™4-TOPO® TA Cloning Kit for Sequencing (Invitrogen K4575-02) manual. Briefly, 2 µl of the PCR product, 2 µl of water, 1 µl of the pCR™4-TOPO® vector, and 1 µl of the included salt solution were combined in a tube, mixed, and incubated for 5 min at room temperature. The reaction was then placed on ice and 2 µl of this TOPO® Cloning reaction was added to a thawed vial of ONE-SHOT® chemically competent TOP10 *Escherichia coli* cells (Invitrogen K4575-02) and mixed without pipetting. The reaction was incubated on ice for 5-30 min. Cells were then heat-shocked for 30 sec at 42° C. without shaking. Tubes were immediately transferred to ice. 250 µl of room temperature SOC medium was added. The tube was capped and shaken horizontally at 200 rpm at 37° C. for 1 h. Next, 50 µl from each transformation was spread onto a pre-warmed LB agar plate containing 50 µg/ml of carbenicillin. Plates were incubated at 37° C. overnight, colonies were picked the next day, and plasmid purification was performed. Sequences were verified and particular wells containing 15H6 VH and VL and 19B12 VH and VL sequences each in a TOPO® vector were selected for use as source vectors in restriction-free cloning.

ii. Restriction-Free Cloning into mIgG2a

Heavy and light chain variable regions in the TOPO® vectors were amplified by setting up a PCR mix in the following way for the LC: 0.5 µl of template DNA (miniprep source vector), 4 µl of 15H6 VL forward primer, 4 µl of 15H6 VL reverse primer, 2 µl of 10 mM dNTPs, 20 µl of 5×HF Buffer, 1 µl of PHUSION® polymerase (F-549L, Thermo Scientific, 2 U/µl), and 68.5 µl of water. The reaction mix for cloning the HC was set up the same way except that 15H6 VH forward and reverse primers were used. 19B12 PCR mixes were set up in the same way as the 15H6 mixes except that 19B12 primers were used. The primer sequences were as follows:

```
15H6 VL forward primer nucleotide sequence:
                                        (SEQ ID NO: 144)
GCA ACT GCA ACT GGA GTA CAT TCA CAA
ATT GTT CTC TCC CAG TCT CC.

15H6 VL reverse primer nucleotide sequence:
                                        (SEQ ID NO: 145)
GGA TAC AGT TGG TGC AGC ATC AGC CCG
TTT GAT TTC CAG CTT GG.

15H6 VH forward primer nucleotide sequence:
                                        (SEQ ID NO: 146)
GCA ACT GCA ACT GGA GCG TAC GCC CAG
GTC CAG CTG CAG CAG TCT GG.

15H6 VH reverse primer nucleotide sequence:
                                        (SEQ ID NO: 147)
GGG CCC TTG GTG GAG GCT GAG GAG ACG
GTG ACT GAG GTT CCT TGA CCC.

19B12 VL forward primer nucleotide sequence:
                                        (SEQ ID NO: 148)
GCA ACT GCA ACT GGA GTA CAT TCA AAC
ATT GTG GTG ACC CAA TCT CC.

19B12 VL reverse primer nucleotide sequence:
                                        (SEQ ID NO: 149)
GGA TAC AGT TGG TGC AGC ATC AGC CCG
CTT TAT TTC CAG CTT GG.

19B12 VH forward primer nucleotide sequence:
                                        (SEQ ID NO: 150)
GCA ACT GCA ACT GGA GCG TAC GCC GAG
GTG AAG CTG GTG GAA TCT GGG GGA GG.

19B12 VH reverse primer nucleotide sequence:
                                        (SEQ ID NO: 151)
GGG CCC TTG GTG GAG GCT GAG GAG ACG
GTG ACT GCG GTT CCT TGA CCC.
```

The PCR cycling conditions were as follows:
98° C. for 30 seconds
35 cycles of [980° C. for 15 seconds, 68° C. for 30 seconds, 72° C. for 35 seconds]
72° C. for 10 minutes Amplified VH and VL were used as primers to amplify template DNA by setting up the PCR mix in the following way for 15H6 LC: 1.25 µl of template mIgG2a PRK vector DNA (1:10 dilution of miniprep), 0.5 µl of 15H6 VL PCR product (100-200 ng/µl), 1 µl of 10 mM dNTPs, 10 µl of HF Buffer (5×), 1 µl of PHUSION® polymerase, and 35.75 µl of water. The 15H6 HC PCR mix was set the same way except that the 15H6 VH PCR product was used. The 19B12 PCR mixes were set up the same way except that 19B12 PCR products were used.

The PCR cycling conditions were as follows:
98° C. for 30 seconds
25 cycles of [98° C. for 15 seconds, 68° C. for 30 seconds, 72° C. for 4 minutes]
72° C. for 10 minutes 18 µl of PCR reaction was then transferred to a new tube and digested with 2 µl of DpnI (#RO176L, NEB 20,000 U/ml) for 2 h at 37° C., with the tube spun periodically. 30 µl of competent NOVABLUE SINGLES™ competent cells (Novagen, 70181) were transformed with 1 µl of DpnI digest according to the manufacturer's instructions. Briefly, cells were thawed, DNA was added, and cells were incubated on ice for 5 min before being heat-shocked for 30 sec, placed back on ice for 2 min, followed by addition of SOC medium. 25 µl or 50 µl were plated on 50 µg/ml carbenicillin-containing plates and set at 37° C. overnight. Colonies were picked the next day, plasmid purification was performed via miniprep, and plasmids were sequenced.

iii. Antibody Purification

Automated purification from 293 cell supernatants was performed on a Tecan Freedom EVO® 200 liquid handling system with a 500 ml MCA96 head. Briefly, IgGs were captured using tip columns that were custom-packed with 20 ml MABSELECT SURE™ resin (Glygen Corp., Columbia, Md. & GE Healthcare, Pittsburgh, Pa.). After washing with 1×PBS pH 7.4, IgGs were eluted into 160 ml of 50 mM phosphoric acid, pH 3, and neutralized with 12 ml of 20×PBS pH 11. MABSELECT SURE™ tip columns were stripped in 0.1 M NaOH and regenerated with 1×PBS pH 7.4 for consecutive use of up to 15 times. Similarly, Fabs were captured using tip columns packed with 20 mL GAMMA-BIND™ Plus resin (Glygen Corp & GE Healthcare) and were subsequently washed with 1×PBS pH 7.4. Fabs were eluted into 190 ml of 10 mM citrate, pH 2.9, and neutralized with 19 ml 0.4 M Tris pH 8.7. GAMMABIND™ Plus tip columns were stripped with 6 M guanidine and regenerated with 1×PBS pH 7.4 for consecutive use of up to 15 times.

iv. Recombinant 15H6 and 19B12 Antibodies Retain Original Blocking Activities

Figure 7B:
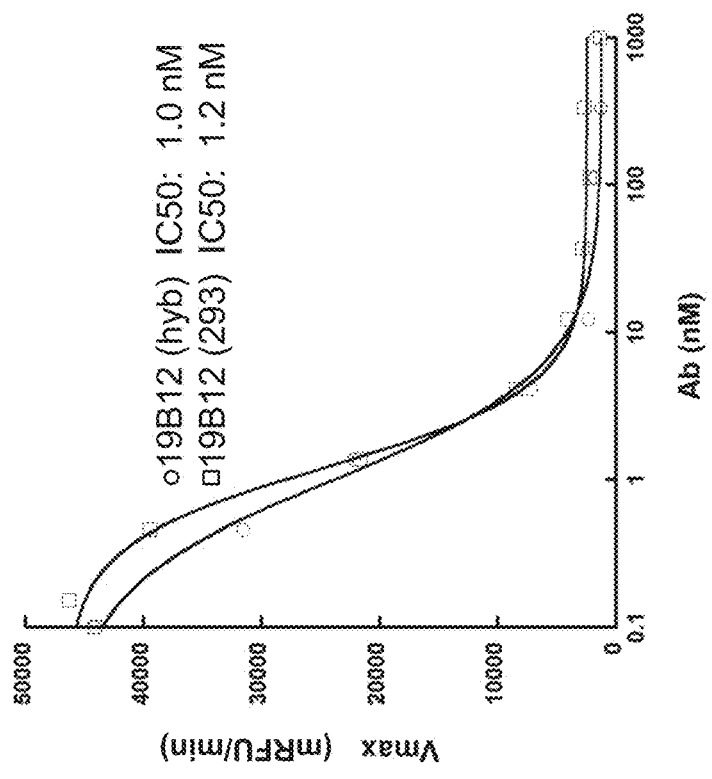
FIGS. 7A-7B are graphs showing the results of a FRET-based blocking assay using mIgG antibody clone 15H6 (FIG. 7A) or clone 19B12 (FIG. 7B) purified from hybridoma supernatant ("hyb") or recombinantly expressed from 293 cells ("293"). The graphs plot Vmax (mRFU/min) as a function of antibody concentration (nM). 3 nM of huHtrA1-FL was used in each assay. The IC50 values for the indicated antibody clones are also shown.
Figure 7A:
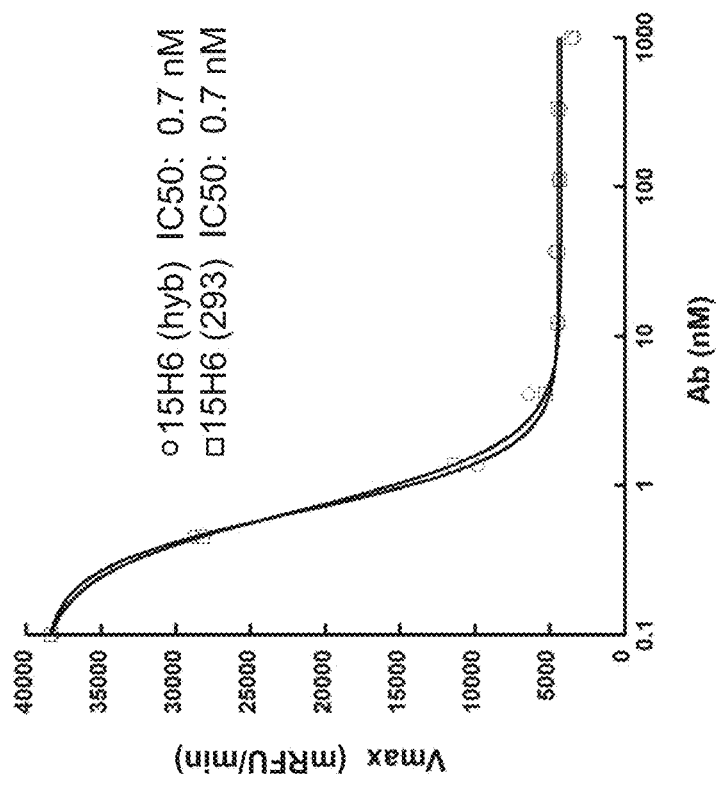
Figure 9A:
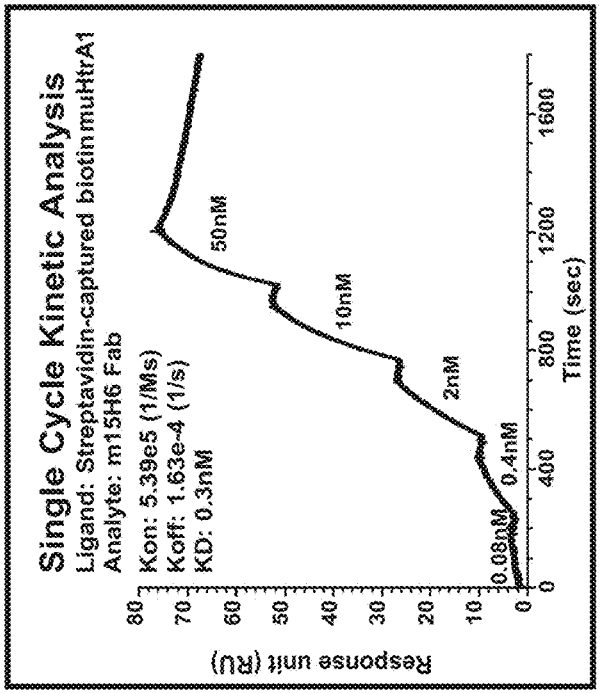
FIGS. 9A-9D are graphs showing the results of BIACORE™ surface plasmon resonance (SPR) analysis of binding of m15H6 or h15H6.v1 to streptavidin-captured biotinylated human or murine HtrA1. Single cycle kinetic analysis was employed. The graphs show response units (RU) as a function of time (sec).
Figure 9B:
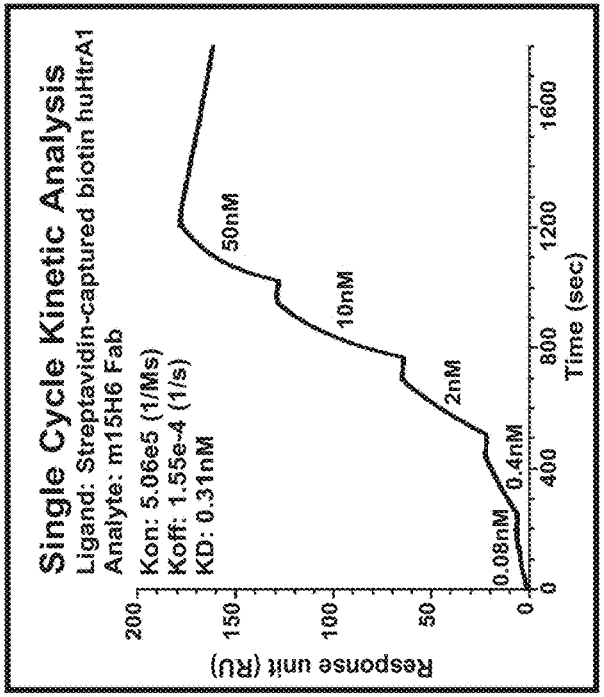
Figure 9C:
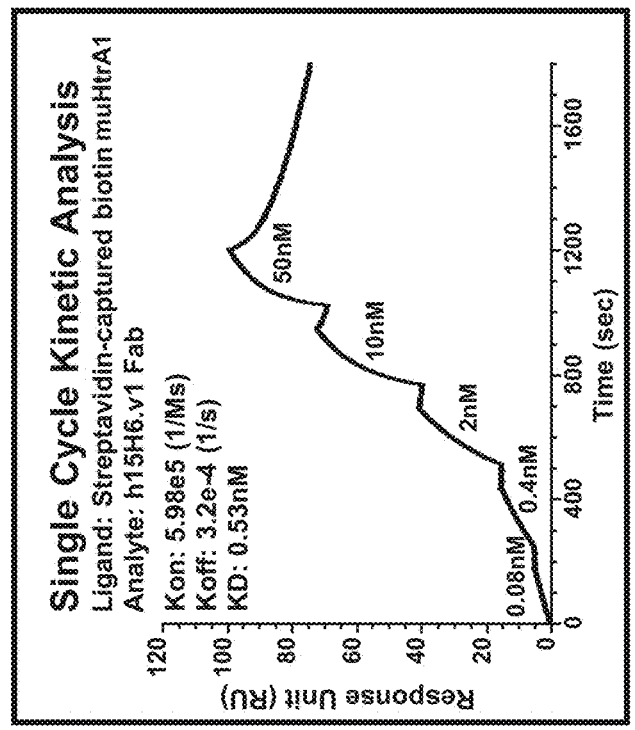
Figure 9D:
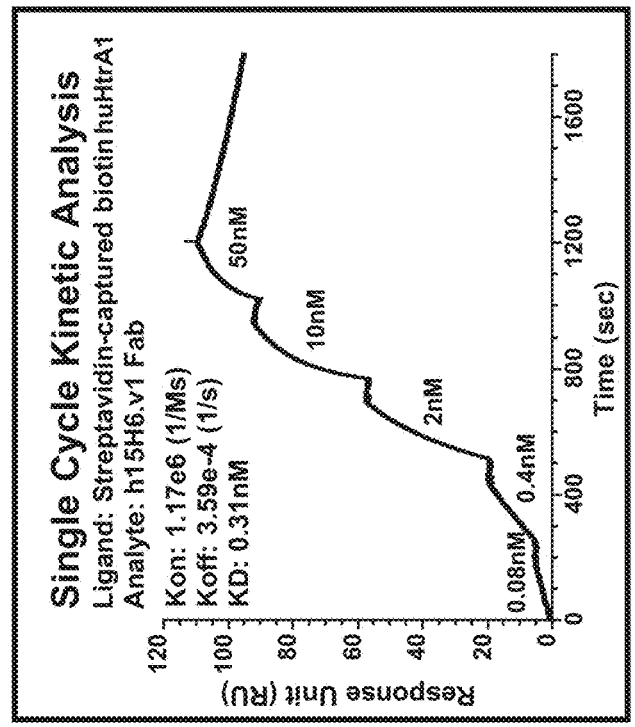

The ability of the recombinant 15H6 and 19B12 antibodies to inhibit huHtrA1-FL activity was evaluated using the FRET blocking assay described in Section C above. Both recombinant antibodies retained their original blocking activities as determined from hybridoma-derived antibodies (FIGS. 7A and 7B). Recombinant 15H6 antibody had an IC50 of approximately 0.7 nM, while recombinant 19B12 antibody had an IC50 of approximately 1.2 nM, which mirrored the activity of the hybridoma-derived antibodies (FIGS. 7A and 7B).

Example 2: Humanization of Anti-HtrA1 Hybridoma Antibodies 15H6 and 19B12

A. Humanization of Anti-HtrA1 Antibody 15H6

Figure 8A:
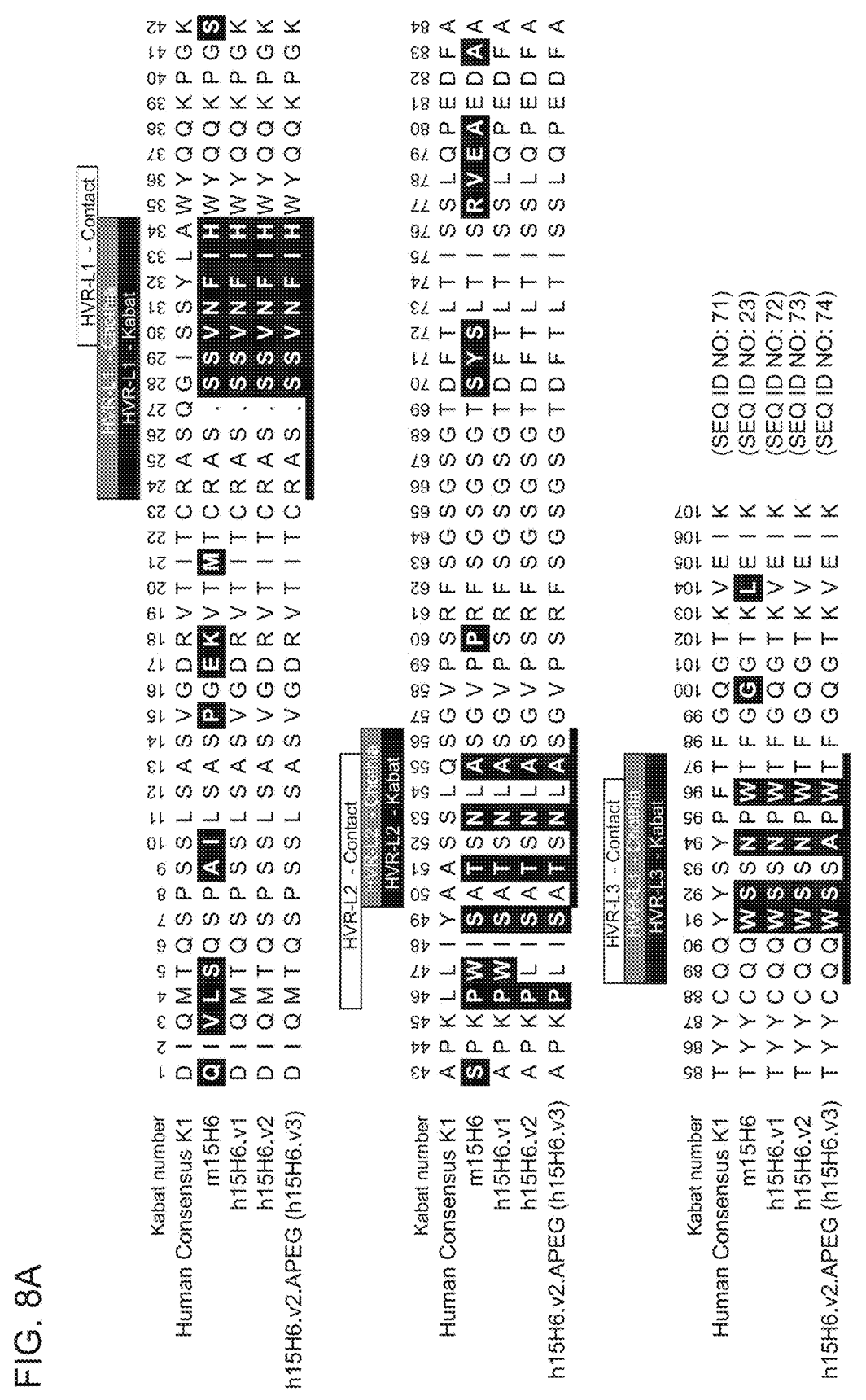
Figure 8B:
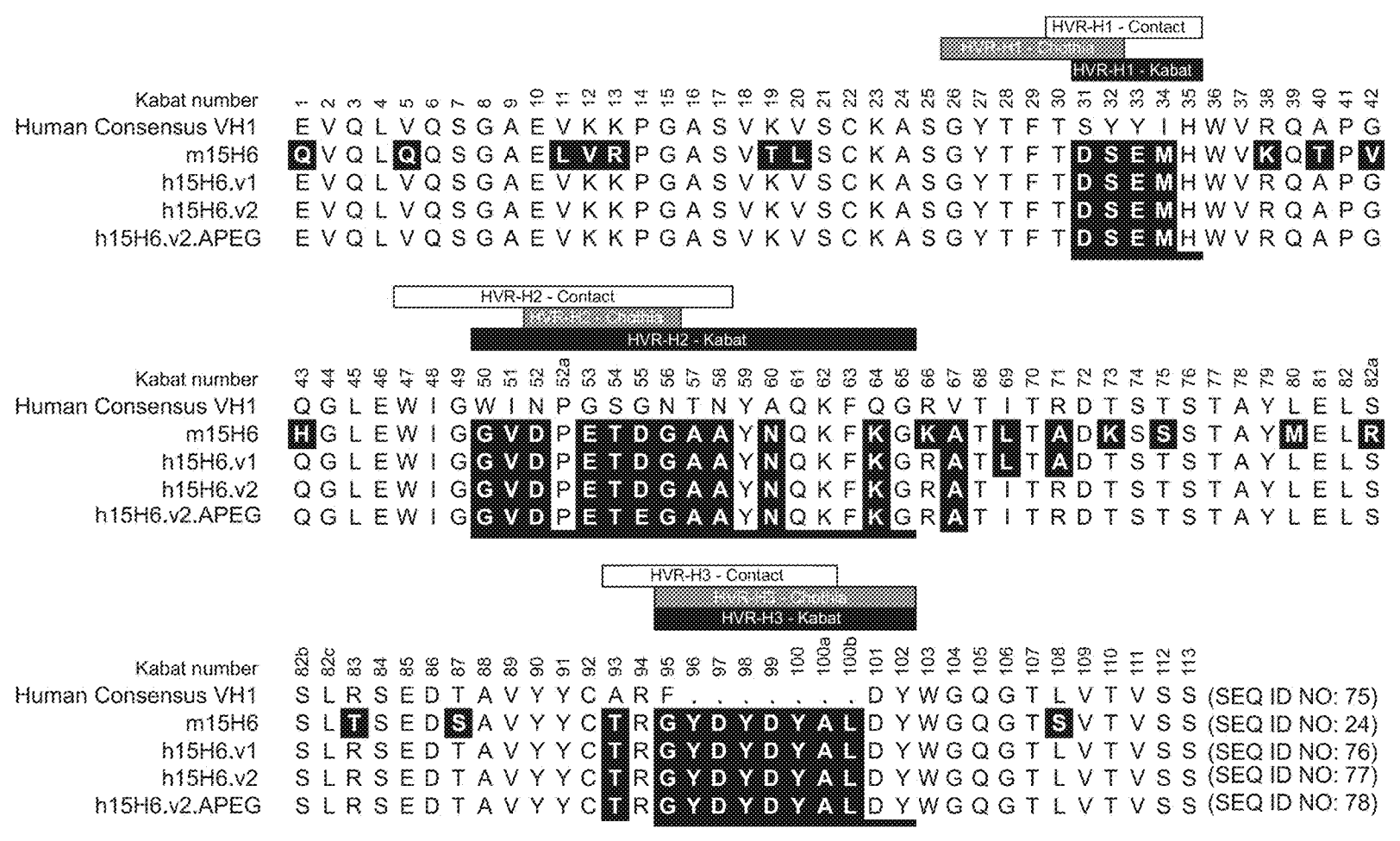

The light chain variable region (VL) and heavy chain variable region (VH) sequences of murine 15H6 antibody (also referred to as m15H6) were aligned with human antibody consensus sequences, and human consensus light chain kappa I (huK1) and human consensus heavy chain subgroup I (huVH1) were identified as the closest human frameworks (FIGS. 8A and 8B).

The hypervariable regions (HVRs) of the m15H6 light chain and heavy chain were grafted into huκI and huVH1 consensus acceptor frameworks, respectively, by Kunkel mutagenesis (see, e.g., Kunkel et al., Methods Enzymol. 154: 367-382, 1987) using separate oligonucleotides for each hypervariable region to generate antibody clone h15H6.v1 (FIGS. 8A and 8B). In this process, positions 24-34 in HVR-L1, 50-56 in HVR-L2 and 89-97 in HVR-L3 of the m15H6 VL were grafted to the huκI consensus acceptor, and positions 26-35 in HVR-H1, 49-65 in HVR-H2, and 95-102 in HVR-H3 of the m15H6 VH were grafted to the huGI consensus acceptor. Positions 46, 47 and 49 in framework region 2 of the light chain (FR-L2), and positions 67, 69, 71, and 93 in framework region 3 of the heavy chain (FR-L3) were also included in the humanization process because Foote and Winter have analyzed antibody and antigen complex crystal structures and found these positions to be part of the framework residues acting as "Vernier" zone, which may adjust HVR structure and fine-tune to fit to antigen (Foote et al., *J. Mol. Biot* 224:487-499, 1992) (FIGS. 8A-8B). The binding affinity of m15H6 and h15H6.v1 in Fab format for human and murine HrtA1 was measured by BIACORE™ surface plasmon resonance (SPR) binding analysis as described in Subsection ii of Section C below (FIGS. 9A-9D). Table 5 summarizes the results of this analysis.

TABLE 5

Kinetic Binding Analysis of m15H6 and h15H6.v1 to HtrA1

| Clone | huHtrA1 | | | muHtrA1 | | |
|---|---|---|---|---|---|---|
| | $k_{on}$ (1/Ms) | $K_{off}$ (1/s) | KD (nM) | $k_{on}$ (1/Ms) | $K_{off}$ (1/s) | KD (nM) |
| m15H6 Fab | $5.06 \times 10^5$ | $1.55 \times 10^{-4}$ | 0.31 | $5.39 \times 10^5$ | $1.63 \times 10^{-4}$ | 0.3 |
| h15H6.v1 Fab | $1.17 \times 10^6$ | $3.59 \times 10^{-4}$ | 0.31 | $5.98 \times 10^5$ | $3.2 \times 10^{-4}$ | 0.53 |

Figure 10B:
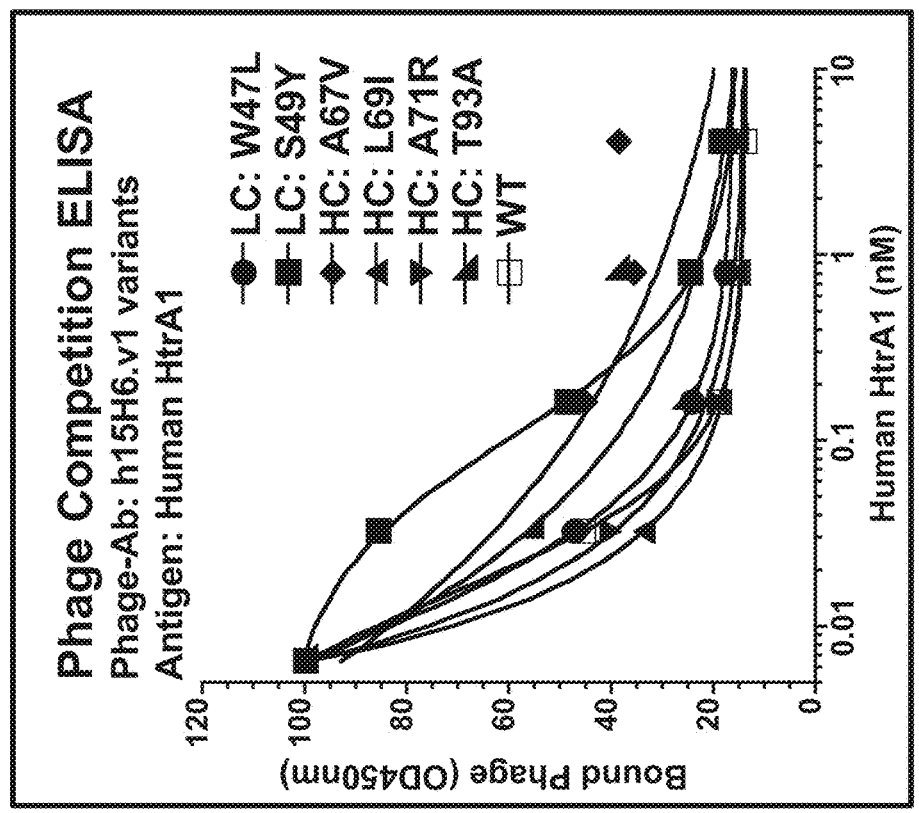
FIGS. 10A-10B are graphs showing the results of phage competition ELISA experiments for binding of the indicated h15H6.v1 Fab variants to murine (FIG. 10A) or human (FIG. 10B) HtrA1. The graphs show bound phage ($OD_{450\ nm}$) as a function of HtrA1 concentration (nM).
Figure 10A:
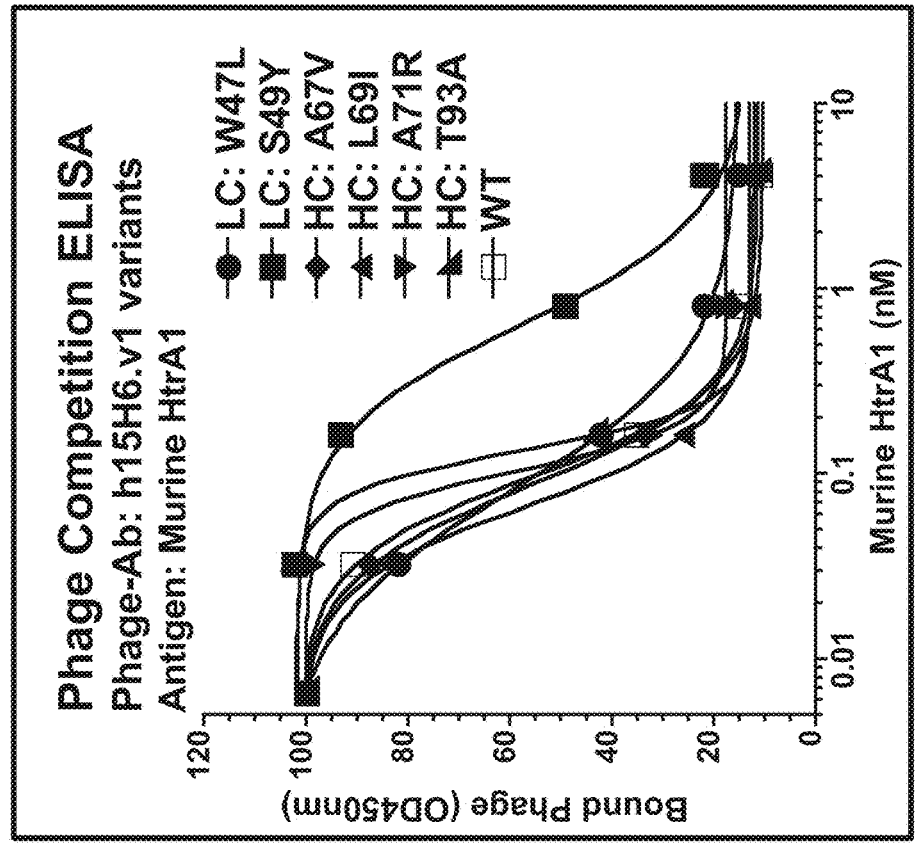

To further evaluate the importance of murine Vernier residues in h15H6.v1, this antibody was displayed on phage and individual Vernier murine residues (LC: P46, W47, S49; HC: A67, L69, A71 and T93) were replaced with human residues (LC: L46, L47, Y49; HC: V67, 169, R71 and A93) to generate point mutation variants. All 7 variants were subject to phage competition ELISA against human or murine HtrA1 to determine the binding affinities (in terms of phage IC50, see Subsection i of Section C below) The results indicated that the LC-P46L variant totally abolished h15H6.v1 binding to both human and murine HtrA1. The LC-S49Y variant reduced binding with human and murine HtrA1 about 10-fold (FIGS. 10A and 10B). The HC variants HC-A67V and HC-T93A both only affected binding to murine HtrA1 but not human HtrA1 (FIGS. 10A and 10B). The other variants, LC-W47L, HC-L691, and HC-A71R, did not show any significant drop in binding to human and murine HtrA1 (FIGS. 10A and 10B). Therefore, antibody clone h15H6.v1 was further engineered by adding the following mutations: LC-W47L, HC-L691, and HC-A71R to generate antibody clone h15H6.v2 (see FIGS. 8A and 8B).

Chemical stability analysis of antibody clone h15H6.v2 identified several potentially unstable residues or residue pairs in HVRs: W91 in HVR-L3 (oxidation), N94 P95 in HVR-L3 (clipping), and D55 G56 in HVR-H2 (isomerization). See, e.g., Example 4 below. To address W91 oxidation in HVR-L3, 2 variants (LC-W91Y and LC-W91 L) were generated and produced as Fabs for BIACORE™ SPR binding analysis. The results, summarized in Table 6 below, indicated that position LC-W91 is important for binding affinity, and the substitutions impacted binding to human and murine HtrA1 by about 20-50 fold (FIGS. 11A and 11B).

For the clipping at positions LC-N94 LC-P95 of HVR-L3, four variants of h15H6.v2 (LC-N94A LC-P95 (also referred to as AP), LC-N94E LC-P95 (also referred to as EP), LC-N94Q LC-P95 (also referred to as QP), and LC-N94S LC-P95 (also referred to as SP)) were generated and produced as Fabs for BIACORE™ binding analysis. The results indicated that AP and EP variants showed similar binding affinity to human HtrA1, and QP and SP variants had an approximate 2-fold reduction in binding affinity to human HtrA1 (FIGS. 12A-12B). A table summarizing the results of this analysis is shown in FIG. 12B.

Figures 13A, 13B:
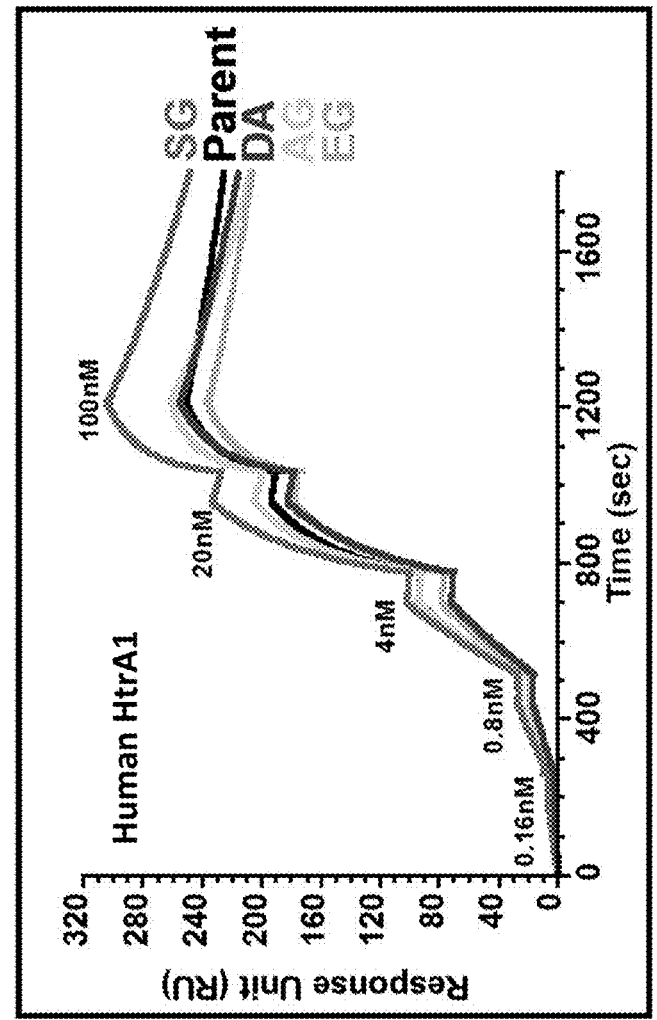
FIG. 13A is a graph showing the results of BIACORE™ SPR analysis comparing binding of antibody clone h15H6.v2 (parent) and the indicated variants at VH position 55 and/or 56 (i.e., HC-D55A HC-G56 (AG), HC-D55E HC-G56 (EG), HC-D55S HC-G56 (SG) and HC-D55 HC-G56A (DA)) to huHtrA1. The antibodies used were in Fab format. The graph shows response units (RU) as a function of time (sec).
FIG. 13B is a table that summarizes the results of the BIACORE™ SPR analysis shown in FIG. 13A.

For the isomerization at residues HC-D55 HC-G56 of HVR-H2, four variants (HC-D55A HC-G56 (also referred to as AG), HC-D55E HC-G56 (also referred to as EG), HC-D55S HC-G56 (also referred to as SG), and HC-D55 HC-G56A (also referred to as DA)) were generated and produced as Fabs for BIACORE™ binding analysis. The results indicated only the EG variant showed comparable binding affinity against human HtrA1, and the rest of the variants at heavy chain positions 55 and/or 56 had a 2-to 3-fold reduction in binding affinity to human HtrA1 (FIGS. 13A and 13B). A table summarizing the results of this analysis is shown in FIG. 13B.

Figures 14A, 14B:
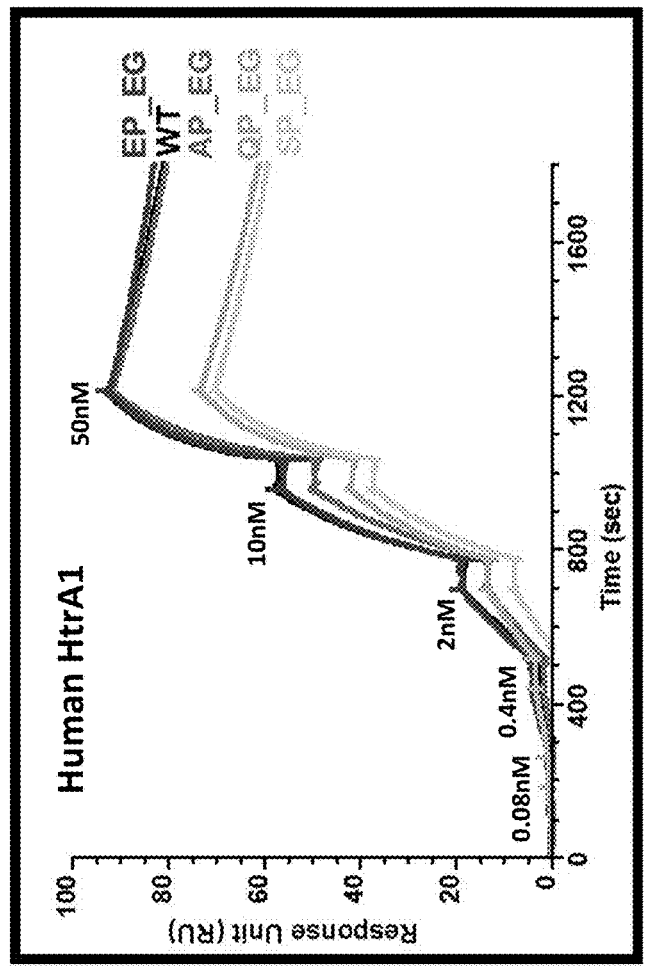
FIG. 14A is a graph showing the results of BIACORE™ SPR analysis comparing binding of antibody clone h15H6.v2 ("parent") and the indicated combination variants at VL position 94 and VH position 55 and/or 56 to huHtrA1. AP_EG: LC-N94A LC-P95 HC-D55E HC-G56 (also referred to as "h15H6.v2.APEG" and "h15H6.v3"). EP_EG: LC-N94E LC-P95 HC-D55E HC-G56. QP_EG: LC-N94Q LC-P95 HC-D55E HC-G56. SP_EG: LC-N94S LC-P95 HC-D55E HC-G56.
FIG. 14B is a table that summarizes the results of the BIACORE™ SPR analysis shown in FIG. 14A.
Figures 14C, 14D:
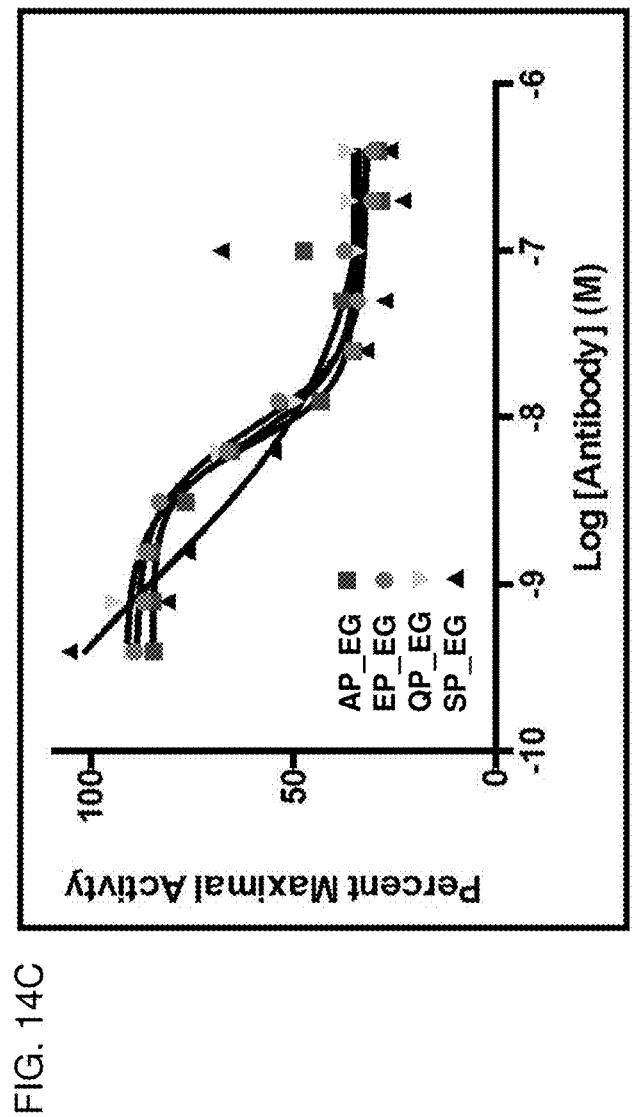
FIG. 14C is a graph showing the results of a FRET-based blocking assay testing the ability of h15H6.v2 IgG, h15H6.v2 Fab, and the indicated combination variants at VL position 94 and VH position 55 and/or 56 to inhibit the activity of HtrA1. The graph plots percent maximal activity as a function of log antibody concentration (M).
FIG. 14D is a table showing the IC50 values for each of the antibody clones tested in FIG. 14C.
Figure 16A:
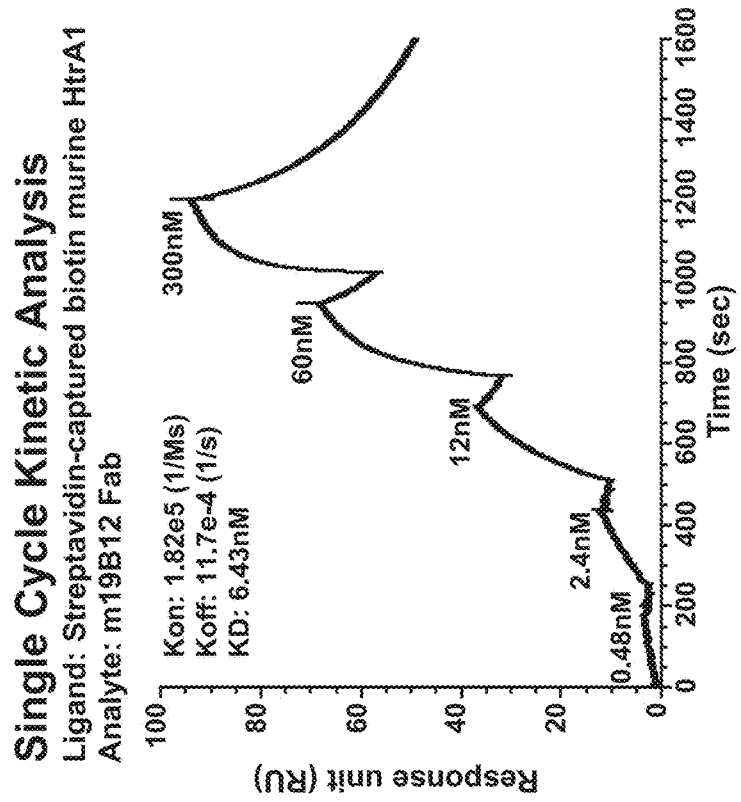
FIGS. 16A-16D are graphs showing the results of BIACORE™ SPR analysis of binding of antibody clone m19B12 or h19B12.v1 to human or murine HtrA1. Single cycle kinetic analysis was employed. The graphs show response units (RU) as a function of time (sec).
Figure 16B:
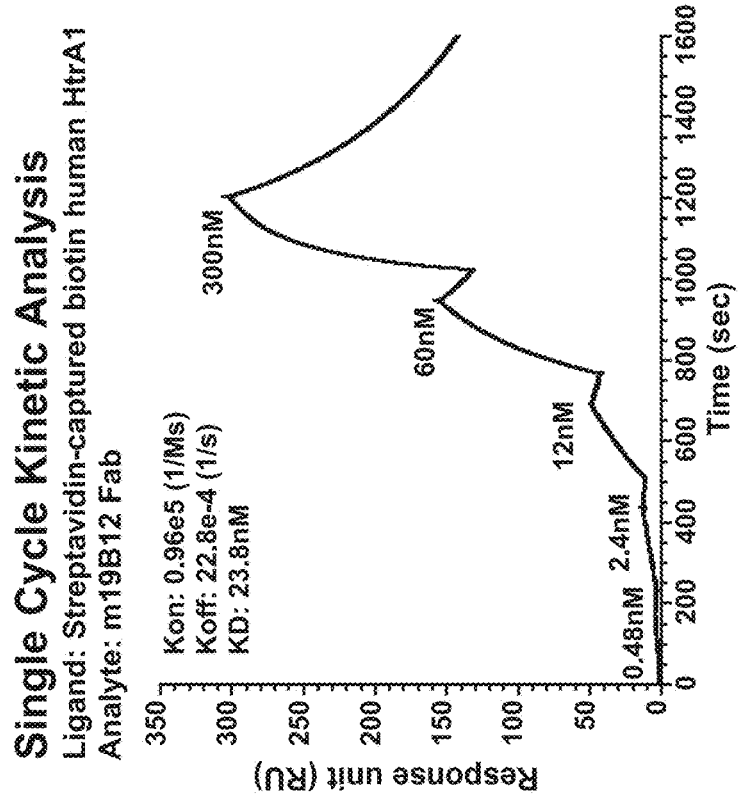
Figure 16C:
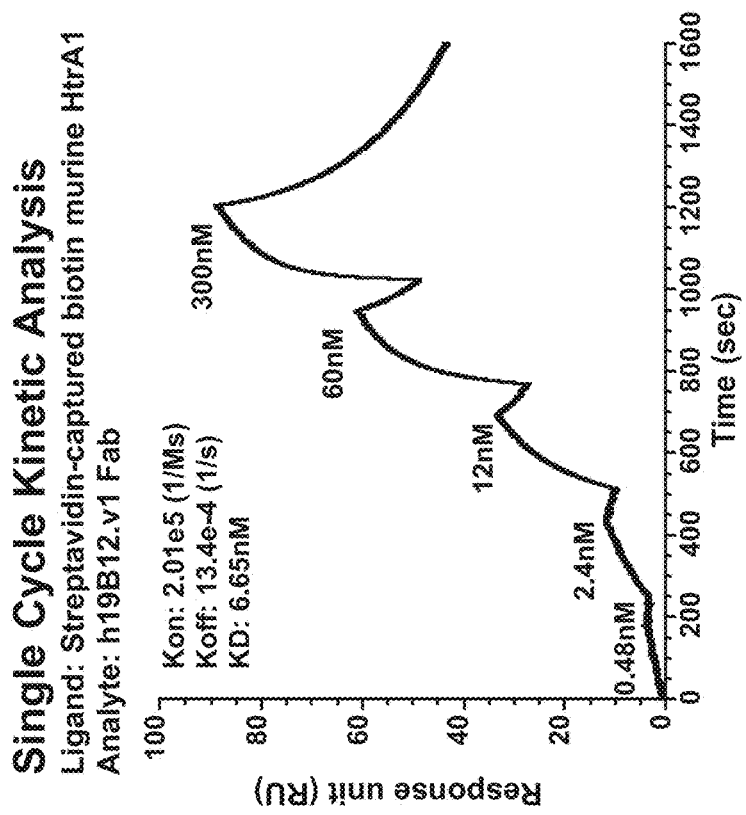
Figure 16D:
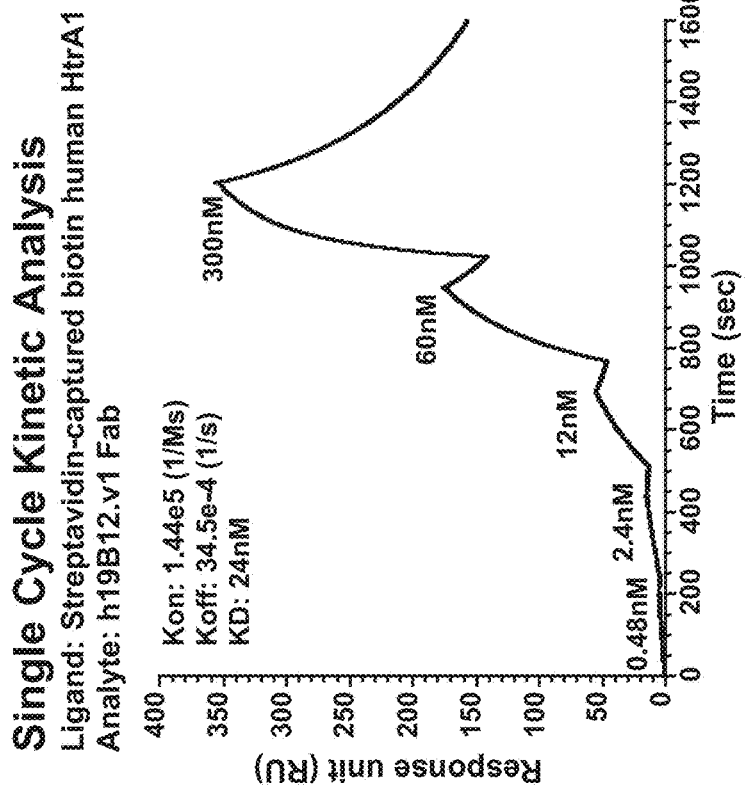

Based on these results, both of the variants AP (HVR-L3) and EG (HVR-H2) were introduced into the sequence of antibody clone h15H6.v2 to generate antibody clone h15H6.v2.APEG (also referred to as h15H6.v3 or AP_EG) (see FIGS. 8A and 8B). This clone was also compared with several other variants of h15H6.v2, including LC-N94E LC-P95 HC-D55E HC-G56 (also referred to as EP_EG); LC-N94Q LC-P95 HC-D55E HC-G56 (also referred to as QP_EG); and LC-N94S LC-P95 HC-D55E HC-G56 (also referred to as SP_EG). BIACORE™ SPR analysis indicated that h15H6.v2.APEG retained a comparable binding affinity to h15H6.v2 (FIGS. 14A and 14B). A table summarizing the results of this analysis is shown in FIG. 14B. The ability of these variants to block the activity of HtrA1 activity was determined using the FRET-based blocking assay described in Example 1 (FIGS. 14C and 14D). The pI of these variants in Fab format was also determined using the software program SMACK (see, e.g., Sharma et al. *Proc. Natl. Acad. Sci. USA* 111: 18601, 2014) and is shown in Table 7 as compared to the anti-VEGF Fab ranibizumab (LUCENTIS®).

TABLE 6

Kinetic Binding Analysis of h15H6.v2 LC-W91 Variants to HtrA1

| Clone | huHtrA1 | | | muHtrA1 | | |
|---|---|---|---|---|---|---|
| | $k_{on}$ (1/Ms) | $K_{off}$ (1/s) | KD (nM) | $k_{on}$ (1/Ms) | $K_{off}$ (1/s) | KD (nM) |
| H15H6.v2 | $6.9 \times 10^5$ | $1.2 \times 10^{-4}$ | 0.2 | $3.6 \times 10^5$ | $1.5 \times 10^{-4}$ | 0.4 |
| H15H6.v2 LC-W91L | $1.5 \times 10^5$ | $1.6 \times 10^{-3}$ | 10.7 | $1.2 \times 10^5$ | $9.1 \times 10^{-4}$ | 7.6 |
| H15H6.v2 LC-W91Y | $3.3 \times 10^5$ | $3.7 \times 10^{-3}$ | 11.2 | $2.4 \times 10^5$ | $1.7 \times 10^{-3}$ | 7.1 |

TABLE 7

| Antibody Clone | pI |
| --- | --- |
| h15H6.v2.APEG (h15H6.v3) | 8.25 |
| EP_EG | 7.45 |
| QP_EG | 8.25 |
| SP_EG | 8.25 |
| Ranibizumab | 8.55 |

B. Humanization of Anti-HrtA1 Hybridoma Antibody 19812

The amino acid sequences of the VL and VH of murine antibody 19B12 (also referred to as m19B12) were aligned with human consensus sequences, and human consensus light chain kappa IV (huK4) and human consensus heavy chain subgroup Ill (huVH3) were identified as the closest human frameworks (FIGS. 15A-15B).

The hypervariable regions of the m19B12 light chain and heavy chain were grafted into huK4 and huVH3 consensus acceptor frameworks, respectively, by Kunkel mutagenesis using separate oligonucleotides for each hypervariable region to generate a direct HVR-graft variant, referred to herein as antibody clone h19B12.v1. In this process, positions 24-34 in HVR-L1, 50-56 in HVR-L2 and 89-97 in HVR-L3 of the 19B12 VL were grafted to the huK4 consensus acceptor, and positions 26-35 in HVR-H1, 50-65 in HVR-H2, and 95-102 in HVR-H3 of the 19B12 VH were grafted to the huGlll consensus acceptor (FIGS. 15A-15B).

The binding affinity of m19B12 and h19B12.v1 (in Fab format) were determined using BIACORE™ SPR (FIGS. 16A-16D) using the approach described in Subsection ii of Section C below. The results of this analysis are summarized in Table 8 below. The equilibrium binding constant (KD) of h19B12.v1 to human HtrA1 improved approximately 2-fold following humanization (Table 8) as compared to m19B12.

ii. Antibody Affinity Determinations by BIACORE™

To determine the binding affinity of anti-HtrA1 Fabs by single-cycle kinetics, (SPR) measurement with a BIACORE™ T100 instrument was used. Briefly, a series S sensor chip CM5 was activated with 1-ethyl-3-(3-dimethylamino-propyl)carbodiimide hydrochloride (EDC) and N-hydroxysuccinimide (NHS) reagents according to the supplier's instructions, and streptavidin (Pierce) was coupled to achieve approximately 2500 response units (RU), followed by blocking un-reacted groups with 1 M ethanolamine.

For kinetics measurements, biotinylated human or murine HtrA1-PD-His was first injected at 10 µl/min flow rate to capture approximately 150 RU at 3 different flow cells (FC), except for FC1 (which served as a reference), and then 5-fold serial dilutions of anti-HtrA1 Fab in HBS-P buffer (0.01M HEPES pH 7.4, 0.15 M NaCl, 0.005% surfactant P20) from low (0.48 nM) to high (300 nM) were injected (flow rate: 30 µl/min) one after the other in the same cycle with no regeneration between injections. The sensorgram was recorded and subject to reference and buffer subtraction before evaluating by BIACORE™ T100 Evaluation Software (version 2.0). Association rates ($k_{on}$) and dissociation rates ($k_{off}$) were calculated using a simple one-to-one Langmuir binding model. The equilibrium dissociation constant (KD) was calculated as the ratio $k_{off}/k_{on}$.

Example 3: Affinity Maturation of Anti-HtrA1 Antibody Clone h15H6.v2

A. h15H6. v2 Affinity Maturation NNK Library Construction and Panning

To further improve the affinity of anti-HtrA1 antibody clone h15H6.v2, phage libraries were constructed from variant h15H6.v2 in Fab-amber format for monovalent Fab phage display with either light chain HVR residues (i.e., HVR-L1, HVR-L2, and HVR-L3) or heavy chain HVR

TABLE 8

Kinetic Binding Analysis of m19B12 or h19B12.v1 to HtrA1

| | huHtrA1 | | | muHtrA1 | | |
| --- | --- | --- | --- | --- | --- | --- |
| Clone | $k_{on}$ (1/Ms) | $K_{off}$ (1/s) | KD (nM) | $k_{on}$ (1/Ms) | $K_{off}$ (1/s) | KD (nM) |
| m19B12 | $0.96 \times 10^5$ | $22.8 \times 10^{-4}$ | 23.8 | $1.82 \times 10^5$ | $11.7 \times 10^{-4}$ | 6.43 |
| h19B12.v1 | $1.5 \times 10^5$ | $1.6 \times 10^{-3}$ | 10.7 | $1.2 \times 10^5$ | $9.1 \times 10^{-4}$ | 7.6 |

C. Materials and Methods i. Phage Competition ELISA to Determine Phage IC50

Figure 17:
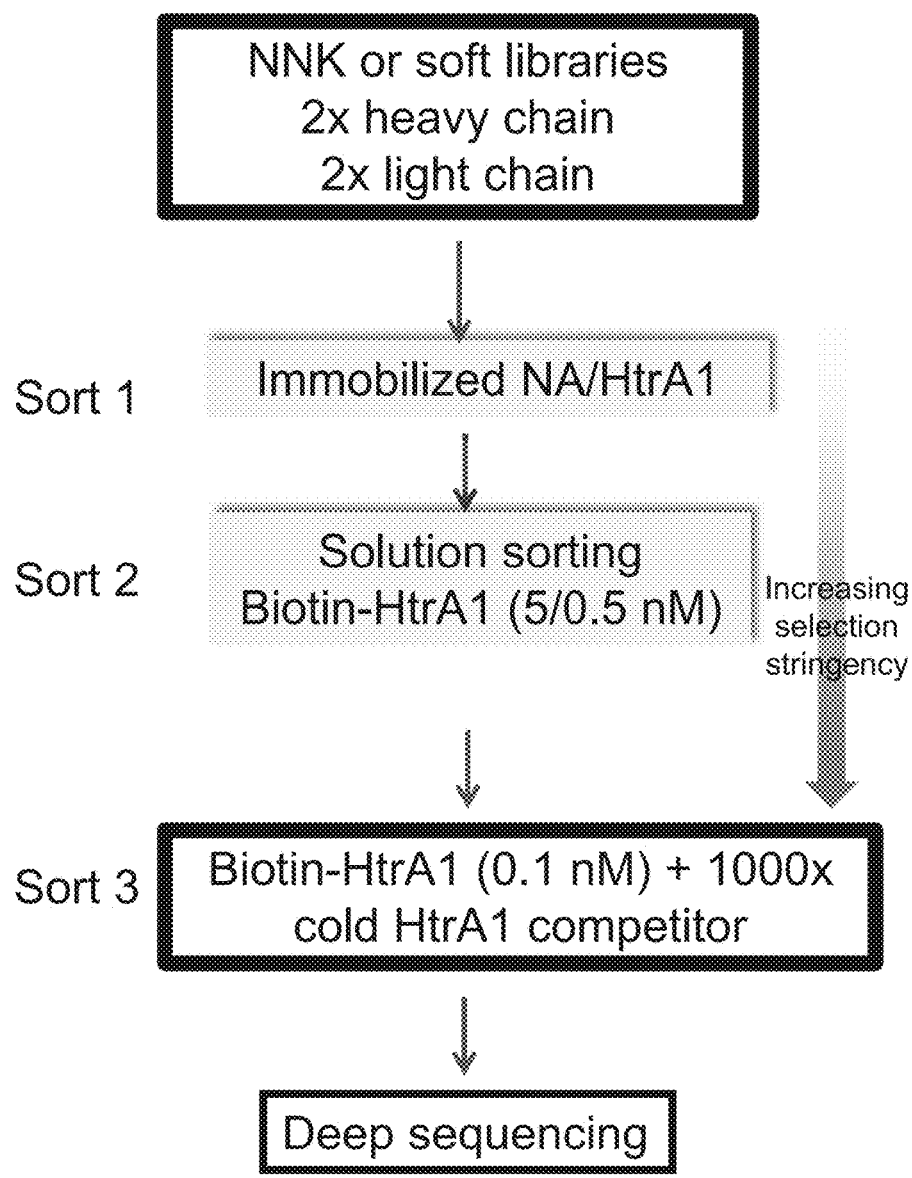
FIG. 17 is a schematic diagram outlining the phage panning strategy used for NNK deep scanning mutagenesis of the HC and LC HVRs of h15H6.v2 for affinity maturation.

MAXISORP™ microtiter plates were coated with human HtrA1-PD-His at 2 µg/ml in PBS for 2 h and then blocked with PBST buffer (0.5% BSA and 0.05% TWEEN®20 in PBS) for 1 h at room temperature. Phage purified from culture supernatants were incubated with serially-diluted human or murine HtrA1 in PBST buffer in a tissue-culture microtiter plate for 1 h, after which 80 µl of the mixture was transferred to human HtrA1-coated wells for 15 min to capture unbound phage. The plate was washed with PBT buffer (0.05% TWEEN®20 in PBS), and HRP-conjugated anti-M13 antibody (Amersham Pharmacia Biotech) was added (1:5000 in PBST buffer) for 40 min. The plate was washed with PBT buffer and developed by adding tetramethylbenzidine substrate (Kirkegaard and Perry Laboratories, Gaithersburg, Md.). The absorbance at 450 nm was plotted as a function of target concentration in solution to determine phage IC50. This was used as an affinity estimate for the Fab clone displayed on the surface of the phage.

residues (i.e., HVR-H1, HVR-H2, and HVR-H3) residues randomized using the NNK degenerate codon that encodes for all 20 amino acids with 32 codons (see, e.g., Brenner et al., Proc. Natl, Acad. Sci. USA 89(12): 5381-5383, 1992). Libraries were designed to allow one NNK mutation in each of the three light chain or heavy chain HVRs. The resultant library DNA was electroporated into E. coli XL1 cells, yielding approximately $10^9$ transformants. In some instances, soft randomization libraries and NNK epistasis were employed as described in PCT/US2015/055672. Phage libraries were incubated with 750 mM NaCl in SUPERBLOCK™ PBS buffer (Pierce) and 0.05% TWEEN® 20 for 30 min and then applied on neutravidin-captured biotinylated HtrA1-His tag for first round panning to reduce non-specific charged interaction between HtrA1 and phage. In the subsequent two rounds using decreasing concentration of biotinylated huHtrA1-PD-His antigen with 1000× non-biotinylated HtrA1 as competitor in solution to increase the selection stringency. See FIG. 17 for a schematic diagram of the panning strategy.

B. Deep Sequencing of h 15H6. v2 Affinity Maturation Libraries

For deep sequencing, phagemid double stranded DNA was isolated from *E. coli* XL-1 cells carrying phagemid vectors from the initial phage library and from the third round of selection. Purified DNA was used as template for a limited cycle PCR-based amplification of VL and VH regions using PHUSION® DNA polymerase (New England Biolabs). PCR products were purified by agarose gel extraction and clean-up (Qiagen Gel Extraction Kit). Eluted amplicon DNA was used as the basis for deep sequencing library preparation with standard Illumina library preparation methods, using a TRUSEQ™ DNA Sample Prep kit (lllumina).

Adapter-ligated libraries were subjected to a single cycle of PCR and sequenced on the Illumina MISEQ®, using paired-end sequencing with an insert size of 200 bp or 300 bp as appropriate to cover the entire length of the amplicon.

C. Deep Sequencing Analysis of h15H6.v2 Affinity Maturation Libraries

Figure 18A:
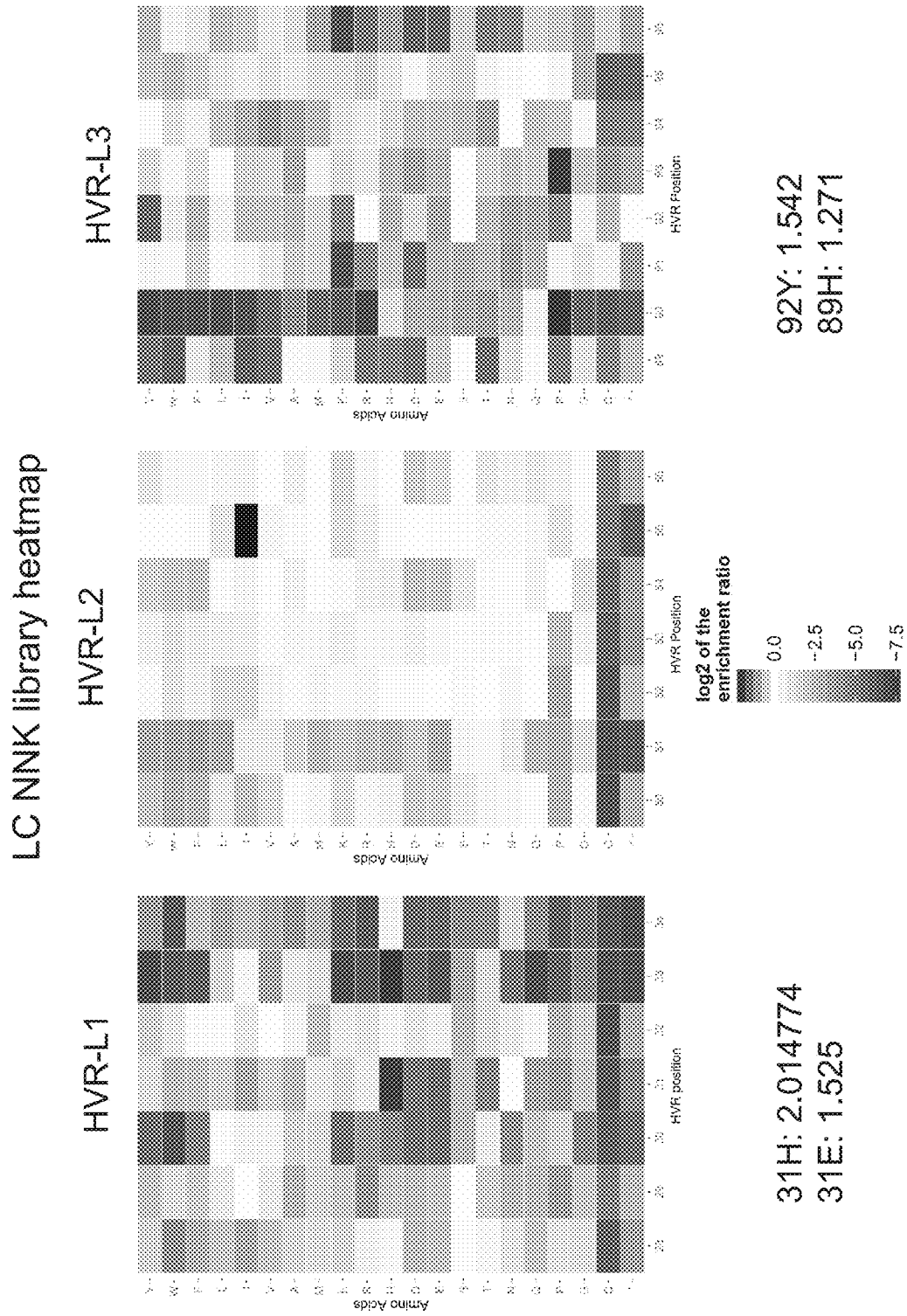
FIGS. 18A-18B show heatmaps of the log 2 of the enrichment ratio for mutations at the indicated VH (FIG. 18A) or VL (FIG. 18B) HVR positions calculated by dividing the frequency of a given mutation at a given position in the sorted sample with the frequency of the very same mutation in the unsorted sample. The enrichment ratios of exemplary mutations are indicated under the heat maps.
Figure 18B:
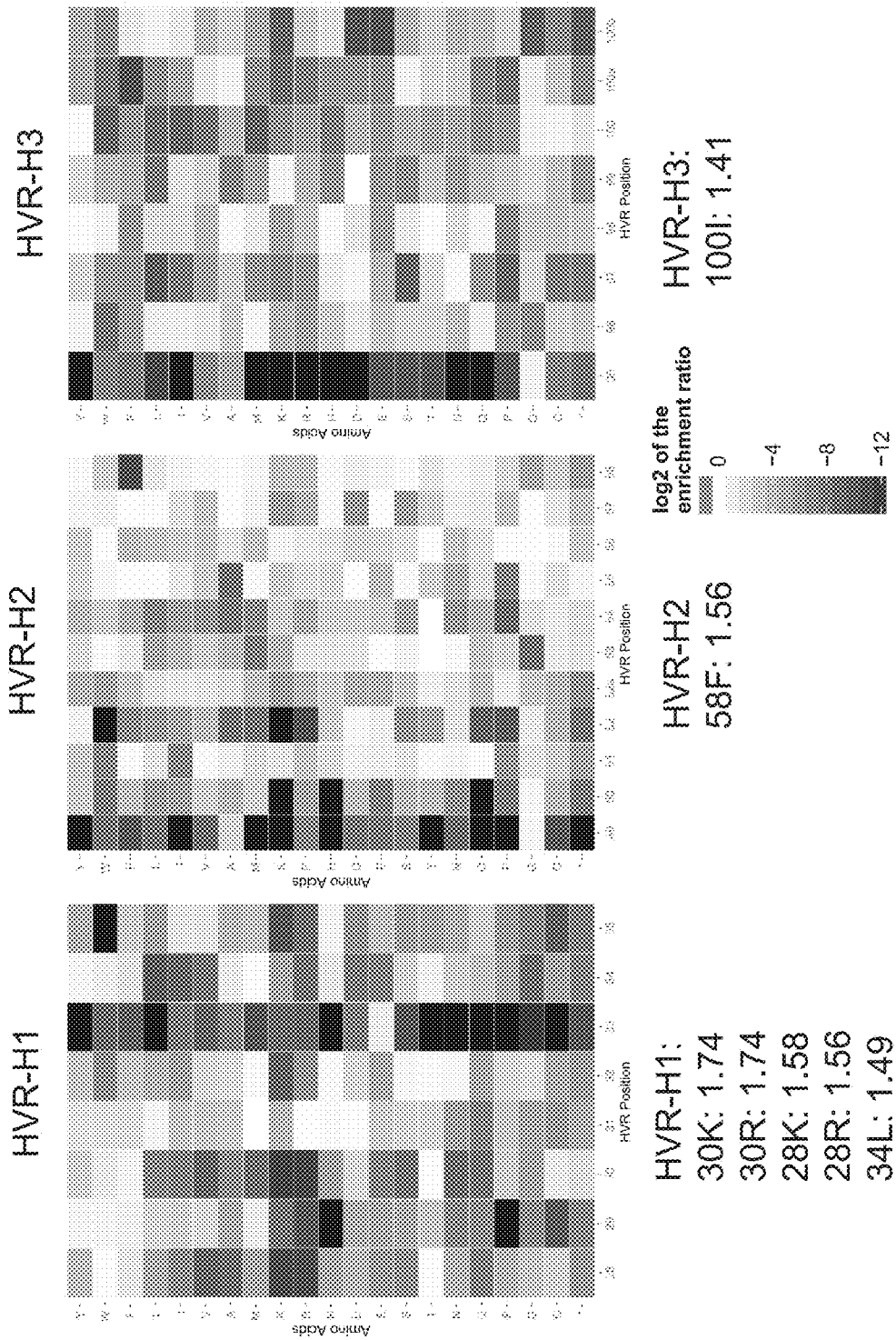

Sequencing data were analyzed using the statistical programming language R (see, e.g., R Core Team, *R: A language and environment for statistical computing*, 2013) and the ShortRead package (see Morgan et al., *Bioinformatics* 25(19): 2607-2608, 2009). Quality control (QC) was performed on identified HVR sequences, where each HVR sequence was checked for the correct length and was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Fowler et al., *Nature Methods* 7(9): 741-746, 2010). Heatmaps depicting the enrichment ratios for each mutation in light chain HVR positions and heavy chain HVR positions are shown in FIGS. 18A and 18B, respectively.

Single mutations from the light chain or heavy chain libraries with high enrichment ratio were selected to synthesize for cloning into a mammalian Fab expression construct containing a Flag tag to generate Fab-Flag tag fusion proteins. Plasmids encoding the heavy or light chain were transfected to 293T cells for 30 ml expression and Fabs were purified with an anti-Flag column.

The purified Fabs containing single mutations were used to determine binding affinity using BIACORE™ SPR analysis (see Section D below). The affinity data for single mutations are summarized in Table 9. The off rates ranged from about 0.0013 to about 0.004, compared with a value of about 0.0016 for h15H6.v2. Variant LC3 (LC-N31E) improved the off-rate 2- to 3-fold over 15H6.v2.

TABLE 9

Binding Affinity of h15H6.v2 Mutations Identified by Deep Scanning Mutagenesis

| Antibody Variant | Mutation | $k_{on}$ (1/Ms) | $k_{off}$ (1/s) | KD (M) | VL SEQ ID NO: | VH SEQ ID NO: |
|---|---|---|---|---|---|---|
| h15H6.v2 | | 7.22E+05 | 1.58E−04 | 2.20E−10 | 73 | 77 |
| LC7 | LC-S92Y | 5.78E+05 | 1.93E−04 | 3.35E−10 | 87 | 77 |
| HC3 | HC-T28K | 4.56E+05 | 1.71E−04 | 3.74E−10 | 73 | 95 |
| HC2 | HC-T30R | 3.66E+05 | 1.64E−04 | 4.49E−10 | 73 | 94 |
| HC1 | HC-T30K | 3.47E+05 | 1.65E−04 | 4.75E−10 | 73 | 93 |
| LC3 | LC-N31E | 2.70E+05 | 1.30E−04 | 4.80E−10 | 83 | 77 |
| HC5 | HC-M34L | 5.11E+05 | 2.46E−04 | 4.81E−10 | 73 | 97 |
| LC5 | LC-N53E | 4.41E+05 | 2.12E−04 | 4.81E−10 | 85 | 77 |
| LC4 | LC-N53H | 4.13E+05 | 2.13E−04 | 5.17E−10 | 84 | 77 |
| HC8 | HC-Y100I | 3.93E+05 | 2.37E−04 | 6.03E−10 | 73 | 100 |
| HC7 | HC-A58F | 2.71E+05 | 1.65E−04 | 6.11E−10 | 73 | 99 |
| HC9 | HC-A100aP | 3.40E+05 | 2.10E−04 | 6.18E−10 | 73 | 101 |
| LC6 | LC-Q89H | 3.90E+05 | 2.51E−04 | 6.42E−10 | 86 | 77 |
| HC4 | HC-T28R | 3.31E+05 | 2.12E−04 | 6.43E−10 | 73 | 96 |
| LC2 | LC-N31H | 2.28E+05 | 1.90E−04 | 8.36E−10 | 82 | 77 |
| LC8 | LC-S92K | 3.43E+05 | 3.97E−04 | 1.16E−09 | 88 | 77 |
| LC1 | LC-S29R | 1.48E+05 | 2.29E−04 | 1.55E−09 | 81 | 77 |
| LC9 | LC-S93I | 1.88E+05 | 4.04E−04 | 2.15E−09 | 89 | 77 |
| HC6 | HC-E53A | 1.01E+05 | 2.60E−04 | 2.58E−09 | 73 | 98 |
| LC10 | LC-F32V, LC-S92K | 2.53E+05 | 2.13E−03 | 8.42E−09 | 90 | 77 |

D. Combination of Selected Variants for Further Affinity Improvement

Most of the single mutations from the heavy chain or light chain NNK library did not improve the binding affinity to HtrA1 over parental clone h15H6.v2 (Table 9). The variants with the slowest off rates were selected from both light chain (LC3, LC4, and LC7) and heavy chain (HC1, HC2, HC3, and HC5) variants to generate combination mutants. These combination mutants included both a variant light chain and a variant heavy chain. BIACORE™ kinetic analysis was performed (as described below in Section C) using the combination mutants. Combination mutants LC3.HC3, LC3.HC1, and LC7.HC2 had 2-3 fold improved affinity improvement over the parental Fab (h15H6.v2) (Table 10).

TABLE 10

Kinetic Analysis of Combination Mutant Binding to HtrA1

| Sample | $k_{on}$ (1/Ms) | $k_{off}$ (1/s) | KD (M) | VL SEQ ID NO: | VH SEQ ID NO: |
|---|---|---|---|---|---|
| LC3.HC3 | 8.01E+05 | 4.93E−05 | 6.16E−11 | 83 | 95 |
| LC3.HC1 | 8.85E+05 | 7.95E−05 | 8.89E−11 | 83 | 93 |
| LC7.HC2 | 1.97E+06 | 1.89E−04 | 9.55E−11 | 87 | 94 |
| LC3.HC5 | 5.77E+05 | 1.02E−04 | 1.76E−10 | 83 | 97 |
| h15H6.v2 | 7.22E+05 | 1.58E−04 | 2.20E−10 | 73 | 77 |
| LC3.HC2 | 3.62E+05 | 1.09E−04 | 3.02E−10 | 83 | 94 |
| LC7.HC3 | 7.09E+05 | 2.37E−04 | 3.35E−10 | 87 | 95 |
| LC5.HC2 | 2.94E+05 | 2.11E−04 | 7.19E−10 | 85 | 94 |
| LC7.HC5 | 4.06E+05 | 3.03E−04 | 7.45E−10 | 87 | 97 |

TABLE 10-continued

Kinetic Analysis of Combination Mutant Binding to HtrA1

| Sample | $k_{on}$ (1/Ms) | $k_{off}$ (1/s) | KD (M) | VL SEQ ID NO: | VH SEQ ID NO: |
|---|---|---|---|---|---|
| LC7.HC1 | 3.47E+05 | 2.67E−04 | 7.72E−10 | 87 | 93 |
| LC4.HC1 | 2.68E+05 | 2.28E−04 | 8.52E−10 | 84 | 93 |
| LC5.HC5 | 3.37E+05 | 2.96E−04 | 8.77E−10 | 85 | 97 |
| LC3 | 1.27E+05 | 1.15E−04 | 9.05E−10 | 83 | 77 |
| LC5.HC3 | 2.33E+05 | 2.51E−04 | 1.08E−09 | 85 | 95 |
| LC5.HC1 | 2.08E+05 | 2.30E−04 | 1.10E−09 | 85 | 93 |
| LC7 | 1.37E+05 | 1.88E−04 | 1.37E−09 | 87 | 77 |
| LC4.HC5 | 2.12E+05 | 2.97E−04 | 1.40E−09 | 84 | 97 |
| LC4.HC3 | 1.10E+05 | 2.40E−04 | 2.18E−09 | 84 | 95 |
| LC4.HC2 | 2.78E+04 | 2.22E−04 | 7.98E−09 | 84 | 94 |

Next, LC mutants (LC37=LC3_LC7, LC347=LC3_LC4_LC7) and HC mutants (HC13=HC1_HC3, HC23=HC2_HC3) were further combined. These mutants were further modified by incorporating the HVR-L3 N94A and HVR-H2 D55E variants (i.e., AP_EG, see Example 2) to avoid self-cleavage and deamidation for affinity kinetic analysis.

Figure 21A:
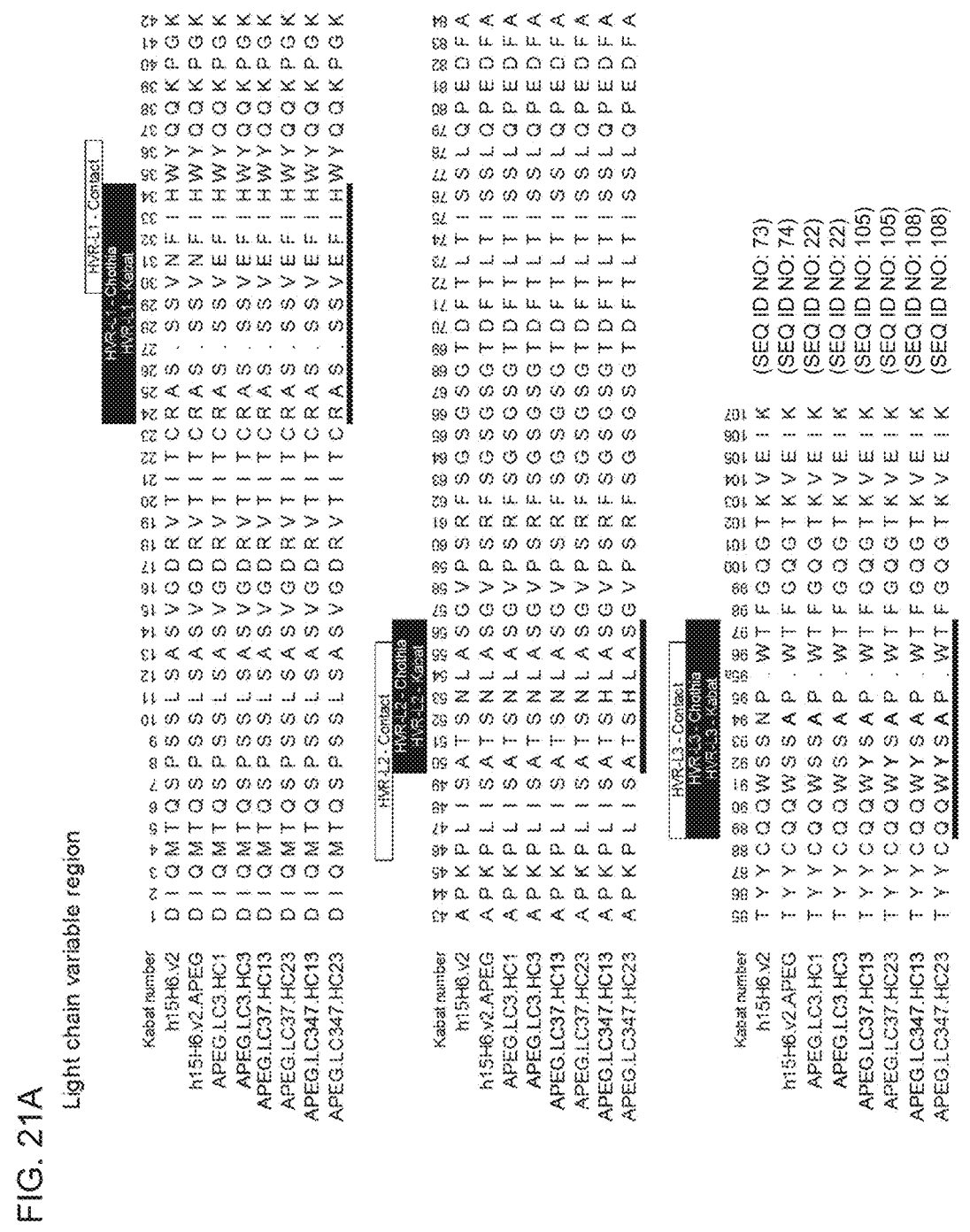
Figure 21B:
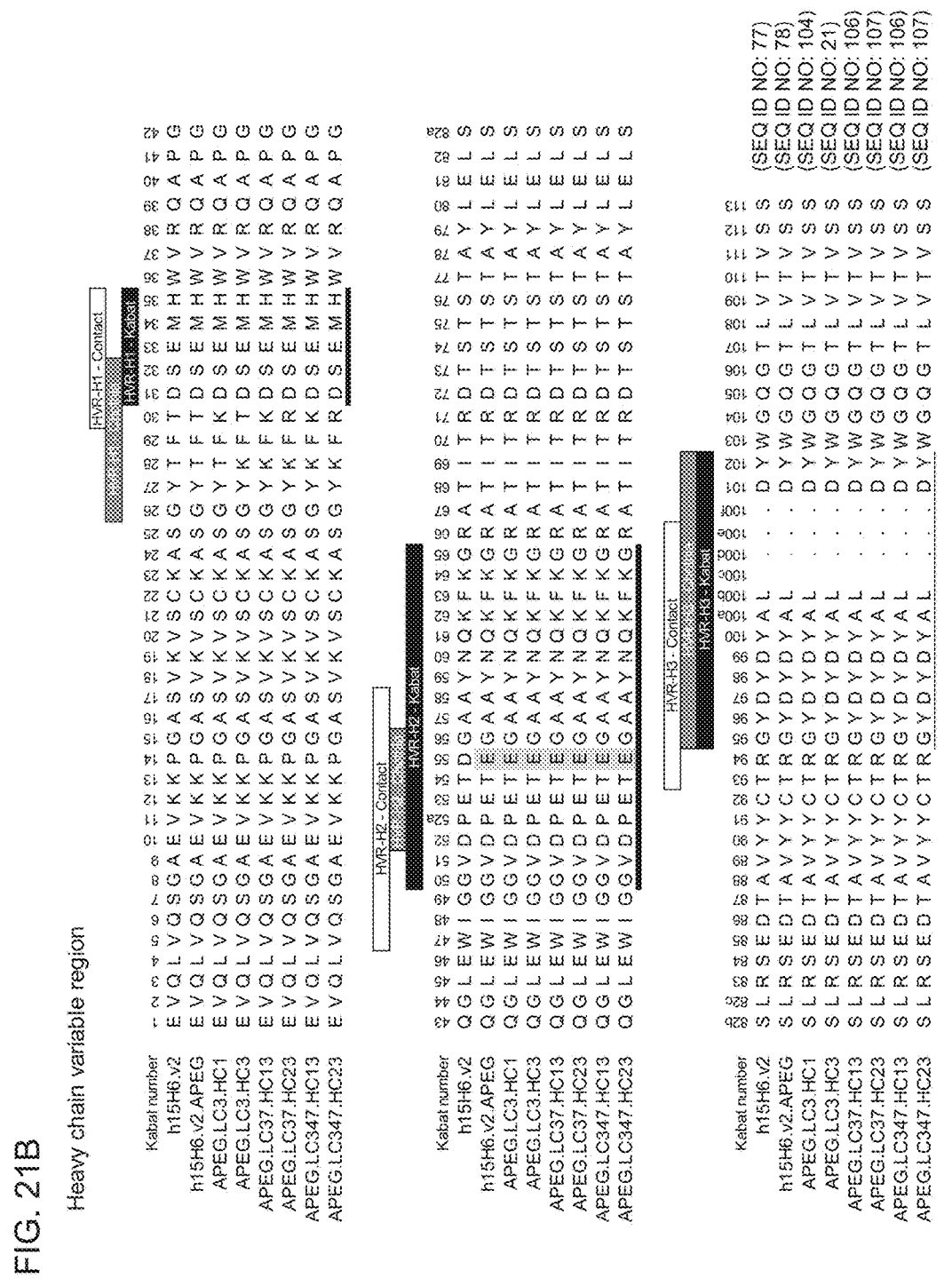

APEG.LC3.HC1, APEG.LC3.HC3 (h15H6.v4), APEG.LC37.HC13, APEG.LC37.HC23, APEG.LC347.HC13, and APEG.LC347.HC23 were the top clones, with 3- to 5-fold improvements, on average, over h15H6.v2 (FIG. 20). The VL and VH amino acid sequences of these variants are shown in FIGS. 21A and 21B, respectively. The sequences of these clones were analyzed by potential risk of oxidation on HVR-L3 W91 using in silico analysis (Sharma et al. Proc. Natl. Acad. Sci. USA 111: 18601, 2014). APEG.LC3.HC3 (h15H6.v4), APEG.LC37.HC13, and APEG.LC347.HC13 were ranked as equivalent risk as h15H6.v3. Others have higher risk than h15H6.v2.

E. Fab Affinity Determination by BIACORE® SPR

To determine the binding affinity of selected Fab variants for HtrA1, SPR measurement with a BIACORE™ T200 instrument was performed. Briefly, a series S sensor chip CM5 was activated with 1-EDC and NHS reagents according to the supplier's instructions, and anti-His antibody was coupled to achieve 200-300 response units (RU), then following by blocking un-reacted groups with 1 M ethanolamine. For kinetics measurements, approximately 5 nM of huHtrA1-PD-His was first injected at 10 µl/min flow rate to capture approximately 100 RU at 2 different flow cells (FC), except for FC1 (which served as a reference). Next, 5-fold serial dilutions of Fab in HBS-P buffer (0.01 M HEPES pH 7.4, 0.15M NaCl, 0.005% surfactant P20) from low (0.8 nM) to high (50 nM) were injected (flow rate: 30 µl/min). The binding responses on HtrA1 were corrected by subtracting of RU from a blank flow cell. The sensorgram was recorded and subject to reference and buffer subtraction before evaluating by BIACORE® T200 Evaluation Software (version 2.0). Association rates ($k_{on}$) and dissociation rates ($k_{off}$) were calculated using a simple one-to-one Langmuir binding model. The equilibrium dissociation constant (KD) was calculated as the ratio of $k_{off}/k_{on}$.

F. inhibitory Activity of h15H6. v2 Variants in an HtrA1 FRET-based Blocking Assay (H2-Opt Blocking Assay)

Selected affinity matured h15H6.v2 variants were tested for the ability to inhibit HtrA1 activity. In vitro FRET-based blocking assays using the H2-Opt substrate ((Mca)IRRVSYSF(Dnp)KK) were performed. The H2-Opt blocking assays were performed as described in Example 3 of U.S. Patent Application Publication No. 2013/0129743A1, which is incorporated by reference herein in its entirety. Briefly, the peptide H2-Opt (Mca-iRRVSYSF(Dnp)KK) (SEQ ID NO: 152), originally described as a substrate for HtrA2 (see, e.g., Martins et al., J. Biol. Chem. 278:49417-27, 2003), was synthesized on Fmoc-Lys(Boc)-wang resin using standard coupling procedures with HBTU. Fmoc-Lys(DNP)-OH (Anaspec) was incorporated in the P5' position. The peptide was synthesized up to P5 (Mca, 7-Methoxy-coumarin, Aldrich) and then cleaved from the solid support using trifluoroacetic acid, triisoproplysilane and water for 2 hours at room temperature. Peptide was precipitated from ethyl ether, extracted with acetic acid, acetonitrile, water and lyophilized. Crude labeled peptide was dissolved and purified on preparative reverse phase C18 column using acetonitrile/water. Purified fractions were pooled, lyophilized, and analyzed by liquid chromatography/mass spectrometry (PE/Sciex) and found to be consistent with their calculated masses.

HtrA1 was incubated in 96-well black optical bottom plates (Nalge Nunc Int., Rochester, N.Y.) with anti-HtrA1 antibodies serially diluted in assay buffer (50 mM Tris-HCl, pH 8.0, 200 mM NaCl, 0.25% CHAPS) for 20 min at 37° C. A 10 mM stock solution of the peptide substrate Mca-IRRVSYSF(Dnp)KK (SEQ ID NO: 152) (H2-Opt) in DMSO was diluted in water to 12.5 µM, pre-warmed at 37° C. and then added to the reaction mixture. The increase of fluorescence signal (excitation 328 nm, emission 393 nm) was measured on a SPECTRAMAX® M5 microplate reader (Molecular Devices, Sunnyvale, Calif.) and the linear rates of H2-Opt cleavage (mRFU/min) determined.

Figure 22B:
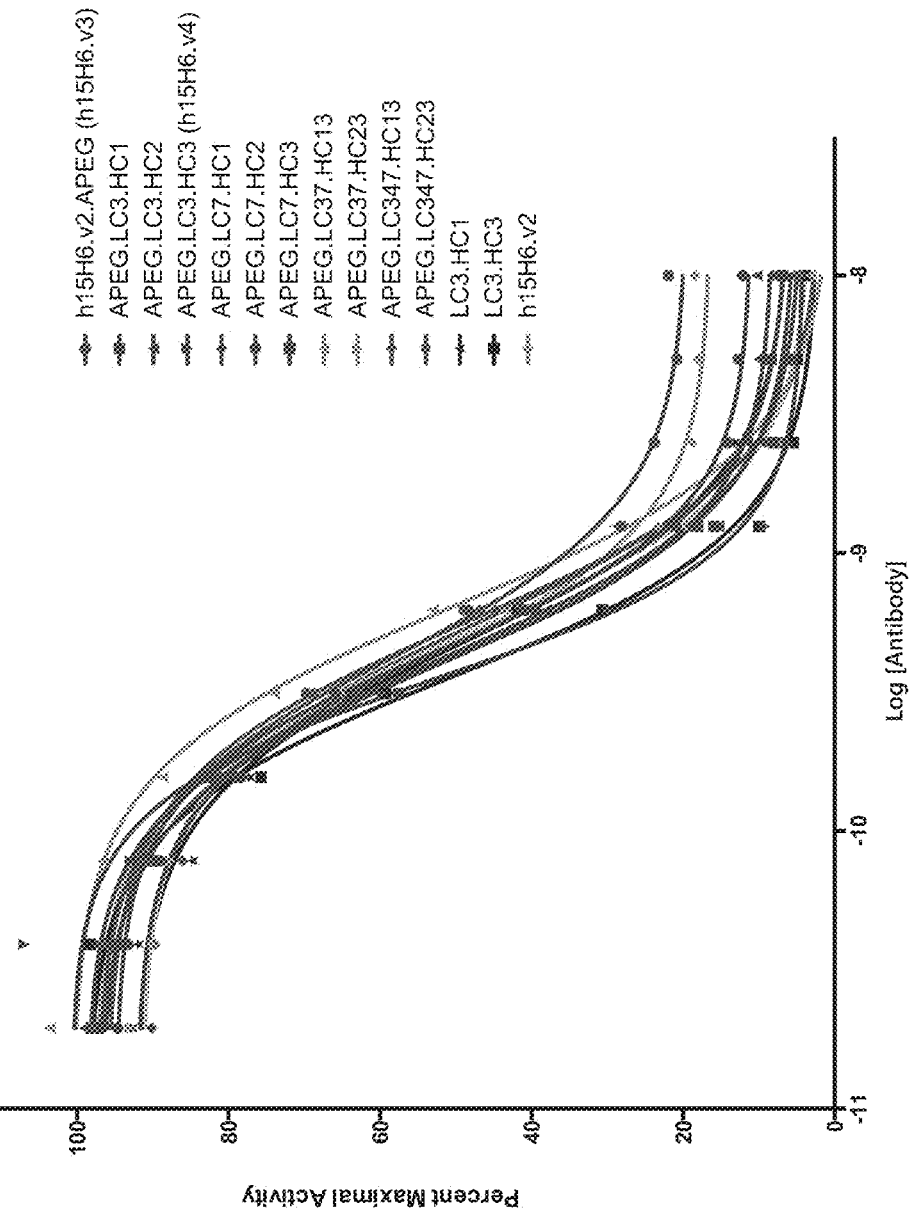
FIG. 22B is a graph showing an exemplary plot of results from an H2-Opt activity assay using recombinant HtrA1 depicted in FIG. 22A. The assay conditions included 400 pM HtrA1, and 2.5 pM substrate. The buffer was 50 mM Tris, 200 mM NaCl, 0.25% CHAPS, pH 8.3. These data are from the second repeat of the three independent experiments in FIG. 22A.
Figure 23A:
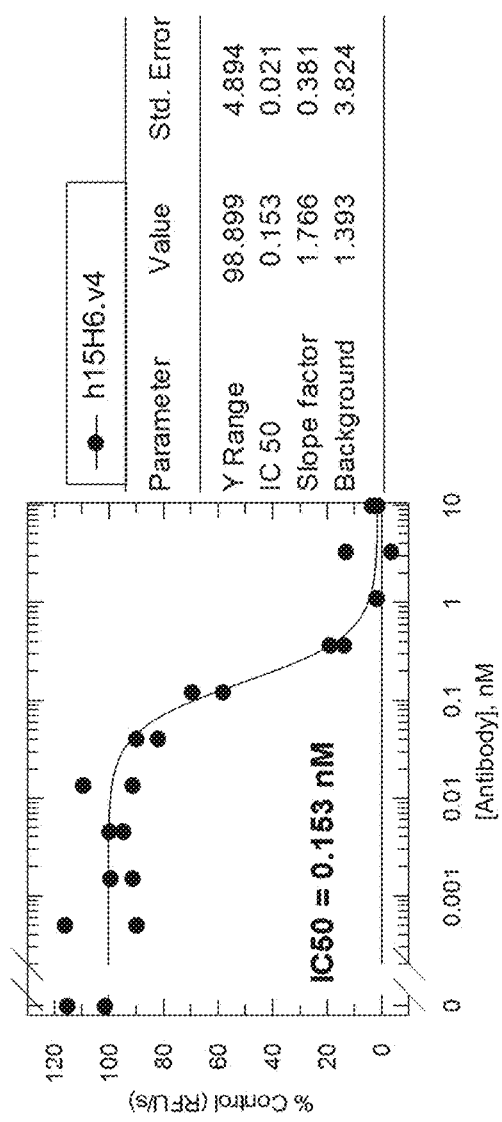
FIGS. 23A-23D are graphs showing the results from an H2-Opt activity assay for the indicated h15H6 antibody variant formats analyzed using an RFU/s rate approach. The graphs show percentage of control (RFU/S) as a function of antibody concentration (nM) for h15H6.v4 IgG monoclonal antibody (mAb) (FIG. 23A), a positive control anti-HtrA1 antibody (YW505.94A IgG, see, e.g., WO 2013/055998) (FIG. 23B), h15H6.v4 Fab (FIG. 23C), and 15H6.v2 Fab (FIG. 23D). A table next to each graph shows the IC50, Y range, slope factor, and background from each analysis.
Figure 23B:
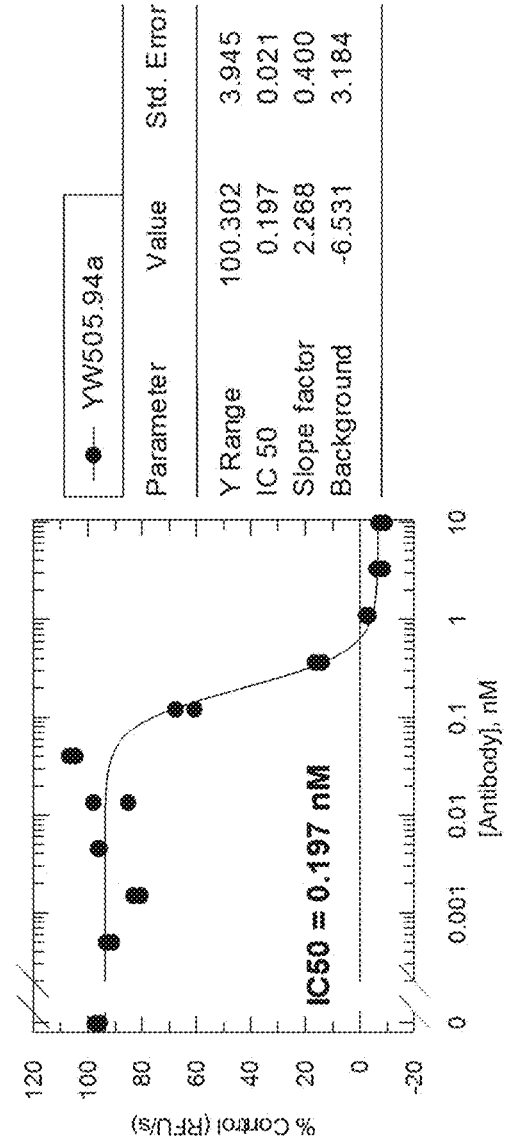
Figure 23C:
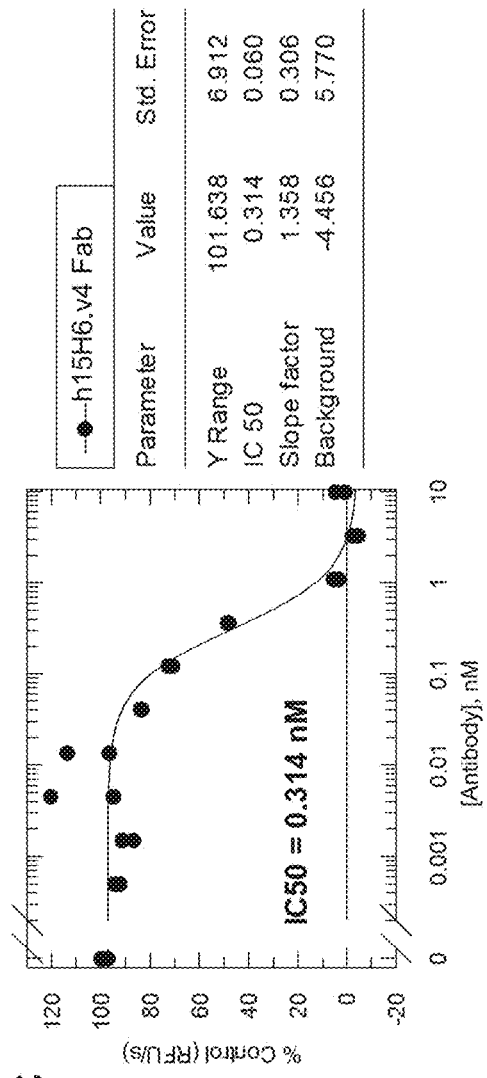
Figure 23D:
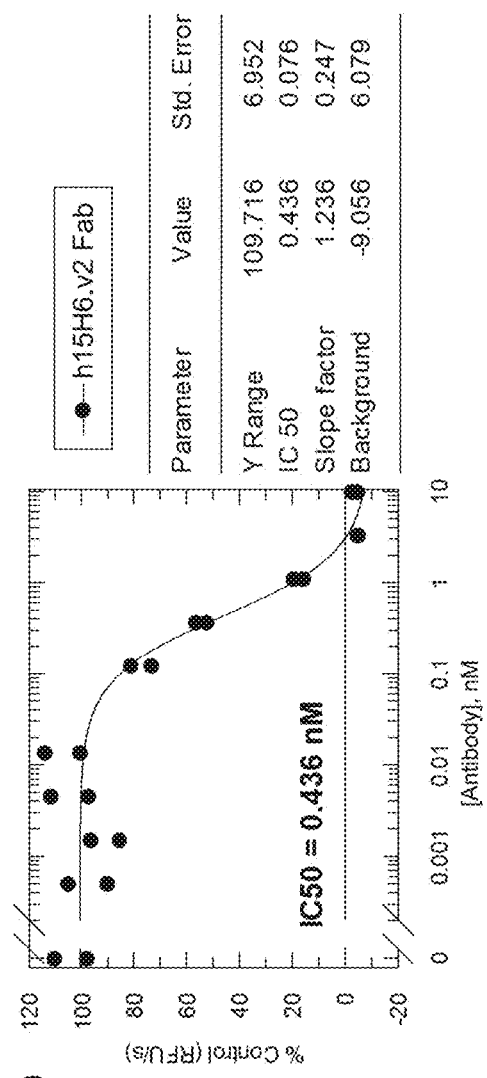
Figure 23E:
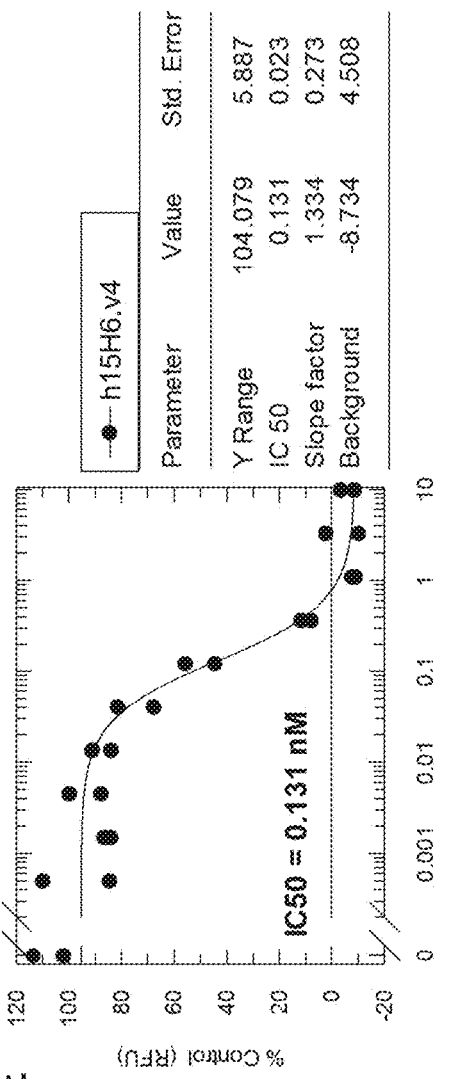
FIGS. 23E-23H are graphs showing the results from an H2-Opt activity assay for the indicated h15H6 antibody variant formats analyzed using an endpoint (RFU) approach. The graphs show percentage of control (RFU/S) as a function of antibody concentration (nM) for h15H6.v4 IgG Mab (FIG. 23E), a positive control anti-HtrA1 antibody (YW505.94A IgG) (FIG. 23F), h15H6.v4 Fab (FIG. 23G), and 15H6.v2 Fab (FIG. 23H). A table next to each graph shows the IC50, Y range, slope factor, and background from each analysis.
Figure 23F:
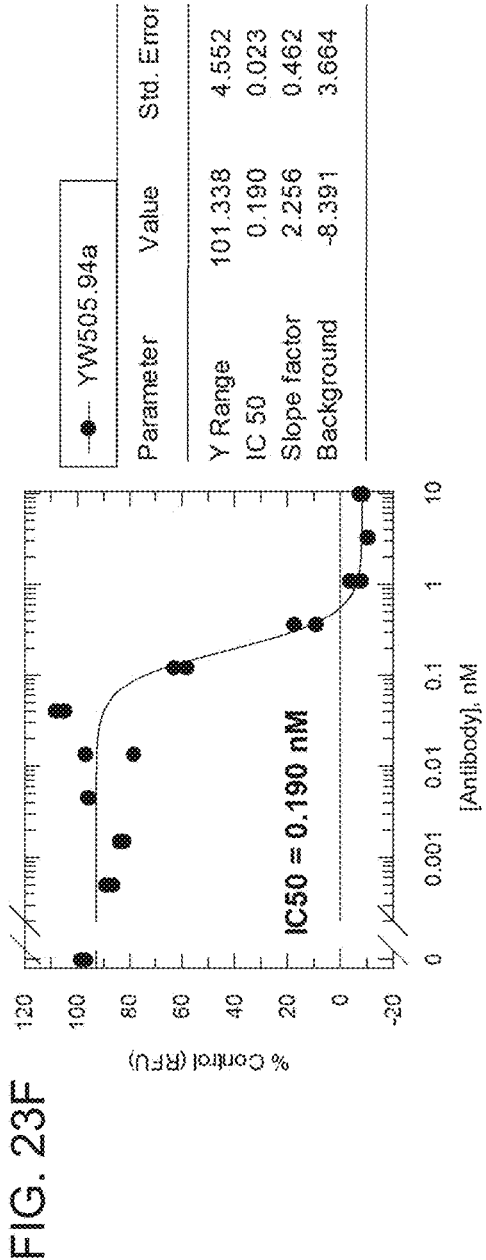
Figure 23G:
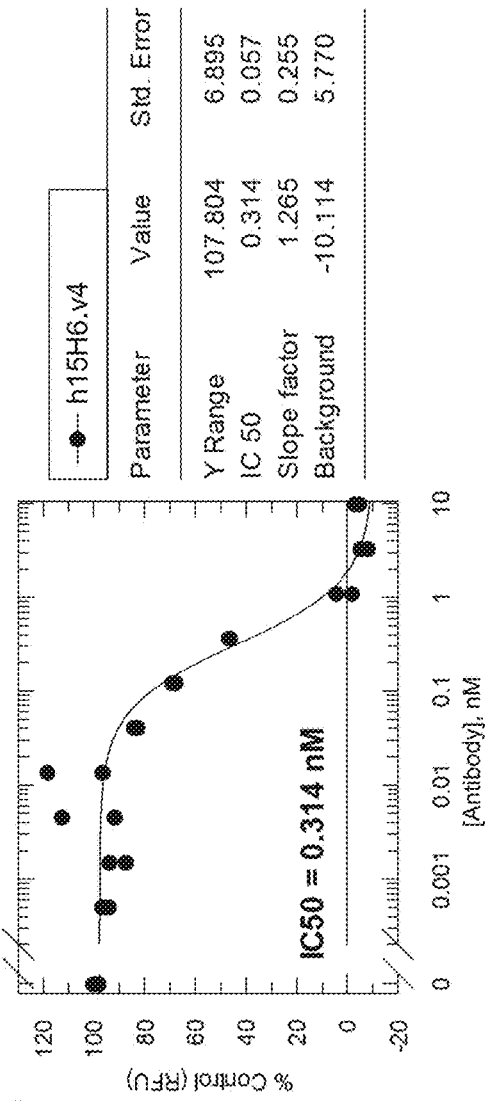
Figure 23H:
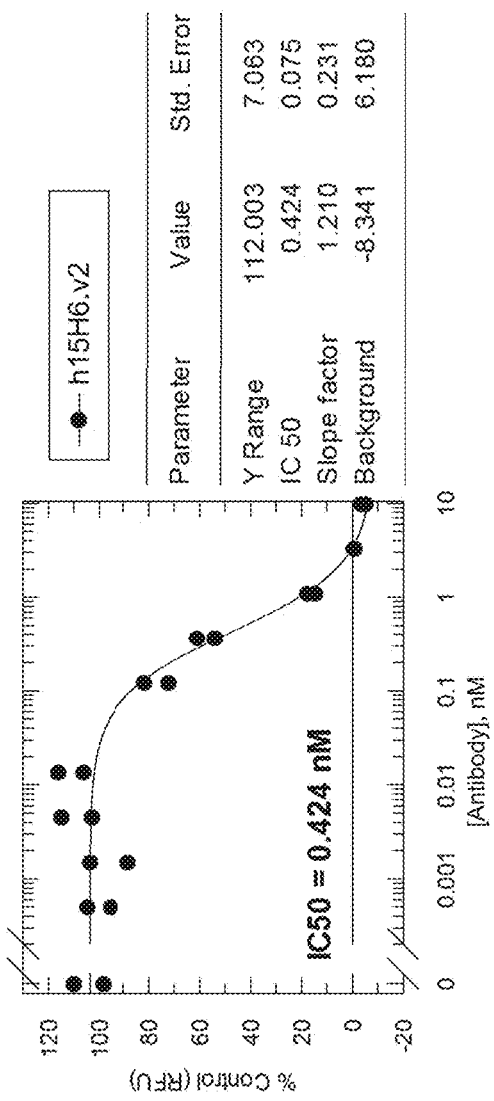

FIG. 22A shows a summary of the results of three independent H2-Opt assay experiments performed essentially as described above. Most of the clones had IC50 values in the range of about 0.4 nm to about 0.5 nM, as compared to about 0.39 nM for h15H6.v2. The anti-HtrA1 antibody APEG.LC3.HC3 (also referred to as h15H6.v4) showed the best IC50 value at about 0.386 nM in this assay (FIG. 22A). FIG. 22B shows a representative plot from this analysis. In general, the affinity matured h15H6.v2 variants showed improved maximal inhibition of HtrA1 compared to h15H6.v2 (FIG. 22A), with the maximal inhibition values ranging from about 78% to about 96%.

The FRET-based H2-Opt blocking assay was used to evaluate the ability of different antibody formats of the h15H6.v2 variants, including h15H6.v4, to inhibit HtrA1 activity. The H2-Opt assay was performed essentially as described above, except that the assay conditions were: 1 nM huHtrA1-PD enzyme, 1.25 µM H2-Opt substrate, 50 mM Tris pH 8, 200 mM NaCl, 0.25% CHAPS. The results were analyzed based on the relative fluorescent units (RFU)/s rate (50-1000 s) or the endpoint RFU values at 2000 s. FIGS. 23A-23H show the results of an exemplary independent experiment comparing the ability of h15H6.v2 in Fab format, and h15H6.v4 in IgG or Fab formats, to inhibit the activity of huHtrA1-PD. The anti-HtrA1 antibody YW505.94a (see WO2013/055988) served as a positive control. FIGS. 24A and 24B show a summary of the IC50 and IC90 results, respectively, from a first set of three independent experiments analyzed using the RFU/s approach. FIGS. 25A and 25B show a summary of the IC50 and IC90 results, respectively, from a second set of three independent experiments analyzed using the RFU/s or the endpoint RFU approach for h15H6.v4 Fab.

G. Blocking Ability of APEG.LC3. HC3 (h 15H6.v4) in a Mass Spectrometry-Based Activity Assay The ability of APEG.LC3.HC3 (h15H6.v4) to inhibit huHtrA1-PD-mediated cleavage of an intact full-length substrate (α-casein) was assessed using a mass spectrometry (MS)-based activity assay. In this example, the anti-HtrA1 antibody h15H6.v4 was compared to a small molecule inhibitor of HtrA proteases, ucf-101, which has been described as an antagonist to HtrA2 (also known as Omi) (Cilenti et al., *J. Biol. Chem.* 278(13):11489-11494, 2003). Tandem Mass Tag (TMT) isobaric mass tagging labels were employed for MS-based quantitation of α-casein cleavage by HtrA1 in the presence of h15H6.v4 or ucf-101. α-casein has three P1' residues that can be cleaved by HtrA1: Ser72, Thr95, and Ser157.

TMTDUPLEX™ isobaric mass tagging reagents were used to differentially label α-casein standards and assay samples for quantitation of intact α-casein. The TMTDUPLEX™ reagents are sets of isobaric compounds (i.e., same mass and structure, also called isotopomers) that are NHS-activated for covalent, irreversible labeling of primary amines (—NH2) groups. Each isobaric reagent contains a different number of heavy isotopes in the mass reporter tag moiety, which results in a unique reporter mass during tandem MS/MS for sample identification and relative quantitation.

100 mM triethylammonium bicarbonate, 100 nM huHtrA1, 100 µg/mL α-casein, and inhibitor (i.e., ucf-101 or h15H6.v4) were incubated (final volume 20 µL) at 37° C. for 18 hours (digested solution). Separately, a similar solution was generated without inhibitor and incubated identically (control solution). h15H6.v4 Fab was tested at concentrations ranging from 3.12 nM to 100 nM, while the positive control small molecule inhibitor ucf-101 was tested at concentrations ranging from 2 nm to 250 nM.

Tandem mass tag (TMTDUPLEX™) stock solutions were generated as recommended by vendor (Thermo Fisher Scientific). 5 µL of TMT-126 was added to the digested solution and 5 µL of TMT-127 was added to the control solution. After 1 h incubation at room temperature, the above solutions were combined on an equal volume basis. The samples were run on LC-MS and quantitated by fragmentation of most intense ion peaks using higher-energy C-trap dissociation (HCD); the reporter ion intensity ratio of 126/127 after fragmentation was used to determine the concentration in the digested solution.

Figure 26A:
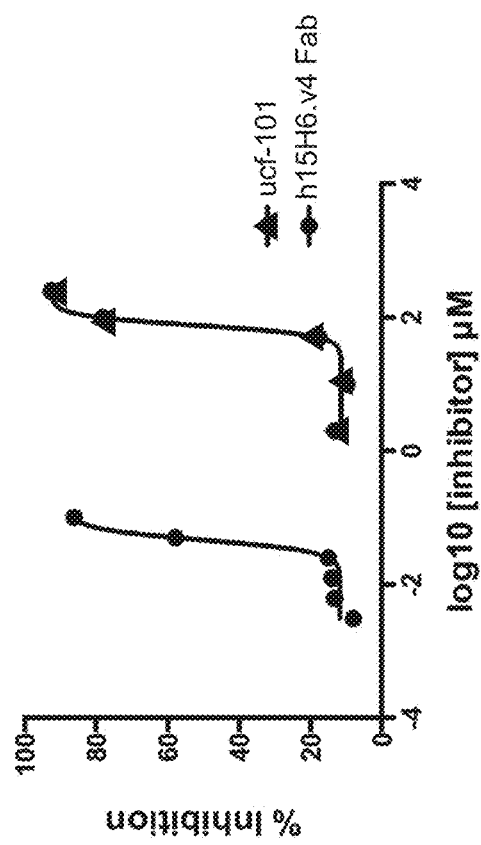
FIG. 26A is a graph showing an intact α-casein titration curve. The experimental concentration is plotted as a function of theoretical spike-in concentration (μg/ml). The correlation coefficient ($R^2$) was 0.999.
Figure 26B:
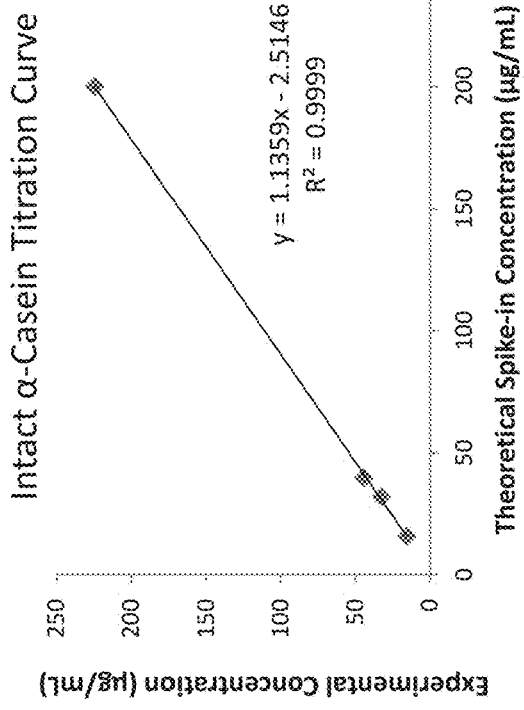
FIG. 26B is a graph showing the results of a mass-spectrometry-based HtrA1 activity assay. The ability of APEG.LC3.HC3 (h15H6.v4) to inhibit Htra1-PD activity was assessed as described in Example 3, section G. The small molecule inhibitor ucf-101 served as a positive control.

A titration curve showed that the assay accurately quantified intact α-casein (FIG. 26B). In this assay, h15H6.v4 Fab inhibited the huHtrA1-PD-mediated cleavage of intact α-casein with an IC50 of about 45 nM (IC90=about 71 nM). This value was markedly improved compared to the small molecule inhibitor ucf-101, which had an IC50 of 77 µM.

Figure 27A:
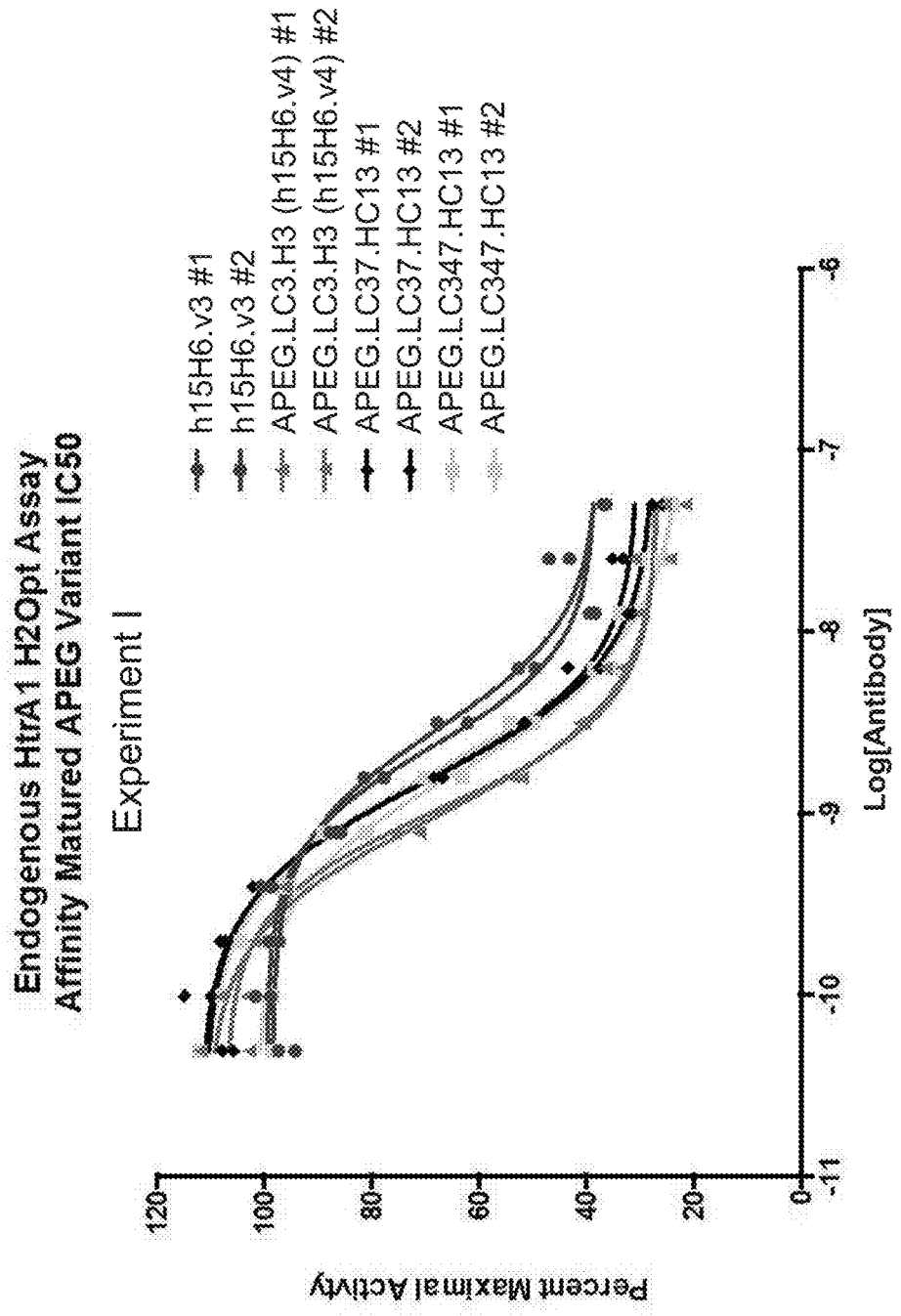
FIGS. 27A-27B are graphs showing the results from two independent endogenous HtrA1 activity assays, Experiment I (FIG. 27A) and Experiment II (FIG. 27B). For each antibody Fab, #1 and #2 indicate separate dilution series of the same antibody, with initial dilutions performed separately. The two dilution series were run on the same plate with other reagents being from the same preparation.
Figure 27B:
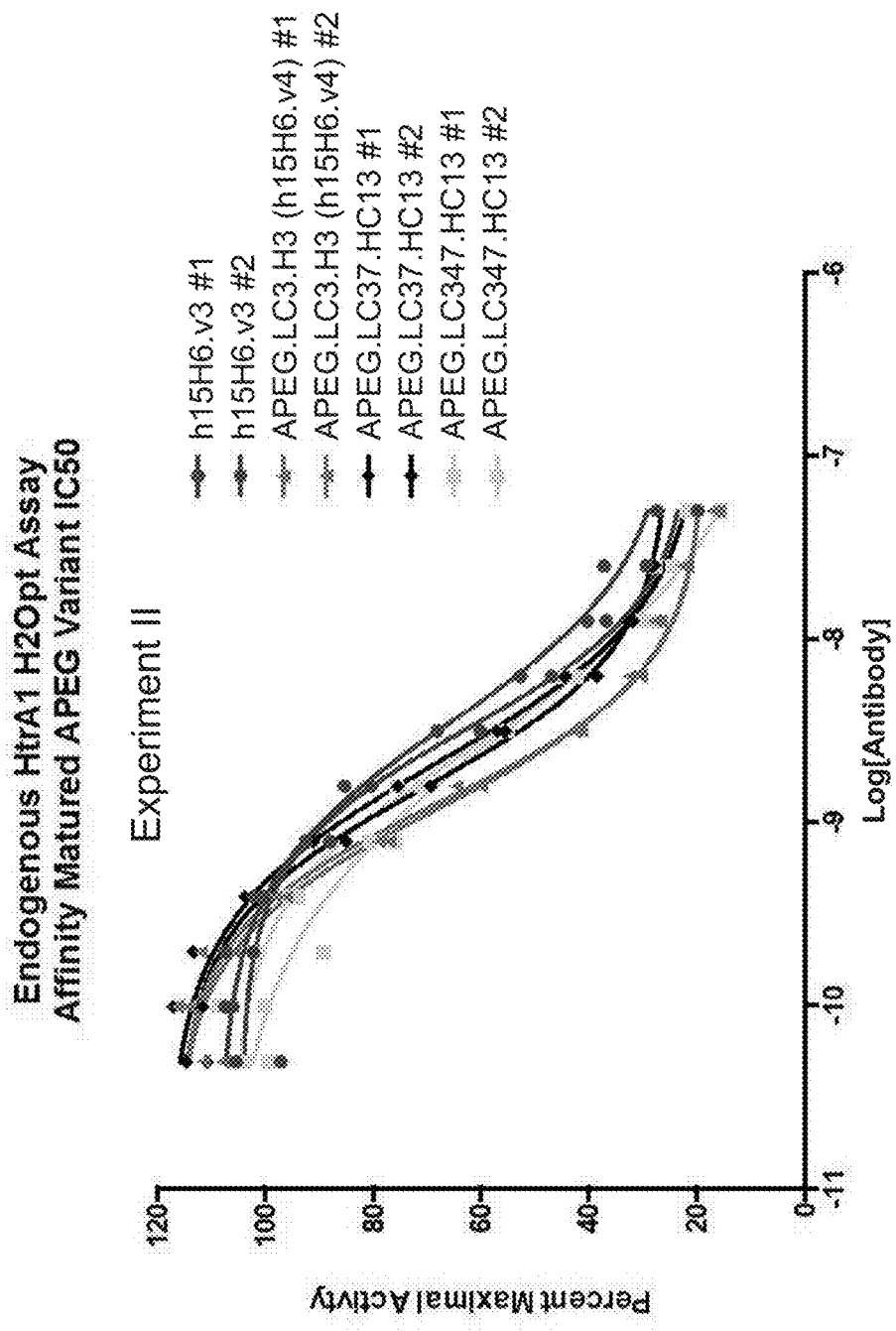
Figure 31A:
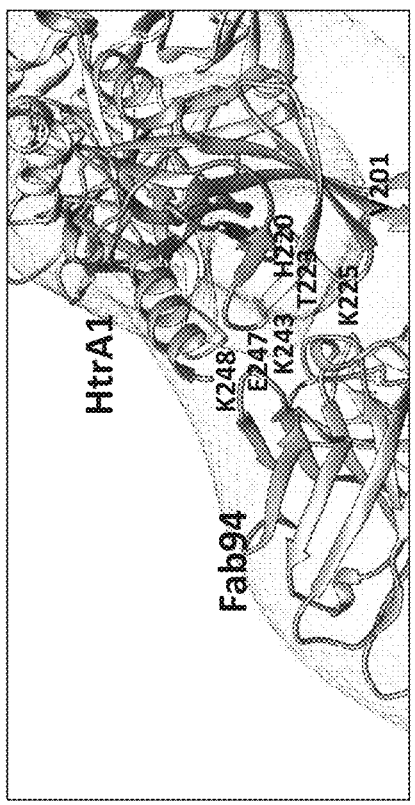
FIGS. 31A-31B depict the binding of YWV505.94 Fab (as described in WO 2013/055998) to HtrA1. When the amino acids designated in FIG. 31A are replaced with alanine, the binding affinity of the YW505.94 Fab for the mutated protein is reduced. The structure shown in FIG. 31B was generated using electron microscopy as described in Ciferri et al. (2015) Biochem. J. 472(2):169-81. The circle shows the epitope for the YW505.94 Fab on the HtrA1 protein. The YW505.94 Fab binds to loops "B" and "C" of the HtrA1 protein.
Figure 31B:

H. Blocking Ability of h15H6. v2 Affinity Matured Variants in an Endogenous HtrA1 Activity Assay The ability of h15H6.v2 affinity matured variants to inhibit endogenous HtrA1 activity in a rabbit eye model was assessed. For the endogenous HtrA1 activity assay, media from HtrA1-secreting cells (human C32 melanoma cells) was used as the source of HtrA1. See, e.g., Ciferri et al. *Biochem J.* Sep. 18, 2015, DOI: 10.1042/BJ20150601. Note that in the endogenous assay, there is an approximate 10-fold higher concentration of HtrA1 compared to the recombinant HtrA1 H2-Opt assay (see, e.g., FIG. 28), which is considered to explain the different IC50 values observed in the H2-Opt assays using endogenous HtrA1 and recombinant HtrA1. FIGS. 27A-27C show results from the Endogenous HtrA1 Assay. In particular, clone APEG.LC3.HC3 (h15H6.v4) had an IC50 of about 1.125 nM (FIG. 27C), with a maximal inhibition of about 80.1%.

I. Summary of Properties for Selected h15H6.v2 Variants

The kinetic binding and inhibitory activity of selected derivatives of the anti-HtrA1 antibody clone h15H6.v2 were compared using BIACORE SPR analysis and the FRET-based H2-Opt activity assay. To determine maximal inhibition, positive and negative controls were used to determine 0% inhibition (enzyme only, no inhibitor) and 100% inhibition (no enzyme). The results of this comparison are shown in FIG. 28.

Example 4: Molecular Assessment Analysis of Anti-HtrA1 Antibodies

Anti-HtrA1 antibody clones h15H6.v2, h15H6.v2.APEG (also referred to as h15H6.v3), and APEG.LC3.HC3 (also referred to as h15H6.v4) were tested in molecular assessment (MA) analyses for stability properties. The anti-HtrA1 antibody clone h19B12.v1 was also tested. Briefly, the anti-HtrA1 antibodies (1 mg/ml) were tested for stress under chemical conditions with AAPH (2,2-azobis(2-amidinopropane) dihydrochloride), a small molecule known to generate free radicals (see, e.g., Ji et al., *J. Pharmn Sci.* 98(12):4485-4500, 2009), as well as under thermal conditions at varying pH (a two-week thermal stress test at 40° C., pH 5.5) (see, e.g., Zhang et al., *J. Chromatography A* 1272:56-64, 2013).

Table 11 shows a comparison between the results of MA analyses for h15H6.v2 and h15H6.v3. Notably, LC-W91 in HVR-L3 had increased oxidation following AAPH stress in both h15H6.v2 and h15H6.v3 (about 84.5% and about 86.4%, respectively). Table 12 shows results of MA analysis for h15H6.v4. Surprisingly, the oxidation at LC-W91 in HVR-L3 for h15H6.v4 was reduced compared to h15H6.v2 and h15H6.v3, with only a 26.5% increase in oxidation following AAPH stress compared to approximately 84.5-86.4% increase in oxidation for h15H6.v2 and h15H6.v3. This improvement was unexpected because APEG.LC3.HC3 has only two substitutions compared to h15H6.v3, i.e., HC-T28K in the FR-H1 region and LC-N31E in HVR-L1, both of which were introduced to improve affinity and neither of which was expected to impact oxidation of LC-W91. The h15H6.v4 antibody used in this MA analysis was prepared using a single-column purification procedure. When the MA analysis for h15H6.v4 was repeated using antibody prepared using a two-column purification procedure, LC-W91 was shown to be unstable under AAPH stress. It is believed that the results of the AAPH stress assessment performed with material purified using the two-column purification was different from the results obtained using material purified by a single-column purification procedure because the single-column purified material contained a contaminant that interfered with the AAPH stress assessment.

TABLE 11

MA Properties of h15H6.v2 and h15H6.v3

| Stress | h15H6.v2 | h15H6.v3 |
|---|---|---|
| Thermal Stress | $D^{31}S^{32}$ in HVR-H1 is stable<br>$D^{55}G^{56}$ in HVR-H2 is unstable - 5.8% increase in isomerization<br>$D^{52}P^{52a}$ in HVR-H2 is stable | Not determined |
| AAPH Stress | $M^{34}$ in HVR-H1 is stable<br>$W^{91}$ in HVR-L3 is unstable - 84.5% increase in oxidation (3.7% in control and 88.2% in AAPH)<br>$W^{96}$ in HVR-L3 is stable | M in HVR-H1 is stable<br>W in HVR-H3 is stable<br>$W^{91}$ in HVR-L3 is unstable - 86.4% increase in oxidation (0.1% in control and 86.5% in AAPH)<br>$W^{96}$ in HVR-L3 is stable |
| Size | Monomer loss (0.9%) is acceptable | Not determined |
| Charge | Main peak loss (14.3%) is acceptable | Not determined |
| LC/MS | Masses are as expected | Not determined |

TABLE 12

MA Properties of h15H6.v4 (APEG.LC3.HC3)

| Stress | h15H6.v4 (APEG.LC3.HC3) |
|---|---|
| Thermal Stress | $D^{31}S^{32}$ in HVR-H1 is stable<br>$D^{52}P^{52a}$ in HVR-H2 is stable<br>$D^{97}Y^{98}$ in HVR-H3 is stable<br>$D^{99}Y^{100}$ in HVR-H3 is stable<br>$D^{101}Y^{102}$ in HVR-H3 is stable |
| AAPH Stress | $M^{34}$ in HVR-H1 is stable<br>$W^{91}$ in HVR-L3 is stable - 26.5% increase in oxidation (0.5% in control and 27.0% in AAPH stress)<br>$W^{96}$ in HVR-L3 is stable |
| Size | Monomer loss (0.1%) is acceptable |
| Charge | Main peak loss (3.7%) is acceptable |
| LC/MS | Masses are as expected |

Table 13 shows the results of MA analysis for the anti-HtrA1 antibody clone h19B12.v1. HC-N52a HC-G53 in HVR-H2 were determined to be unstable, with a 49% increase in deamidation. Accordingly, substitutions at these HVR-H2 positions of h19B12.v1 (e.g., HC-N52aE, HC-N52aS, HC-N52aS, and HC-N52a HC-G53A) are expected to improve stability.

TABLE 13

MA Properties of h19B12.v1

| Stress | h19B12.v1 |
|---|---|
| Thermal Stress | $D^{61}T^{62}$ in HVR-H2 is stable<br>$D^{100}G^{100a}$ in HVR-H3 is stable<br>$D^{27c}S^{27d}$ in HVR-L1 is stable<br>$N^{91}N^{92}$ in HVR-L3 is stable<br>$D^{94}P^{95}$ in HVR-L3 is stable |
| AAPH Stress | $N^{52a}G^{53}$ in HVR-H2 is unstable (49% change in deamidation) ($t_0$: 15% to $t_{4\ wk}$: 64%)<br>$M^{100d}$ in HVR-H3 is stable<br>$M^{33}$ in CDR-L1 is stable<br>$M^{34}$ in CDR-H1 is stable |
| Size | Monomer loss (1.8%) is acceptable |
| Charge | Main peak loss (56.3%) is unacceptable |
| LC/MS | Masses are as expected |

Example 5: Structure of h15H6.v4 Fab Bound to HtrA1

The structure of h15H6.v4 Fab bound to HtrA1 was determined by X-ray crystallography and electron microscopy. The results demonstrated that the h15H6.v4 Fab HtrA1 epitope is formed primarily by amino acids that comprise the turn of the LA loop of HtrA1.

Peptide Synthesis:

Peptides corresponding to regions of the HtrA1 protein were generated using methods well known in the art. See, for example, Atherton, E., et al (1978). *J. Chem Soc. Chem. Commun.* 13:537-539.

Crystallization:

The h15H6.v4 Fab (1 mL) at 10 mg/ml in 0.15M NaCl, 20 mM Tris pH 7.5 was incubated overnight at 4° C. with 1 mg of peptide (3 fold molar excess peptide/protein) containing amino acids in the LA loop of HtrA1. The Fab-peptide complex was crystallized using 2M ammonium sulfate, 0.2M potassium acetate.

X-ray Refinement:

An h15H6.v4 Fab/HtrA1 peptide crystal was harvested and preserved for diffraction analysis by immersion in a cryo-protectant solution made from addition of 30% glycerol to mother liquor followed by sudden immersion in liquid nitrogen. Data were collected at SSRL beamline 12-2 and processed using XDS (Kabasch W (2010) *Acta Crystallogr D Biol Crystallogr.* 266:125-32). Molecular replacement for the Fab-peptide complex was achieved using the Fab structure as a search probe in CCP4 (Winn M D et al (2011) *Acta Crystallogr D Biol Crystallogr.* 67:235-42). After rigid body refinement, Fo-Fc density could be seen for the peptide. A portion of the HtrA protease domain residues from loop A (RKLPFSKREVPV) (PDB 3TJO) were then fit into the density essentially as described in Emsley et al. (2010) *Acta Crystallogr D Biol Crystallogr.* 66:125-32.

Several rounds of refinement in Phenix (Adams P D et al (2010) *Acta Crystallogr D Bioc Crystalogr.* 66:213-21) were utilized. A final round of refinement in Buster (Bricogne G et al. (2011) brought the R values to R=16.8%, Rfree=19.8% 2.1 Å resolution.

Electron Microscopy (EM) Structure of Fab 15H6. v4 Bound to HtrA1

For EM imaging, 4 µl of HtrA1-hFab15H6.v4 complex was incubated for 30 sec on a freshly glow discharged continuous carbon 400-mesh copper grid (Electron Microscopy Sciences). After incubation, the sample was negatively stained using a solution of 2% (w/v) uranyl formate (SPI Supplies). Excess stain solution was blotted away with Watman paper and the grid was air-dried. HtrA1-Fab15H6.v4 sample was analyzed on a Tecnai-12 BioTween (FEI) equipped with a LaB6 filament and operated at 120 keV under low dose conditions. Images were collected using a 4 k×4 k CCD camera (Gatan Inc.) at a nominal magnification of ×62,000 (2.22 Å per pixel). 27346 particles, having a box size of 128px were semi-automatically picked, using the swarm algorithm available under the e2dogpicker.py routine included into EMAN2 distribution (Tang L et al. (2007) *J. Chem. Inf. Model.* 47:1438-45). These particles were then subjected to reference free 2D classification using the software suite Relion (Scheres SH (2012) *J. Struct. Biol.*180:519-30). Given the flexibility between the HTRA1 trimer and the bound Fabs, the 3D classification algorithm of Relion was used to generate five 3D volumes using as a starting model the crystal structure of HtrA1 trimer (PDB ID 3TJO) low pass filtered to a resolution of 60 Å. Each of these volumes was finally refined using the Refine3D algorithm in Relion. Atomic densities of the HTRA1 trimer and the crystal structure of the Fab15H6.v4 were fitted into the EM density using the fit in map algorithm in Chimera (Pettersen E F et al., 2004). *J. Comput. Chem.* 25:1605-12 (2004).

Validation of Structure of Fab 15H6. v4 Fab Bound to HtrA1 Using Alanine Substitutions The structural studies described above demonstrated that the Fab15H6.v4 Fab interacts closely with loop "A" of the HtrA1 protein. To confirm this, a peptide corresponding to residues 190-201 of the human HtrA1 sequence (where the numbering corresponds to the numbering of the precursor protein) was synthesized and tested for binding to h15H6.v4 Fab using surface plasmon resonance (SPR) as described above. The peptide (LA-pep1) showed a strong binding interaction with 15H6.v4 Fab having a KD value of 0.4 nM. See Table 14.

Alanine substitutions in this peptide sequence reduce (LA-pep2, LA-pep5) or completely abolish (LA-pep3, LA-pep4, LA-pep5) the binding to 15H6.v4 Fab. These biophysical results are consistent with the structural studies described above and in FIGS. 32A and 32B and demonstrate that the binding epitope for 15H6.v4 is formed primarily by amino acids that comprise the turn of LA Loop of HtrA1.

In contrast, the YW505.94 Fab did not bind to LA-pep1, nor to any of the mutant forms (Table 14). This indicates that, despite the fact that the YW505.94 Fab and the h15H6.v4 compete with each other to bind to HtrA1, the epitopes of these two Fabs are distinct. The YW505.94 Fab epitope is centered at loops B and C, whereas the epitope of 15H6.v4 Fab mainly comprises the tip of the LA loop. Although it is not intended that the present invention be bound by any particular mechanism, it is possible that the close interaction between h15H6.v4 and the LA loop of HtrA1 accounts for the significantly improved affinity and potency of this antibody when compared with YW505.94.

TABLE 14

HtrA1 Loop A (LA) peptides binding to 15H6.v4 Fab and to YW505.94 Fab

| Name | Peptide | AA change | h15H6.v4 Fab $K_D$ (nM) | h15H6.vr Fab Affinity loss** | YW505.94 Fab $K_D$ (nM) |
|---|---|---|---|---|---|
| LA-pep1 | RKLPFSKREVPV | | | | |
| LA-pep2 | AKLPFSKREVPV | R1A | 321 | 810 | NB |
| LA-pep3 | RKAPFSKREVPV | L3A | NB* | >2,500 | NB |
| LA-pep4 | RKLAFSKREVPV | P4A | NB | >2,500 | NB |
| LA-pep5 | RKLPASKREVPV | F5A | 4.53 | 11 | NB |
| LA-pep6 | RKLPFSKAEVPV | R8A | NB | >2,500 | NB |

*NB-no binding detected up to 1 µM, **affinity loss = $K_D$ mutant/$K_D$ wild-type.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds HtrA1, or an antigen-binding fragment thereof, wherein the antibody comprises a binding domain comprising the following six hypervariable regions (HVRs):
   (a) an HVR-H1 comprising the amino acid sequence of DSEX$_1$H (SEQ ID NO: 1), wherein X$_1$ is Met or Leu;
   (b) an HVR-H2 comprising the amino acid sequence of GVDPETX$_2$GAAYNQKFKG (SEQ ID NO: 2), wherein X$_2$ is Glu or Asp;
   (c) an HVR-H3 comprising the amino acid sequence of GYDYDYALDY (SEQ ID NO: 3);
   (d) an HVR-L1 comprising the amino acid sequence of RASSSVX$_3$FIH (SEQ ID NO: 4), wherein X$_3$ is Glu or Asn;
   (e) an HVR-L2 comprising the amino acid sequence of ATSX$_4$LAS (SEQ ID NO: 5), wherein X$_4$ is Asn, His or Glu; and
   (f) an HVR-L3 comprising the amino acid sequence of QQWX$_5$SX$_6$PWT (SEQ ID NO: 6), wherein X$_5$ is Ser or Tyr and X$_6$ is Ala or Asn.

2. The antibody, or antigen-binding fragment thereof, of claim 1, wherein the antibody comprises:
   (a) a variable heavy (VH) domain comprising an amino acid sequence having at least 95% sequence identity to the amino acid sequence of SEQ ID NO: 21; and
   (b) a variable light (VL) domain comprising an amino acid sequence having at least 95% sequence identity to the amino acid sequence of SEQ ID NO: 22.

3. The antibody, or antigen-binding fragment thereof, of claim 1, which is an antibody fragment that binds to HtrA1.

4. The antibody, or antigen-binding fragment thereof, of claim 3, wherein the antibody fragment is a Fab, a Fab'-SH, an Fv, an scFV, or a (Fab')$_2$ fragment.

5. The antibody, or antigen-binding fragment thereof, of claim 4, wherein the antibody fragment is a Fab.

6. The antibody, or antigen-binding fragment thereof, of claim 5, wherein the Fab comprises a truncation in the upper hinge of the heavy chain constant region.

7. The antibody, or antigen-binding fragment thereof, of claim 6, wherein the heavy chain constant region terminates at position 221 (EU numbering).

8. The antibody, or antigen-binding fragment thereof, of claim 1, wherein the antibody is a monoclonal antibody, a humanized antibody, or a bispecific antibody.

9. The antibody, or antigen-binding fragment thereof, of claim 1, wherein the antibody is a full-length antibody.

10. A pharmaceutical composition comprising the antibody, or antigen-binding fragment thereof, of claim 1 and at least one pharmaceutically acceptable carrier, excipient, or diluent.

11. An isolated antibody that specifically binds HtrA1, or an antigen-binding fragment thereof, wherein the antibody comprises a binding domain comprising the following six HVRs:
   (a) an HVR-H1 comprising the amino acid sequence of DSEMH (SEQ ID NO: 7);
   (b) an HVR-H2 comprising the amino acid sequence of GVDPETEGAAYNQKFKG (SEQ ID NO: 8);
   (c) an HVR-H3 comprising the amino acid sequence of GYDYDYALDY (SEQ ID NO: 3);
   (d) an HVR-L1 comprising the amino acid sequence of RASSSVEFIH (SEQ ID NO: 9);
   (e) an HVR-L2 comprising the amino acid sequence of ATSNLAS (SEQ ID NO: 10); and
   (f) an HVR-L3 comprising the amino acid sequence of QQWSSAPWT (SEQ ID NO: 11).

12. A pharmaceutical composition comprising the antibody, or antigen-binding fragment thereof, of claim 11 and at least one pharmaceutically acceptable carrier, excipient, or diluent.

13. An isolated nucleic acid encoding the antibody, or antigen-binding fragment thereof, of claim 11.

14. The nucleic acid of claim 13, wherein the antibody, or antigen-binding fragment thereof, comprises:
   (a) a VH domain comprising an amino acid sequence having at least 95% sequence identity to the amino acid sequence of SEQ ID NO: 21; and
   (b) a VL domain comprising an amino acid sequence having at least 95% sequence identity to the amino acid sequence of SEQ ID NO: 22.

15. The nucleic acid of claim 14, wherein the VH domain comprises the amino acid sequence of SEQ ID NO: 21 and the VL domain comprises the amino acid sequence of SEQ ID NO: 22.

16. The nucleic acid of claim 15, wherein the antibody, or antigen-binding fragment thereof, is a full-length antibody comprising a heavy chain comprising the amino acid sequence of SEQ ID NO: 160 and a light chain comprising the amino acid sequence of SEQ ID NO: 159.

17. A vector comprising the isolated nucleic acid of claim 13.

18. A host cell comprising the vector of claim 17.

19. The host cell of claim 18, wherein the host cell is a mammalian cell.

20. The host cell of claim 19, wherein the mammalian cell is a Chinese hamster ovary (CHO) cell or a 293 cell.

21. The host cell of claim 18, wherein the host cell is a prokaryotic cell.

22. The host cell of claim 21, wherein the prokaryotic cell is *Escherichia coli*.

23. A method of producing an antibody that specifically binds HtrA1, or an antigen-binding fragment thereof, the method comprising:
   (a) culturing the host cell of claim 18; and
   (b) recovering the antibody, or antigen-binding fragment thereof, from the host cell or host cell culture medium.

24. The method of claim 23, wherein the antibody, or antigen-binding fragment thereof, comprises:
   (a) a VH domain comprising the amino acid sequence of SEQ ID NO: 21; and
   (b) a VL domain comprising the amino acid sequence of SEQ ID NO: 22.

25. An isolated antibody that specifically binds HtrA1, or an antigen-binding fragment thereof, wherein the antibody comprises a VH domain comprising the amino acid sequence of SEQ ID NO: 21 and a VL domain comprising the amino acid sequence of SEQ ID NO: 22.

26. The antibody, or antigen-binding fragment thereof, of claim 25, which is an antibody fragment that binds to HtrA1.

27. The antibody, or antigen-binding fragment thereof, of claim 26, wherein the antibody fragment is a Fab, a Fab'-SH, an Fv, an scFV, or a (Fab')$_2$ fragment.

28. The antibody, or antigen-binding fragment thereof, of claim 27, wherein the antibody fragment is a Fab.

29. The antibody, or antigen-binding fragment thereof, of claim 28, wherein the Fab comprises a truncation in the upper hinge of the heavy chain constant region.

30. The antibody, or antigen-binding fragment thereof, of claim 29, wherein the heavy chain constant region terminates at position 221 (EU numbering).

31. The antibody, or antigen-binding fragment thereof, of claim 25, wherein the antibody is a monoclonal antibody, a bispecific antibody, or a humanized antibody.

32. The antibody, or antigen-binding fragment thereof, of claim 25, wherein the antibody is a full-length antibody.

33. A pharmaceutical composition comprising the antibody, or antigen-binding fragment thereof, of claim 25 and at least one pharmaceutically acceptable carrier, excipient, or diluent.

34. An isolated antibody that specifically binds HtrA1, wherein the antibody is a full-length antibody comprising a heavy chain comprising the amino acid sequence of SEQ ID NO: 160 and a light chain comprising the amino acid sequence of SEQ ID NO: 159.

35. A pharmaceutical composition comprising the antibody, or antigen-binding fragment thereof, of claim 34 and at least one pharmaceutically acceptable carrier, excipient, or diluent.

36. An isolated antibody that specifically binds HtrA1, or antigen-binding fragment thereof, wherein the antibody comprises a binding domain comprising the following six HVRs:
 (a) an HVR-H1 comprising the amino acid sequence of DSEMH (SEQ ID NO: 7);
 (b) an HVR-H2 comprising the amino acid sequence of GVDPETEGAAYNQKFKG (SEQ ID NO: 8);
 (c) an HVR-H3 comprising the amino acid sequence of GYDYDYALDY (SEQ ID NO: 3);
 (d) an HVR-L1 comprising the amino acid sequence of RASSSVEFIH (SEQ ID NO: 9);
 (e) an HVR-L2 comprising the amino acid sequence of ATSNLAS (SEQ ID NO: 10); and
 (f) an HVR-L3 comprising the amino acid sequence of QQWSSAPWT (SEQ ID NO: 11); and
 wherein the antibody comprises a heavy chain comprising an amino acid sequence having at least 95% sequence identity to the sequence of SEQ ID NO: 156.

37. The antibody, or antigen-binding fragment thereof, of claim 36, wherein the heavy chain comprises an amino acid sequence having at least 96% sequence identity to the sequence of SEQ ID NO: 156.

38. The antibody, or antigen-binding fragment thereof, of claim 37, wherein the heavy chain comprises an amino acid sequence having at least 97% sequence identity to the sequence of SEQ ID NO: 156.

39. The antibody, or antigen-binding fragment thereof, of claim 38, wherein the heavy chain comprises an amino acid sequence having at least 98% sequence identity to the sequence of SEQ ID NO: 156.

40. The antibody, or antigen-binding fragment thereof, of claim 39, wherein the heavy chain comprises an amino acid sequence having at least 99% sequence identity to the sequence of SEQ ID NO: 156.

41. The antibody, or antigen-binding fragment thereof, of claim 40, wherein the heavy chain comprises the amino acid sequence of SEQ ID NO: 156.

42. The antibody, or antigen-binding fragment thereof, of claim 41, which comprises a heavy chain comprising the amino acid sequence of SEQ ID NO: 160 and a light chain comprising the amino acid sequence of SEQ ID NO: 159.

43. A pharmaceutical composition comprising the antibody, or antigen-binding fragment thereof, of claim 36 and at least one pharmaceutically acceptable carrier, excipient, or diluent.

44. An isolated antibody that specifically binds HtrA1, or antigen-binding fragment thereof, wherein the antibody comprises:
 (a) a VH domain comprising the amino acid sequence of SEQ ID NO: 21; and
 (b) a VL domain comprising the amino acid sequence of SEQ ID NO: 22; and
 wherein the antibody comprises a heavy chain comprising an amino acid sequence having at least 95% sequence identity to the sequence of SEQ ID NO: 156.

45. The antibody, or antigen-binding fragment thereof, of claim 44, wherein the heavy chain comprises an amino acid sequence having at least 96% sequence identity to the sequence of SEQ ID NO: 156.

46. The antibody, or antigen-binding fragment thereof, of claim 45, wherein the heavy chain comprises an amino acid sequence having at least 97% sequence identity to the sequence of SEQ ID NO: 156.

47. The antibody, or antigen-binding fragment thereof, of claim 46, wherein the heavy chain comprises an amino acid sequence having at least 98% sequence identity to the sequence of SEQ ID NO: 156.

48. The antibody, or antigen-binding fragment thereof, of claim 47, wherein the heavy chain comprises an amino acid sequence having at least 99% sequence identity to the sequence of SEQ ID NO: 156.

49. The antibody, or antigen-binding fragment thereof, of claim 48, wherein the heavy chain comprises the amino acid sequence of SEQ ID NO: 156.

50. A pharmaceutical composition comprising the antibody, or antigen-binding fragment thereof, of claim 44 and at least one pharmaceutically acceptable carrier, excipient, or diluent.

51. An isolated antibody that specifically binds HtrA1, or antigen-binding fragment thereof, which is an antibody fragment comprising a heavy chain which comprises the amino acid sequence of SEQ ID NO: 160 and a light chain which comprises the amino acid sequence of SEQ ID NO: 159.

52. A pharmaceutical composition comprising the antibody, or antigen-binding fragment thereof, of claim 51 and at least one pharmaceutically acceptable carrier, excipient, or diluent.

* * * * *

UNITED STATES PATENT AND TRADEMARK OFFICE
CERTIFICATE OF CORRECTION

PATENT NO. : 10,421,822 B2
APPLICATION NO. : 16/168503
DATED : September 24, 2019
INVENTOR(S) : Robert F. Kelley et al.

It is certified that error appears in the above-identified patent and that said Letters Patent is hereby corrected as shown below:

In the Specification

Column 14, Line 67, replace "m1 5H6" with --m15H6--.

Column 15, Line 16, replace "m1 5H6" with --m15H6--.

Column 16, Line 61, replace "2.5 pM" with --2.5 µM--.

Column 18, Line 9, replace "YWV505.94" with --YW505.94--.

Column 25, Line 60, replace "10-10M" with --$10^{-10}$M--.

Column 26, Line 62, replace "% O/amino" with --% amino--.

Column 27, Line 2, replace "XIY" with --X/Y--.

Column 28, Line 14, replace "HtrA11" with --HtrA1--.

Column 35, Lines 52-53, replace "3 capital letters in italics, e.g., NNK, NNS, XYZ, DVK" with --3 capital letters in italics, e.g., *NNK, NNS, XYZ, DVK*--.

Column 38, Line 44, replace "Arg1197" with --Arg197--;
    Line 57, replace "Leu1192" with --Leu192--;
    Line 59, replace "Leu1192" with --Leu192--.

Column 40, Line 19, replace "GVPSRFSGSGSS" with --GVPSRFSGSGS--.

Column 48, Line 5, replace "Factor 20 D" with --Factor D--.

Column 49, Line 21, replace "EGGVXN" with --EGGVX$_1$N--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,421,822 B2

Column 50, Line 18, replace "90%/I" with --90%--.

Column 52, Line 67, replace "1.7 nriM" with --1.7 nM--.

Column 54, Line 55, replace "(ko)" with --$k_{off}$--.

Column 60, Line 28, replace "WINTYTGETTYAXDFKG" with --WINTYTGETTYAX$_1$DFKG--.

Column 62, Line 32, replace "*immunol.*" with --*Immunol.*--.

Column 63, Line 29, replace "lie" with --Ile--;
    Line 30, replace "Gin" with --Gln--.

Column 64, Line 30, replace "Gin" with --Gln--;
    Line 35, replace "Gin" with --Gln--;
    Line 39, replace "Gin" with --Gln--.

Column 67, Line 18, replace "*Immrunol.*" with --*Immunol.*--.

Column 70, Line 11, replace "YO, NSO" with --Y0, NS0--.

Column 71, Line 8, replace "YO, NSO" with --Y0, NS0--.

Column 73, Line 48, replace "HtrA11" with --HtrA1--.

Column 76, Lines 64-65, replace "hyd roxymethylcellu lose" with --hydroxymethylcellulose--.

Column 82, Line 28, replace "*Deiiv.*" with --*Deliv.*--.

Column 84, Line 60, replace "anti-HtrA1 10" with --anti-HtrA1--.

Column 89, Line 32, replace "Farster" with --Förster--.

Column 90, Line 49, replace "SUPERSCRIPT@" with --SUPERSCRIPT®--.

Column 93, Line 47, replace "980" with --98--.

Column 95, Line 6, replace "*Biot*" with --*Biol.*--.

Column 97, Line 13, replace "19812" with --19B12--.

Column 98, Line 31, replace "h 156H6. v2" with --h156H6.v2--.

Column 99, Line 1, replace "h 156H6. v2" with --h156H6.v2--.

Column 101, Line 60, replace "inhibitory" with --Inhibitory--.

CERTIFICATE OF CORRECTION (continued)
U.S. Pat. No. 10,421,822 B2

Column 102, Line 2, replace "Mca-iRRVSYSF" with --Mca-IRRVSYSF--.

Column 104, Line 29, replace "*Pharmn*" with --*Pharm.*--.

Column 105, Line 5, replace "unstable" with --<u>unstable</u>--;
      Line 9, replace "unstable" with --<u>unstable</u>--;
      Line 10, replace "unstable" with --<u>unstable</u>--;
      Line 29, replace "stable" with --<u>stable</u>--;
      Line 54, replace "$t_{4\ wk}$" with --$t_{4wk}$--.

Column 106, Line 50, replace "*Bioc Crystalogr.*" with --*Biol Crystallogr.*--;
      Line 54, replace "15H6. v4" with --15H6.v4--.

Column 27, Line 54, replace "lie" with --Ile--.

Column 70, Line 63, replace "$T_M 4$" with --TM4--.

Column 76, Line 63, replace "coascervation" with --coacervation--.

Column 91, Line 61, replace "dithioreitol" with --dithiothreitol--.